(12) United States Patent
Horwitz

(10) Patent No.: US 7,993,915 B2
(45) Date of Patent: Aug. 9, 2011

(54) METHODS AND MATERIALS FOR INCREASING EXPRESSION OF RECOMBINANT POLYPEPTIDES

(75) Inventor: Arnold M. Horwitz, San Leandro, CA (US)

(73) Assignee: XOMA Technology Ltd., Berkeley, CA (US)

( * ) Notice: Subject to any disclaimer, the term of this patent is extended or adjusted under 35 U.S.C. 154(b) by 696 days.

(21) Appl. No.: 11/673,539

(22) Filed: Feb. 9, 2007

(65) Prior Publication Data

US 2007/0281334 A1     Dec. 6, 2007

Related U.S. Application Data

(62) Division of application No. 10/404,724, filed on Mar. 31, 2003, now Pat. No. 7,192,737.

(60) Provisional application No. 60/368,530, filed on Mar. 29, 2002.

(51) Int. Cl.
*C12N 5/00*     (2006.01)
(52) U.S. Cl. ............. 435/325; 435/252.33; 435/254.21; 435/320.1; 536/23.53; 536/23.5
(58) Field of Classification Search .................. None
See application file for complete search history.

(56) References Cited

U.S. PATENT DOCUMENTS

| | | | |
|---|---|---|---|
| 4,880,741 | A | 11/1989 | Davidow et al. |
| 5,998,174 | A | 12/1999 | Glorioso et al. |
| 2002/0019049 | A1 | 2/2002 | Lok |
| 2003/0203447 | A1 | 10/2003 | Horwitz |

FOREIGN PATENT DOCUMENTS

WO     20040033693 A1     4/2004

OTHER PUBLICATIONS

Ciafre, et al., "A Plasmid Family Containing Two Different Expression Cassettes Suitable for Immunomodulation and Genetic Immunization" Plasmid 40:84-89 (1998) Article No. PL981339.
Papa, et al., "Development of a Multigenic Plasmid Vector for HCV DNA Immunization," Res. Virol. 149:315-319 (1998).
Huynh, et al., "Construction of Modular and Versatile Plasmid Vectors for the High-level Expression of Single or Multiple Genes in Insects and Insect Cell Lines", J. Mol. Biol 288:13-20 (1999).
New, et al., "Co-expression of two gene products in the CNS using double-cassette defective herpes simplex virus vectors," Molecular Brain Research 37:317-323 (1996).
PCT International Search Report, Application No. PCT/US03/10154 dated Aug. 21, 2003 (4 pages).
Cao, M.-X., et al., "*Agrobacterium*-mediated multiple gene transformation in rice using a single vector", J. Integrative Plant Biology 47:233-242 (1999).
Baculovirus Expression Vector System Manual, 6th Edition, May 1999, Pharmingen.
Cloning Vectors: A Laboratory Manual, Elsevier, 1985, pp. VIII-B-b-i-3.
Yang, V.W., et al., "High-efficiency transformation of *Pichia stipitis* Based on Its URA3 Gene and a Homologous Autonomous Replication Sequence, ARS2", Applied and Environmental Microbiology, 1994, 60(12):4245-4254.

*Primary Examiner* — Jim Ketter
(74) *Attorney, Agent, or Firm* — John M. Polo

(57) ABSTRACT

The present invention provides novel methods and materials for increasing the expression of recombinant polypeptides. Methods and materials of the invention allow increased expression of transcription units that include recombinant DNA sequences which encode polypeptides of interest. The present invention provides expression vectors which contain multiple copies of a transcription unit encoding a polypeptide of interest separated by at least one selective marker gene and methods for sequentially transforming or transfecting host cells with expression vectors to increase transcription unit dosage and expression.

50 Claims, 46 Drawing Sheets

Figure 3.
A.
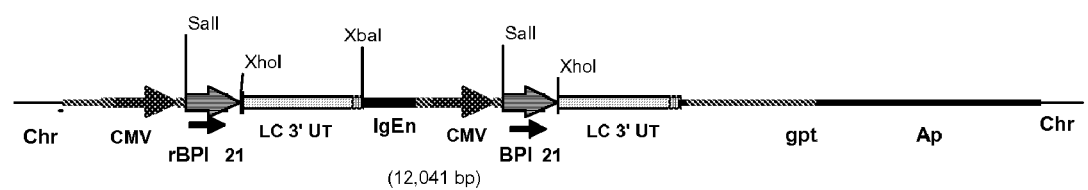
B.
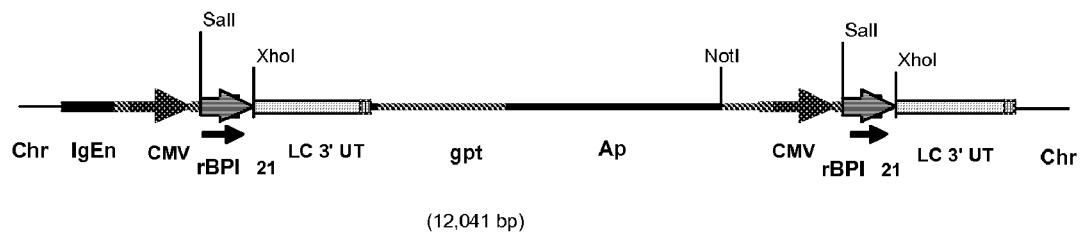

Figure 13.

| Variable Region | No. of Changes | Amino Acids 1-59 |
|---|---|---|
| Risk Line | | LHLHLHLMLLMLHLMLLLHLHLHLHMHHHHHHHHHHHHHMHLMLLMHMHH HHHHHHL |
| Mouse | | DIVMTQAAFSNPVTLGTSGSISCRSSKSLLHSNGITYLYWYLQKPGQSPQLLIYQ MSNL |
| Human | | DIVMTQSPLSLPVTPGEPASISCRSSQSLLHSLN-----WYLQKPGQSPQLLIYLVSNR |
| Low Risk | 4 | DIVMTQSALSNPVTLGESGSISCRSSKSLLHSNGITYLYWYLQKPGQSPQLLIYQM SNR |
| Low plus Moderate Risk | 8 | DIVMTQSPLSLPVTPGEPGSISCRSSKSLLHSNGITYLYWYLQKPGQSPQLLIYQM SNR |
| Variable Region | No. of Changes | Amino Acids 60-112 |
| Risk Line | | MMLHMLMHLHLHLHLLHLHLHLLHLLLHLHHHHHHHHHHHHHHHLHHLHLLL |
| Mouse | | ASGVPDRFSSSGSGTDFTLRISRVEAEDVGVYYCAQNLELPRTFGGGTKLEMK (SEQ ID NO: 80) |
| Human | | ASGVPDRFSGSGSGTDFTLKISRVEAEDVGVYYCMQAXQXPXTFGQGTKVEIK (SEQ ID NO: 81) |
| Low Risk | 2 | ASGVPDRFSSSGSGTDFTLKISRVEAEDVGVYYCAQNLELPRTFGQGTKLEMK (SEQ ID NO: 82) |
| Low plus Moderate Risk | 2 | ASGVPDRFSSSGSGTDFTLKISRVEAEDVGVYYCAQNLELPRTFGQGTKLEMK (SEQ ID NO: 83) |

Figure 15.

| Variable Region | No. of Changes | Amino Acids 1-59 |
|---|---|---|
| Risk Line | | MHLHLHLHMLLMLMLLLHLHLHLHMHHHHHHHHHHHHMHLMLLMHMHHHHH HHHHHHHH |
| Mouse | | QIQLVQSGPELKKPGETVKISCKASGYTFTKYGMNWVKQAPGKGLKWMGWIN TYTEEPT |
| Human | | QVQLVQSGAEVKKPGXSVKVSCKASGYTFXSYXIXWVRQAPGQGLEWMGXIX PXGXT-X |
| Low Risk | 3 | QIQLVQSGPE<u>V</u>KKPGE<u>S</u>VKISCKASGYTFTKYGMNWVKQAPG<u>Q</u>GLKWMGWIN TYTEEPT |
| Low plus Moderate Risk | 6 | QIQLVQSG<u>AE</u>VKKPGE<u>S</u>VKISCKASGYTFTKYGMNWV<u>R</u>QAPG<u>Q</u>G<u>LE</u>WMGWIN TYTEEPT |
| Variable Region | No. of Changes | Amino Acids 60-116 |
| Risk Line | | MHMMHMLMHLHLHLMLLMLHLHLHLLHLLLHLHMHHHHHHHHHHHHHLHHL HLHLL |
| Mouse | | YGDDFKGRFAFSLETSASTANLQINNLKSEDTATYFCARFGSAVDYWGQGTSV TVSS (SEQ ID NO: 84) |
| Human | | YAQKFQGRVTITXDXSTSTAYMELSSLRSEDTAVYYCARXXXXXXXWGQGTLV TVSS (SEQ ID NO: 85) |
| Low Risk | 10 | YGDDFKGRF<u>TFTL</u>DTS<u>T</u>STA<u>YLEISSLR</u>SEDTATYFCARFGSAVDYWGQGT<u>L</u>VT VSS (SEQ ID NO: 86) |
| Low plus Moderate Risk | 14 | YG<u>QK</u>F<u>Q</u>GRF<u>TFTL</u>DTS<u>T</u>STA<u>YLEISSLR</u>SEDTA<u>V</u>YFCARFGSAVDYWGQGT<u>L</u>VT VSS (SEQ ID NO: 87) |

Figure 23.
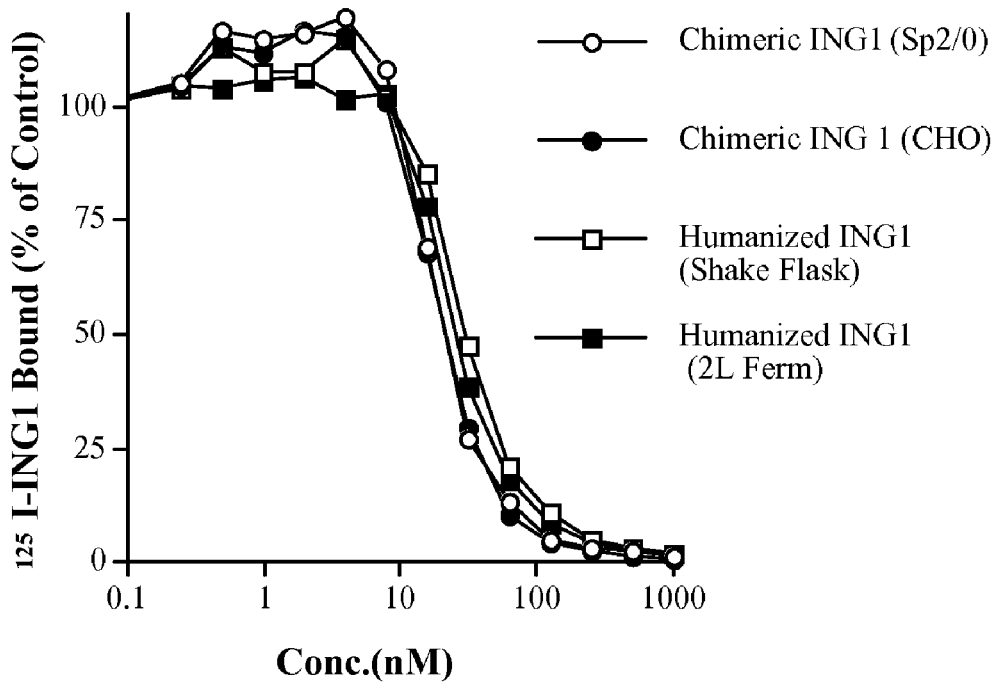
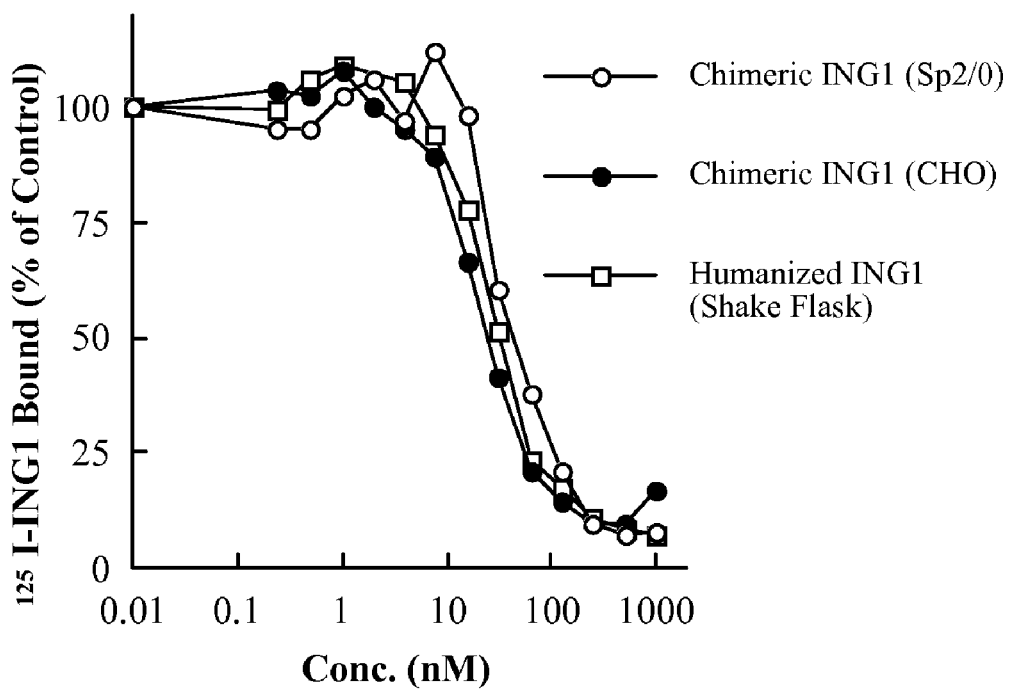

Figure 28.
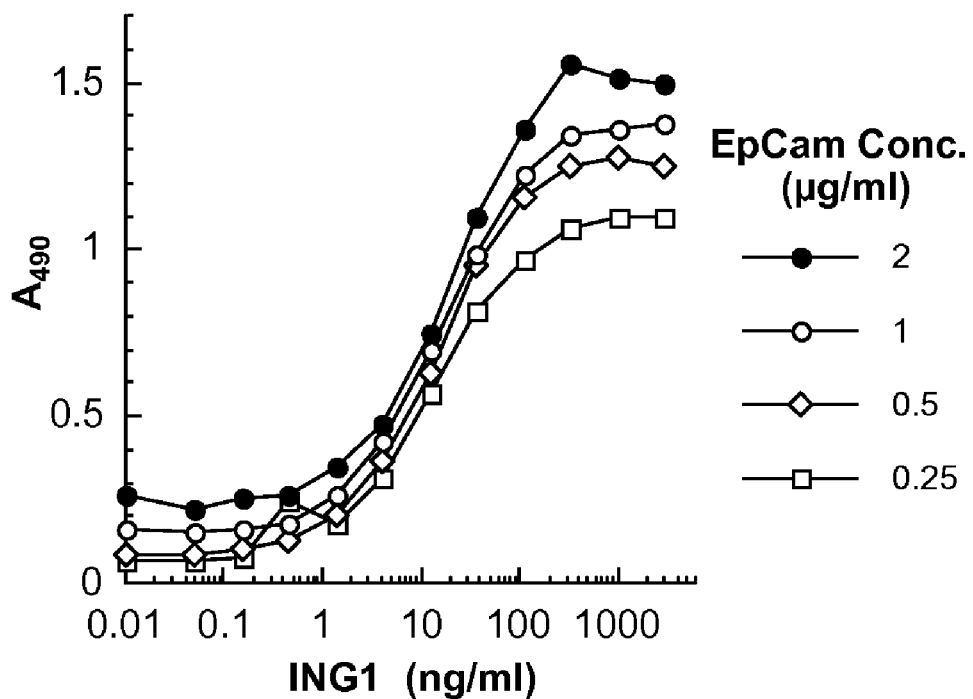
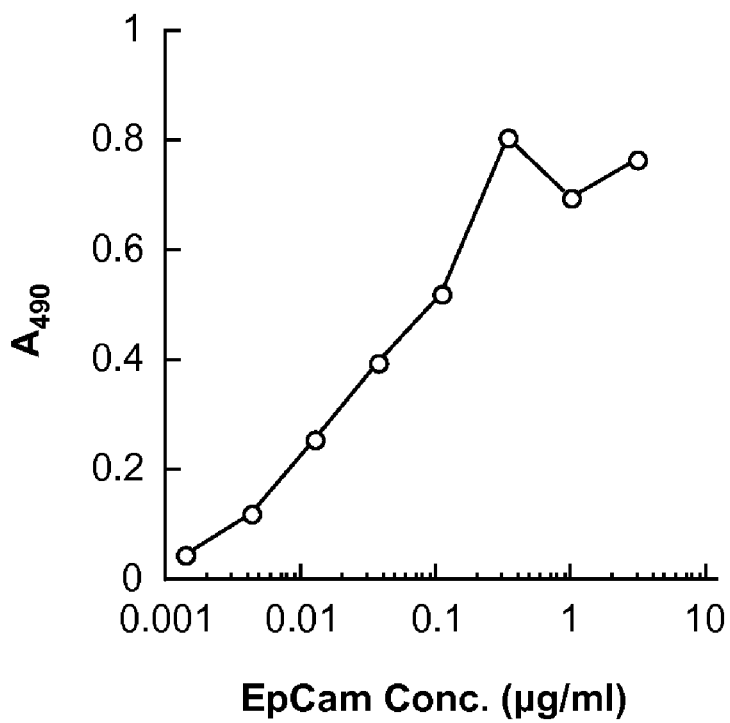

Figure 33.

```
  1 ATG GGA TGG AGC TGT ATC ATC CTC TTC TTG GTA GCA ACA GCT ACA GGT
  1▶ M   G   W   S   C   I   I   L   F   L   V   A   T   A   T   G

49 GTC CAC TCC|GAC ATC CAG ATG ACC CAG AGC CCA AGC AGC CTG AGC GCC
 17▶ V   H   S | D   I   Q   M   T   Q   S   P   S   S   L   S   A
              +1

97 AGC GTG GGT GAC AGA GTG ACC ATC ACC TGT AAA GCA AGT AAG AGC ATT
 33▶ S   V   G   D   R   V   T   I   T   C   K   A   S   K   S   I

145 AGC AAT TAT TTA GCC TGG TAC CAG CAG AAG CCA GGT AAG GCT CCA AAG
 49▶ S   N   Y   L   A   W   Y   Q   Q   K   P   G   K   A   P   K

193 CTG CTG ATC TAC TAT GGG TCA ACT TTG CGA TCT GGT GTG CCA AGC AGA
 65▶ L   L   I   Y   Y   G   S   T   L   R   S   G   V   P   S   R

241 TTC AGC GGT AGC GGT AGC GGT ACC GAC TTC ACC TTC ACC ATC AGC AGC
 81▶ F   S   G   S   G   S   G   T   D   F   T   F   T   I   S   S

289 CTC CAG CCA GAG GAC ATC GCC ACC TAC TAC TGC CAA CAG TAT TAT GAA
 97▶ L   Q   P   E   D   I   A   T   Y   Y   C   Q   Q   Y   Y   E

337 AGA CCG CTC ACG TTC GGC CAA GGG ACC AAG GTG GAA ATC AAA CGA ACT
113▶ R   P   L   T   F   G   Q   G   T   K   V   E   I   K   R   T

385 GTG GCT GCA CCA TCT GTC TTC ATC TTC CCG CCA TCT GAT GAG CAG TTG
129▶ V   A   A   P   S   V   F   I   F   P   P   S   D   E   Q   L

433 AAA TCT GGA ACT GCC TCT GTT GTG TGC CTG CTG AAT AAC TTC TAT CCC
145▶ K   S   G   T   A   S   V   V   C   L   L   N   N   F   Y   P

481 AGA GAG GCC AAA GTA CAG TGG AAG GTG GAT AAC GCC CTC CAA TCG GGT
161▶ R   E   A   K   V   Q   W   K   V   D   N   A   L   Q   S   G

529 AAC TCC CAG GAG AGT GTC ACA GAG CAG GAC AGC AAG GAC AGC ACC TAC
177▶ N   S   Q   E   S   V   T   E   Q   D   S   K   D   S   T   Y

577 AGC CTC AGC AGC ACC CTG ACG CTG AGC AAA GCA GAC TAC GAG AAA CAC
193▶ S   L   S   S   T   L   T   L   S   K   A   D   Y   E   K   H

625 AAA GTC TAC GCC TGC GAA GTC ACC CAT CAG GGC CTG AGC TCG CCC GTC
209▶ K   V   Y   A   C   E   V   T   H   Q   G   L   S   S   P   V

673 ACA AAG AGC TTC AAC AGG GGA GAG TGT TAG    (SEQ ID NO: 67)
225▶ T   K   S   F   N   R   G   E   C          (SEQ ID NO: 68)
```

Figure 34.

```
                                                                        +1
   1 ATG GGA TGG AGC TGT ATC ATC CTC TTC TTG GTA GCA ACA GCT ACA GGT GTC CAC TCC|CAG
   1▶ M   G   W   S   C   I   I   L   F   L   V   A   T   A   T   G   V   H   S  Q

61 GTC CAA CTG CAG GAG AGC GGT CCA GGT CTT GTG AGA CCT AGC CAG ACC CTG AGC CTG ACC
  21▶ V   Q   L   Q   E   S   G   P   G   L   V   R   P   S   Q   T   L   S   L   T

121 TGC ACC GTG TCT GGC TTC ACC TTC ACC GAT TAC CTT CTG CAC TGG GTG AGA CAG CCA CCT
  41▶ C   T   V   S   G   F   T   F   T   D   Y   L   L   H   W   V   R   Q   P   P

181 GGA CGA GGT CTT GAG TGG ATT GGA TGG ATT GAT CCT GAG GAT GGT GAA ACA AAG TAT GGT
  61▶ G   R   G   L   E   W   I   G   W   I   D   P   E   D   G   E   T   K   Y   G

241 CAG AAG TTT CAA AGC AGA GTG ACA ATG CTG GTA GAC ACC AGC AAG AAC CAG TTC AGC CTG
  81▶ Q   K   F   Q   S   R   V   T   M   L   V   D   T   S   K   N   Q   F   S   L

301 AGA CTC AGC AGC GTG ACA GCC GCC GAC ACC GCG GTC TAT TAT TGT GCA AGA GGC GAA TAT
 101▶ R   L   S   S   V   T   A   A   D   T   A   V   Y   Y   C   A   R   G   E   Y

361 AGA TAC AAC TCG TGG TTT GAT TAC TGG GGT CAA GGC TCA CTA GTC ACA GTC TCC TCA GCC
 121▶ R   Y   N   S   W   F   D   Y   W   G   Q   G   S   L   V   T   V   S   S   A

421 TCC ACC AAG GGC CCA TCG GTC TTC CCC CTG GCA CCC TCC TCC AAG AGC ACC TCT GGG GGC
 141▶ S   T   K   G   P   S   V   F   P   L   A   P   S   S   K   S   T   S   G   G

481 ACA GCG GCC CTG GGC TGC CTG GTC AAG GAC TAC TTC CCC GAA CCG GTG ACG GTG TCG TGG
 161▶ T   A   A   L   G   C   L   V   K   D   Y   F   P   E   P   V   T   V   S   W

541 AAC TCA GGC GCC CTG ACC AGC GGC GTG CAC ACC TTC CCG GCT GTC CTA CAG TCC TCA GGA
 181▶ N   S   G   A   L   T   S   G   V   H   T   F   P   A   V   L   Q   S   S   G

601 CTC TAC TCC CTC AGC AGC GTG GTG ACC GTG CCC TCC AGC AGC TTG GGC ACC CAG ACC TAC
 201▶ L   Y   S   L   S   S   V   V   T   V   P   S   S   S   L   G   T   Q   T   Y

661 ATC TGC AAC GTG AAT CAC AAG CCC AGC AAC ACC AAG GTG GAC AAG AAA GTT GAG CCC AAA
 221▶ I   C   N   V   N   H   K   P   S   N   T   K   V   D   K   K   V   E   P   K

721 TCT TGT GAC AAA ACT CAC ACA TGC CCA CCG TGC CCA GCA CCT GAA CTC gcG GGG GcA CCG
 241▶ S   C   D   K   T   H   T   C   P   P   C   P   A   P   E   L   A   G   A   P

781 TCA GTC TTC CTC TTC CCC CCA AAA CCC AAG GAC ACC CTC ATG ATC TCC CGG ACC CCT GAG
 261▶ S   V   F   L   F   P   P   K   P   K   D   T   L   M   I   S   R   T   P   E

841 GTC ACA TGC GTG GTG GTG GAC GTG AGC CAC GAA GAC CCT GAG GTC AAG TTC AAC TGG TAC
 281▶ V   T   C   V   V   V   D   V   S   H   E   D   P   E   V   K   F   N   W   Y

901 GTG GAC GGC GTG GAG GTG CAT AAT GCC AAG ACA AAG CCG CGG GAG GAG CAG TAC AAC AGC
 301▶ V   D   G   V   E   V   H   N   A   K   T   K   P   R   E   E   Q   Y   N   S

961 ACG TAC CGT GTG GTC AGC GTC CTC ACC GTC CTG CAC CAG GAC TGG CTG AAT GGC AAG GAG
 321▶ T   Y   R   V   V   S   V   L   T   V   L   H   Q   D   W   L   N   G   K   E

1021 TAC AAG TGC AAG GTC TCC AAC AAA GCC CTC CCA GCC CCC ATC GAG AAA ACC ATC TCC AAA
 341▶ Y   K   C   K   V   S   N   K   A   L   P   A   P   I   E   K   T   I   S   K

1081 GCC AAA GGG CAG CCC CGA GAA CCA CAG GTG TAC ACC CTG CCC CCA TCC CGG GAT GAG CTG
 361▶ A   K   G   Q   P   R   E   P   Q   V   Y   T   L   P   P   S   R   D   E   L

1141 ACC AAG AAC CAG GTC AGC CTG ACC TGC CTG GTC AAA GGC TTC TAT CCC AGC GAC ATC GCC
 381▶ T   K   N   Q   V   S   L   T   C   L   V   K   G   F   Y   P   S   D   I   A

1201 GTG GAG TGG GAG AGC AAT GGG CAG CCG GAG AAC AAC TAC AAG ACC ACG CCT CCC GTG CTG
 401▶ V   E   W   E   S   N   G   Q   P   E   N   N   Y   K   T   T   P   P   V   L

1261 GAC TCC GAC GGC TCC TTC TTC CTC TAC AGC AAG CTC ACC GTG GAC AAG AGC AGG TGG CAG
 421▶ D   S   D   G   S   F   F   L   Y   S   K   L   T   V   D   K   S   R   W   Q

1321 CAG GGG AAC GTC TTC TCA TGC TCC GTG ATG CAT GAG GCT CTG CAC AAC CAC TAC ACG CAG
 441▶ Q   G   N   V   F   S   C   S   V   M   H   E   A   L   H   N   H   Y   T   Q

1381 AAG AGC CTC TCC CTG TCT CCG GGT AAA TGA      (SEQ ID NO: 71)
 461▶ K   S   L   S   L   S   P   G   K   •      (SEQ ID NO: 72)
```

Figure 38.
A. Growth
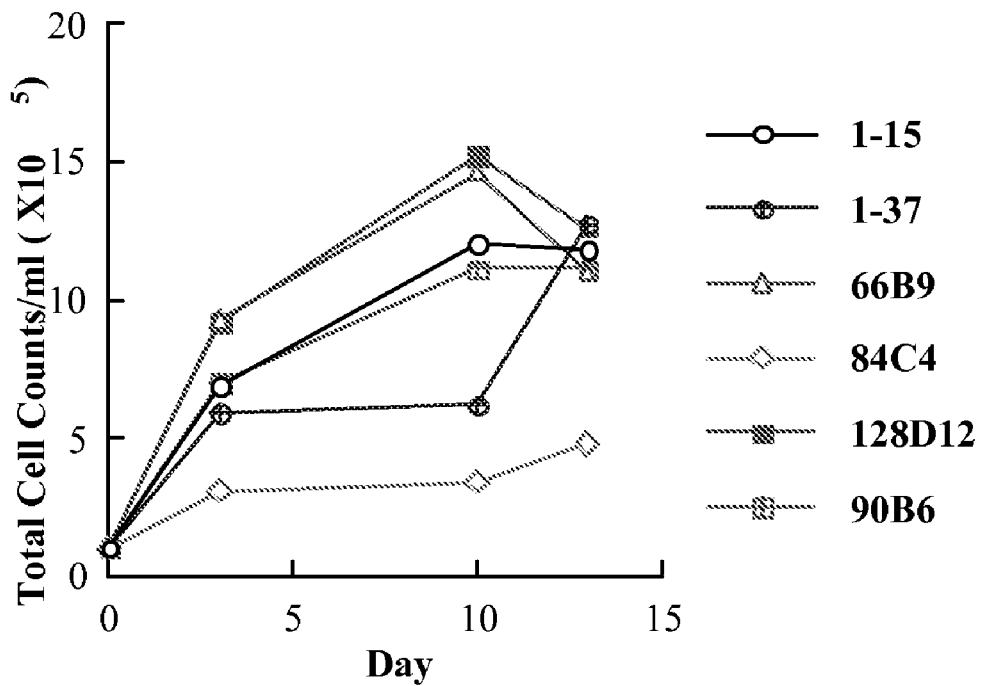
B. Productivity
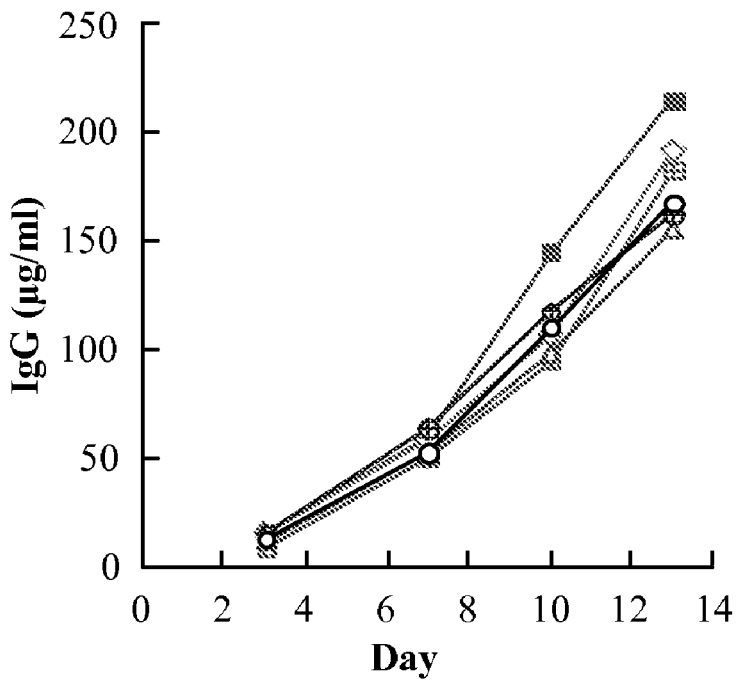

Figure 39.
A. Clone 264E2
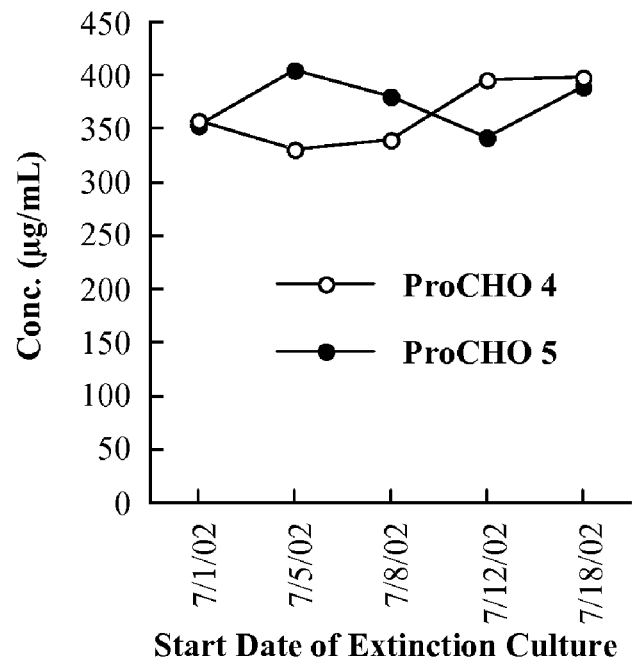
B. Clone 254G12
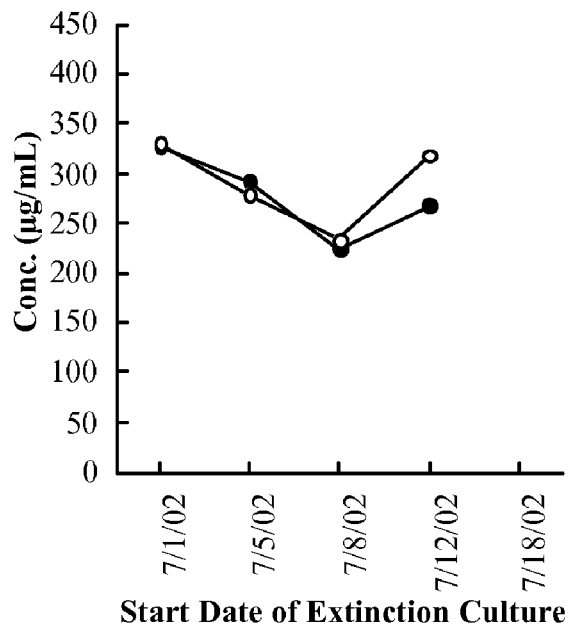

Figure 44.
A. pING2054: "single gene" vector.
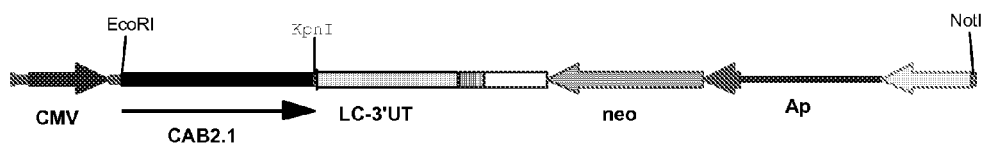
B. pING2055: "two-gene" vector.
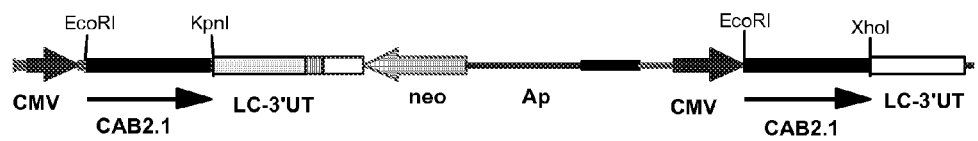

Figure 45.
A. Growth.
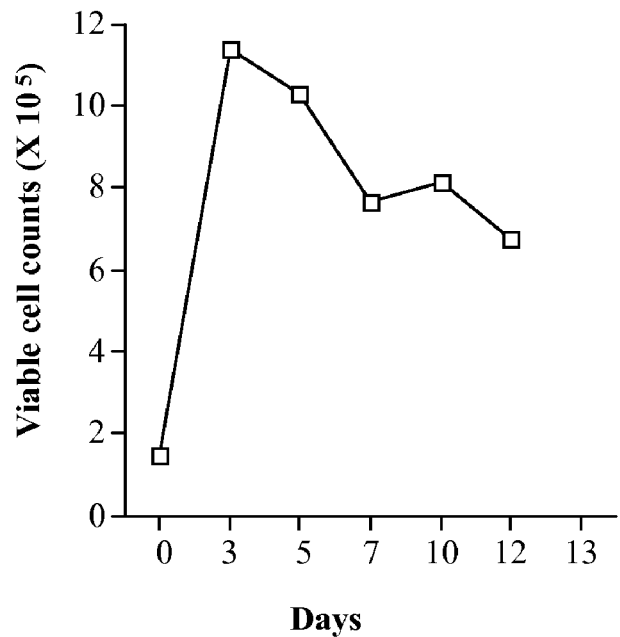
B. Productivity
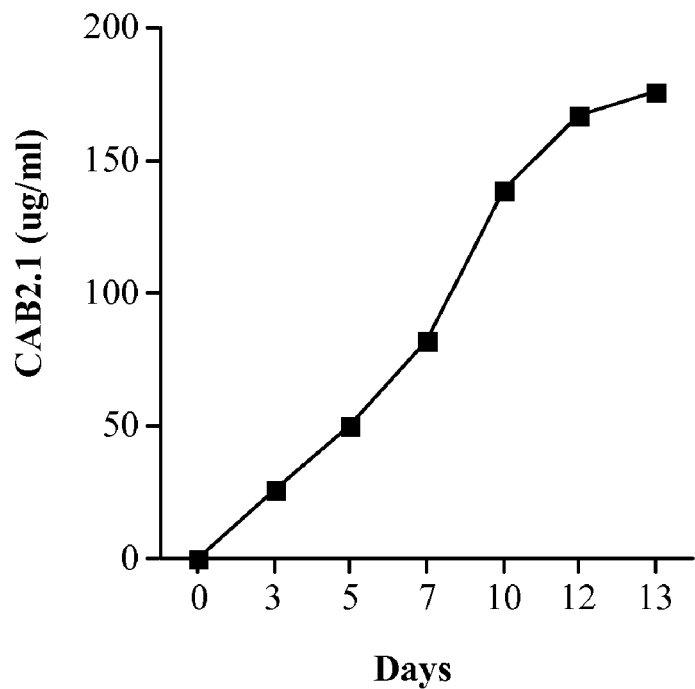

METHODS AND MATERIALS FOR INCREASING EXPRESSION OF RECOMBINANT POLYPEPTIDES

RELATED APPLICATIONS

This application is a divisional of U.S. application Ser. No. 10/404,724, filed Mar. 31, 2003, now U.S. Pat. No. 7,192,737, which claims the benefit of U.S. Provisional Application No. 60/368,530, filed Mar. 29, 2002, the disclosures of which are incorporated by reference herein in their entirety.

BACKGROUND OF THE INVENTION

Recombinant polypeptide compositions are increasingly being used in a wide variety treatments or therapies across the health-related fields. Recombinant polypeptides are being used in diagnostic procedures, as tools in preventative medicine, and to directly save lives through administrative therapies. In addition, recombinant polypeptides are found in a wide array of both health and cosmetic products, used to increase the quality of life. Complex polypeptide products are also routinely used in research laboratories both as end-products of analyses themselves and as agents in assays for the study or preparation of other molecules. Such uses often lead to the discovery of the causes of disease and an understanding of the underlying disease mechanism(s), furthering development toward diagnoses and/or viable treatments. Recombinant polypeptide products also play a vital role in a variety of industrial settings, in areas ranging from farming to the processing of food materials and the raising of livestock to the catalytic degradation of both natural and synthetic by-products and waste materials.

The production of polypeptides for preclinical and clinical evaluation often requires multigrain quantities [Kelley, *Bio/Technology* 14: 28-31 (1996)]. Industrial applications using such polypeptides generally require even greater quantities and the costs of production are often prohibitive. While there are a variety of ways to chemically synthesize simple polypeptides when the amino acid sequence is known, this method of production has problems with respect to larger polypeptides, e.g., uncertain deviations from native conformational folding, an absence of intracellular post-translational modification, and reduced or limited bioactivity. For these and other reasons, recombinant DNA technology is the most common production method of choice and offers the greatest potential for large-scale production at high efficiency and reasonable cost. Accordingly, the production of useful quantities of these important polypeptides is typically generated through standard recombinant DNA technology, especially where the polypeptide of interest is ultimately modified or where it only occurs naturally in very small amounts.

Current recombinant DNA techniques used for expressing polypeptides can exhibit numerous limitations, including, for example, significant production costs for materials and reagents and low product yield. In addition, production can be time consuming and can require substantial monitoring with limited control. These, as well as other problems and limitations involved in production of recombinant polypeptides, along with inefficiencies in current methods for producing recombinant polypeptides, ultimately can result in a significant toll in costs, resources, health and life itself. Thus, given the fundamental role and countless uses for recombinant polypeptides and the limitations current methods for recombinant polypeptide production, it is of primary importance to employ a method of recombinant gene expression that maximizes protein production and, ultimately, saves time, money and other resources. Accordingly, there exists a need for methods that can increase, maximize and/or optimize the production of recombinant polypeptides.

Several factors can influence recombinant expression in mammalian cells, including promoter strength, the context of the translation initiation region, the efficiency of the 3' untranslated region to polyadenylate and terminate transcription, the insertion site of the randomly integrated recombinant gene in the host chromosome, and the number of integrated copies of the gene that is being expressed. Of these factors, the choice of promoter and 3' untranslated regions can significantly impact expression levels. Viral promoters are often used because they are thought to promote high expression levels. The optimal translation initiation sequence, ACCATGG, also known as the Kozak box, can promote more efficient polypeptide synthesis and, therefore, higher expression levels.

One strategy employed for increasing expression of polypeptides uses expression vectors containing multiple integrated copies of a desired gene. Improvements in recombinant polypeptide expression in mammalian cells can be achieved in this manner by effectively increasing the gene dosage in a transfected host cell. Increases in gene copy number are most commonly achieved by gene amplification using cell lines deficient in an enzyme such as dihydrofolate reductase (DHFR) or glutamine synthetase (GS) in conjunction with expression vectors containing genes encoding these enzymes and agents such as methotrexate (MTX), which inhibits DHFR, and methionine sulfoxamine (MSX), which inhibits GS. Using expression vectors containing the recombinant gene under control of a strong promoter and genes encoding DHFR or GS, DHFR$^+$ and GS$^+$ transfectants, respectively, are first obtained and gene amplification is then achieved by growing the transfectants in progressively increasing concentrations of MTX or MSX.

While gene amplification can result in higher levels of expression, it has several drawbacks. First, cell lines that have mutations in the genes encoding the selective enzymes are generally used for gene amplification. In the case of DHFR, both chromosomal copies need to be mutated and, consequently, these cell lines can be less robust than wildtype cells. This can ultimately lead to cells which secrete lower net amounts of the protein of interest as compared to more robust cells that thrive and are stable. In the case of GS, the lymphoid cell line NSO is naturally GS$^-$, but CHO-K1, another commonly-used cell line, is GS$^+$ and requires selection directly for MSX-resistant transfectants. A second problem with current methods of gene amplification is that the amplification can result in cell lines that are unstable in the absence of selective pressure, thus requiring the maintenance of selective pressure. Finally, current methods for gene amplification can be exceedingly time-consuming and can require up to several months to complete with a proportional allocation of both resources and costs. Another strategy for increasing expression of polypeptides uses sequential transfections with expression vectors, each containing single copies of a desired gene but with different selective marker genes such as gpt, neo and his. Gene copy number for the first transfection is one, from the second transfection, two and so on. While this approach can achieve higher levels of expression, it has drawbacks in that the number of gene copies increases only modestly even after three sequential transfections.

Therefore, in view of all these problems, novel ways to increase gene expression through increased gene copy number by methods that do not depend on the use of mutant cell lines and current methods for gene amplification would be highly desirable.

For all the foregoing reasons, there is a need in the art for improved methods of expressing polypeptides of interest at increased net concentrations from stable cell lines, while maximizing efficiency and minimizing expenditure of time, resources, and costs in production. Furthermore, there is a need for expression vectors and stable cell lines harboring and/or integrating into their chromosomes such vectors that are capable of efficiently producing secreting high concentrations of valuable and useful polypeptide products.

SUMMARY OF THE INVENTION

The present invention provides novel methods and materials for increasing the expression of recombinant polypeptides. In one aspect, the present invention is directed to novel methods for efficiently increasing the expression of recombinant polypeptides from host cells, thus satisfying the need for producing increased concentrations of valuable proteins and polypeptides of interest. The benefits of such methods can include minimizing time, resources and/or costs of production. In another aspect, the present invention is directed to novel vectors comprising multiple copies of a recombinant DNA sequence encoding, for example, a recombinant polypeptide of interest, separated by at least one selective marker gene and cell lines harboring such vector constructs, thus satisfying the need for vectors and host cells, including stable cell lines, which are capable of efficiently producing increased concentrations of valuable and/or useful polypeptide products.

According to the present invention, the number of transcription units, i.e., recombinant DNA sequences which encode a recombinant polypeptide of interest, introduced into a host cell is increased so that there are more copies of the transcription unit to express. This is achieved by incorporating at least two copies of the transcription unit on the same vector. In certain embodiments, each transcription unit copy is placed under control of its own promoter and 3' untranslated region. Increasing transcription unit dosage and expression is achieved by transfection with such a vector. Performing additional transformations or transfections with additional vectors, for example, a second and then third sequential transformation or transfection with such vectors, each containing at least two transcription unit copies can yield further increases in transcription unit dosage and expression relative to a vector with only a single transcription unit copy. Preferably, each additional vector for each sequential transformation or transfection contains a different selective marker gene.

While integration into a host cell chromosome of a linear DNA sequence containing two transcription unit copies on the same vector can increase gene dosage and therefore expression, it could also lead to instability due to homologous recombination. According to the present invention, such potential instability, especially during the early stages of cell line development, is overcome by the design of the vector so that a gene encoding a selective marker is positioned between at least two identical or similar transcription units encoding a recombinant polypeptide of interest. Preferably, the vector is linearized (e.g., via a unique restriction enzyme site prior to transfection or transformation such that the selective marker gene is positioned between at least two and no more than 8 transcription unit copies, each transcription unit encoding recombinant polypeptide(s) of interest. For example, the vector comprises as [(transcription unit)$_x$-selective marker gene-(transcription unit)$_x$], wherein x=1-4. Using such a vector, any homologous recombination between, for example, two identical or similar transcription unit DNA sequences would then potentially delete or inactivate the gene encoding resistance to the selective agent. Thus, cells transfected or transformed with such a vector and that underwent homologous recombination would not be able to grow in the presence of the selective agent. Application of at least some selective pressure should promote maintenance of transcription unit copies from such novel vectors.

One aspect of the invention involves the design, construction and use of vectors, preferably mammalian expression vectors containing at least two copies of a transcription unit encoding a recombinant polypeptide of interest to be expressed, each under control of a promoter and a 3' untranslated region and positioned so that, when the vector is linearized by digestion at a unique restriction enzyme site, at least two transcription unit copies are separated by a selective marker gene in the linear sequence. According to the aspect of the invention, the design or configuration includes positioning the selective marker gene between at least two transcription units for example, [(transcription unit)-selective marker gene-(transcription unit)], which will in turn stabilize the linear vector DNA with that position of the selective marker gene between transcription units integrated into a host cell chromosome. In contrast, homologous recombination between at least two copies of the transcription unit can lead to the loss of at least one of the transcription units and the selective marker gene. As an additional benefit, this aspect of the present invention can yield a vector that has multiple enhancers. As an example, the multiple enhancers can include several from promoters controlling transcription unit expression and one from a promoter controlling the selective marker gene(s). Because enhancers are known to act bi-directionally and also at a distance, this vector design or configuration can lead to increased transcription and consequently increased net concentrations of the polypeptide of interest.

Another aspect of the invention also provides for the use of vectors containing two or more transcription units (preferably between two and no more than eight) with various selective marker genes, including, for example, gpt, neo or his, for selection of mammalian cell transfectants. By use of these additional selective marker genes, transfectants can be obtained with multiple copies of a transcription unit and further increased by performing a number of sequential transfections with vectors according to the invention.

In addition to selective marker genes such as gpt, neo and his for selection of transfectants, the vector configuration as described herein can be used in conjunction with genes encoding amplifiable selective marker genes such as DHFR or GS. Amplification of such vectors may yield transfectants with vector DNA integrated into a host cell chromosome so that transcription units are separated by the DHFR or GS marker gene.

The present invention provides multiple transcription unit vectors, including, those containing for example, two, three, four, five, six, seven and eight and so on, copies of a transcription unit with DNA sequences encoding a recombinant polypeptide or interest. Preferably, there are at least two and no more than eight transcription units. Such vectors are constructed with at least one selective marker gene positioned between or separating the transcription units in a manner that allows the stable integration into a host cell chromosome and reduction, avoidance or nullification of homologous recombination. Vectors comprising multiple copies of a transcription unit each separated by a selective marker gene, wherein the transcription unit encodes a polypeptides are provided by the invention. All such permutations of multiple transcription unit copies are contemplated by this invention as one skilled in the art would recognize from the disclosure herein.

An aspect of the present invention includes vectors containing transcription units which encode subunits of dimeric or higher order multimeric proteins. According to the invention, transcription units encoding different subunits of a multimeric protein, each under control of a promoter and a 3' untranslated region, are separated by a selective marker gene. For multimeric proteins encoded by at least two distinct genes (for instance, immunoglobulin light and heavy chains or at least the variable regions of immunoglobulin light and heavy chains), transcription units encoding the desired subunits are first linked with or without an internal ribosome entry site (IRES) and this bi (or poly) transcription unit can be placed under the control of a promoter and a 3' untranslated region. These transcription units then can be combined to construct vectors with at least two copies of a bi-cistronic unit separated by a selective marker gene. For example, vectors comprise [(transcription unit-IRES-transcription unit)-selective marker gene-(transcription unit-IRES-transcription unit)]. Also, for example, vectors can comprise [(transcription unit-transcription unit)-selective marker-(transcription unit-transcription unit)]. In certain embodiments, each transcription unit copy is placed under control of its own promoter (P) and 3' untranslated region (3' UT). For example, vectors can comprise [(P-transcription unit-3' UT)-(CP-transcription unit-3' UT)-selective marker gene-(P-transcription unit-3' UT)-(CP-transcription unit-3' UT)-].

The present invention provides methods of producing a recombinant polypeptide and/or of increasing the expression of a transcription unit comprising the following steps:
(a) culturing under selective conditions cells which have been transformed or transfected with a vector containing multiple copies of a transcription unit separated by at least one selective marker gene wherein the transcription unit encodes a polypeptide; and
(b) expressing the polypeptide from the multiple copies of the transcription units.

According to the present invention, the number of copies of the transcription unit on the vector is at least two, but can be three, four, five, six, seven, eight, etc. Preferably, the number of copies of the transcription unit is at least two and not more than eight on any vector. Each vector containing at least two transcription units separated by a selective marker gene can be introduced into host cells. Additional vectors, each preferably with a different selective marker gene, can be sequentially introduced into the host cells to further increase gene dosage and expression. Preferred host cells include Chinese hamster ovary (CHO) cells, such as CHO-K1 cells. The methods of the present invention also allow for transcription units encoding any polypeptide product of interest, including, for example, multimeric protein products, such as immunoglobulins.

The present invention provides methods for constructing vectors or segments thereof comprising building an expression vector or cloning vector with multiple copies of a transcription unit separated by at least one selective marker gene. According to the invention, the number of multiple copies of the transcription unit is at least two. Preferably, the number of multiple copies of the transcription unit on a single vector is less than or equal to eight.

The present invention provides vectors comprising multiple copies of a transcription unit encoding recombinant mammalian polypeptides of interest separated by at least one selective marker gene. According to the invention, the number of multiple copies of the transcription unit on the vector or transformed/transfected into host cells is at least two. Preferably, the number of multiple copies of the transcription unit is equal to or less than eight. Multiple vectors can be used and multiple transformations or transfections can be carried out to produce clones and cell lines expressing the polypeptide of interest. Exemplary vectors are described herein containing a transcriptional unit encoding a BPI protein product, for example, a BPI fragment, BPI analog, BPI variant or BPI-derived peptide. An exemplary expression vector described herein contains a transcriptional unit encoding $rBPI_{21}$. The present invention further provides vectors containing transcription units encoding different subunits of a multimeric protein, including vectors containing transcription units encoding antibody light and heavy chains, or at least the variable regions of light and heavy chains.

According to the present invention, vectors contain selective marker genes which can vary, but may include a gpt, neo or his gene. A vector according to the present invention can also include multiple copies of a transcription unit in a direct repeat orientation and/or in an inverted repeat orientation. Additionally, the present invention provides a vector containing multiple copies of transcription units that are identical or similar. Such copies can be homologous copies, for example, at least 25% homologous. Accordingly, the copies can be identical or similar by any percentage between 25% and 100% homologous, preferably identical or similar by at least 80%, including 80%, 81%, 82%, 83%, 84%, 85%, 86%, 87%, 88%, 89%, 90%, 91%, 92%, 93%, 94%, 95%, 96%, 97%, 98%, 99%.

The present invention further embodies all variations of vectors or segments thereof within the scope and spirit of this disclosure or as may be understood or contemplated by one skilled in the art through this disclosure and/or the art.

The present invention provides host cells comprising vectors or segments thereof, [(transcription unit)$_x$-selective marker gene-(transcription unit)$_x$], wherein x=1-4 as disclosed herein. According to the invention, host cells include any or all eukaryotic host cell types. By way of example, eukaryotic host cell types may include any mammalian cell, for example, the Chinese hamster ovary (CHO) cell line, the DHFR$^+$ CHO-K1 cell line, the DHFR$^-$ DUKX-B11 (DXB11) cell line or DG-44 cell line. Eukaryotic host cell types may also include plant, insect, and yeast cells. In addition, the present invention provides any stable cell line comprising vectors or segments thereof within the scope and spirit of this disclosure or as may be understood or contemplated by one skilled in the art through this disclosure and/or the art. Such cells may be propagated by any means, and may include cells in an attached or suspension state with any growth or support medium or sustaining solution.

In view of all the current problems and limitations in the art, including those discussed hereinabove, there are many advantages of the present invention over the art, including increased recombinant polypeptide production, increased production efficiency, greater control and/or regulation over the quantities of polypeptide expressed, increased stability of cell lines, and/or decreased costs for materials, reagents, and/or other resources. For example, the present invention provides methods of vector construction that, when such vectors are linearized, minimize or avoid homologous recombination of multiple copies of transcription units by separating transcription units containing DNA sequences encoding polypeptides of interest with at least one selective marker gene. As another example, the present invention provides methods to further increase expression through sequential transfections with multiple-transcription unit constructs. This leads to clones and/or cell lines which can produce substantially increased levels of polypeptides of interest, while still maintaining viability and stability in growth medium.

While various modifications may be suggested by those versed in the art, it should be understood that this invention contemplates all embodiments within the scope of the patent warranted hereon and all such modifications as reasonably and properly come within the scope of this contribution to the art.

BRIEF DESCRIPTION OF THE DRAWINGS

These and other features, aspects, and advantages of the present invention will become better understood with reference to the following description, appended claims, and accompanying drawings wherein:

FIG. 3A shows the structure of vector pING1737 linearized with XbaI.

FIG. 3B shows the structure of vector pING1737 linearized with NotI.

FIG. 13 shows the amino acid changes (underlined) made during human engineering of the ING-1 light chain variable region, including mouse and human light chain variable region sequences, risk line for human engineered method, and low as well as moderate risk changes.

FIG. 15 shows the amino acid changes (underlined) made during human engineering of the ING-1 heavy chain variable region, including mouse and human heavy chain variable region sequences, risk line for human engineered method, and low as well as moderate risk changes.

FIG. 23 shows competition binding results for human engineered low risk ING-1.

FIG. 28 shows a direct binding ELISA for human engineered (low risk) ING-1 with soluble Ep-CAM.

FIG. 33 depicts the DNA and amino acid sequence for an anti-CD18 light chain (designated LDP-01 or LDP-1 LC).

FIG. 34 depicts the DNA and amino acid sequence for an anti-CD18 heavy chain (designated LDP-01 or LDP-1 HC).

FIG. 38 shows the growth and productivity of various anti-CD18 producing clones, including 1-15, 1-37, 66B9, 84C4, 128D12, 90B6.

FIG. 39 shows the level of expression from clones 264EZ and 254G12 in additional commercially available media, including ProCH04 and ProCH05.

FIG. 44 shows the structure of vectors pING2054 and pING2055 linearized with XbaI.

FIG. 45 shows the growth and productivity of Clone 3G8 neo Subclone G5F1.

DETAILED DESCRIPTION

Figure 1:
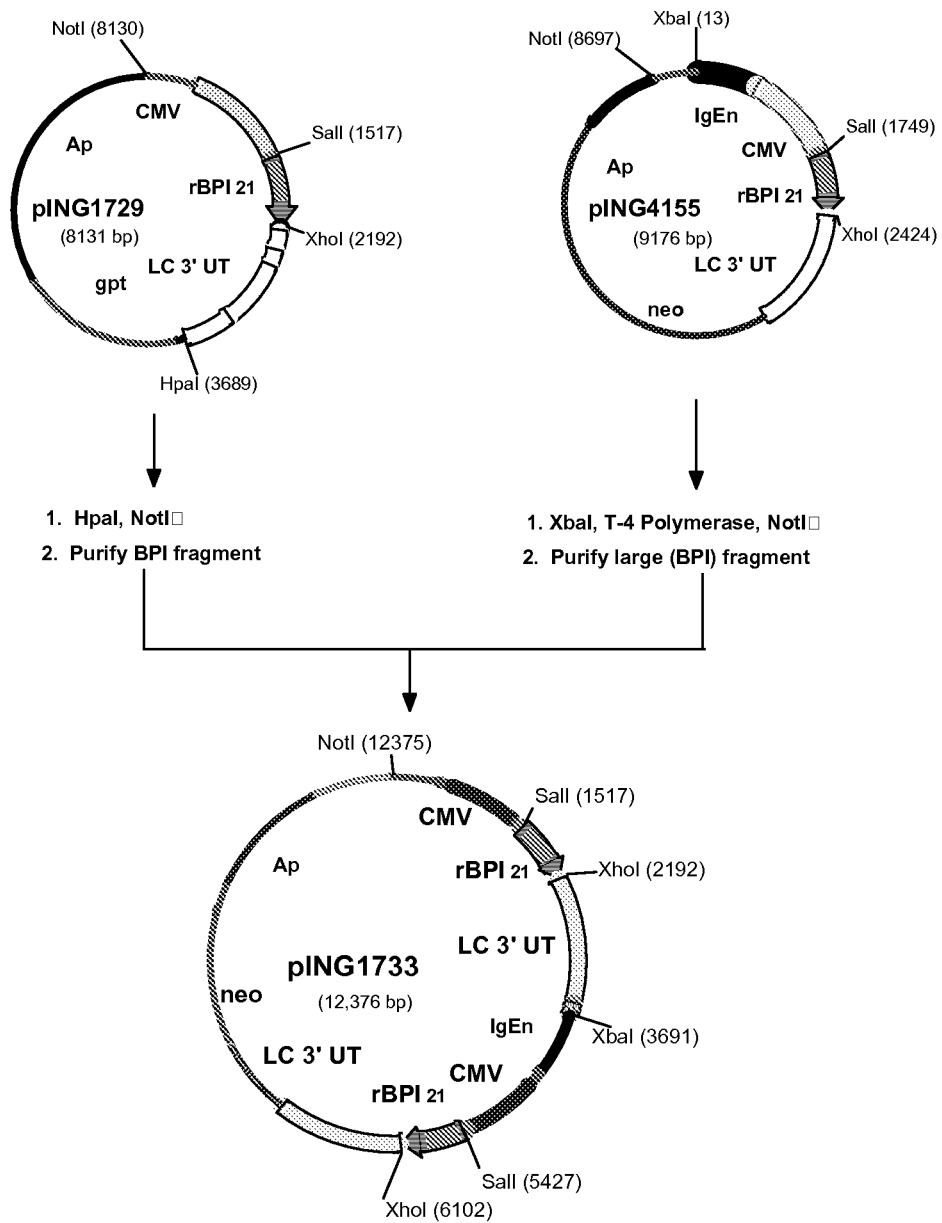
FIG. 1 depicts a construction map for vector pING1733.

The present invention provides novel materials and methods for increasing the expression of recombinant polypeptides, including expression from stable cell lines. Novel expression vectors are provided comprising multiple copies of a transcription unit containing a recombinant DNA sequence which encodes a polypeptide of interest, separated by a selective marker gene. Cell lines harboring these vector constructs are also provided that are capable of expressing the polypeptides encoded by the transcription units. Methods of increasing expression of any polypeptide of interest, including multimeric polypeptides such as immunoglobulins, are provided. An exemplary polypeptide described herein is a BPI protein product, such as $rBPI_{21}$. Another exemplary polypeptide is an immunoglobulin, or a polypeptide comprising at least the variable regions of the light and heavy chains of an immunoglobulin. As described herein, two or more copies of a recombinant gene are inserted into an expression vector wherein the genes are separated by various selective marker genes such as gpt, neo or his, in order to prepare and/or select cell transformants or transfectants, preferably mammalian cell transformants or transfectants and to reduce, minimize or avoid homologous recombination. An increase in net yield of recombinant polypeptide product from host cells harboring these vector constructs is achieved.

Examples of polypeptides expressed through use of the methods of the present invention can include any polypeptide of interest. Expressed recombinant polypeptides of the invention can include any sequences known or contemplated in the art. Polypeptides of interest can be produced by any means through use of the methods disclosed herein, including transformation or transfection of host cells such as mammalian cells with the disclosed vector constructs. Polypeptide production can be provided by any means in a host cell, including accumulation in an intracellular compartment or secretion from the cell into a culture supernatant. Host cells of the present invention may be propagated or cultured by any method known or contemplated in the art, including but not limited to growth in culture tubes, flasks, roller bottles, shake flasks or fermentors. Isolation and/or purification of polypeptide products may be conducted by any means known or contemplated in the art.

In accordance with the invention, vectors were designed that contain multiple copies of a transcription unit encoding a polypeptides of interest. Two-transcription unit vectors were constructed and used to prepare cell lines expressing the encoded polypeptides. Two of these two-transcription unit vectors were used in sequential transfections with cells to produce cell lines, which produce approximately twice the level of polypeptide as a cell line which contained a single two-transcription unit vector or two one-transcription unit vectors as a result of sequential transfection. This increased productivity appeared to result from a two-fold increase in specific productivity and not merely from an increase in cell density. The examples herein demonstrate that increased expression can be achieved through increased transcription unit dosage in a non-amplified expression system through the methods of the present invention in at least two different employed strategies with surprising effectiveness. First, by positioning the selective marker gene between multiple copies of transcription units encoding the gene of interest, the problem of homologous recombination can be avoided and high producing, stable cell lines can be developed which express multiple copies of this gene. Second, by sequentially transfecting cells in the methods of the present invention, the number of multiple integrated copies of transcription units can be increased stepwise to increase expression levels. The present invention contemplates the use of any transcription unit encoding any polypeptide of interest.

The present invention thus provides vectors comprising multiple copies of transcription units that are identical or similar. An aspect of the present invention includes vectors containing transcription units which encode subunits of dimeric or higher order multimeric proteins. Such copies can be homologous copies, for example, at least 25% homologous. Accordingly, the copies can be identical or similar by any percentage between 25% and 100% homologous. Percent sequence identity can be determined by standard methods that are commonly used to compare the similarity in position of the amino acids of two polypeptides. Using a computer program such as BLAST or FASTA, two polypeptides are aligned for optimal matching of their respective amino acids (either along the full length of one or both sequences, or along a pre-determined portion of one or both sequences). The programs provide a default opening penalty and a default gap penalty, and a scoring matrix such as PAM 250 [a standard scoring matrix; see Dayhoff et al., in: *Atlas of Protein Sequence and Structure*, vol 5, supp. 3 (1978)] can be used in conjunction with the computer program. For example, the percent identity can then be calculated as: the total number of identical matches multiplied by 100 and then divided by the sum of the length of the longer sequence within the matched span and the number of gaps introduced into the longer sequences in order to align the two sequences.

Transcription Unit refers to a DNA sequence encoding a polypeptide and can include a promoter and/or a 3' untranslated region.

DNA sequence or recombinant DNA sequence refers to any natural or synthetic DNA sequence derived using molecular biology and/or cloning techniques including, but not limited to, cDNA sequences, genomic sequences, polymerase chain reaction (PCR)-amplified DNA sequences, as well as any chemically-synthesized DNA sequences obtained using techniques known by those of ordinary skill in the art. Recombinant DNA sequences for use in the present invention may be derived from any native or natural source, including prokaryotic DNA sequences or eukaryotic DNA sequences, from sources such as mammalian, plant, yeast, bacterial or viral sources, or from any synthetic or non-natural source, such as chemically-synthesized oligonucleotides.

Polypeptide refers to a molecule comprising a polymer of amino acids linked together by a peptide bond(s). Polypeptides include polypeptides of any length, including proteins (e.g., $\geq 50$ amino acids) and peptides (e.g., 2-49 amino acids) [Alberts et al., *Molecular Biology of the Cell*, 3rd Ed., (1994)]. Polypeptides include proteins or peptides of any activity or bioactivity, including, for example, bioactive polypeptides, such as enzymatic proteins or peptides (e.g., protases, kinases, phosphatases), receptor proteins or peptides, transporter proteins or peptides, bactericidal and/or endotoxin-binding proteins or peptides, structural proteins or peptides, immune proteins or peptides (e.g., antibodies or antigen-binding portions thereof), cytokine proteins or peptides, toxins, chemotherapeutic agents, antibiotics, hormones, growth factors, vaccines, or the like. For example, polypeptides include, but are not limited to, full length proteins, fragments, analogs, variants or derivatives of proteins, fusion proteins, chimeric proteins, multimeric proteins or their subunits. Peptides include, but are not limited to, anti-microbial peptides, herbicidal peptides, peptide hormones, neuropeptides, toxins or the like.

Bioactive polypeptide refers to a polypeptide product exhibiting bioactivity akin to that of a protein or peptide innately produced within a living organism for a physiological purpose, as well as to intermediates which can be processed into such proteins and peptides, as by cleavage away of DNA sequences encoding superfluous protein, folding, combination (as in the case of the A and B chains of insulin or the heavy and light chains of immunoglobulins), post-translational modification, etc.

Vector refers to an agent or vehicle for carrying polynucleotide sequences (e.g., DNA or RNA). Thus, vectors are said to contain (i.e., comprise) such polynucleotide sequences.

Cloning vector refers to an agent or vehicle that may be capable of autonomously replicating, including but not limited to plasmids, phagemids, or phage, comprising a polynucleotide molecules, including a DNA molecule, to which one or more additional polynucleotide segments, including DNA segments, can be or have been added.

Expression vector refers to a vector into which one or more transcriptional and translational regulation sequence(s) have been incorporated.

Promoter refers to a site on a DNA molecule to which an RNA polymerase and/or any associated factors attaches and at which transcription is initiated. Promoters may include those well-known in the art, including from SV40, HSV, bovine growth hormone, thymidine kinase, MPSV, mouse beta globin, human EF1, MSV-LTR, RSV, MMTV-LTR, CMV, MLV, Chinese hamster elongation factor, mouse Abelson LTR, human C-fos promoter or the like. Promoters for yeast, insect, plant and/or bacterial expression are also well-known in the art.

Enhancer refers to a control element that can increase expression of a gene or genetic sequence.

Selective marker or selectable marker refers to a gene or any genetic material that encodes for a phenotype that may encourage or inhibit the growth of a cell or organism in the absence or presence of a chosen compound or condition. Selective maker genes may include gpt, res, his genes, or also genes for adenosine deaminase (ADA), thymidine kinese (TK), adenine phosphoribosyl transferase (APRT), zeocin resistance gene, hygromycin resistance gene, or puromycin resistance gene.

Transformation or transfection refers to the introduction of genetic material, such as a vector, including a cloning or expression vector, into a recipient host cell that changes the genotype and results in a phenotypic change in the recipient cell. A host cell or those colonies resulting from a host cell that has undergone successful transformation or transfection is said to be transformed or transfected or may be referred to as a transformant or transfectant.

The present invention specifically provides for the development of exemplary vectors, including two and four transcription unit expression vectors which are functional and selectable in a host cell.

Figure 2:
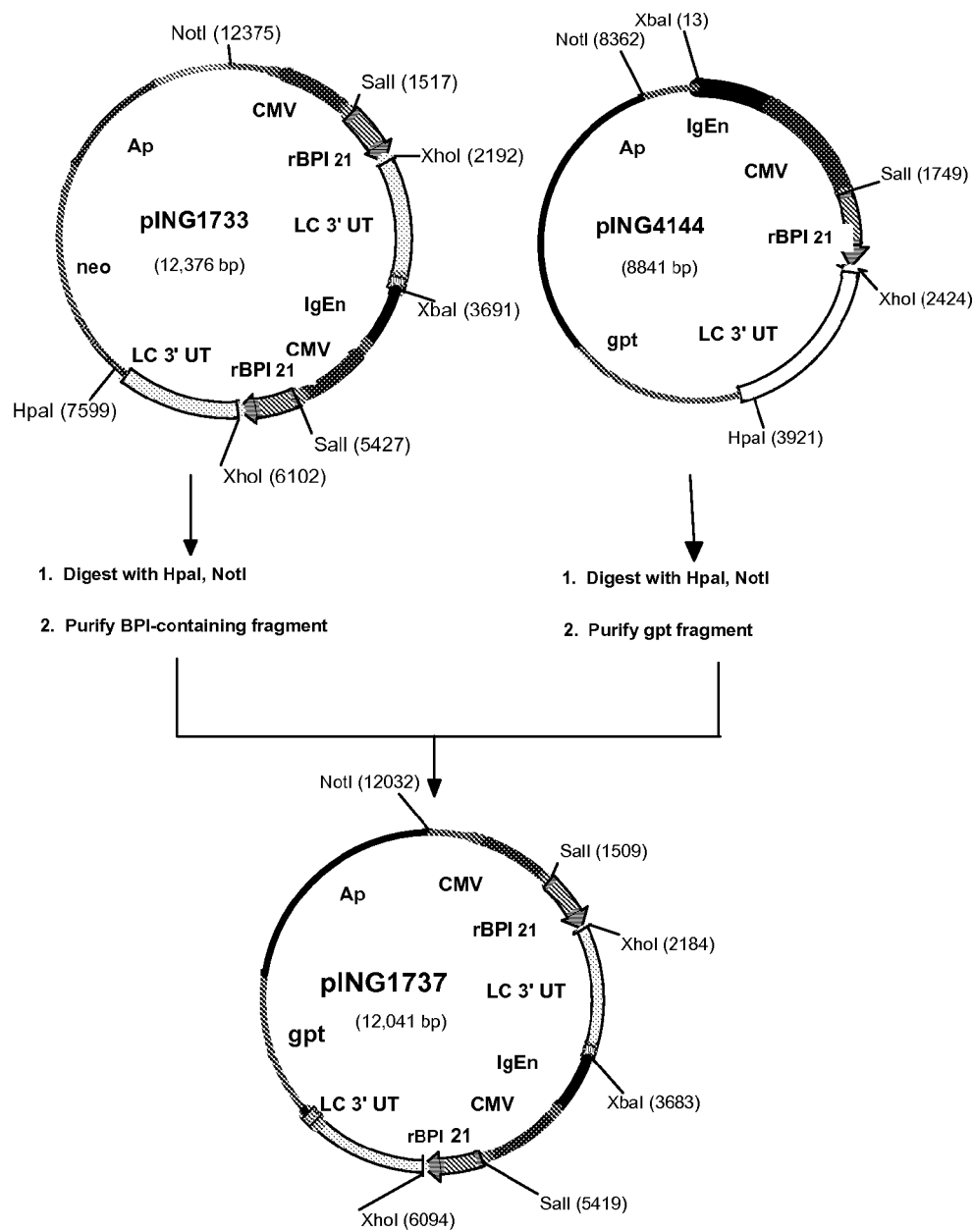
FIG. 2 depicts a construction map for vector pING1737.

A series of exemplary vectors have been constructed containing two copies of a gene encoding a BPI protein product, $rBPI_{21}$, each under the control of a hCMV promoter and mouse light chain 3' untranslated region with 0, 1 or 2 copies of a human heavy chain enhancer and either a gpt or neo gene for selection of transformants or transfectants. The vectors also differed in the orientation of $rBPI_{21}$ genes on the vector. Initial testing of these vectors indicated that a preferred configuration was represented by the gpt vector, pING1737 (FIG. 2). This vector and its neo version, pING1733 (FIG. 1) were selected for use in full-scale cell line development.

According to the present invention, the presence of two copies of a $rBPI_{21}$ gene and flanking promoter and 3' untranslated region sequences in pING1737 and pING1733 should promote higher expression through increased gene dosage. However, one potentially adverse consequence of this configuration could be instability of the integrated DNA as a result of recombination between two homologous $rBPI_{21}$ and flanking sequences leading to elimination of one of the $rBPI_{21}$ copies and lower expression. To reduce the chance of recombination, these vectors have been designed according to the invention so that when linearized at a unique XbaI site, the $rBPI_{21}$ genes would be separated by the selective marker gene as integrated into a host cell chromosome. This configuration would have the greatest potential stability in the chromosome, at least as long as the transfectants were maintained in the presence of selective agent(s), because homologous recombination between the gene copies of $rBPI_{21}$ would also eliminate selective marker gene(s). To evaluate the effect of gene placement on both gene expression and clone stability, both configurations were tested in cell line development for $rBPI_{21}$ expression described in the examples that follow.

Bactericidal/permeability-increasing protein (BPI) is a protein isolated from the granules of mammalian polymorphonuclear leukocytes (PMNs or neutrophils), which are blood cells essential in the defense against invading microorganisms. Human BPI protein has been isolated from PMNs by acid extraction combined with either ion exchange chromatography [Elsbach, *J. Biol. Chem.*, 254: 11000 (1979)] or *E. coli* affinity chromatography [Weiss, et al., *Blood* 69: 652 (1987)]. BPI obtained in such a manner is referred to herein as natural BPI and was initially shown by Elsbach and Weiss to have bactericidal activity against gram-negative bacteria. The molecular weight of human BPI is approximately 55,000 daltons (55 kD). The amino acid sequence of the entire human BPI protein and the nucleic acid sequence of DNA encoding the protein have been reported in FIG. 1 of [Gray, et al., *J. Biol. Chem.* 264: 9505 (1989)].

BPI protein products have a wide variety of beneficial activities. BPI protein product refers to and includes naturally and recombinantly produced BPI protein; natural, synthetic, and recombinant biologically active polypeptide fragments of BPI protein; biologically active polypeptide variants of BPI protein or fragments thereof, including hybrid fusion proteins and multimer of monomers; biologically active polypeptide analogs of BPI protein or fragments or variants thereof, including cysteine-substituted analogs; and BPI-derived peptides. U.S. Pat. Nos. 5,198,541 and 5,641,874, the disclosures of which are incorporated herein by reference, discloses recombinant genes encoding and methods for expression of BPI proteins including recombinant BPI holoprotein, referred to as rBPI and recombinant fragments of BPI. U.S. Pat. No. 5,439,807 and corresponding International Publication No. WO 93/23540 (PCT/US93/04752), which are all incorporated herein by reference, disclose novel methods for the purification of recombinant BPI protein products expressed in and secreted from genetically transformed or transfected mammalian host cells in culture and disclose how one may produce large quantities of recombinant BPI products suitable for incorporation into stable, homogeneous pharmaceutical preparations.

Biologically active fragments of BPI (BPI fragments) include biologically active molecules that have the same or similar amino acid sequence as a natural human BPI holoprotein, except that the fragment molecule lacks amino-terminal amino acids, internal amino acids, and/or carboxy-terminal amino acids of the holoprotein, including those described in U.S. Pat. Nos. 5,198,541 and 5,641,874. Nonlimiting examples of such fragments include an N-terminal fragment of natural human BPI of approximately 25 kD, described in [Ooi et al., *J. Exp. Med.*, 174: 649 (1991)], or the recombinant expression product of DNA encoding N-terminal amino acids from 1 to about 193 to 199 of natural human BPI, described in [Gazzano-Santoro et al., *Infect. Immun.* 60: 4754-4761 (1992)], and referred to as $rBPI_{23}$. In that publication, an expression vector was used as a source of DNA encoding a recombinant expression product ($rBPI_{23}$) having the 31-residue signal sequence and the first 199 amino acids of the N-terminus of the mature human BPI, as set out in FIG. 1 of [Gray et al., supra], except that valine at position 151 is specified by GTG rather than GTC and residue 185 is glutamic acid (specified by GAG) rather than lysine (specified by AAG). Recombinant holoprotein (rBPI) has also been produced having the sequence (SEQ ID NOS: 1 and 2) set out in FIG. 1 of [Gray et al., supra], with the exceptions noted for $rBPI_{23}$ and with the exception that residue 417 is alanine (specified by GCT) rather than valine (specified by GTT). Another fragment consisting of residues 10-193 of BPI has been described in U.S. Pat. No. 6,013,631, continuation-in-part U.S. application Ser. No. 09/336,402, filed Jun. 18, 1999, and corresponding International Publication No. WO 99/66044 (PCT/US99/13860), all of which are incorporated herein by reference. Other examples include dimeric forms of BPI fragments, as described in U.S. Pat. Nos. 5,447,913, 5,703,038, and 5,856,302 and corresponding International Publication No. WO 95/24209 (PCT US95/03125), all of which are incorporated herein by reference. Preferred dimeric products include dimeric BPI protein products wherein the monomers are amino-terminal BPI fragments having the N-terminal residues from about 1 to 175 to about 1 to 199 of BPI holoprotein. A particularly preferred dimeric product is the dimeric form of the BPI fragment having N-terminal residues 1 through 193, designated $rBPI_{42}$ dimer.

Biologically active variants of BPI (BPI variants) include but are not limited to recombinant hybrid fusion proteins, comprising BPI holoprotein or biologically active fragment thereof and at least a portion of at least one other polypeptide, or dimeric forms of BPI variants. Examples of such hybrid fusion proteins and dimeric forms are described in U.S. Pat. No. 5,643,570 and corresponding International Publication No. WO 93/23434 (PCT/US93/04754), which are all incorporated herein by reference and include hybrid fusion proteins comprising, at the amino-terminal end, a BPI protein or a biologically active fragment thereof and, at the carboxy-terminal end, at least one constant domain of an immunoglobulin heavy chain or allelic variant thereof.

Biologically active analogs of BPI (BPI analogs) include but are not limited to BPI protein products wherein one or more amino acid residues have been replaced by a different amino acid. For example, U.S. Pat. Nos. 5,420,019, 5,674,834 and 5,827,816 and corresponding International Publication No. WO 94/18323 (PCT/US94/01235), all of which are incorporated herein by reference, disclose polypeptide analogs of BPI and BPI fragments wherein a cysteine residue is replaced by a different amino acid. A stable BPI protein product has been described that is the expression product of DNA encoding from amino acid 1 to approximately 193 to 199 of the N-terminal amino acids of BPI holoprotein, but wherein the cysteine at residue number 132 is substituted with alanine. This product is designed $rBPI_{21}\Delta cys$ or $rBPI_{21}$. Production of this N-terminal analog of BPI, $rBPI_{21}$, has been described in [Horowitz et al., *Protein Expression Purification*, 8: 28-40 (1996)]. Similarly, an analog consisting of residues 10-193 of BPI in which the cysteine at position 132 is replaced with an alanine (designated rBPI(10-193)C132A or rBPI(10-193)ala$^{132}$) has been described in U.S. Pat. No. 6,013,631, continuation-in-part U.S. application Ser. No. 09/336,402, filed Jun. 18, 1999, and corresponding International Publication No. WO 99/66044 (PCT US/99/13860), all of which are incorporated herein by reference. Other examples include dimeric forms of BPI analogs; e.g. U.S. Pat. Nos. 5,447,913, 5,703,038, and 5,856,302 and corresponding International Publication No. WO 95/24209 (PCT/US95/03125), all of which are incorporated herein by reference.

Other BPI protein products useful according to the methods of the invention are peptides derived from or based on BPI produced by synthetic or recombinant means (BPI-derived peptides), such as those described in International Publication No. WO 97/04008 (PCT/US96/03845), which corresponds to U.S. application Ser. No. 08/621,259 filed Mar. 21, 1996, and International Publication No. WO 96/08509 (PCT/US95/09262), which corresponds to U.S. Pat. No. 5,858,974, and International Publication No. WO 95/19372 (PCT/US94/10427), which corresponds to U.S. Pat. Nos. 5,652,332 and 5,856,438, and International Publication No. WO94/20532 (PCT/US94/02465), which corresponds to U.S. Pat. No. 5,763,567 which is a continuation of U.S. Pat. No. 5,733,873, which is a continuation-in-part of U.S. application Ser. No. 08/183,222, filed Jan. 14, 1994, which is a continuation-in-part of U.S. application Ser. No. 08/093,202 filed Jul. 15, 1993 (corresponding to International Publication No. WO 94/20128 (PCT/US94/02401)), which is a continuation-in-part of U.S. Pat. No. 5,348,942, as well as International Application No. PCT/US97/05287, which corresponds to U.S. Pat. No. 5,851,802, the disclosures of all of which are incorporated herein by reference. Methods of recombinant peptide production are described in U.S. Pat. No. 5,851,802 and International Publication No. WO 97/35009 (PCT/US97/05287), the disclosures of which are incorporated herein by reference. Three separate functional domains within the BPI sequence have been identified and designate regions of the amino acid sequence of BPI that contribute to the total biological activity of the protein (Domain I—from about amino acid 17 to about amino acid 45; Domain II—from about amino acid 65 to about amino acid 99; and Domain III—from about amino acid 142 to about amino acid 169). The biological activities of peptides derived from or based on these functional domains (i.e., BPI-derived peptides) may include LPS binding, LPS neutralization, heparin binding, heparin neutralization or antimicrobial including antifungal and antibacterial (including e.g., anti-gram-positive and anti-gram-negative) activity.

Many utilities of BPI protein products, including $rBPI_{23}$ and $rBPI_{21}$, have been described due to the wide variety of biological activities of these products.

Exemplary vectors have been developed according to the invention, with multiple transcription units encoding an exemplary polypeptide of interest, $rBPI_{21}$. Using such vectors, exemplary clones and cell lines have been developed. For example, a CHO-K1 cell line, Clone 689, has been developed, as detailed in the following examples, which secretes up to ~125 µg/ml of $rBPI_{21}$ in shake flasks. This cell line was developed using a novel expression vectors containing two copies of the $rBPI_{21}$ gene, each under the control of the human immediate early cytomegalovirus (hCMV) promoter and the mouse light chain 3' untranslated region, and either the gpt (pING1737) or neo (pING1733) genes for selection of mycophenolic acid or G418-resistant transfectants, respectively. These vectors were designed so that when linearized at a unique XbaI restriction site prior to transfection, the two copies of the $rBPI_{21}$ transcription unit are separated by the selective marker gene. This configuration provides a selective pressure against recombination because recombination between the two $rBPI_{21}$ genes would result in deletion of the selective marker gene, and thereby results in enhanced stability of clones developed with these vectors.

As detailed in the following examples, a total of ~500 mycophenolic acid-resistant transfectants were screened from a pING1737 transfection. The highest-secreting transfectants, based on the 24 well plate cultures, were adapted to suspension growth in Ex-Cell 301 medium supplemented with 2% Fetal Bovine Serum (FBS) and tested in shake flask tests with S-Sepharose beads. The highest producer, Clone 51, consistently secreted ~50 µg/ml in shake flask tests. This level is similar to that produced by Clone 228 which contains two $rBPI_{21}$ gene copies as a result of a sequential transfection with vectors each containing one $rBPI_{21}$ gene. Clone 51 maintained this productivity level in the absence of selection for up to 14 weeks and was subsequently re-transfected with the neo vector, pING1733, for selection of G418-resistant transfectants. A total of 1253 clones were screened and Clone 689 was the highest producer at ~100 µg/ml based on results of initial shake flask tests. Clone 689 was adapted to growth in Ex-Cell 301 medium without FBS and re-designated Clone 689b. This clone maintained its productivity during passage in the absence of selection for at least 12 weeks.

As further detailed in the following examples, the results of initial shake flask tests indicated that after adaptation to Ex-Cell 301 medium without FBS, Clone 689b secreted ~75-80 µg/ml compared to ~50 µg/ml for Clone 228. Typically, these tests were performed with 250 ml flasks that are closed for the entire 12 days of incubation until the beads are harvested. It was discovered that by periodically opening the flasks (thus allowing gas exchange to occur), the expression levels for Clone 689 increased to ~125 µg/ml compared to ~60 µg/ml for Clone 228 under the same conditions. Clones 228 and 689 produced ~4 and 9 pg/cell/day, respectively, during the period when the cells were at their highest levels of viability, indicating that increased gene dosage resulted in increased specific productivities. Consistent with these results, Northern blot analysis revealed that Clone 689 expressed almost 2-fold higher levels of $rBPI_{21}$ mRNA than Clone 228. Several research cell banks based on these clones have been prepared.

An additional series of exemplary vectors comprising multiple transcription units encoding anti-Ep-CAM immunoglobulin polypeptides were developed, including vectors containing two genes encoding mouse-human chimeric or human engineered anti-Ep-CAM antibody light plus heavy chains, each under the control of a hCMV promoter and mouse light chain 3' untranslated region with 0, 1 or 2 copies of a human heavy chain enhancer and either a gpt or neo gene for selection of transformants or transfectants. The vectors also differed in the orientation of light and heavy chains genes on the vector.

ING-1 is a mouse-human chimeric antibody comprising variable regions from the mouse antibody Br-1 and human constant regions (see, e.g., U.S. Pat. No. 5,576,184). It is now known that the mouse anti-carcinoma antibody Br-1 binds the Epithelial Cell Adhesion Molecule (Ep-CAM). This murine antibody was first made and characterized by Colcher et al. from the B38.1 hybridoma cell line (described in U.S. Pat. No. 4,612,282). The ING-1 antibody is a mouse-human chimeric version of Br-1 and was previously developed and expressed in Sp2/0 cells using vectors pING2207 encoding the mouse-human chimeric ING-1 light chain mammalian and pING2225 encoding the mouse-human chimeric ING-1 heavy chain (see, e.g., U.S. Pat. No. 5,576,184).

Antibody products that target Ep-CAM derived from the ING-1 antibody produced by cell line HB9812 as deposited with the ATCC (see, e.g., U.S. Pat. No. 5,576,184) have a variety of beneficial activities for diagnostic, prognostic and/or therapeutic uses involving diseases, disorders or conditions related to the expression of Ep-CAM, including for use with Ep-CAM-positive tumor cells, particularly the metastasis of Ep-CAM positive tumor cells. ING-1 antibody product refers to and includes an antibody heavy and/or light chain protein comprising at least an antibody variable region wherein the heavy and/or light chain variable region binds to Ep-CAM and wherein the heavy and/or light chain variable region shares at least 80% (including, for example, at least 80%, 81%, 82%, 83%, 84%, 85%, 86%, 87%, 88%, 89%, 90%, 91%, 92%, 93%, 94%, 95%, 96%, 97%, 98%, 99%) sequence identity with the murine heavy and/or light chain variable regions of the ING-1 antibody produced by cell line HB9812 as deposited with the ATCC.

Exemplary vectors have been developed according to the invention, with multiple transcription units encoding an exemplary immunoglobulin polypeptide of interest, including mouse-human chimeric or human engineered anti-Ep-CAM antibodies derived from the ING-1 antibody produced by cell line HB9812 as deposited with the ATCC. Using such vectors, exemplary clones and cell lines have been developed. For example, a CHO-K1 cell line, Clone 146, has been developed, as detailed in the following examples, which secretes up to ~60 μg/ml of immunoglobulin polypeptides in shake flasks and about 200 mg/L in a fermentor. This cell line was developed using a novel expression vector pING1937 containing two genes, one copy each of the low risk human engineered ING-1 light and heavy chain genes and a neo (G418-resistant) gene, each under the control of a human cytomegalovirus (hCMV) promoter and mouse light chain 3' untranslated region, and a neo gene for selection of G418-resistant transfectants.

The present invention provides for increasing expression and production of human engineered anti-Ep-CAM immunoglobulin polypeptides through a second transfection of an exemplary cell line with a second multiple transcription unit vector. For example, Clone 373 was developed, as detailed in the following examples by transfecting a subclone of Clone 146, Clone 146.3, with the expression vector pING1959 which is similar to pING1937 except that it contains a gpt selective marker gene. Clone 373 expressed ~225 and ~257 μg/ml of the human engineered anti-Ep-CAM antibody as determined by shake flask results in Ex-Cell 301 medium.

A series of exemplary vectors have also been constructed containing four genes, two copies of each of the low risk human engineered ING-1 light and heavy chain genes (pING1965, four gene vector), each under the control of a hCMV promoter and mouse light chain 3' untranslated region with 0, 1 or 2 copies of a human heavy chain enhancer and either a gpt or neo gene for selection of transformants or transfectants. Using such vectors, exemplary clones and cell lines have been developed. For example, a CHO-K1 cell line, Clone 17, has been developed, as detailed in the following examples, which secretes up to ~216 μg/ml in ExCell 301 medium supplemented with 1% FBS and ~214 μg/ml in ExCell 301 medium without FBS supplementation. This cell line was developed using a novel expression vector pING1964 containing four genes, two copies each of the low risk human engineered ING-1 light and heavy chain genes and the neo (G418-resistant) gene, each under the control of a human cytomegalovirus (hCMV) promoter and mouse light chain 3' untranslated region.

An additional series of exemplary vectors comprising multiple transcription units encoding anti-CD18 immunoglobulin polypeptides, including vectors containing two genes encoding anti-CD18 antibody light and heavy chains, each under the control of a hCMV promoter and mouse light chain 3' untranslated region with 0, 1 or 2 copies of a human heavy chain enhancer and either a gpt or neo gene for selection of transformants or transfectants. The vectors also differed in the orientation of light and heavy chains genes on the vector. The anti CD-18 antibody was originally developed as a rat antibody YFC51.1.1 to the human lymphocyte surface antigen CD18 and later humanized by CDR grafting as described in U.S. Pat. Nos. 5,985,279 and 5,997,867.

Antibody products that target CD18 have a wide variety of beneficial activities. For example, anti-CD18 adhesion of neutrophils to endothelial cells and restenosis in primate model with stents and balloon angioplasty. Anti-CD18 protein product refers to and includes anti-CD18 antibodies that comprise CDRs derived from the YFC 5.1.1.1 antibody (see, e.g., U.S. Pat. No. 5,985,279). Anti-CD18 antibody product refers to and includes an antibody heavy and/or light chain protein comprising at least an antibody variable region wherein the heavy and/or light chain variable region binds to CD18, wherein the CDRs are those of the YFC 5.1.1.1 antibody as shown in SEQ ID NOS: 3-8 and 11-16 of U.S. Pat. No. 5,985,279, and wherein the heavy and/or light chain variable region shares at least 80% (including, for example, at least 80%, 81%, 82%, 83%, 84%, 85%, 86%, 87%, 88%, 89%, 90%, 91%, 92%, 93%, 94%, 95%, 96%, 97%, 98%, 99%) sequence identify with the murine heavy and/or light chain variable regions of the YFC 5.1.1.1 antibody.

Exemplary vectors have been developed according to the invention, with multiple transcription units encoding additional exemplary immunoglobulin polypeptides of interest, including humanized anti-CD18 immunoglobulin. Using such vectors, exemplary clones and cell lines have been developed. For example, a CHO-K1 cell line, Clone 128D12, has been developed, as detailed in the following examples, which secrets ~200 μg/ml of immunoglobulin in shake flasks. This cell line was developed using a novel expression vector pING2052 containing two genes, one copy each of the anti-CD18 light and heavy chain genes and a neo (G418-resistance) gene, each under the control of a human cytomegalovirus (hCMV) promoter and mouse light chain 3' untranslated region, and a neo gene for selection of G418-resistant transfectants, respectively.

The current invention provides for increasing expression and production of anti-CD18 immunoglobulin through a second transfection of an exemplary cell line with a second multiple transcription unit vector. For example, Clone 264E2 was developed by sequential transfection of Clone 128D12, with the expression vector pING2057 which is similar to pING2052 except that it contains a his selective marker gene. Clone 264E2 in several shake flask tests in Ex-Cell 301 medium produced approximately 1.5 to greater than two times as much immunoglobulin polypeptides as Clone 128D12 as measured by Protein A-HPLC.

An additional series of exemplary vectors comprising multiple transcription units encoding complement inhibitory polypeptides were developed, including vectors containing multiple copies of the complement inhibitory peptide designated CAB2.1 (see, e.g., U.S. Pat. Nos. 5,866,402; 6,316,253; and 6,451,539). For example, a vector was constructed containing two copies of a gene encoding a CAB2.1 polypeptide each under the control of a hCMV promoter and mouse light chain 3' untranslated region and either a neo or his gene for selection of transformants or transfectants. Initial testing of these vectors indicated that a preferred configuration was represented by the vector, pING2055 with a neo gene for selection. This vector and its his version, pING2056 were selected for use in full-scale cell line development.

Complement Activation Blocker-2 (CAB2.1) is a chimeric or fusion protein consisting of two human complement inhibitory proteins, membrane cofactor protein (MCP, CD46) at its N-terminus and decay accelerating factor (DAF, CD55) at its C-terminus. CAB2.1 protein has been isolated from CHO-DuKX-B11 DHFR⁻ cells transfected with a vector containing the CAB2.1 gene along with the DHFR gene for selection in the presence of methotrexate either by affinity chromatography with MCP-specific Mab (GB24) or by employing acid precipitation, anion exchange chromatography, immobilized metal affinity chromatography, and hydrophobic interaction chromatography [Higgins et al., *J. Immunol.* 158: 2872-2881 (1989)]. CAB2.1 obtained in such a manner was initially shown by Higgins [Higgins et al., *J. Immunol.* 158: 2872-2881 (1988)] to possess both factor 1 cofactor activity and decay-accelerating activity, and to inactivate both the classical and alternative pathways of complement activation by inactivating C3/C5 convertases. The molecular weight of CAB2.1 is approximately 110,000 daltons (110 kD). The amino acid sequence of the entire CAB2.1 protein and the nucleic acid sequence of DNA encoding the protein have been reported (see, e.g., U.S. Pat. No. 6,316, 253).

CAB2.1 protein products have therapeutic potential for the prevention of complement mediated lysis of normal tissue, for example in the treatment of acute human diseases in which excessive complement activation causes damage to normal tissues. Some diseases in which complement is known to be activated include systemic lupus erythematosus, acute myocardial infarction, burn, sepsis, and adult respiratory distress syndrome. CAB2.1 protein product refers to and includes recombinantly produced CAB2.1 protein; complement inhibitory polypeptide fragments of CAB2.1 protein; complement inhibitory polypeptide variants of CAB2.1 protein or fragments thereof; including hybrid fusion proteins and multimer of monomers; complement inhibitory analogs of CAB2.1 protein or fragments or variants thereof; and complement inhibitory CAB2.1-derived peptides. Complement inhibitory fragments of CAB2.1 include biologically active molecules that have the same or similar amino acid sequence as a full length CAB2.1, except that the fragment molecule lacks amino-terminal amino acids, internal amino acids, and/or carboxy-terminal amino acids of the full length CAB2.1. Complement inhibitory analogs of CAB2.1 include but are not limited to CAB2.1 protein products wherein one or more amino acid residues have been replaced by a different amino acid. Other CAB2.1 protein products useful according to the methods of the invention are complement inhibitory peptides derived from or based on CAB2.1 produced by synthetic or recombinant means (CAB2.1-derived peptides).

Using vectors encoding CAB2.1, exemplary clones and cell lines expressing CAB2.1 were developed. For example, a CHO-K1 cell line, Clone 217B4 was developed, as detailed in the following examples, which secreted up to about 200 µg/ml of CAB2.1 in shake flasks. This cell line was developed using novel expression vectors containing one and two copies of the CAB2.1 gene, each under the control of a human cytomegalovirus (hCMV) promoter and mouse light chain 3' untranslated region, and either a neo (pING2054) or his (pING2056) genes for selection of G418-resistant or histinol transfectants, respectively.

Other aspects, versions, and advantages of the present invention will be understood upon consideration of the following illustrative examples, wherein Example 1 addresses the construction of vectors according to the present invention that comprise multiple copies of a given transcription unit encoding a polypeptide of interest; Example 2 addresses development of an rBPI$_{21}$-Producing CHO-K1 cell line, Clone 51, by transfection with a two-transcription unit vector, pING1737; Example 3 addresses transfection of Clone 51 with a second two-transcription unit vector, pING1733, to yield the exemplary Clone 689; Example 4 addresses a third sequential transfection with a two-transcription unit vector, pING1753, to yield the exemplary Clone 341 and subclones thereof; and Example 5 addresses sequential transfection with a two-transcription unit vectors lacking an Ig enhancer, pING1744 and pING1915, to yield the exemplary Clones 338 and 58, respectively. Example 6 addresses the construction of additional vectors according to the present invention that comprise multiple copies of a given transcription unit, including those encoding immunoglobulin polypeptides; Example 7 includes development of a mouse-human chimeric ING-1 producing CHO-K1 cell line, Clone 40, by transfection with a two-transcription unit vector, pING1932 and the development of Clone 146, by transfection with a two-transcription unit vector, pING1937; Example 8 addresses the development of Clones 259 and 373 by sequential transfection of Clone 146 with a two-transcription unit vector pING1957 and Clone 373 by sequential transfection of Subclone 146.3 with a two-transcription unit vector pING1959; Example 9 addresses the development of Clone 132 by sequential transfection of Clone 373 with a two-transcription unit vector pING1957; Example 10 addresses the development of Clones 53 and 157 by transfection with a two-transcription unit vector pING1959, containing one copy of each of the light and heavy chain genes of a human engineered anti-EpCAM antibody, and the development of Clone 17 transfected with a four-transcription unit vector pING1964, containing two copies of each of the light and heavy chain genes of a human engineered anti-EpCAM antibody; Example 11 addressing the binding activity of exemplary immunoglobulin polypeptides, including those encoding anti-Ep-CAM immunoglobulin polypeptides; Example 12 addresses the cloning of soluble Ep-CAM and the development of a direct binding ELISA assay with soluble Ep-CAM; Example 13 addresses the construction of additional expression vectors according to the present invention that contain multiple copies of a given transcription unit, including those encoding additional immunoglobulin polypeptides; Example 14 addresses the development of an anti-CD18 antibody-producing clone 128D12 by transfection with a two-transcription unit vector pING2052; Example 15 addresses the development of an anti-CD18 antibody-producing clone 264E2 by sequential transfection of clone 128D12 with the two-transcription unit vector pING264E2; Example 16 addresses the use of a number of additional cell culture media for anti-CD18 antibody production in selected cell lines; Example 17 addresses the construction of expression vectors that contain multiple copies of a given transcription unit, including those encoding complement inhibitory polypeptides; Example 18 addresses the development of Clone 3G8 and its Subclone G5F1 transfected with CAB2.1-encoding vectors, including a single-transcription unit neo vector pING2054 and Clones 156B8 and 176C6 transfected with a two-transcription unit neo vector pING2055; Example 19 addresses the development of additional CAB2.1-producing clones by sequential transfection of Clone 3G8 with the two-transcription unit his vector pING2056 followed by subcloning of the top producing clones.

EXAMPLE 1

Construction of Vectors

This example describes the construction of vectors that contain (i.e., comprise) multiple copies of an exemplary transcription unit. Exemplary vector constructs are also described containing multiple copies of exemplary gene sequences encoding a polypeptide of interest.

A. Construction of Expression Vectors Containing Two $rBPI_{21}$ Genes and a Single Copy of the Mouse Immunoglobulin Heavy Chain Enhancer The expression vectors, pING1729, pING4144, pING4151 and pING4155 were used as the source of DNAs encoding $rBPI_{21}$ sequences (SEQ ID NO: 3 and 4). Plasmids pING4144 and pING4151 have been described in co-owned U.S. Pat. No. 5,674,834 by Theofan et al. pING4155 is similar to pING4144 and pING4151 except that it contains the neo gene for selection of G418-resistant transfectants. pING1729 is similar to pING4144 except that it lacks the mouse immunoglobulin heavy chain enhancer. This vector was constructed by deleting a ~700 bp HindIII restriction fragment containing the enhancer.

The plasmid pING1733 was constructed from pING4155 and pING1729 (FIG. 1). pING4155 was first digested with XbaI, which cuts at a unique site adjacent to the Ig enhancer. The XbaI-digested DNA was treated with T4 DNA polymerase in the presence of deoxyribonucleotides, which fills in the 4 bp 5' extension to make the ends blunt, and then digested with NotI, which cuts at a unique site within the vector ~500 bp counterclockwise to XbaI on a circular map. The resulting ~8700 bp vector fragment was gel purified. pING1729 was digested with NotI and HpaI and a ~3700 bp restriction fragment containing the human cytomegalovirus (hCMV) promoter, the gene encoding $rBPI_{21}$ and the mouse kappa light chain 3' untranslated region was gel purified. Ligation of these restriction fragments re-created the XbaI site and retained the NotI site. The resulting vector, pING1733 (FIG. 1), contains the neo gene for selection of G418-resistant transfectants, two copies of the $rBPI_{21}$ gene each under the control of the CMV promoter and mouse kappa light chain 3' untranslated region and one IgG enhancer unit.

The plasmid pING1737 is similar to pING1733 except that it contains the gpt instead of the neo gene for selection of mycophenolic acid-resistant transfectants and was constructed from pING1733 and the gpt vector, pING4144 (FIG. 2). pING1733 and pING4144 were each digested with HpaI and NotI and a 7600 bp restriction fragment from pING1733 (containing the two $rBPI_{21}$ transcription units) and a 4400 bp restriction fragment from pING4144 (containing the gpt gene) were ligated. As with pING1733, pING1737 contains two copies of the $rBPI_{21}$ gene each under control of the CMV promoter with one Ig enhancer and unique XbaI and NotI sites. Digestion of pING1737 with NotI (FIG. 3A) or XbaI (FIG. 3B) yields linear plasmids identical to pING1733 digested with the same restriction enzymes except that they contain the gpt instead of the neo gene.

Figure 4:
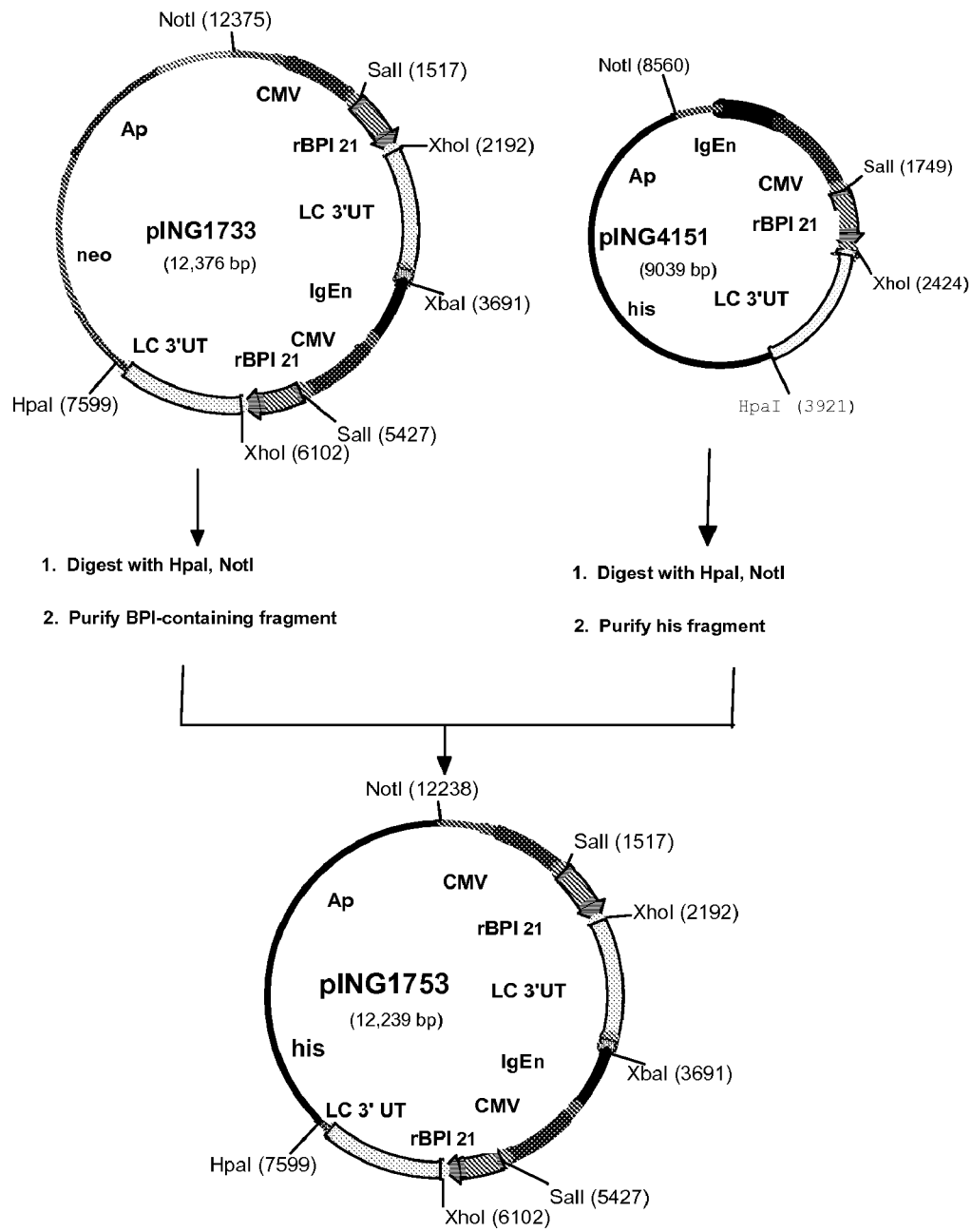
FIG. 4 depicts a construction map for vector pING1753.

The plasmid pING1753 was constructed in a similar manner to pING1737 except that the vector, pING4151, containing the his gene for selection of histidinol-resistant transfectants, was used instead of the gpt-containing vector, pING4144. Both plasmids were digested with HpaI and NotI and the fragment containing the two $rBPI_{21}$ transcription units from pING1733 and the fragment containing the his gene from pING4151 were gel purified and ligated (FIG. 4). As with pING1737 and pING1733, pING1753 contains two copies of the $rBPI_{21}$ gene each under control of the CMV promoter with one Ig enhancer and unique XbaI and NotI sites. Digestion of pING1753 with XbaI or NotI yields linear plasmid maps similar to those of pING1733 and pING1737 digested with the same restriction enzymes except that pING1753 contain the his instead of the neo or gpt genes.

Digestion of pING1733, 1737 or 1753 at the unique XbaI site each yields a linear restriction fragment containing both copies of the $rBPI_{21}$ gene configured so that the selection marker gene, neo gpt or his, is positioned between the two identical $rBPI_{21}$ transcription units. For example, pING1733 viewed as linear XbaI-digested DNA, the order of elements within the vector is as follows: IgG enhancer, CMV promoter, $rBPI_{21}$ gene, light chain 3' untranslated region, neo gene, bla (Amp$^r$) gene, CMV promoter, $rBPI_{21}$ gene, light chain 3' untranslated region. Digestion of pING1733 at a unique NotI site yields a linear restriction fragment with the two $rBPI_{21}$ transcription units being adjacent to each other and the selective marker gene positioned outside of the these two recombinant $rBPI_{21}$ transcription units. Viewed as linear NotI-digested DNA, the order of elements within the vector is as follows: CMV promoter, $rBPI_{21}$ gene, light chain 3' untranslated region, IgG enhancer, CMV promoter, $rBPI_{21}$ gene, light chain 3' untranslated region, neo gene, bla (Amp$^r$) gene.

B. Construction of an Expression Vector Containing Two $rBPI_{21}$ Genes Without the Immunoglobulin Heavy Chain Enhancer The expression vector pING1744 (FIG. 5) was constructed using pING1732 and pING1740 as the source of DNAs encoding $rBPI_{21}$. pING1732 is similar to pING1729 except that it contains the neo gene. pING1740 was constructed by first cloning a multilinker site between the NotI and HindIII sites of pING1732 to generate pING1736, which contains the neo gene encoding resistance to G418. This linker destroyed the original NotI site and introduced a new NotI site adjacent to a XbaI site. The neo gene from pING1736 was then replaced with the gpt gene from pING4144 by ligating a 2090 bp XmnI-XhoI fragment containing the multilinker, the CMV promoter and the $rBPI_{21}$ gene from pING1736 with a 5600 bp XmnI-XhoI fragment from pING4144 containing the gpt gene. To construct pING1744, a ~3700 bp HpaI-NotI $rBPI_{21}$-containing fragment from pING1732 was ligated with a ~7700 bp fragment from pING1740 generated by digestion with XbaI, treatment with T-4 DNA polymerase and deoxyribonucleotides to blunt end, and then digestion with NotI (FIG. 5). pING1744 contains the gpt gene for selection of mycophenolic acid-resistant transfectants and two copies of the rBPI$_{21}$ gene each under the control of the CMV promoter and mouse kappa light chain 3' untranslated region. This vector lacks the Ig enhancer. Digestion of pING1744 at a unique XbaI site yields a linear restriction fragment containing both copies of the rBPI$_{21}$ gene configured so that the gpt selective marker gene is positioned between the two identical rBPI$_{21}$ transcription units. Viewed as linear DNA, the order of elements within the expression vector is as follows: CMV promoter, rBPI$_{21}$ gene, light chain 3' untranslated region, gpt gene, bla (Amp$^r$) gene, CMV promoter, rBPI$_{21}$ gene, light chain 3' untranslated region (FIG. 6).

EXAMPLE 2

Development and Characterization of Transfected Clones and Cell Lines

This example describes the development and characterization of clones and cell lines transfected with an exemplary vector following an embodiment of the present invention. The development and characterization of an rBPI$_{21}$-producing CHO-K1 cell line, Clone 51, is described from a transfection with a two-gene vector as described in Example 1. The CHO-K1 cell line used for the development of Clone 51 was obtained from ATCC (CCL61). The cells were grown in Ham's F12 culture medium supplemented with 10% FBS.

Prior to transfection, 40 µg of pING1737 was linearized with either NotI or XbaI. CHO-K1 cells from Research Cell Bank C1754 were transfected with either NotI- or XbaI-digested pING1737 using electroporation by the procedure of [Andreason, et al., *BioTechniques* 6: 650 (1988)]. Following a 48-hour recovery period in Ham's F12 medium supplemented with 10% FBS, the cells were trypsinized, diluted in selective medium (Ham's F12 medium supplemented with 10% fetal bovine serum (FBS), 292 mg/L glutamine, $10^5$ units/L penicillin, 100 mg/L streptomycin, and 0.01 M HEPES, 250 mg/L xanthine and 25 mg/L mycophenolic acid [MPA]) and $\sim 1 \times 10^4$ cells/well were transferred to 96-well plates. The cells were incubated at 37° C. in a CO$_2$ incubator.

Starting at about 2 weeks of incubation, culture supernatants from 96-well plate wells containing only one colony per well were screened using the BPI sandwich ELISA by the procedure of [White, et al. *J. Immunol. Methods* 167: 227-235 (1988)]. Approximately 500 clones each were screened for cells transfected with the NotI- and XbaI-digested pING1737. The 42 clones from the NotI-digested pING1737 (NotI clones) and the 26 clones from the XbaI-digested pING1737 (XbaI clones) secreting the highest levels of rBPI$_{21}$ were transferred to Ham's F12 selective medium in 24-well plates. The cells were grown to confluence, and the master and replica 24-well plate cultures were prepared. To assess productivity, the cells in the replica plate were grown to confluence in the Ham's F12 medium (48-72 hours), the medium removed and replaced with 1 ml/well of serum-free medium (HB-CHO, Irvine Scientific) plus 40 µl of sterile S-Sepharose beads and the cells incubated for an additional seven days. The S-Sepharose beads were then removed, washed once with ~1 ml of Tris buffer (20 mM Tris, pH 7.4, 0.1 M NaCl), and the rBPI$_{21}$ was eluted from the beads with 1 ml 1.5 M NaCl in 20 mM sodium acetate pH 4.0. The level of secreted rBPI$_{21}$ eluted from the S-Sepharose beads was quantitated using the sandwich ELISA. The results demonstrated that the top transfectants from each group secreted up to ~3 µg/ml. The top 10 XbaI clones (including, for example, clones 51 and 127) and top 11 NotI clones (including, for example, clones 255 and 266) were chosen for further study.

Cells from the 24-well plate cultures were transferred to 24-well plate wells containing Ex-Cell 301 medium (JRH Biosciences, Lenexa, Kans.) supplemented with 25 µg/ml MPA and 250 µg/ml xanthine (Selective Ex-Cell 301 medium) plus 10% FBS. At confluency, the cells from the 24-well plate wells were transferred to 125 ml Erlenmeyer flasks containing 20 ml selective Ex-Cell 301 medium supplemented with 2% FBS. The clones were maintained in Erlenmeyer flasks in the selective Ex-Cell 301 medium containing 2% FBS during the screening period.

An initial productivity test was performed for the top 11 NotI and 10 XbaI clones. At this stage, the cells were growing in selective Ex-Cell 301 medium and supplemented with 2% FBS. They were transferred to a 250 ml Erlenmeyer (shake) flask containing a total volume of 50 ml of Ex-Cell 301 medium plus 2% FBS (includes inoculum) and 2 ml of SP-Sepharose (Big Beads) and grown at 37° C., 100 RPM for 12 days. As controls, Clone 180 (which contains a single copy of the rBPI$_{21}$ gene) and Clone 228 (which contains two copies of the rBPI$_{21}$ gene from two successive transfections of single copies of the rBPI$_{21}$ gene) were also included in this test. Following incubation, the beads were removed, washed with low salt buffer (20 mM sodium phosphate, pH 7.0, 0.15 M NaCl) and the rBPI$_{21}$ eluted in 20 mM sodium acetate (pH 4.0) buffer containing 1.5 M NaCl. The rBPI$_{21}$ level in the eluates was measured by ion exchange HPLC. The results indicated that three clones from the transfection with NotI-digested DNA and two from the transfection with XbaI-digested DNA expressed rBPI$_{21}$ at levels similar to those of Clone 228. The results further indicated that both rBPI$_{21}$ gene copies in pING1737 were being maximally expressed at least in some of the clones.

Upon continued growth of these clones as suspension cells in selective Ex-Cell 301 medium (supplemented with 2% FBS), those arising from transfection with the NotI-digested DNA eventually lost productivity gradually over the course of a ten week period from a range of ~37-60 µg/ml to ~5-35 µg/ml rBPI$_{21}$ even though selection was maintained. This outcome was not entirely unexpected as the two rBPI$_{21}$ genes were positioned in tandem and could be subject to recombination. By comparison, Clone 51, arising from transfection with the XbaI-digested pING1737, maintained or increased its productivity for the 10 week period of the study. These results indicated that the placement of the selective marker (gpt) gene between the two rBPI$_{21}$ genes with the integrated expression vector can help maintain both rBPI$_{21}$ gene copies in the transfectants.

During the course of additional passages of Clone 51, the FBS content was gradually reduced until a serum-free condition was achieved. Clone 51 growing in Ex-Cell 301 medium without FBS was redesignated as Clone 51b.

The stability of Clones 51 and 51b in Ex-Cell 301 medium with and without 2% FBS supplementation, respectively, was examined. For this test, the cells were maintained in a 125 ml Erlenmeyer flask containing 25 ml of Ex-Cell 301 medium with (Clone 51) or without (Clone 51b) 2% FBS and with or without full selection and passage twice each week. Once a week, a shake flask test was set up and performed as described above. The stability study for Clone 51 and Clone 51b lasted 16 weeks. For the Clone 51b study, the level of expression was compared to that of Clone 228 maintained in selective Ex-Cell 301 medium. The results of the Clone 51 stability study demonstrated that after an initial drop in expression levels, the cells in selective and non-selective medium maintained similar rBPI$_{21}$ expression levels at least out to week 11. Clone 51b maintained similar productivity in the presence and absence of selection during the entire 18 week course of the experiment. Throughout the course of the Clone 51b study, productivity was equal to or greater than that of Clone 228, which also contains two rBPI$_{21}$ genes as a consequence of sequential transfection with vectors containing one rBPI$_{21}$ gene.

EXAMPLE 3

Increasing Expression Through a Second Sequential Vector Transfection: Development and Characterization of Transfected Clones and Cell Lines This example describes the further increase in expression and production of polypeptides through a second transfection of an exemplary cell line with a second multi-transcription unit vector. The development and characterization of an rBPI$_{21}$-producing CHO-K1 cell line, Clone 689, is described. Clone 689 was developed by transfecting Clone 51 cells as described in Example 2 adapted to Ex-Cell 301 medium supplemented with 2% FBS with the neo expression vector, pING1733 (FIG. 1) digested with XbaI prior to transfection. Clone 51 cells still growing in selective Ex-Cell 301 medium supplemented with 2% FBS (rather than completely adapted to serum-free growth) were used to allow prompt initiation of the second transfection.

A. Transfection of Clone 51 with pING1733

Clone 51 cells growing in selective Ex-Cell 301 medium supplemented with 2% FBS, MPA and xanthine were electroporated with 40 µg of XbaI-digested pING1733. Following a 48-hour recovery period in non-selective Ex-Cell 301 medium supplemented with 2% FBS, the cells were placed in selective medium (Ex-Cell 301 medium supplemented 0.8 mg/ml G418 and 2% FBS) and transferred to 96-well plates at ~1×10$^4$ cells/well. The MPA and xanthine were not included in the medium at this time. The cells were placed in a CO$_2$ incubator at 37° C. Two additional transfections were performed as above.

B. Screening and Section of Clone 689

A total of 1,253 clones were screened at the 96-well level from the three transfections. The 125 clones secreting the highest rBPI$_{21}$ levels were transferred to selective Ex-Cell 301 medium (250 µg/ml xanthine, 25 µg/ml mycophenolic acid and 0.8 mg/ml G418) supplemented with 2% FBS in 24-well plates. Although the transfectants had been selected in 96-well plates in Ex-Cell 301 with 2% FBS, they initially grew poorly when transferred to the 24-well plates with this medium. This problem was solved by temporarily increasing the FBS concentration to 4%. The cells were grown to confluence, and then master and replica 24-well plate cultures were prepared as described above for Clone 51. To screen for productivity in the 24-well plate cultures, the cells were transferred to 1 ml of selective Ex-Cell 301 medium containing 4% FBS plus 40 µl of sterile S-Sepharose beads and they were incubated until extinct (7-10 days). The S-Sepharose beads were removed, washed once with ~1 ml of Tris buffer (20 mM Tris, pH 7.4, 0.1 M NaCl), and the rBPI$_{21}$ was eluted from the beads into 1 ml of the same buffer containing 1.5 M NaCl. The level of secreted rBPI$_{21}$ eluted from the S-Sepharose beads was quantitated using the sandwich ELISA. The top 46 clones were transferred from the 24-well plate to a 125 ml Erlenmeyer (shake) flask containing 25 ml of Ex-Cell 301 supplemented with 4% FBS and selective agents at one-half the concentration used for selection of transfectants. Shake flask tests were performed with these clones in the Ex-Cell 301 medium with 4% FBS. From these and subsequent tests, a number of high producing clones were identified (including, for example, clones 357, 548, 689, and 815). The results of these tests indicated that Clone 689 was the top producer at ~100 µg/ml. Subsequent shake flask tests confirmed that Clone 689 was the best producer with an average of 104.3+ 1.99 µg/ml in six tests in Ex-Cell 301 medium with 4% FBS. Vials of Clone 689 were frozen (designated Research Cell Bank C3043). Clone 689 was maintained in Ex-Cell 301 medium supplemented with 4% FBS and used for the initial stability study set forth below.

C. Adaptation of Clone 689 to Ex-Cell 301 Medium Without FBS

Clone 689 was adapted to growth in Ex-Cell 301 medium without FBS by reducing the serum level by one half at each passage. The adaptation to serum-free growth was completed and vials were frozen (designated Research Cell Bank C3056).

A second, more aggressive adaptation of Clone 689 to Ex-Cell 301 medium without FBS was undertaken. Prior to this adaptation, a vial of research cell bank C3043 had been thawed and placed in culture. This Ex-Cell 301-adapted clone was designated as Clone 689b and a research cell bank, (designated C3071), was prepared. Additional research cell banks (designated C3131 and C3287) were also prepared.

Although Clone 689 produced ~100 µg/ml in the initial shake flask tests, including one test immediately following its adaptation to growth in serum-free medium, its productivity slowly dropped over the course of 6 weeks on continued passage unit it leveled out to ~75-80 µg/ml. As with Clone 51, it is not clear why a decline was observed.

D. Stability of Clone 689

Three stability studies were performed with Clone 689. As controls, the expression levels of Clones 228 and 180 (both in selective Ex-Cell 301 medium) were also monitored as a part of these studies. The first study was initiated with Clone 689 adapted to growth in Ex-Cell 301 medium supplemented with 4% FBS with and without selection (mycophenolic acid, xanthine, G418) in 125 ml Erlenmeyer flasks (25 ml cells/flask). The cultures were incubated at 37° C., 100 RPM and passaged twice each week. Once each week, the cells were also inoculated into 50 ml of non-selective Ex-Cell 301 medium supplemented with 2% FBS and 2.5 ml sterile SP-Sepharose beads (Big Beads). These cultures were then grown at 37° C. for 12 days after which the beads were collected, washed and the rBPI$_{21}$ eluted and analyzed by HPLC as above. This study was completed after a total of 14 weeks. The results demonstrated that after an initial decline through week 6 for cells grown both in the presence and absence of selection (similar to that observed with Clone 51), thereafter Clone 689 maintained similar productivity (~75-80 µg/ml) in the presence and absence of selection at least through the eleventh week, after which productivity of cells grown without selection seemed to decline very slightly through week 14 to a level of ~65-70 µg/ml. The second study was performed with Clone 689b, resulting from the second adaptation of Clone 689 to completely FBS-free medium. This study was conducted for a total of 14 weeks. For both studies, the cultures were incubated in Ex-Cell 301 medium with and without selection and evaluated for productivity as described above. The results of the Clone 689b stability study demonstrated that there was no significant decrease in expression levels in the absence of selection out to 14 weeks. A similar result was obtained with the Clone 689 cells that had been initially adapted to Ex-Cell 301.

E. Growth and Productivity

The average productivity of Clone 689 was at least ~1.5 fold higher than Clone 228 and Clone 51. Since productivity is a function of both specific productivity and cell density, tests were conducted to determine if relative expression levels for various clones were reflected in specific productivity differences. Therefore, growth and productivities of Clone 180 (1 copy), Clones 228 and 51 (2 copies), and Clone 689 (~4 copies) were compared in shake flask tests. For each clone, cells were grown to logarithmic phase and inoculated at 1-2×10$^5$ cells/ml into seven 250 ml Erlenmeyer flasks each containing 50 ml of Ex-Cell 301 medium supplemented with 2% FBS and 2% S-Sepharose (big beads). One flask was dedicated for each time point. Previous studies had indicated that a high concentration (>100 µg/ml) of rBPI$_{21}$ was inhibitory for CHO-K1 cell growth. Therefore, a flask without SP-Sepharose was also inoculated for each clone to compare the growth with and without beads. The cells were incubated at 37° C. and SP-Sepharose was harvested from flasks at Days 2, 3, 4, 5, 8 and 12.

The cell growth results for cultures with and without SP-Sepharose indicated that there were no significant growth differences with and without SP-Sepharose beads even for the highest producers. These results suggested that the secreted rBPI$_{21}$ did not significantly influence cell growth under conditions where it was not absorbed by the SP-Sepharose beads. The greatest growth was observed with Clone 180 (maximum cell density of ~3.5×10$^6$ cells/ml) followed by Clone 228 (maximum cell density of ~3×10$^6$ cells/ml). The next highest density was Clone 689 (maximum cell density of ~2.5×10$^6$ cells/ml) and Clone 51 displayed the lowest maximum cell density although this result may actually be a consequence of cell clumping.

The results of productivity tests for cultures supplemented with SP-Sepharose demonstrated that as previously observed, the maximum productivities of Clones 228 and 51 were ~2 times that of Clone 180 (~50 vs. 25 µg/ml) while the productivity of Clone 689 was ~1.5 times that of Clone 228, at least when measured at Day 5 (the day Clone 228 achieved its maximum productivity). However, Clone 689 slowly accumulated up to ~100 µg/ml by Day 12 in this test.

The above results indicated that the relative expression levels in the shake flasks for Clones 180, 228, 51 and 689 were directly proportional to gene dosage, assuming that as with Clones 180 and 228, Clones 51 and 689 received only one copy of the plasmids from each transfection. To confirm that this increased yield resulted from a higher specific productivity (pg/cell/day), we estimated this value from Days 2 to 4 for Clone 180 and Days 3 to 5 for the other cell lines at which time the cell viabilities were high (>90%) and the cultures were at or approaching their maximum cell densities. This calculation was made by dividing the average daily production during these 2 days by the average cell density during this period. The results demonstrated that the specific productivity for Clone 689 (~9 pg/cell/day) was about twice that of Clone 228 (~4 pg/cell/day) which, in turn, was about twice that of Clone 180 (~2 pg/cell/day). Clone 51, which was from the initial transfection with the 2-gene vector and served as the parent for Clone 689, had almost the same specific productivity as Clone 689, although this value is probably inflated due to the abnormally low cell counts as a result of cell clumping.

F. Effect of Culture Conditions on rBPI$_{21}$ Expression by Clone 689

Typically, shake flask tests were performed in Erlenmeyer flasks that were sealed after inoculation and only re-opened after the 12-day incubation period. Under these conditions, Clone 689, on average has produced ~75-80 µg/ml compared to ~45-50 µg/ml for Clone 228.

As part of the evaluation of the growth characteristics of Clone 689 in the presence of S-Sepharose, an experiment was performed in which cells were inoculated with ~1×10$^5$ cells/ml into three flasks containing Ex-Cell 301 with 2% FBS and S-Sepharose. One of the flasks remained sealed during the course of the experiment, as is usually the case, while the other two were used to perform cell counts at days 2-7, 9, 11. After day 11, the S-Sepharose was removed, washed, eluted and the levels of rBPI$_{21}$ determined by HPLC. Surprisingly, while cells in the sealed flask expressed rBPI$_{21}$ at 75 µg/ml as expected, cells in the flasks from which samples were taken for cell counts expressed an average of ~130 µg/ml (for two tests), representing a ~70% increase. As previously observed, the Clone 689 cells achieved a maximum cell density of ~2.5×10$^6$ cells/ml at days 4-5 indicating that the increased rBPI$_{21}$ expression in the "opened" flasks was not due to significantly higher cell densities.

To further examine this phenomenon with Clone 689 and determine if it occurred with other clones, a similar experiment was performed with Clones 180, 228 and 689. The results demonstrated that a similar phenomenon occurred to some extent with all of the tested clones. As before, Clone 689 produced 79 µg/ml in the closed flask and up to 128 µg/ml in the open flask, representing a 62% increase. Clone 228 produced up to 47 and 62 µg/ml in the "closed" and "open" flasks, respectively, representing a 32% increase. Clone 180 expression levels increased ~20% in the open vs. closed flask.

In the initial open flask experiment with Clone 689, we also observed that the media in the flasks that had been opened appeared to be less acidic. To determine if this were the case with the second experiment, the pH values of the culture supernatants from each flask were measured. The results demonstrated that the pH of the media from the flasks that had been opened was 0.2 to 0.5 units higher than that of the flasks which had remained sealed. The greatest pH difference between the closed and open flasks occurred with Clone 689. It is possible that the gas exchange that occurs when the flasks are opened allows the cells to more efficiently utilize glucose and perhaps produce less lactic acid, which may adversely affect both growth and production.

The results of these experiments indicated that future shake flask tests could incorporate the gas exchange step because the highest productivities were observed under these conditions.

G. rBPI$_{21}$ Expression Levels Without S-Sepharose

Previous experiments showed that the presence of S-Sepharose facilitates efficient detection and recovery of rBPI$_{21}$ from the culture supernatants of transfected cells [Horwitz, A. H. et al., *Protein Expr Purif.* 18: 77-85 (2000)]. The loss of rBPI$_{21}$ from the culture supernatants without beads may be due to its interaction with heparan proteoglycans on the surface of the CHO cells.

One potential consequence of achieving higher expression levels is that the surface receptors for rBPI$_{21}$ eventually might be saturated, resulting in elevated levels of rBPI$_{21}$ in the supernatant in the absence of S-Sepharose. To determine if this was the case, the levels of rBPI$_{21}$ expression was compared with and without SP-Sepharose for Clones 180, 228, and 689. The rBPI$_{21}$ levels in the supernatants from cultures without beads were measured by ELISA, while the rBPI$_{21}$ levels eluted from the beads were measured by both ELISA and HPLC. The results demonstrated that the level of rBPI$_{21}$ present both during the production phase and at the end of the incubation period increased with higher expression occurring with Clone 689. However, even for Clone 689, SP-Sepharose beads were still required for optimal detection and recovery of rBPI$_{21}$.

H. RNA Levels

Figure 7:
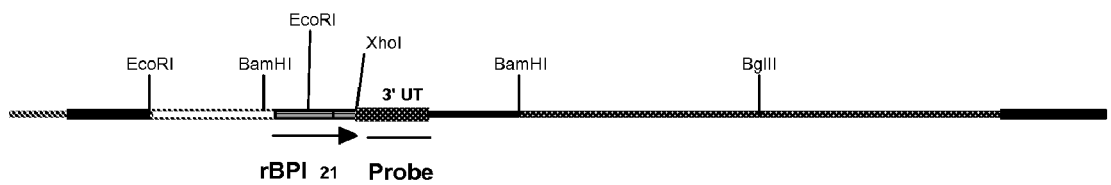
FIG. 7 shows a linear map of vector pING4155 showing the location of binding of an $rBPI_{21}$ probe.
Figure 8:
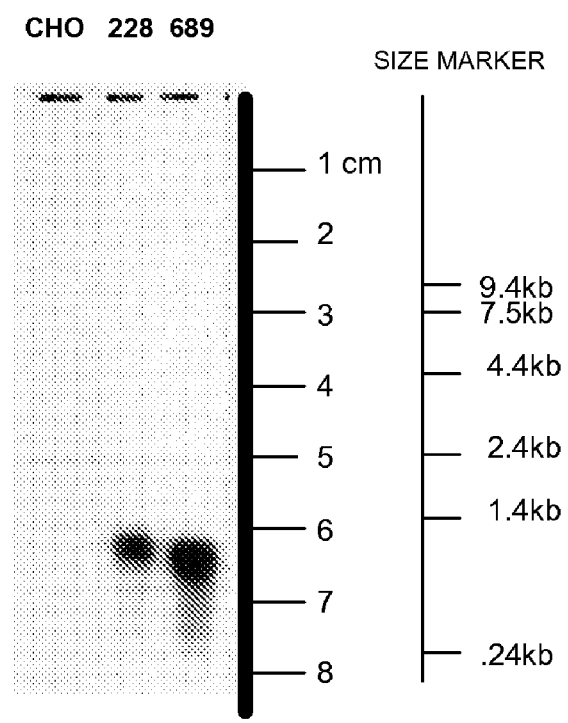
FIG. 8 shows a Northern blot of $rBPI_{21}$ RNA isolated from untransfected CHO-K1 cells, Clone 228 and Clone 689.

Relative levels of rBPI$_{21}$ mRNA were compared for Clones 228 and 689. Clone 228, 689 and untransfected CHO-K1 cells were grown to logarithmic phase in Ex-Cell 301 medium and total cytoplasmic RNA was isolated as described by [Gough *Anal. Biochem.* 173: 93-95 (1988)]. The RNA samples were first checked for the level of ribosomal RNAs and then run on a formamide, 1% agarose gel, blotted to nitrocellulose and hybridized with a $^{32}$P-labeled DNA probe for the light chain 3' untranslated region (FIG. 7). The membrane was washed to remove non-specifically-boundcounts and exposed to X-ray film. The results as shown in FIG. 8 indicate that Clone 689 expressed rBPI$_{21}$ mRNA at an estimated ~1.6× higher level than Clone 228. However, a method such as RNAase protection or quantitative PCR will be needed to provide more accurate quantitation of the mRNA levels.

I. Summary

Thus, in accordance with the invention, vectors were designed that contain (i.e., comprise) multiple copies of a cDNA encoding rBPI$_{21}$. Two of these two-transcription unit vectors were used in sequential transfections with CHO-K1 cells to produce a cell line, Clone 689, which produced approximately twice the rBPI$_{21}$ level as Clone 228 which contained two one-transcription unit vectors as a result of sequential transfection. This increased productivity appeared to result from a two-fold increase in specific productivity (compared to Clone 228), and not merely from an increase in cell density. Indeed, Clone 689 cells did not grow to as high a cell density as Clone 228 cells while producing higher rBPI$_{21}$ levels. In addition, Clone 689 maintained its productivity in the absence of selection for up to 14 weeks, an amount of time sufficient to account for scale-up into large fermenters. This example demonstrates that increased expression can be achieved through increased transcription unit dosage in a non-amplified expression system through the methods of the present invention in at least two different employed strategies with surprising effectiveness. First, by positioning the selective marker gene between multiple copies of transcription units encoding the rBPI$_{21}$ gene, the problem of homologous recombination can be avoided and high producing, stable cell lines can be developed which express multiple copies of the rBPI$_{21}$ gene. Second, by sequentially transfecting cells in the methods of the present invention, the number of multiple integrated copies of transcription units can be increased stepwise to increase expression levels. The present invention contemplates the use of any transcription unit encoding any polypeptide of interest and is in no way limited to BPI protein products, as exemplified by rBPI$_{21}$, as would be understood by one skilled in the art.

EXAMPLE 4

Further Increasing Expression by a Third Sequential Vector Transfection: Development and Characterization of Transfected Clones and Cell Lines This example describes the further increase in expression and production by a third sequential transfection of an exemplary cell line with a third multi-transcription unit vector, resulting in clones and cell lines that express increased levels of polypeptide production.

A. Selection of Sequential Transfectants and Development Thereof

Further sequential transfections with multiple copies of transcription units separated by selective marker genes were carried out to test for still further increased expression of the transcription units. A third sequential transfection of Clone 689 with a vector containing two rBPI$_{21}$ genes and a third selective marker might yield expression levels at least 1.5 times those of Clone 689 based on increased gene dosage, assuming that gene dosage could be achieved. Clone 689 was thus sequentially transfected a third time. This cell line was transfected with the vector, pING1753, containing two copies of the rBPI$_{21}$ gene and the his gene as a selective marker for selection of histidinol resistance. Subsequent to transfection and selection, a total of ~500 triple-transfectant clones were screened at the 96 well level and 85 at the 24 well level with S-Sepharose. The top producers secreted up to 1.5 times higher levels (~50 µg/ml) of rBPI$_{21}$ as compared to Clone 689 when tested at the 24-well level, but only secreted ~20-30% higher than Clone 689 in the initial shake flask tests which were performed in closed flasks. A top producing clone (341), was chosen for further study.

B. Production Under Open Flask Conditions

Subsequent to the surprising results as described in Example 3 above of increased expression in shake flasks when gas exchange was allowed, the shake flask tests were again performed, but this time with open flasks. Several triple transfectants were evaluated in open shake flask tests in Ex-Cell 301 medium supplemented with 2% FBS. The results indicated that the expression levels were considerably higher than those previously observed with closed flasks for Clone 341 (the triple transfectant obtained by transfecting Clone 689). In fact, in four separate tests, Clone 341 consistently secreted higher levels (ranging from 107.6 µg/ml to 142.0 µg/ml) than Clone 689 (which ranged from 67.8 µg/ml to 93.4 µg/ml). Thus, expression levels of the triple transfectant, Clone 341, did approximate a 1.5 fold increase in expression at both the 24-well level and in open shake flasks.

C. Adaptation of Clone 341 to 1% FBS

Clone 341 was subsequently tested after adaptation to growth in Ex-Cell 301 medium supplemented with 1% FBS. The triple sequential transfectant had initially been selected in 4% FBS and then adapted to 2% FBS in Ex-Cell 301 medium. Next, Clone 341 was adapted to 1% FBS and re-tested in shake flask tests. The results for eight shake flask tests indicated that this clone maintained its high productivity for at least 33 passages over the 17 weeks in which it was tested with concentrations of rBPI$_{21}$ ranging from 122.6 µg/ml to 144.8 µg/ml.

D. Subcloning of Clone 341 and the Development of Clone 83

Attempts to adapt Clone 341 to completely serum-free conditions were not initially successful. In addition, although the above expression levels were higher than those for the initial closed flask experiments and were slightly higher than those achieved with some subclones of Clone 689, to further improve expression levels and potentially select for a faster growing, higher producing clone, Clone 341 was subcloned. The cells were plated in Ex-Cell 301 medium containing 1% FBS at ~30, 15, 7.5 and 3 cells/well. A total of 69 clones from wells with single colonies were transferred to 24 well plates and then to shake flasks where they were evaluated for productivity. Of these, the top 6 clones were ultimately kept for re-evaluation over 90 days where screening for rBPI$_{21}$ production was periodically conducted. The results of the screening indicated that Clone 83 was identified as the top subclone, secreting in the range of 150-165 µg/ml (compared to ~135 µg/ml for parent Clone 341) in shake flask tests.

E. Productivity and Stability of Clone 341 Subclone, Clone 83

The top 6 subclones were maintained and evaluated for productivity for an additional 8 weeks under full selection. The results demonstrated that Clone 83 had remained the best producer, secreting 180 and 195 µg/ml on two occasions and always outperforming the Clone 341 parent.

The stability of Clone 83 was examined by growing the subclone in Ex-Cell 301 medium in the presence and absence of selection. The cells were passaged twice each week and shake flask tests were set up weekly. The results demonstrated that Clone 83 maintained productivity at a stable range of ~160 µg/ml in the presence of selection. However, while Clone 83 maintained productivity in the absence of selection through at least week 5, by week 7 $rBPI_{21}$ levels had decreased in the absence of selection to ~120 µg/ml. These results suggest that this subclone is stable for at least 5 weeks (10 passages, ~30-35 generations) in the absence of selection. Other Clone 689 subclones were shown to be stable for longer periods of time in the absence of selection. Lower productivity without selection may be due to instability of the integrated DNA encoding histidinol-resistance. If this is the case, high productivity may be maintained by keeping histidinol in the medium during the early scale-up stages.

EXAMPLE 5

Sequential Transfection with a Multiple Transcription Unit Vector Lacking an Enhancer: Development and Characterization of Clones and Cell Lines This example demonstrates that sequential transfections with a multiple transcription unit vector, that effectively increases the expressed amounts of a given transcription unit, even when an enhancer has been removed from the vector. This is shown through the development and characterization of an exemplary clone, Clone 338, transfected with an exemplary vector, pING1744, which contained two $rBPI_{21}$ genes similar to Clone 51, but without the Ig enhancer. The resulting Clone, Clone 338, was then retransfected with a second two-gene ($rBPI_{21}$) vector, pING1915, also without the Ig enhancer, and then characterized. Clone 58 resulted from the sequential transfection and when screened, demonstrated expression of $rBPI_{21}$ at concentrations markedly higher than that of Clone 338, the single transfectant.

A. Transfection with pING1744: Clone 338

Figure 5:
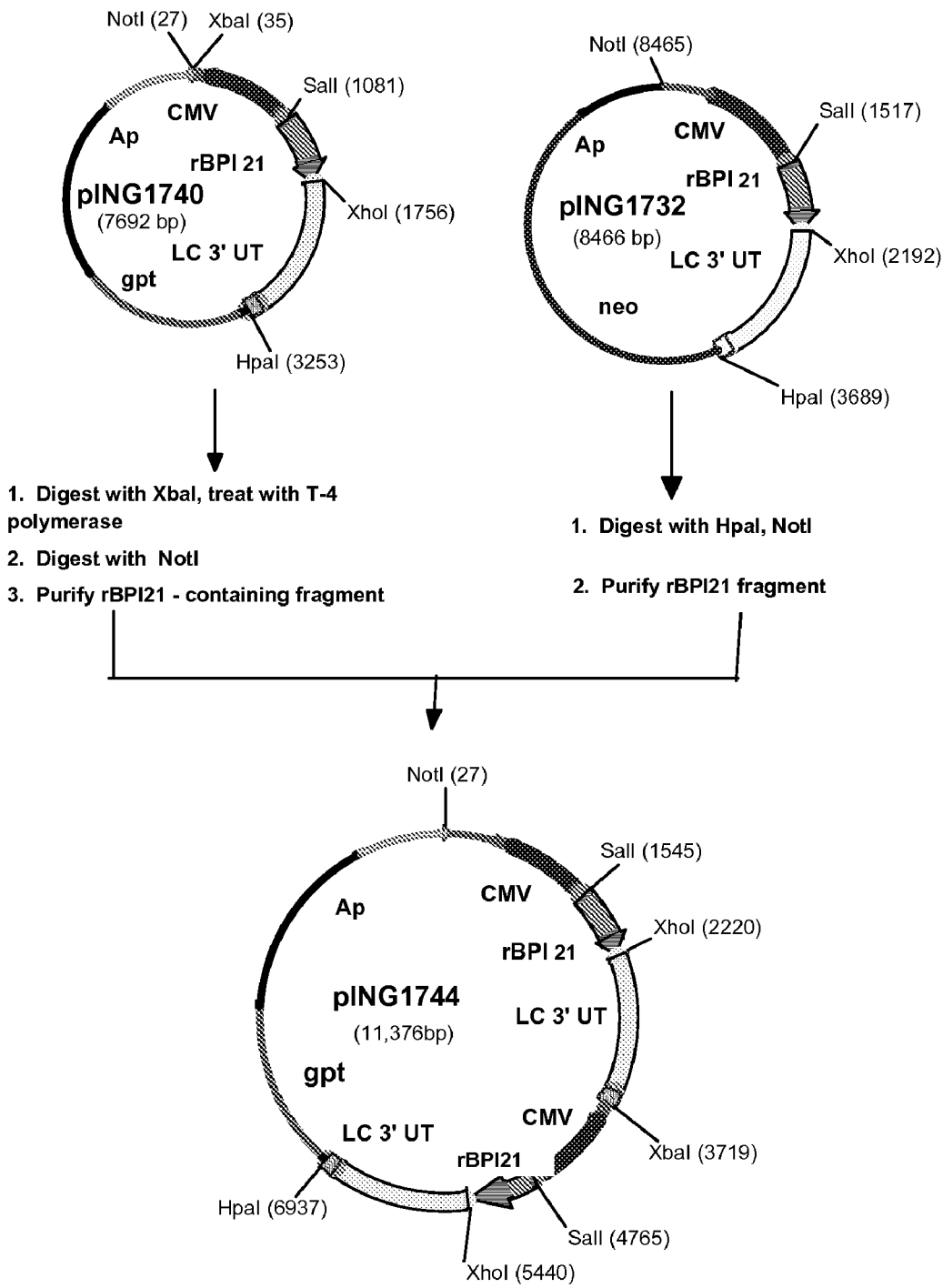
FIG. 5 depicts a construction map for vector pING1744.
Figure 6:
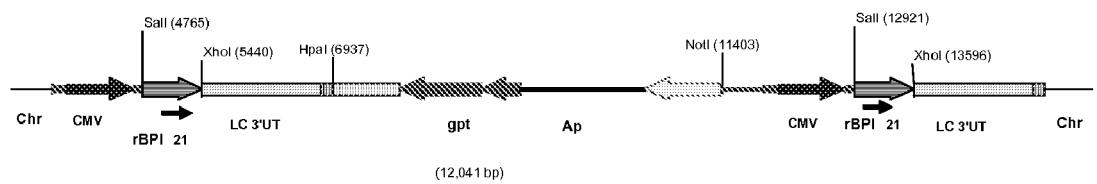
FIG. 6 shows the structure of vector pING1744 linearized with XbaI.

Clone 338 was developed by transfection of attached CHO-K1 cells with the vector pING1744, which contains two $rBPI_{21}$ genes each under the control of the CMV promoter and light chain 3' untranslated region with the gpt gene for selection of MPA-resistant transfectants, but without an Ig enhancer. pING1744 had been first digested at a unique XbaI site prior to transfection so as to place the selective marker gene between the two copies of $rBPI_{21}$ gene (FIG. 5).

Ex-Cell 301-adapted Clone 338 cells initially were grown in the presence of 2% FBS and produced up to ~100 µg/ml in shake flask tests. The cells were subsequently adapted to Ex-Cell 301 medium supplemented with 1% FBS, retaining productivity of 80-100 µg/ml.

B. Stability of Clone 338 with Selection

Selection for mycophenolic acid is relatively poor in Ex-Cell 301 medium and maintenance of the high expression levels suggests that this clone is relatively stable. To further examine stability, cultures were grown in Ex-Cell 301 medium supplemented with 1% FBS and with or without selection. Cells were passaged twice each week and shake flask tests were set up weekly. Results showed that $rBPI_{21}$ was expressed at ~100 µg/ml in the presence and absence of selection through 7 weeks, although there was a slight decline in expression over this period of ~20 µg/ml in the absence of selection. These results suggest that although the cells without selection expressed $rBPI_{21}$ at slightly lower levels, this clone was stable for at least 7 weeks in the absence of selection. The study was discontinued at week 7.

C. Transfection with pING1915: Clone 58

To further optimize expression, Clone 338 adapted to Ex-Cell 301 medium with 1% FBS was re-transfected with pING1915 which is similar to pING1744 except that it contains the neo gene for selection of G418-resistant transfectants, but also lacks an Ig enhancer. A total of ~600 transfectants were screened at the 96 well level and 250 were screened in 24 well plates with S-Sepharose. Results of this screen revealed a number of clones that secreted at 30-60 µg/ml. By comparison, the highest expression levels in 24 well plates for a single two-gene vector with an Ig enhancer generally was ~15 µg/ml, the levels from a sequential transfection with two such two-gene vectors) was ~30-35 µg/ml, and the levels from a third transfection with such two-gene vectors was up to ~45 µg/ml under similar conditions.

The top 76 clones from the ~600 transfectants screened, secreting from ~20 to 64 µg/ml, were transferred to shake flasks and grown in Ex-Cell 301 medium supplemented initially with 4% FBS (to ensure a smooth transition to shake flask growth). Results of an initial shake flask test for two series of transfectants indicated that there were several clones that secreted above the levels of subclones of Clone 689 and Clone 341 (subclones 689.47 and 341.83 from previous sequential transfectants) at the time of the assay.

The top clones were maintained and adapted to Ex-Cell with 2% FBS and re-screened several more times. The results indicated that Clone 58 consistently secreted at levels equal to or better than subclones of Clones 689 and 341 (subclones 689.47 and 341.83), and at markedly higher levels than Clone 338, from which the respective subclones were derived. For example, Clone 338 was screened at secretion levels over a 7 week period from 80.8 µg/ml to 101.4 µg/ml, while a subclone of Clone 689 (689.47) secreted at 112.0 µg/ml to 134.8 µg/ml and a subclone of Clone 341 (341.83) was at 95.2 µg/ml to 121.4 µg/ml over the same period. Comparatively, Clone 58 secreted at 119 µg/ml to 134.4 µg/ml during this same period of testing. Although all of the above tested sequential transfectants of Clone 338 secreted at higher levels than Clone 338, they did not secrete at twice the level although the number of transcription unit copies were effectively doubled through the sequential transfections. This could be due to either growth related differences, limitations in the medium and/or to an inability of the plasmid, pING1915, to generate transfectants that express at the same levels as pING1744, which had been used to generate Clone 338, in these experiments. Nevertheless, this example clearly demonstrates that sequential transfections with vectors containing multiple copies of a transcription unit in accordance with the present invention effectively increases expression levels to substantially higher amounts, even when an enhancer has been removed from the vector.

EXAMPLE 6

Construction of Additional Expression Vectors

This example describes the construction of expression vectors that contain multiple copies of additional exemplary transcription units. Exemplary vector constructs are also described containing multiple copies of exemplary gene sequences encoding polypeptides of interest, for example, immunoglobulin gene sequences including light and/or heavy chain sequences.

A. Construction of Expression Vectors Comprising Mouse-Human Chimeric ING-1 Light Chain Gene Vectors comprising sequences encoding mouse-human chimeric ING-1 light (SEQ ID NOS: 5 and 6) and heavy chains (SEQ ID NOS: 7 and 8) which incorporate the necessary elements for optimal expression in CHO-K1 cells have been constructed. These ING-1 vectors serve both as the starting point for construction of human engineered antibody genes and have been used to develop CHO-K1 cell lines expressing mouse-human chimeric ING-1. The expression vectors described below have a CMV promoter and a mouse kappa light chain 3' un-translated region and transcription units encoding selective gene markers, and light and/or heavy chain sequences.

Figure 9:
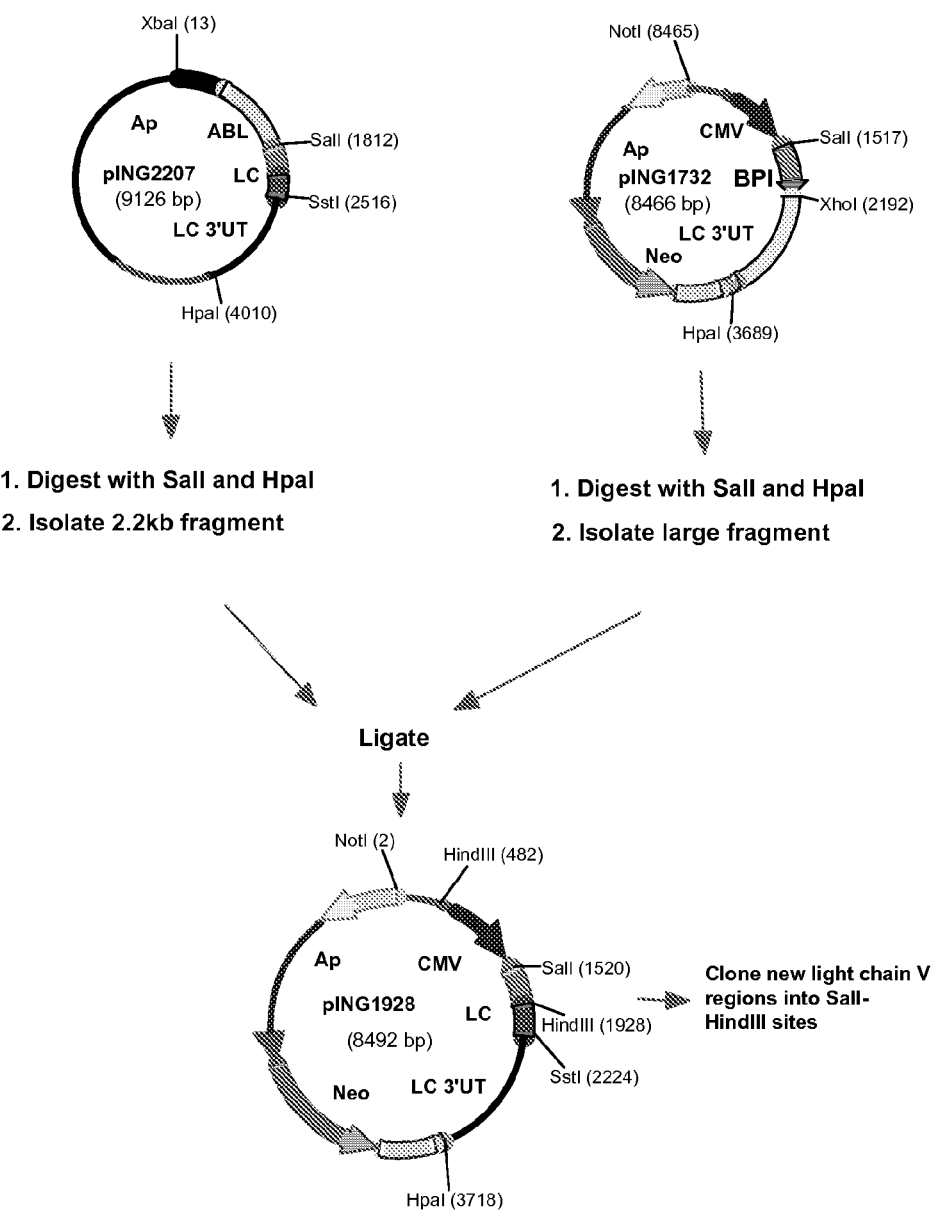
FIG. 9 depicts a construction map for vector pING1928.

A mouse-human chimeric ING-1 light chain vector, pING1928, was constructed by digesting pING2207 (see, e.g., U.S. Pat. No. 5,576,184), comprising a mouse-human chimeric ING-1 light chain gene (SEQ ID NO: 5) fused to a mouse light chain 3' untranslated region, with SalI plus HpaI and isolating the ~2200 bp fragment comprising a light chain (FIG. 9). This fragment was ligated to a ~6300 bp SalI-HpaI vector fragment from pING1732 (described in Example 1 above), placing the mouse-human chimeric ING-1 light chain gene (SEQ ID NO: 5) under control of the CMV promoter and mouse light chain 3' untranslated region (FIG. 9). The sequence of chimeric mouse-human ING-1 light chain is shown as SEQ ID NO: 5. Alternative light chain variable region gene may be cloned into the SalI HindIII sites of pING1928, including human engineered antibody variable region genes sequences as described below.

Figure 10:
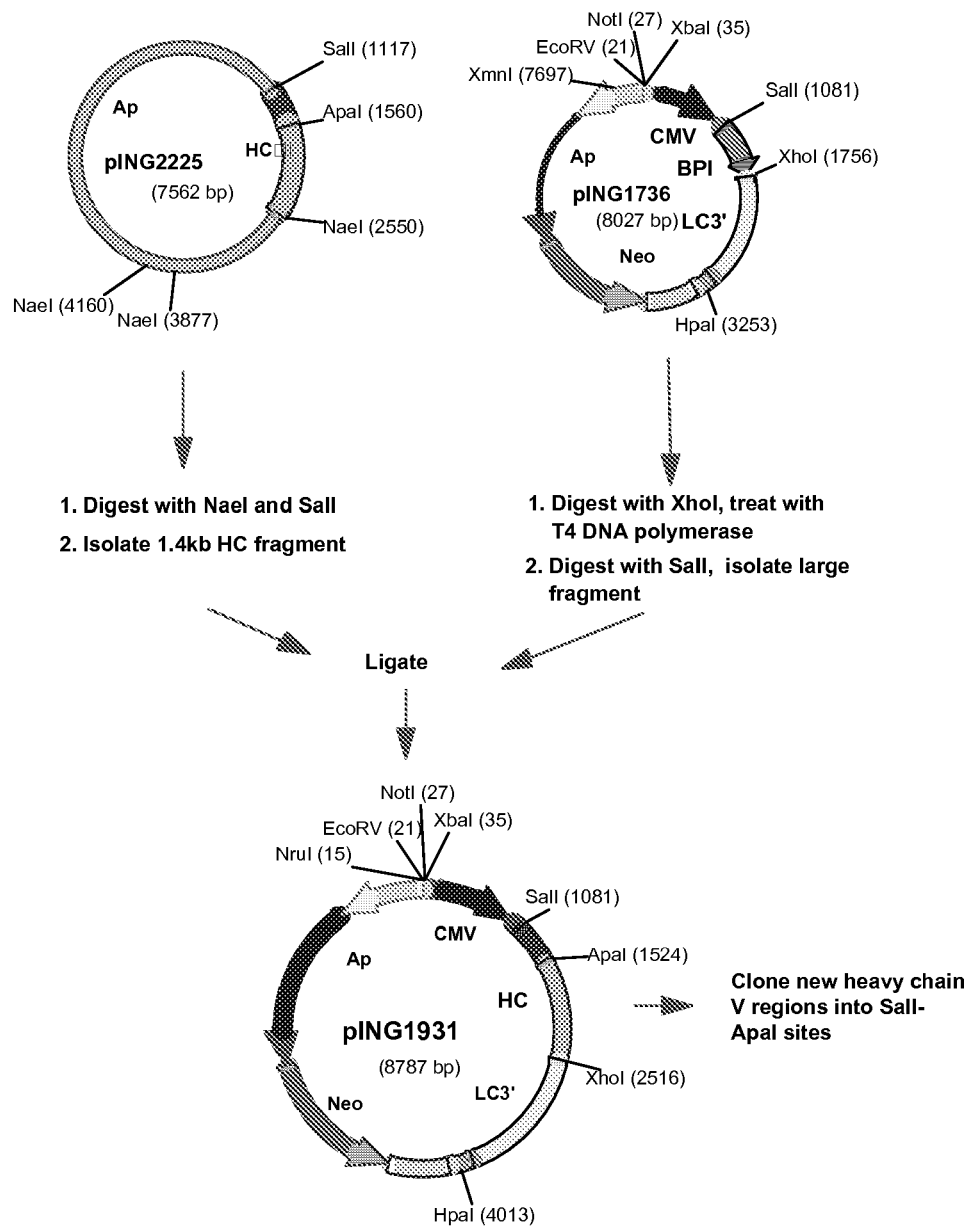
FIG. 10 depicts a construction map for vector pING1931.

B. Construction of Expression Vectors Comprising Mouse-Human Chimeric ING-1 Heavy Chain Gene A mouse-human chimeric ING-1 heavy chain vector (SEQ ID NOS: 7 and 8), pING1931, was constructed by digesting pING2225 (see, e.g., U.S. Pat. No. 5,576,184), comprising a mouse-human chimeric ING-1 heavy chain gene (SEQ ID NO: 7) with SalI plus NaeI and isolating the ~1433 bp fragment comprising the heavy chain gene sequence (FIG. 10). This fragment was ligated to the ~7352 bp vector fragment from pING1736 (described in Example 1 above, similar to pING1740 except that it contains the neo instead of the gpt gene) which had been digested with XhoI, treated with T4 DNA polymerase in the presence of deoxyribonucleotides to blunt end, and then with SalI placing the mouse-human chimeric ING-1 heavy chain gene (SEQ ID NO: 7) under control of the human CMV promoter and the mouse light chain 3' untranslated region (FIG. 10). The sequence of the chimeric mouse-human ING-1 heavy chain is shown as SEQ ID NO: 7. Alternative heavy chain variable region genes may be cloned into the Sal-ApaI sites of pING1931, including human engineered antibody variable region genes as described below.

C. Construction of Mouse-Human Chimeric Light Plus Heavy Chain Expression Vectors Mouse-Human Chimeric (Two Gene Vectors)

Figure 11:
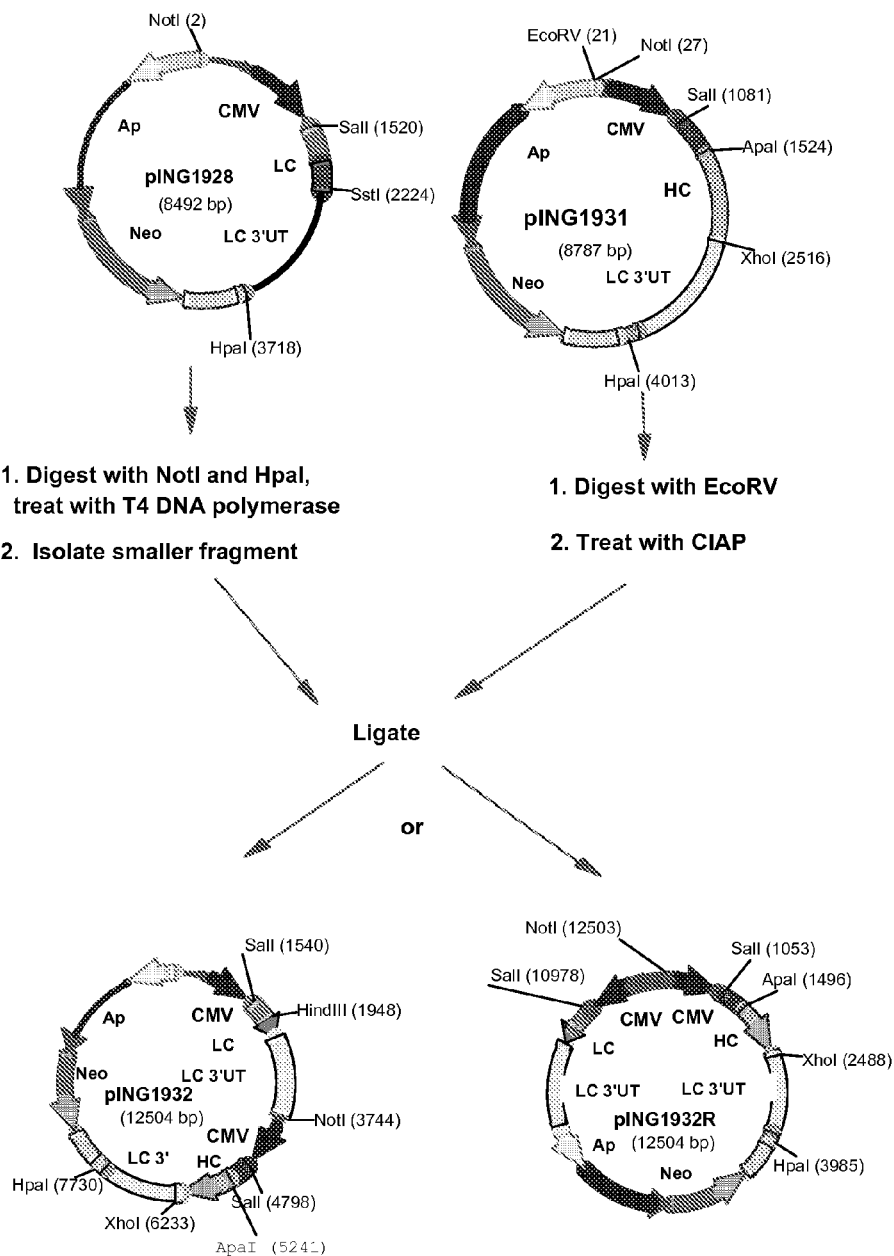
FIG. 11 depicts construction maps for vector pING1932 and pING1932R.

Vectors comprising mouse-human chimeric ING-1 light chain plus heavy chain gene sequences (SEQ ID NOS: 5 and 7) were constructed using pING1928 and pING1931 (FIG. 11). pING1931 was digested with EcoRV and treated with calf intestinal alkaline phosphatase (CIAP). EcoRV cuts at a unique site adjacent (and counterclockwise on a circular map) to a unique NotI site. pING1928 was digested with NotI and HpaI, and then treated with T4 DNA polymerase in the presence of dexoyribonucleotides to blunt end. The ~3720 bp fragment comprising a mouse-human chimeric light chain gene (SEQ ID NO: 5) was purified and ligated with EcoRV-digested pING1931 comprising a mouse-human chimeric heavy chain gene (SEQ ID NO: 7). Both possible orientations, represented by pING1932 and pING1932R, were obtained as shown in FIG. 11.

D. Construction of Expression Vectors Comprising Human Engineered ING-1 Light Chain Gene Human engineering of antibody variable domains has been described by Studnicka [see, e.g., Studnicka et al, U.S. Pat. No. 5,766,886; Studnicka et al., *Protein Engineering* 7: 805-814 (1994)] as a method for reducing immunogenicity while maintaining binding activity of antibody molecules. According to the method, each variable region amino acid has been assigned a risk of substitution. Amino acid substitutions are distinguished by one of three risk categories: (1) low risk changes are those that have the greatest potential for reducing immunogenicity with the least chance of disrupting antigen binding or protein folding (2) moderate risk changes are those that would further reduce immunogenicity, but have a greater chance of affecting antigen binding or protein folding; (3) high risk residues are those that are important for binding (e.g., CDR loops) or for maintaining antibody structure and carry the highest risk that antigen binding or protein folding will be affected.

Figure 12:
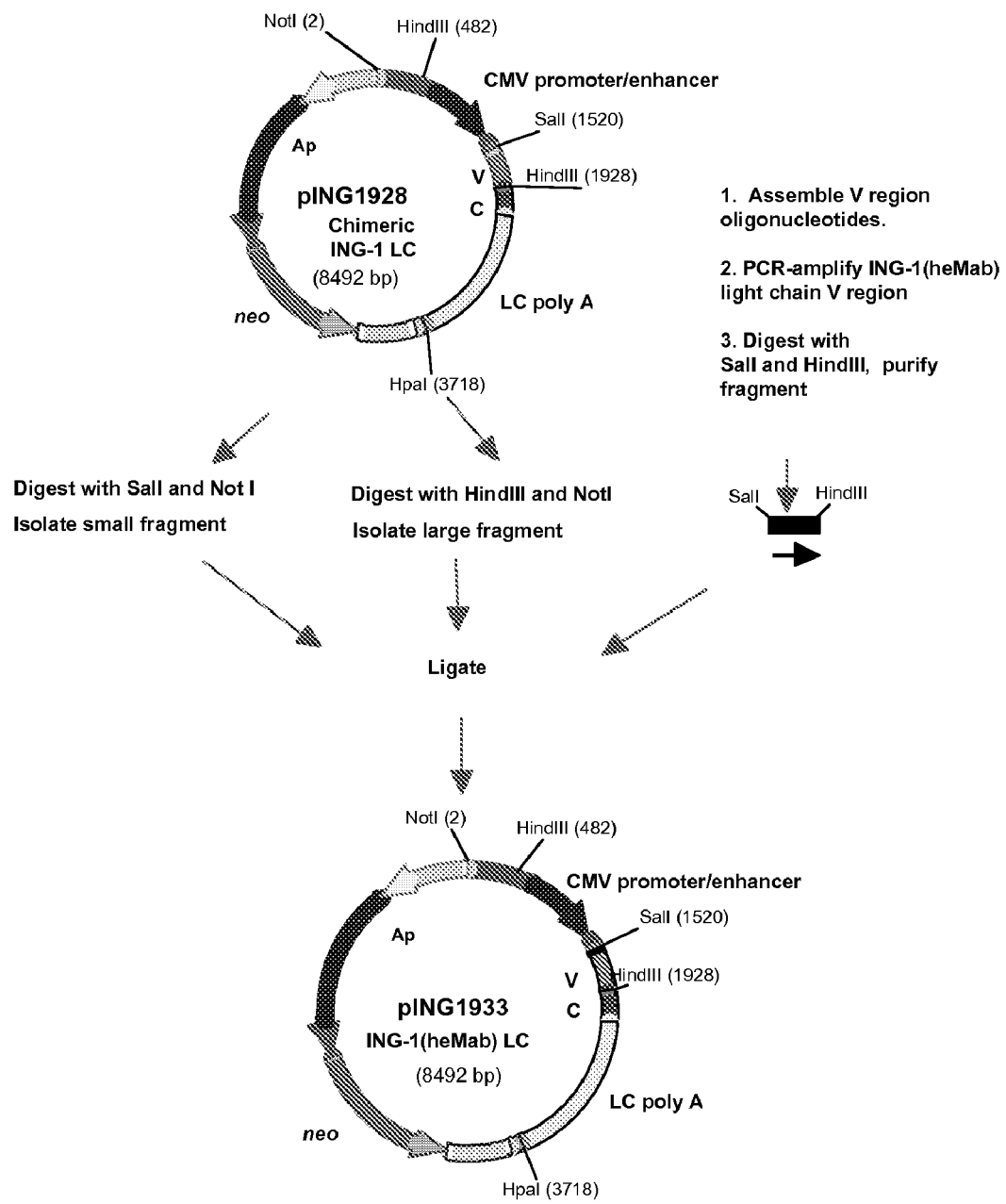
FIG. 12 depicts a construction map for vector pING1933.

A human engineered ING-1 light chain vector, pING1933 (FIG. 12), was constructed by digesting pING1928 (FIG. 9), containing a mouse-human chimeric ING-1 light chain gene, with SalI plus NotI and isolating the ~1518 bp fragment with a CMV promoter and separately digesting pING1928 with HindIII plus NotI and isolating the ~6566 bp fragment comprising a human light chain constant region, a mouse light chain 3' untranslated region and a neo gene for selection of G418-resistant transfectants. These fragments were ligated to a ~400 bp PCR-generated SalI-HindIII fragment comprising an ING-1 light chain variable region human engineered with a total of 6 low risk amino acid substitutions (FIG. 13; SEQ ID NO: 9), placing the low risk human engineered ING-1 light chain gene under control of a CMV promoter and mouse light chain 3' untranslated region. Low risk changes as well as low plus moderate risk changes in an ING-1 light chain variable region are shown in FIG. 13. For the light chain, a total of 6 low risk changes were made for a low risk variable region (SEQ ID NO: 10) as described, and separately a total of 10 low plus moderate risk changes were made for a low plus moderate risk variable region in the light chain (SEQ ID NO: 11 and 12). The vector pING1933 comprises a PCR-generated human engineered ING-1 light chain variable region with 6 low risk changes incorporated. A DNA fragment encoding a low risk modified light chain variable region was constructed using 6 overlapping oligonucleotides KL1 (SEQ ID NO: 13), KL2 (SEQ ID NO: 14), KL3 (SEQ ID NO: 15), KL4 (SEQ ID NO: 16), KL5 (SEQ ID NO: 17), and KL6 (SEQ ID NO: 18). These segments were annealed to each other, extended with DNA polymerase and then the assembled variable region amplified by PCR using 5' forward primer KF (SEQ ID NO: 19) and 3' reverse primer KR (SEQ ID NO: 20), digested with SalI and HindIII to yield a restriction fragment that was cloned directly into expression vector pING1928 to generate pING1933 as shown in FIG. 12. Another expression vector, pING1939, was constructed using a similar method and is like pING1933 except that pING1939 comprises an ING-1 light chain variable region human engineered with the low plus moderate risk changes as shown in FIG. 13 (SEQ ID NO: 11 and 12). The low plus moderate risk modified light chain variable region was constructed using 6 overlapping oligonucleotides, including 5 used in the construction of the low risk modified variable region described above: KL1 (SEQ ID NO: 13), KM2 (SEQ ID NO: 21), KL3 (SEQ ID NO: 15), KL4 (SEQ ID NO: 16), KL5 (SEQ ID NO: 17) and KL6 (SEQ ID NO: 18).

Figure 14:
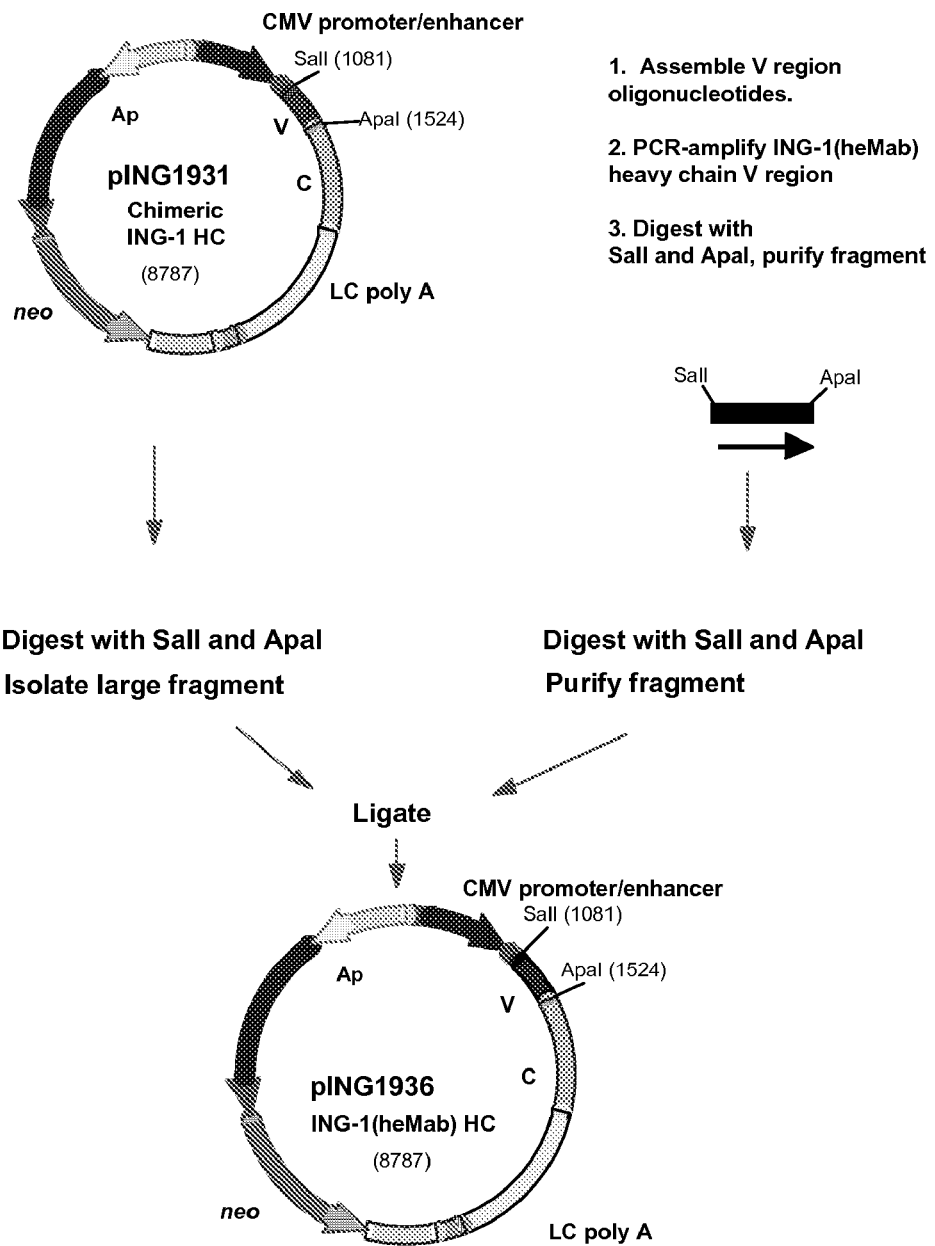
FIG. 14 depicts a construction map for vector pING1936.
Figure 16:
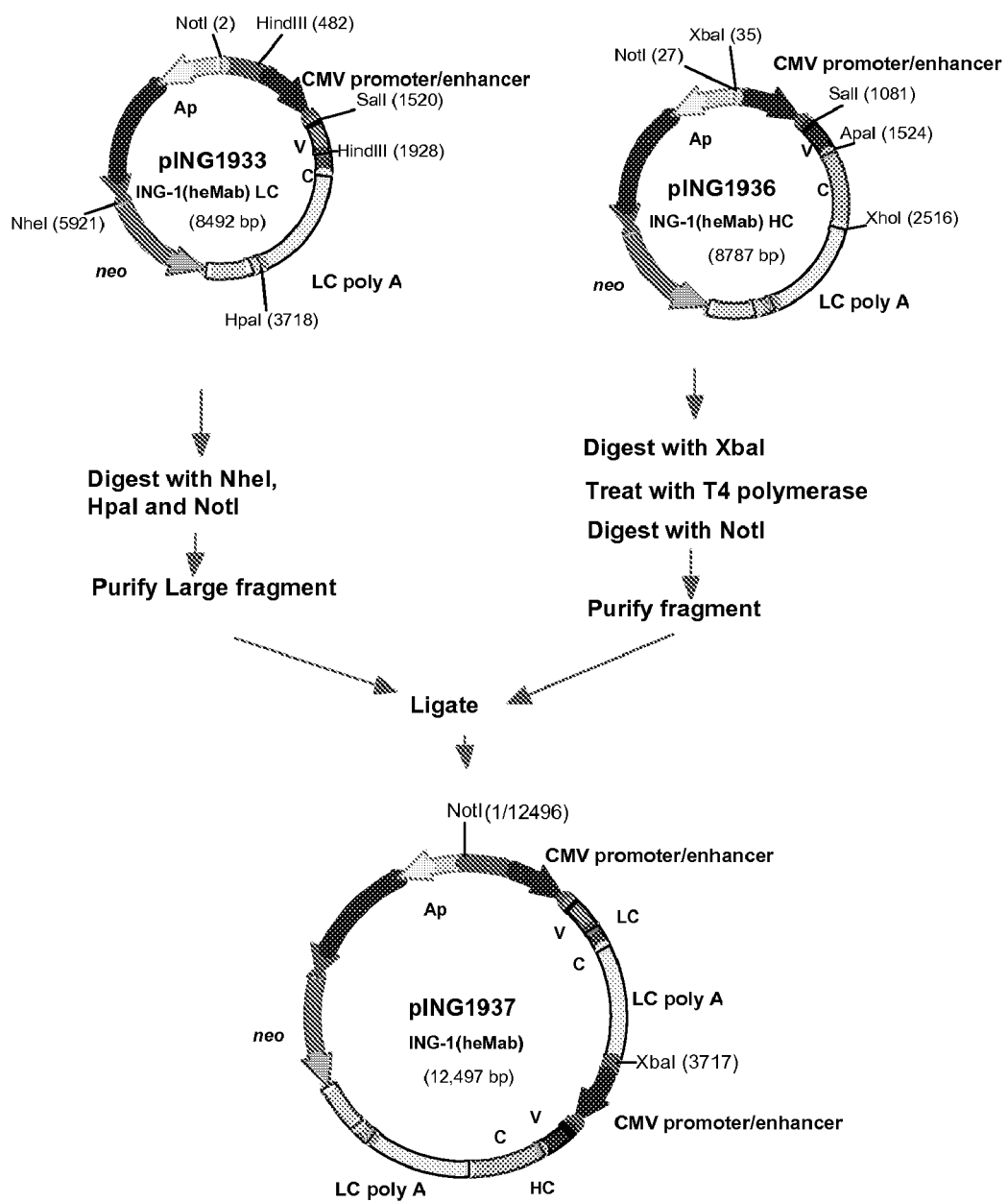
FIG. 16 depicts a construction map for vector pING1937.

E. Construction of Expression Vectors Comprising Human Engineered ING-1 Heavy Chain Gene A human engineered ING-1 heavy chain vector, pING1936 (FIG. 14), was constructed by digesting pING1931, containing mouse-human chimeric ING-1 heavy chain with SalI plus ApaI and isolating the ~8344 bp fragment comprising a CMV promoter, heavy chain constant region, light chain 3' untranslated region and a neo gene for selection of G418-resistant transfectants. This fragment was ligated to the ~450 bp PCR-generated SalI-ApaI fragment comprising an ING-1 heavy chain variable region human engineered with a total of 13 low risk amino acid substitutions (FIG. 15; SEQ ID NO: 22), placing the low risk human engineered ING-1 heavy chain gene under control of a CMV promoter and mouse light chain 3' untranslated region. Low risk changes as well as low plus moderate risk changes in an ING-1 heavy chain variable region are shown in FIG. 15. For the heavy chain, a total of 13 low risk changes were made for a low risk heavy chain variable region (SEQ ID NO: 23) as described, and separately a total of 20 low plus moderate risk changes were made for a low plus moderate risk variable region (SEQ ID NO: 24 and 25). The vector pING1936 separately attached contains a PCR-generated human engineered ING-1 heavy chain variable region with 13 low risk changes incorporated. A DNA fragment encoding the heavy chain variable region was constructed using 6 overlapping oligonucleotides GL1 (SEQ ID NO: 26), GL2 (SEQ ID NO: 27), GL3 (SEQ ID NO: 28), GL4 (SEQ ID NO: 29), GL5 (SEQ ID NO: 30), and GL6 (SEQ ID NO: 31). These segments were annealed to each other, extended with DNA polymerase and then the assembled variable region amplified by PCR using a 5' forward primer GF (SEQ ID NO: 32) and a 3' reverse primer GR (SEQ ID NO: 33), digested with SalI and ApaI to yield a restriction fragment that was cloned directly into expression vector pING1931 to generate pING1936 as shown in FIG. 14. Another expression vector, pING1942, was constructed using a similar method and is like pING1936 except that pING1942 comprises an ING-1 heavy chain variable region human engineered with the low plus moderate risk changes as shown in FIG. 15 (SEQ ID NO: 24 and 25). The low plus moderate risk modified heavy chain variable region was constructed using 6 overlapping oligonucleotides, including 2 used in the construction of the low risk modified variable region described above: GL1 (SEQ ID NO: 26), GM2 (SEQ ID NO: 34), GM3 (SEQ ID NO: 35), GM4 (SEQ ID NO: 36), GM5 (SEQ ID NO: 37), and GL6 (SEQ ID NO: 31).

F. Construction of Expression Vectors Comprising Human Engineered ING-1 Light Plus Heavy Chain Genes (Two Gene Vectors)

A vector pING1937, comprising human engineered ING-1 light plus heavy chain genes, was constructed using pING1933 and pING1936 (FIG. 16). pING1936 was digested with XbaI, treated with T4 polymerase and then digested with NotI. The ~8780 bp restriction fragment was purified. pING1933 was digested with NheI, then NotI and HpaI, and the ~3716 bp fragment comprising a human engineered light chain gene was purified and ligated with the XbaI-NotI-digested pING1936 to generate pING1937, which has a neo gene for selection of G418-resistant transfectants. The variable region DNAs were re-sequenced before being used to construct light plus heavy chain expression vectors. The features of pING1937 are summarized in Table 1.

TABLE 1

Description of pING1937 vector.

| Plasmid region | Start nt | End nt | Description |
|---|---|---|---|
| NotI-HindIII | 1 | 479 | =pUC12 2616-399 (includes pBR322 4291-4361, 2069-2354 and part of lac gene) |
| HindIII-1/2BamHI | 479 | 643 | upstream region of Abelson murine leukemia virus 3' LTR enhancer/promoter (=4627-4804 of Reddy et al., 1983 sequence; ref 8) |
| 1/2HincII-BamHI | 643 | 1414 | hCMV promoter (=−598 to 174 of Boshart et al., ref 1; includes splice donor) |
| BamHI-SalI | 1414 | 1517 | SV40 16S splice acceptor (1654-1741 = SV40 1410-1497) |
| SalI-HindIII | 1517 | 1925 | ING-1(heMab) light chain V region |
| HindIII-NS[a] | 1925 | 2263 | ING-1 light chain(heMab) C region (kappa) |
| NS-BamHI | 2263 | 3582 | LC genomic DNA including poly A site |
| BamHI-1/2BamHI | 3582 | 3889 | upstream region of Abelson murine leukemia virus 3' LTR enhancer/promoter |
| 1/2HincII-BamHI | 3889 | 4660 | hCMV promoter, including splice donor |
| BamHI-SalI | 4660 | 4763 | SV40 16S splice acceptor |
| SalI-ApaI | 4763 | 5206 | ING-1 (heMab) heavy chain V region |
| ApaI-XhoI | 5206 | 6198 | ING-1 heavy chain(heMab) C region (gamma-1) |
| XhoI-BamHI | 6198 | 7562 | LC genomic DNA including poly A site |
| BamHI-1/2BclI | 7562 | 7802 | SV40 polyadenylation (=SV40 2532-2774) |
| 1/2BstYI-NS[a] | 7802 | 8409 | SV40 small T intron (=SV40 4769-4099) |
| 1/2 SalI-NheI | 8409 | 9898 | bacterial neomycin phoshotransferase (neo) gene from pSV2neo (coding region = 9545-8753) |
| NheI-PvuII | 9898 | 10242 | SV40 promoter (=SV40 5172-272) |
| PvuII-NotI | 10242 | 12496 | bacterial origin of replication and beta-lactamase (ampicillin resistance) gene (=pBR322 2069-4290) |

[a]NS - restriction site not identified.

The vector, pING1950, which is similar to pING1937 except that it has a gpt gene for selection of mycophenolic acid-resistant transfectants, was constructed by ligating the ~7696 bp HpaI-NotI fragment from pING1937 (comprising human engineered ING-1 light and heavy chain genes each fused to a CMV promoter and light chain 3' untranslated region) with a ~4441 bp HpaI-NotI fragment from pING4144 (described in Example 1 above) comprising a gene encoding gpt as shown in FIG. 17.

Figure 18:
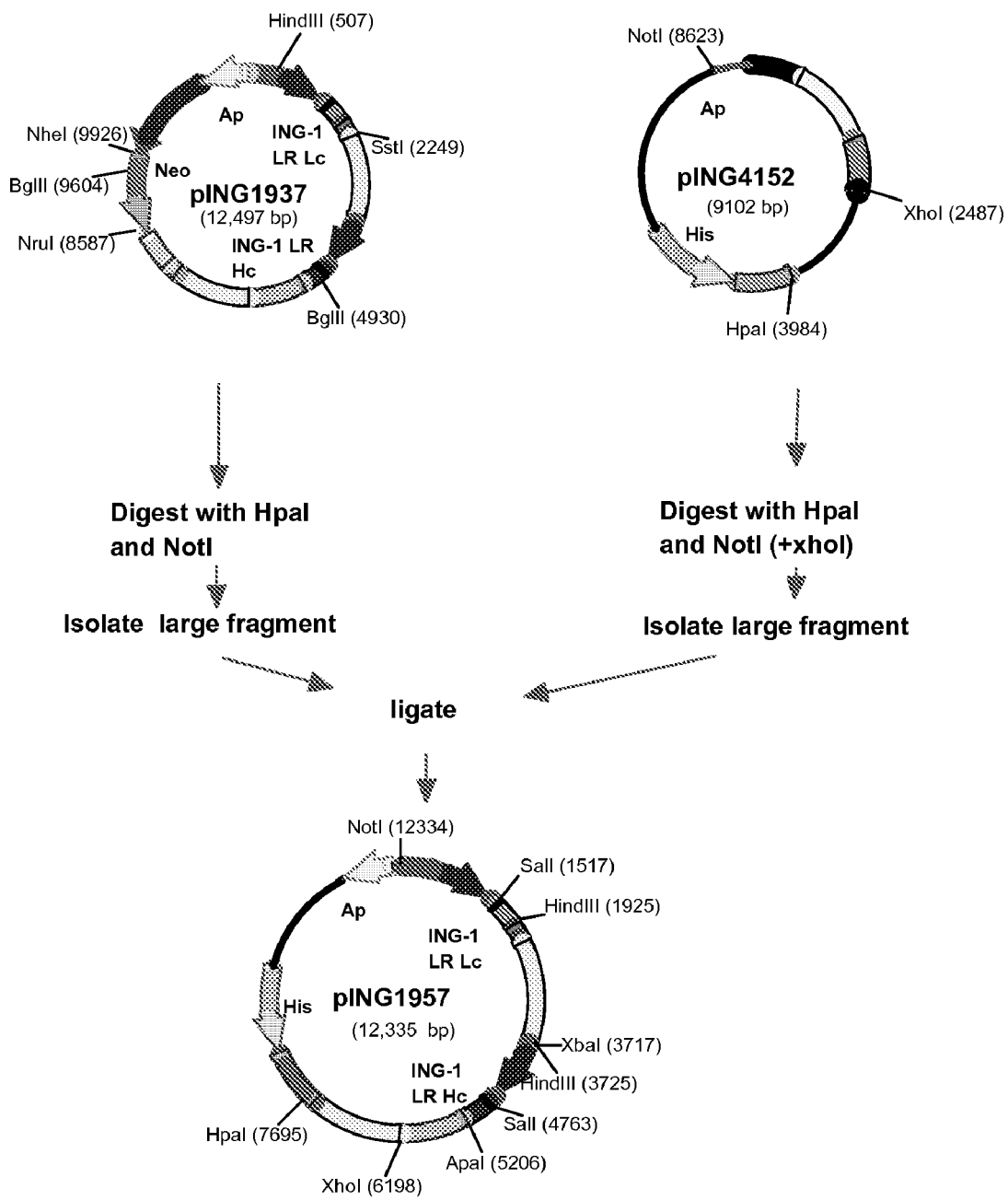
FIG. 18 depicts a construction map for vector pING1957.

The vector, pING1957, which is similar to pING1937 and pING1959 except that it has a his gene for selection of histidinol-resistant transfectants, was constructed by ligating the ~7696 bp HpaI-NotI fragment from pING1937 (as described above) with a ~4639 bp HpaI-NotI fragment from pING4152 (described in Example 1 above) comprising a his gene as shown in FIG. 18.

Another vector pING1944 was constructed by similar methods used in the construction of pING1937 described above, and is similar to pING1937 except that pING1944 was constructed using pING1939 in place of pING1933 and using pING1942 in place of pING1936. The resulting vector, pING1944 comprises light chain and heavy chain variable regions (SEQ ID NOS: 11, 12, 24, 25) with both the low plus moderate risk substitutions as shown in FIGS. 13 and 15. Thus, expression vectors for both low risk ING-1 (pING1937) and low plus moderate risk ING-1 (pING1944) were prepared.

G. Construction of Expression Vectors Comprising Two Copies of Human Engineered ING-1 Light and Heavy Chain Genes (Four Gene Vectors)

Figure 19:
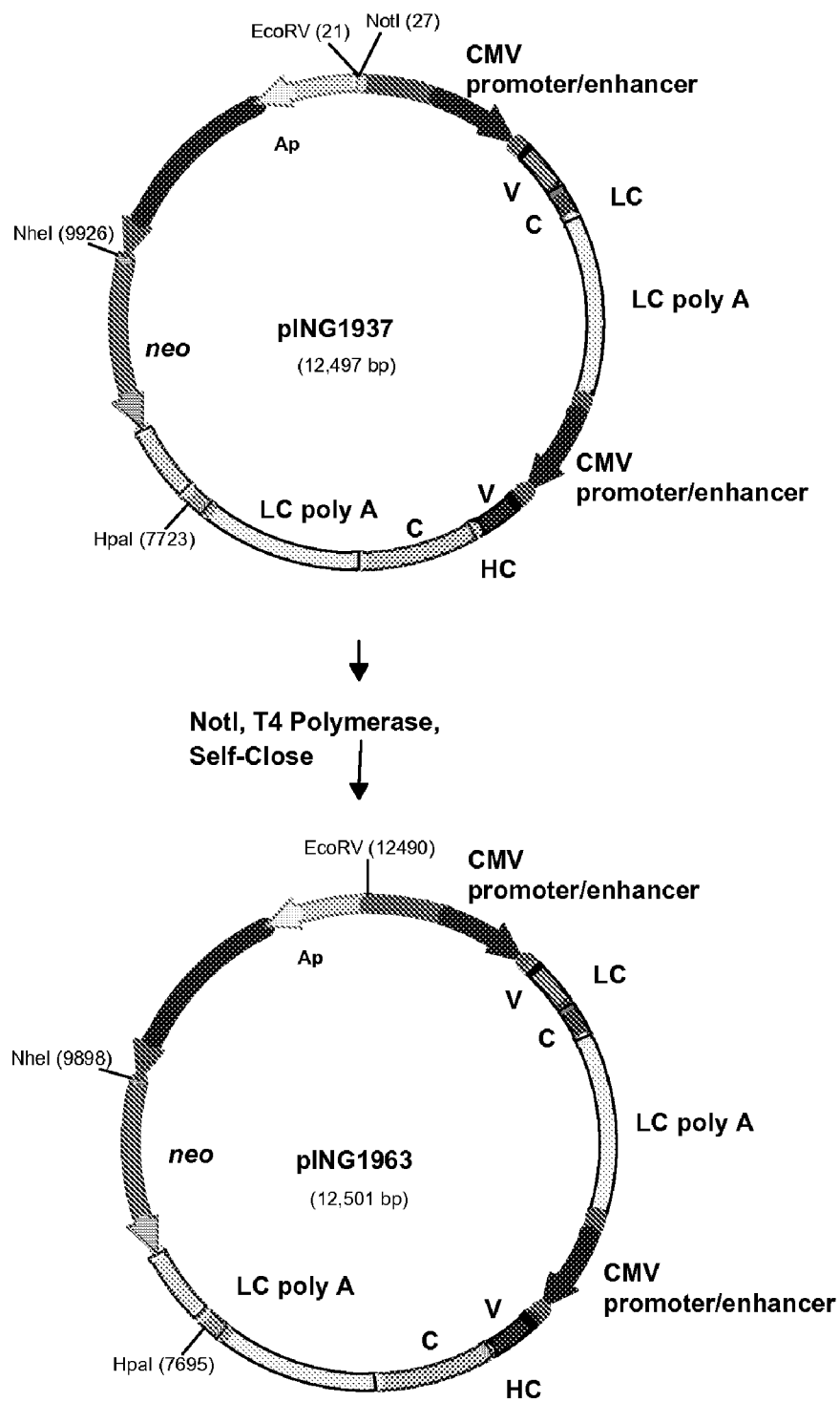
FIG. 19 depicts a construction map for vector pING1963.
Figure 20:
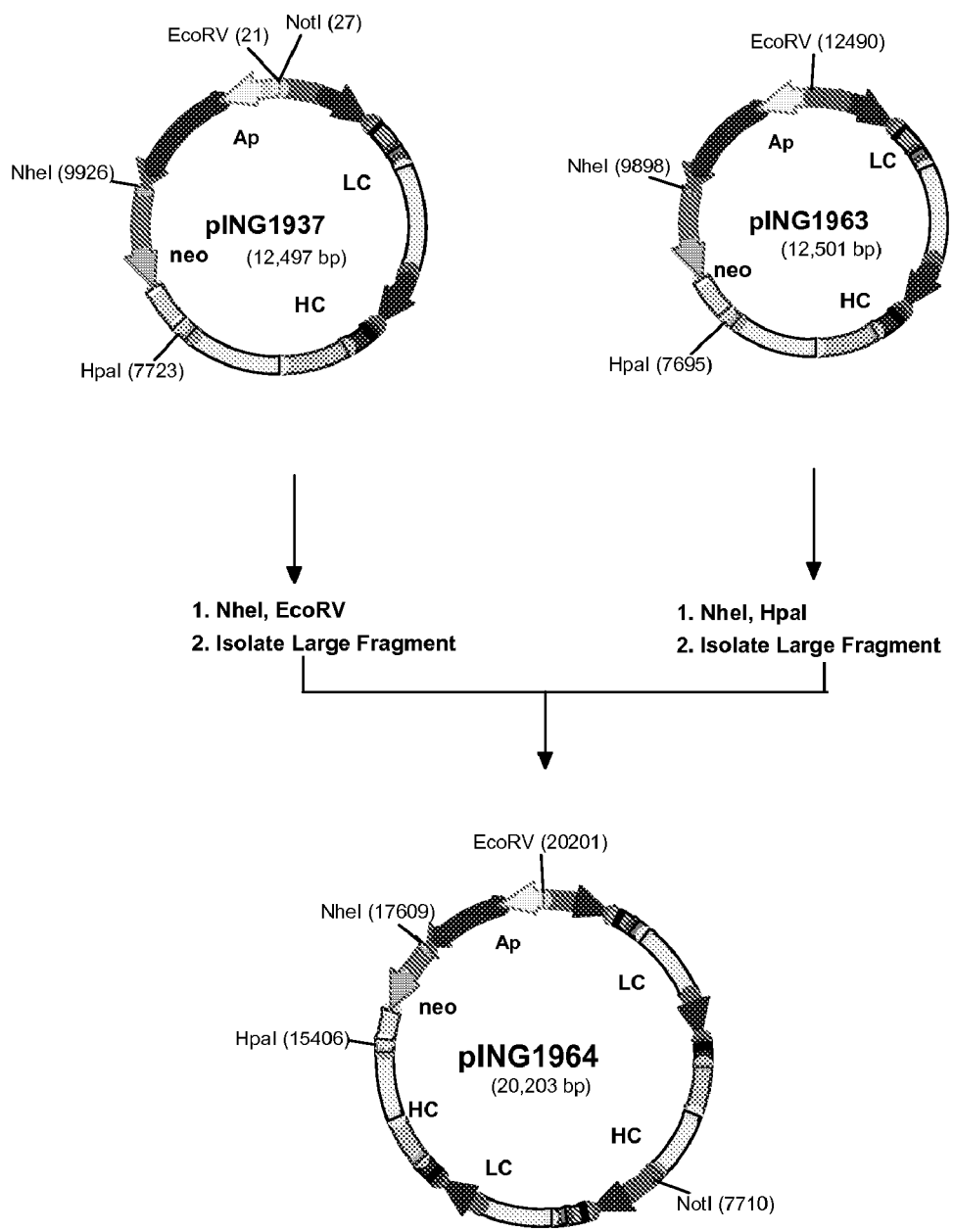
FIG. 20 depicts a construction map for vector pING1964.
Figure 21:
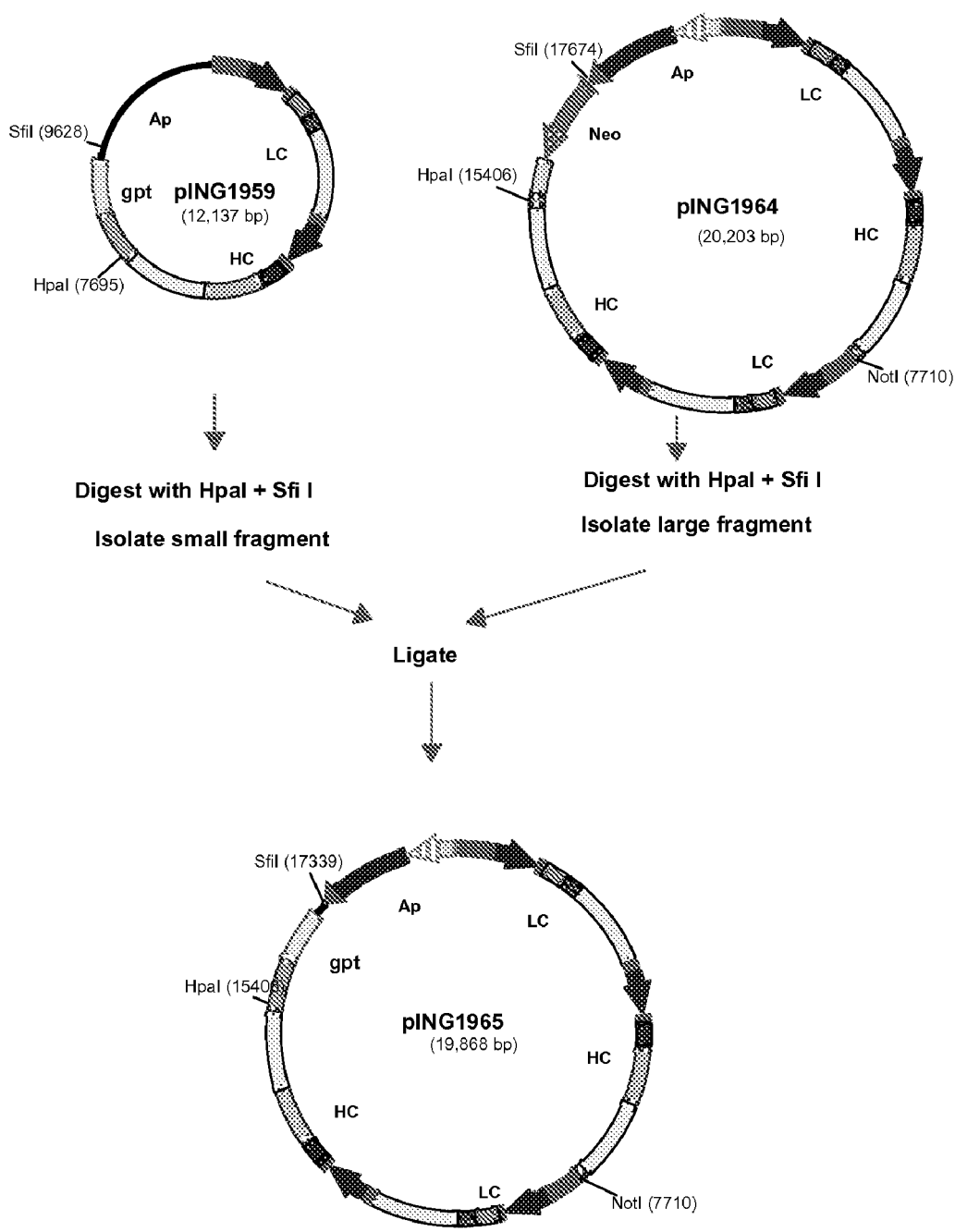
FIG. 21 depicts a construction map for vector pING1965.

A human engineered ING-1 heavy plus light chain vector, pING1937, was treated with NotI, T4 DNA polymerase in the presence of deoxyribonucleotides to blunt end and allowed to self-close, destroying the NotI site and generating the vector pING1963 lacking a NotI site as shown in FIG. 19. The vector pING1937 was then digested with NheI and EcoRV and the ~9905 bp fragment was purified and ligated with the ~10,298 bp NheI-HpaI fragment form pING1963 to generate the vector pING1964 as shown in FIG. 20 which comprises four ING-1 genes (a four gene vector). pING1964 has two copies of human engineered ING-1 light chain genes and two copies of ING-1 heavy chain genes, with each of the four genes under control of a CMV promoter and light chain 3' untranslated region and a neo gene for selection of G418-resistant transfectants. A vector, pING1965, which is similar to pING1964 except that it contains a gpt gene for selection of mycophenolic acid-resistant transfectants was constructed by ligating the 1933 bp HpaI-SfiI fragment from pING1959 with the ~17,935 bp HpaI-SfiI fragment from pING1964 as shown in FIG. 21.

Figure 22:
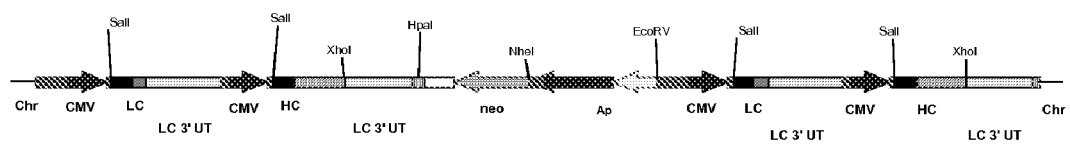
FIG. 22 shows the structure of vector pING1964 linearized with NotI.

Digestion of pING1964 or pING1965 at the unique NotI site yields a linear restriction fragment containing four transcription units: two copies of human engineered ING-1 light plus heavy chain genes configured so that a selective marker gene, neo, or gpt, respectively, is positioned between the two identical light and heavy chain transcription units. Viewed as linear NotI-digested DNA, the order of elements within the vector(s) is as follows: CMV promoter, light chain gene, light chain 3' untranslated region, CMV promoter, heavy chain gene, light chain 3' untranslated region, neo (pING1964) or gpt (pING1965) genes, bla (Amp$^r$) gene, CMV promoter, light chain gene, light chain 3' untranslated region, CMV promoter, heavy chain gene, light chain 3' untranslated region, (FIG. 22).

EXAMPLE 7

Development and Characterization of Additional Transfected Clones and Cell Lines This example describes the development and characterization of additional clones and cell lines transfected with additional exemplary vectors according to the present invention. The development and characterization of immunoglobulin producing cell lines is described from transfections, for example, with two gene vectors as described in Example 6.

A. pING1932 and pING1932R

The expression vectors, pING1932 and pING1932R described in Example 6 were transfected into Ex-Cell 301-adapted CHO-K1 cells. CHO-K1 cells adapted to suspension growth in Ex-Cell 301 medium were typically electroporated with 40 μg of linearized vector. Both pING1932 and pING1932R contain a unique NotI site. In preparation of DNA for transfection, digestion at NotI results in linear DNA such that light and heavy chain genes, under the control of a CMV promoter and light chain 3' untranslated region, are separated by the selective marker gene when inserted into the CHO chromosome. With the pING1932, the heavy and light chains are oriented in the same direction, whereas in pING1932R, they are oriented in opposite directions.

The cells were plated in 96 well plates containing Ex-Cell 301 medium supplemented with 2% FBS and G418. A total of 155 and 168 clones were screened in 96 well plates for pING1932 and pING1932R, respectively. The top 22 clones for each transfection were transferred to 24 well plates containing Ex-Cell 301 medium with FBS.

A productivity test was performed in 24 well plates in Ex-Cell 301 medium with or without 2% FBS. Cells were grown to extinction and culture supernatants tested for levels of secreted antibody by an immunoglobulin ELISA assay for IgG. The results demonstrated that the pING1932 transfectants generally secreted higher levels of immunoglobulin polypeptide than the pING1932R transfectants. Interestingly, in some cases, the levels of secreted immunoglobulin polypeptides were higher in the medium without FBS than in those supplemented with FBS. The top transfectants from each group secreted in the range from about 7 μg/ml IgG to more than about 30 μg/ml IgG.

The top 7 clones from the pING1932 transfection (including, for example, Clones 27, 40 and 82) and the top clone from the pING1932R transfection (Clone 168R) were transferred to shake flasks containing Ex-Cell 301 medium. As soon as the cells were adapted to suspension growth, a shake flask test was performed with these clones in Ex-Cell 301 medium with and without 2% FBS. The cells were grown for up to 10 days in 125 ml Erlenmeyer flasks containing 25 ml media. The flasks were sealed for the most of the incubation period and the levels of immunoglobulin polypeptide in the culture medium were determined by IgG ELISA at the end of the incubation period. The results of the initial shake flask test demonstrated that the top clone (Clone 40) secreted up to ~66 μg/ml. In many cases, there was little difference in productivity between cultures grown with and without FBS.

The initial shake flask test was performed with flasks that were not opened regularly during the incubation period. Because introducing a gas exchange step at least every other day was found to significantly influence the productivity of certain rBPI$_{21}$-producing CHO-K1 clones as described in Examples 3 and 4 above, this approach was evaluated with Clones 27, 40, 82 and 168R. Cells were seeded at 1.5×10$^5$ cells/ml into duplicate 125 ml Ehrlenmeyer flasks in 25 ml Ex-Cell 301 medium supplemented with 1% FBS and incubated at 37° C., 100 RPM. One set of flasks remained sealed for the duration of the incubation, while the other set was opened every day for cell counts and aeration. The results demonstrated that cells grown in flasks that were periodically opened expressed immunoglobulin polypeptide at a higher level (for example, from about 50 μg/ml to about 116 μg/ml) than those in which the flasks remained closed (for example, from about 35 μg/ml to about 81 μg/ml). These results also corresponded to those obtained in the first shake flask test (for example, from about 45 μg/ml to about 66 μg/ml), although the conditions were slightly different (1% FBS in the second test vs. 2% FBS in the first test).

The cultures that were opened periodically were also examined for growth and productivity at various times. The results of this analysis for Clones 27 and 40 indicated that the cells produced mouse-human chimeric antibody during both the log and the stationary phases.

B. pING1937

The expression vector pING1937, comprising one copy each of the human engineered ING-1 low risk light and heavy chain genes and the neo (G418-resistant) gene, was linearized by digested with XbaI followed by transfection into serum-free adapted CHO-K1 cells in Ex-Cell 301 medium. G-418-resistant transfectants were selected and screened for immunoglobulin polypeptide expression. Clone 146 was selected as one of the top transfectants and produced up to about 60 mg/ml in shake flasks and about 200 mg/L in a fermentor.

EXAMPLE 8

Increasing Expression through a Second Sequential Vector Transfection: Development and Characterization of Additional Transfected Clones and Cell Lines This example describes a further increase in expression and production of polypeptides, for example, immunoglobulins, through a second transfection of an exemplary cell line with a second multi-transcription unit vector.

Two additional vectors (as described in Example 6) were employed that were identical to pING1937 each comprising two transcription units, with a low risk human engineered ING-1 light chain gene and a low risk human engineered heavy chain gene, except that they have either a his gene encoding histidinol resistance (pING1957) or a gpt gene encoding mycophenolic acid resistance (pING1959). The development of an ING-1 immunoglobulin producing CHO cell line, Clone 259, is described. Clone 259 was developed by transfecting Clone 146 cells (as described in Example 7) with the his expression vector pING1957. The development of another ING-1 immunoglobulin producing CHO cell line, Clone 373, is also described. Clone 373 was developed by transfecting a subclone of Clone 146, Clone 146.3 cells, with the gpt expression vector pING1959.

A. Transfection of Clone 146 with pING1957 and Development of Clone 259

Clone 146 was transfected with pING1957 in serum-free medium (Ex-Cell 301). First, 650 clones were screened from 2 transfections in 96 well plates. Then, 142 clones were selected from the 96 well plates and then screened from 24 well plates. Finally, 31 clones were selected from the 24 well plates and screened in shake flasks. The results for top producers in Ex-Cell 301 media without FBS of antibody as measured by HPLC demonstrated that the top producers expressed antibody at greater than 2 times higher levels than Clone 146. For example, the top producer, clone 146.2-259, expressed 172 µg/ml and 192 µg/ml in two different tests.

Clone 146.2-259 was subcloned in Ex-Cell 301 medium and screened in a 24 well format. The top subclones were further selected based on shake flask productivity in Ex-Cell 301 serum-free medium. Shake flask results for top producers in Ex-Cell 301 without FBS of expression of immunoglobulin polypeptide as measured by HPLC demonstrated that the top Clone 259 subclones expressed antibody at about 1.5 to 2 times higher levels (e.g., from about 229 µg/ml to about 271 µg/ml) than the parent Clone 259 (e.g., about 116 µg/ml).

B. Transfection of Subclone of Clone 146, Clone 146.3, with pING1959 and Development of Clone 373

Clone 146, the initial pING1937 G418-resistant transfectant was also subjected to subcloning in Ex-Cell medium and one subclone, 146.3, secreted ~121 µg/ml compared to ~65 µg/ml for Clone 146 in Ex-Cell medium.

Since Clone 146.3 secreted at a relatively high level for a single transfection, it was therefore subjected to transfection with pING1959. Serum-free medium (Ex-Cell 301) adapted Clone 146.3 cells were transfected with pING1959 (same as pING1937 except for mycophenolic acid resistance as described in Example 6), plated in Ham's F12 with 5% FBS/mycophenolic acid and xanthene for selection. First, 520 clones were screened from 2 transfections in 96 well plates. Then 106 clones were selected from 24 well plates and screened. Finally, 26 clones were selected from the 24 well plates and screened in shake flasks. The sequential transfection of Clone 146.3 with pING1959 resulted in the selection of Clone 373 which expressed ~225 and ~257 µg/ml immunoglobulin polypeptide as determined by the shake flask results in Ex-Cell 301 medium.

EXAMPLE 9

Further Increasing Expression by a Third Sequential Vector Transfection: Development and Characterization of Additional Transfected Clones and Cell Lines This example describes a further increase in expression and production by a third sequential transfection of an exemplary cell line with a third multi-transcription unit vector, resulting in clones and cell lines that express increased levels of polypeptide production, for example, immunoglobulin production.

Clone 373 as described in Example 8 was chosen for additional studies and was further subjected to another sequential transfection using pING1957 (same as pING1937 except for histidinol resistance) in serum-free medium (Ex-Cell 301) and plated in Ex-Cell 301 supplemented with FBS and histidinol. Once the clones were selected, they were maintained with G418, MPA/xanthine/histidinol.

First, 160 clones were screened from 2 transfections in 96 well plates. Then, 48 clones were selected from the 96 well plates and screened in 24 well plates. Finally, 12 clones were selected from the 24 well plates and screened in shake flasks. Results for shake flask tests in Ex-Cell 301 yielded 8 top producing clones.

The top producing clones displayed an expression level ranging from about 310 to about 370 µg/ml, including Clone 132 which had an expression level of about 317 µg/ml.

EXAMPLE 10

Figure 17:
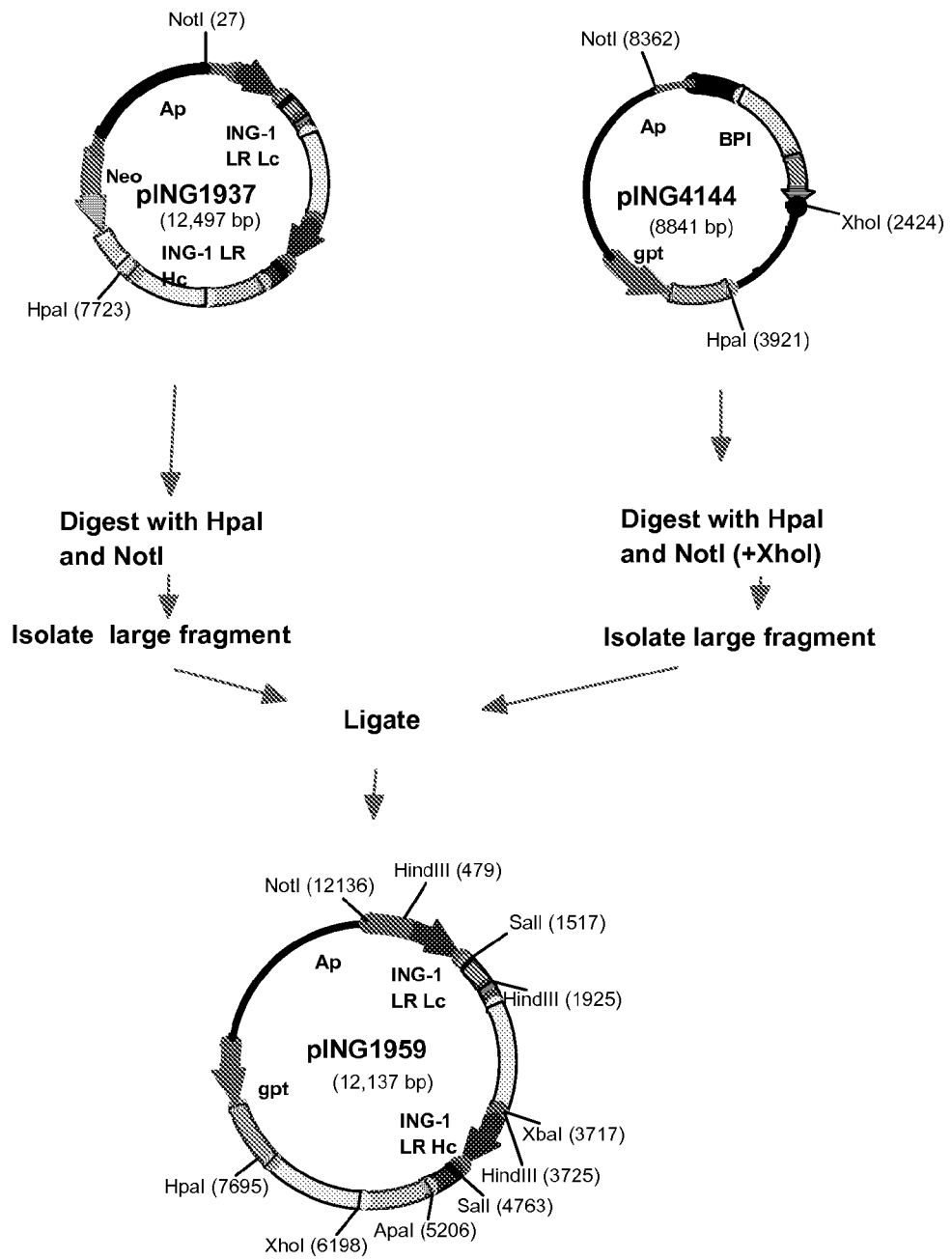
FIG. 17 depicts a construction map for vector pING1959.

Transfection with Additional Multiple Transcription Unit Vectors: Development and Characterization of Additional Transfected Clones and Cell Lines The expression vectors, pING1959 (FIG. 17) and pING1965 (FIG. 21) containing one copy of each of the human engineered ING-1 light and heavy chain genes (pING1959, two gene vector) or two copies of each of the human engineered ING-1 light and heavy chain genes (pING1965, four gene vector) were transfected into CHO-K1 cells. CHO-K1 cells adapted to suspension growth in Ex-Cell 301 medium were electroporated with 40 µg of each linearized vector. After a recovery period of 2 days without selective agent, cells were plated in 96 well plates containing Ham's F12 medium supplemented with 5% FBS, mycophenolic acid and xanthine. A total of 300 and 255 clones were screened in 96 well plates for transfections with pING1959 and pING1965, respectively. For the pING1959 transfections, the top 18 clones were transferred to 24 well plates containing Ex-Cell 301 medium supplemented with 1% FBS. For the pING1965 transfections, the top 40 clones, were transferred to 24 well plates containing Ex-Cell 301 medium supplemented with 1% FBS. All 18 clones from the pING1959 transfection were next transferred to shake flasks containing Ex-Cell 301 medium supplemented with 1% FBS and evaluated for productivity. The top two producers, Clones 53 and 157 secreted ~116 and ~133 µg/ml, respectively in the presence of 1% FBS. In ExCell 301 medium without FBS supplementation Clones 53 and 157 secreted ~117 and ~121 µg/ml, respectively. For the pING1965 transfection, the top 8 clones were transferred to shake flasks and evaluated for productivity. The top producer, Clone 17, secreted ~216 µg/ml in ExCell 301 medium supplemented with 1% FBS and ~214 µg/ml in ExCell 301 medium without FBS supplementation. Accordingly, a cell line transfected with a four gene vector (pING1965) with two copies of each of the human engineered light and heavy chain genes did produce approximately twice as much immunoglobulin polypeptides as cell lines transfected with a two gene vector (pING1959) with one copy of each of the human engineered ING-1 light and heavy chain genes.

EXAMPLE 11

Evaluation of Binding Activity of Immunoglobulin Polypeptides

Vectors constructed according to Example 6 encoding human engineered ING-1 light and heavy chain genes, for example, pING1937 (low risk human engineered ING-1) and pING1944 (low plus moderate risk human engineered ING-1) were linearized by XbaI and used to transfect serum-free adapted CHO-K1 followed by selection of G418-resistant transfectants. Protein was purified from shake flask culture supernatants by passage over a protein A column. To evaluate the binding activity of the produced immunoglobulin polypeptides, competition binding assays with the human carcinoma cell line HT-29 were performed. This colorectal carcinoma cell line expresses a molecule known as Ep-CAM on its surface. Ep-CAM is recognized by immunoglobulin polypeptides having the antigen binding specificity of the mouse-human chimeric ING-1 antibody produced by cell line HB 9812 as deposited with the ATCC.

HTG29 cells were grown to confluency (~2×10$^5$ cells/well) in 96 well plates. Mouse-human chimeric ING-1 was labeled with Na$^{125}$I (Iodo-gen®, Pierce). The competition conditions included in a 100 µl assay volume, 0.1 nM labeled mouse-human chimeric ING-1, 2-fold serial dilutions of unlabeled immunoglobulin polypeptides, for example, as produced by cells transfected with pING1937 and pING1944. The labeled and unlabeled immunoglobulin polypeptides were incubated with HT-29 cells at 4° C. for 5 hours followed by washing. Labeled cells were removed with NaOH and counted. Data analysis was performed using Ligand [Munson and Redbard, *Analytical Biochem.* 107:220-239 (1980)].

Results for competition binding assays using immunoglobulin polypeptides obtained from transfection with the pING1937 (low risk) vector are shown in FIG. 23. The affinities for the mouse-human chimeric ING-1, containing an un-modified ING-1 murine variable domain, and the human engineered ING-1, with its variable domain modified at low risk positions, showed very similar affinities (2-5 nM) (FIG. 23).

Figure 24:
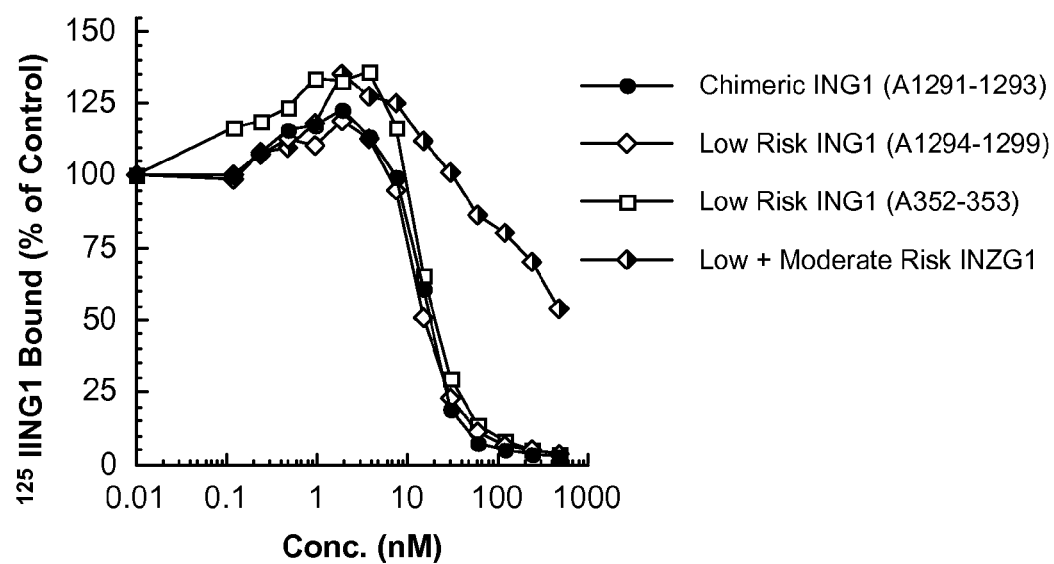
FIG. 24 shows competition binding results for human engineered anti-Ep-CAM antibodies, including low risk as well as low plus moderate risk ING-1 as compared with mouse-human chimeric ING-1.

Human engineered ING-1 modified at the low risk plus moderate risk positions was also evaluated using competition binding assays. Results with the human engineered ING-1 purified from pING1944 transfected cell culture supernatant are shown in FIG. 24. No differences in binding between the mouse-human chimeric and the human engineered (low risk) ING-1 were observed. The human engineered (low plus moderate risk) ING-1 obtained from transfection with the vector pING1944 showed a reduced competition binding activity as shown in FIG. 24.

To examine the contribution of the light and heavy chain moderate risk changes on ING-1 binding activity, immunoglobulin polypeptides were expressed from vectors constructed with either the combination of a low risk light chain with a low plus moderate risk heavy chain or a low risk heavy chain with a low plus moderate risk light chain. Vectors containing both modified ING-1 light chain plus heavy chain were used to transfect serum-free medium-adapted CHO-K1 cells. Approximately 100 clones were screened in microtiter plates to select the top 8 to 10 clones for shake flask evaluation. For production purposes, the best producers were grown in shake flasks and modified ING-1 IgG's were purified on a protein A column followed by concentration determination by $A_{280}$.

Figure 25:
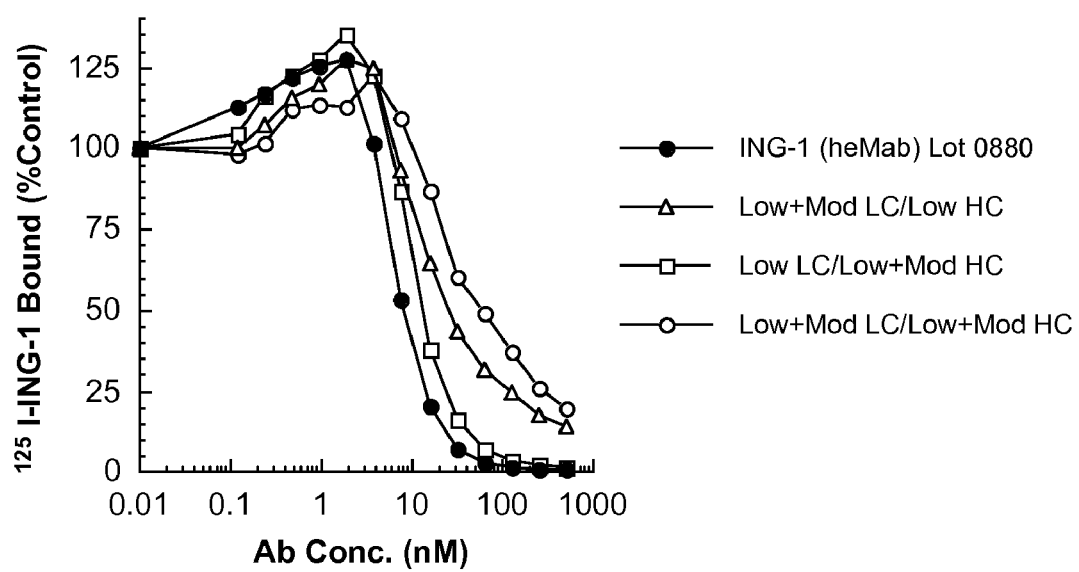
FIG. 25 shows competition binding results for ING-1 with combinations of light and heavy chains modified at either low or low plus moderate risk positions ING-1 (heMab) has both heavy and light chains modified at low risk positions.

Competition binding assays, employing iodinated human engineered (low risk) ING-1 and Ep-CAM-expressing HT-29 cells, were used to characterize modified ING-1 immunoglobulin polypeptides. Exemplary results are shown in FIG. 25. Moderate risk changes made to the light chain appeared to have the greatest impact on binding of the modified ING-1 antibodies tested. Moderate risk changes made to the heavy chain also appeared to affect binding, but to a lesser extent than the light chain changes. The results suggested that the effects observed with individual chains were additive.

Figure 26A:
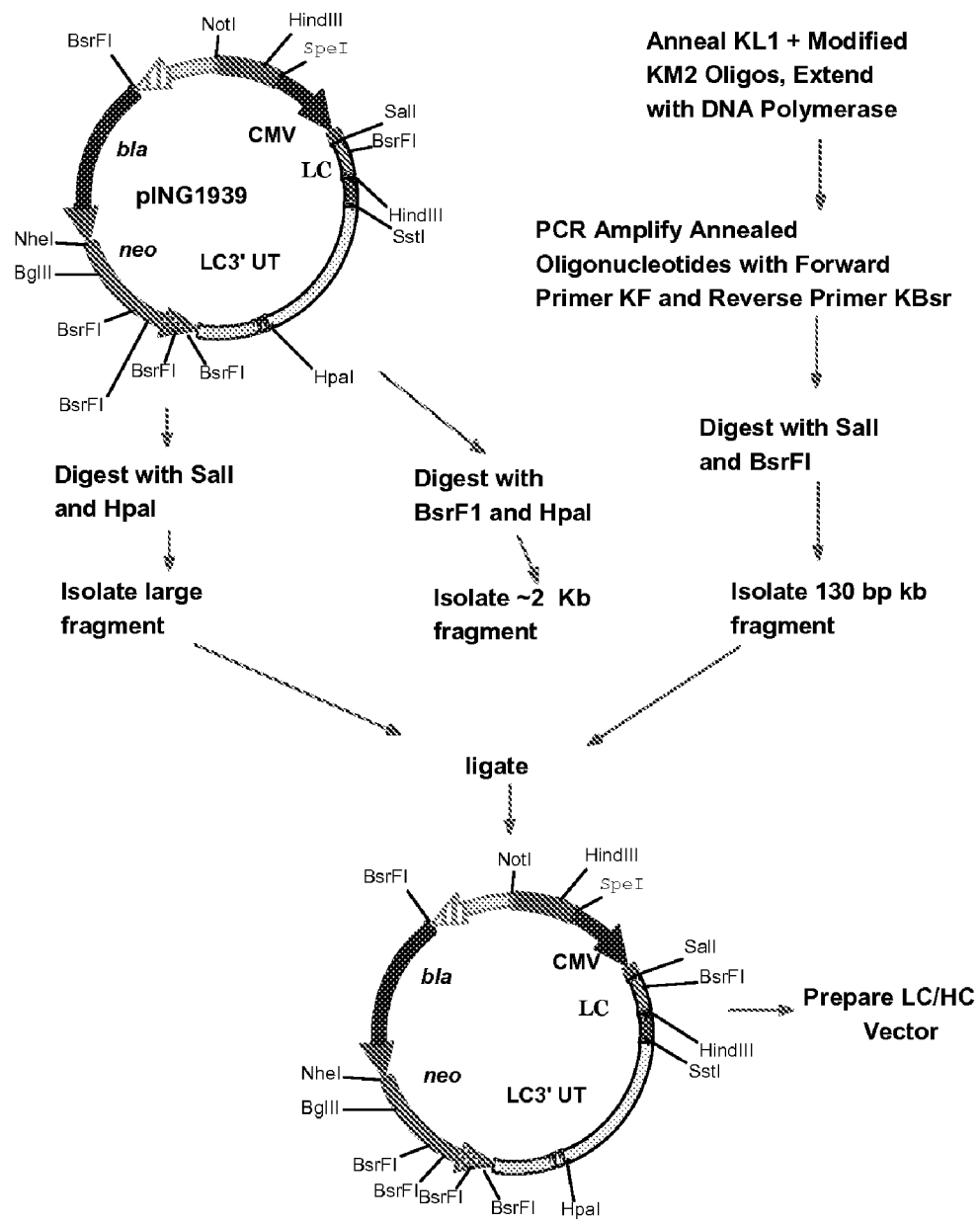
FIG. 26 shows competition binding results for human engineered low risk ht chain with additional P2 or P3) or pair combinations (P1P2 or P1P3) of moderate risk proline changes.

Moderate risk changes include changes involving prolines (see, e.g., FIGS. 13 and 15). The moderate risk ING-1 light chain has 3 prolines introduced within Framework 1 (amino acids 1-59 (SEQ ID NO: 12)), and the moderate risk ING-1 heavy chain has 1 proline removed within framework 1 (amino acids 1-57 (SEQ ID NO: 25)). To examine the effects of proline changes in greater detail, low risk human engineered ING-1 light chain variable regions were constructed with prolines substituted in the low risk human engineered variable regions either one at a time (e.g. Proline1 (P1) (SEQ ID NOS: 38 and 39), Proline2 (P2) (SEQ ID NOS: 40 and 41), Proline3 (P3) (SEQ ID NOS: 42 and 43) or combinations of prolines P1P2 (SEQ ID NOS: 44 and 45), P1P3 (SEQ ID NOS: 46 and 47), P2P3 (SEQ ID NOS: 48 and 49) of the light chain. As is shown in FIG. 13, the total of 3 amino acid positions in the low risk light chain that were changed to proline are within Framework 1. Therefore, all combinations of prolines were incorporated by using two overlapping oligonucleotides. KL1 (SEQ ID NO: 13) remained unchanged, and was as described in Example 6 for the construction of the low risk ING-1 light chain vector pING1933. The second oligonucleotide used was one of 6 variations of the oligonucleotide KM2 (SEQ ID NO: 21) described in Example 6 for the construction of the low plus moderate risk ING-1 light chain vector pING1939. The variation of KM2 chosen depended upon which combinations of prolines were to be introduced into the low risk ING-1 light chain sequence. A low risk light chain variable region was further with the first moderate risk proline (P1) substituted for the alanine at position 8 of the low risk ING-1 light chain (SEQ ID NO: 39). A low risk variable region was modified with the second moderate risk proline (P2) substituted for the leucine at position 15 of the low risk ING-1 light chain [SEQ ID NO: 41]. A low risk variable region was modified with the third moderate risk proline (P3) substituted for the serine at position 18 (SEQ ID NO: 43). By employing one of 6 variations of the KM2 oligonucleotide (SEQ ID NO: 21), each proline residue was first changed separately using the oligonucleotide P1 (SEQ ID NO: 50), P2 (SEQ ID NO: 51), P3 (SEQ ID NO: 52), and then in pairs using the oligonucleotide P1P2 (SEQ ID NO: 53), P1P3 (SEQ ID NO: 54) or P2P3 (SEQ ID NO: 55). The cloning strategy employed to construct expression vectors encoding various ING-1 light chains with different combinations of moderate risk proline residues incorporated into the low risk human engineered ING-1 light chain is shown in FIG. 26A. Subsequent to annealing the modified KM2 variant with the unmodified KL1 oligonucleotide, the annealling reaction was extended with DNA polymerase followed by amplification by PCR employing ING-1 light chain forward primer KF and reverse primer KBsr (SEQ ID NO: 56). The resultant product was then digested with SalI and BsrF1, followed by purification of the resultant 130 base pair fragment corresponding to low risk ING-1 light chain framework 1 region modified by the introduction of proline residues at one of three positions or in various combinations. The vector pING1939 was then digested with SalI and HpaI followed by purification of the large linear vector fragment. The vector pING1939 in a separate reaction was digested with BsrF1 and HpaI followed by purification of line 2 kb fragment.

A three way ligation was performed in which the HpaI end of the pING1939 linear vector first ligates with the HpaI end of the 2 kb fragment comprising the ING-1 light chain minus the framework 1 region. The full length ING-1 light chain is reconstructed when the BsrF1 end of the 130 bp proline modified fragment ligates to the BsrF1 end of the 2 kb fragment comprising the ING-1 light chain minus the framework 1 region. The vector was then closed when the SalI end of the 130 bp proline modified framework 1 region fragment ligates to the SalI end of the pING1939 linear vector. These light chains, modified at various proline positions, were then expressed with the low risk heavy chain.

Figure 26B:
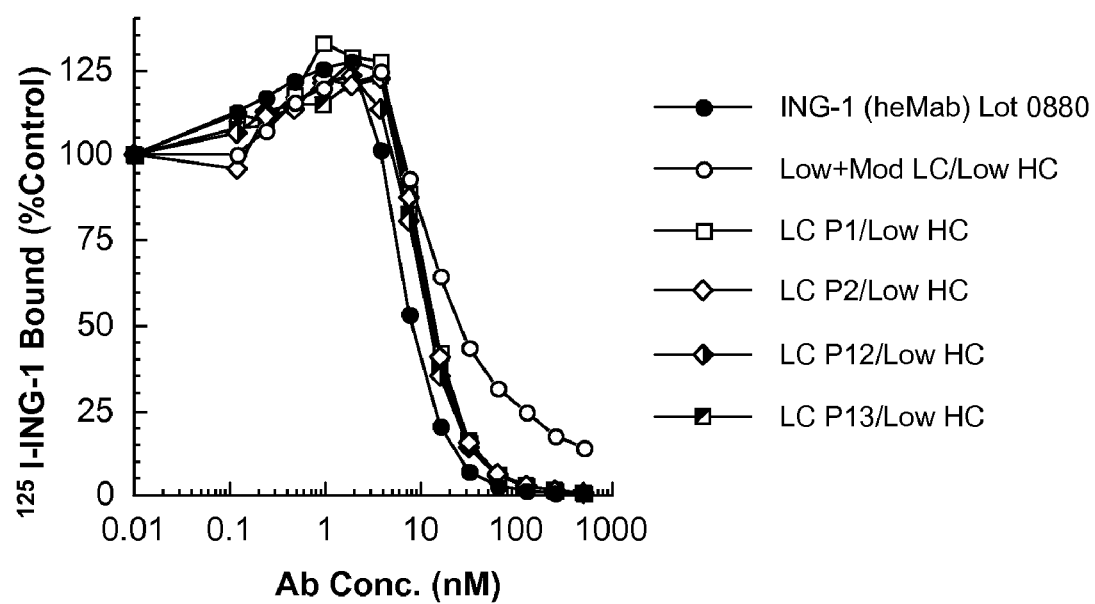

Competition binding assays, again employing iodinated human engineered (low risk) ING-1 and Ep-CAM expressing HT-29 cells, were used to determine the effect of prolines on binding activity. Results for modified ING-1 with a low risk heavy chain in combination with a light chain modified at P1, P2, P1P2, or P1P3 are shown in FIG. 26B. When compared with each other, changes at any one or a combination of two, of the tested prolines, have a similar effect. Changing all three positions to prolines has the greatest effect.

EXAMPLE 12

Cloning and Expression of Soluble Human Ep-CAM and Ep-CAM Binding Assays

Competition binding assays with Ep-CAM expressing cells such as HT-29 cells as described in Example 11 above require the use of isotopes and the maintenance and growth of cells for each assay, with the potential variability as with any cell-based assay. A direct binding ELISA assay with soluble Ep-CAM was also developed and used to evaluate the binding activity of immunoglobulin polypeptides produced by transfected cells according to the invention. For these assays, soluble human Ep-CAM (SEQ ID NOS: 57 and 58) was cloned and expressed. Immunoglobulin polypeptides used included human engineered (low risk) ING-1 from either 2 L or 500 L fermentor runs and soluble sEp-CAM from shake flasks or 2 L fermentors purified by ING-1 affinity chromatography.

Figure 27:
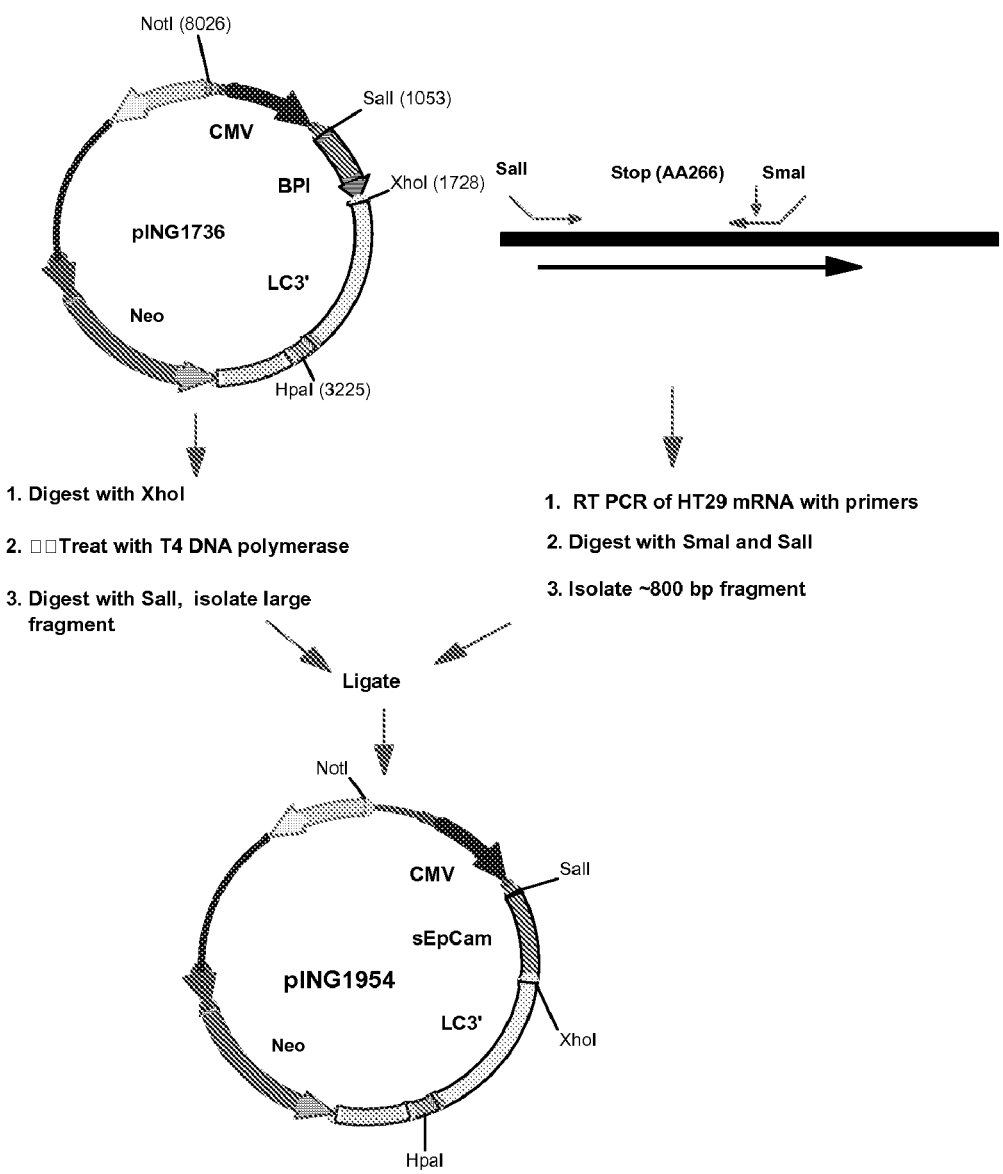
FIG. 27 depicts a construction map for vector pING1954.

Soluble Ep-CAM has previously been expressed in insect cells for expression in and secretion from CHO-K1 cells, truncated Ep-CAM (sEp-CAM) was cloned into an expression vector with the CMV promoter and the neo gene encoding for G418-resistance. The cloning strategy is outline in FIG. 27. The vector pING1736 (described in Example 6 above) was digested with XhoI, followed by treatment with T4 DNA polymerase to blunt end. The blunt-ended linear vector was then digested with SalI and the large fragment was isolated. The Ep-CAM gene was obtained from HT-29 mRNA using a RT PCR reaction which incorporated a 5' SalI site, a 3' SmaI site, and truncated the Ep-CAM gene by introducing a stop codon at amino acid position 266 (SEQ ID NO: 57 or 58). Without that stop codon the Ep-CAM sequence comprises 314 amino acids as shown in (SEQ ID NOS: 59 and 60). For the RT PCR, two primers were used, an Ep-CAM forward primer (SEQ ID NO: 61) and an Ep-CAM reverse primer (SEQ ID NO: 62). The RT PCR reaction was digested with SmaI and SalI and the resultant ~800 base pair fragment was purified and ligated with the digested pING1736 large fragment to produce vector pING1954.

Serum-free medium adapted CHO-K1 cells were then transfected with linearized pING1954. Transfectants were then selected in Ex-Cell 301 with 2% FBS. Screening was performed in 24 well plates, and shake flask formats by direct ELISA. Detection was performed with ING-1 followed by peroxidase-labeled goat anti-human IgG. 150 clones, adapted to grow without FBS were transferred to 24 well plates. The cells were grown to extinction and 50 μl supernatant was used to pre-coat the Immulon II plates. The top 6 clones were then transferred to shake flasks. The productivity for Clone 51 was subsequently estimated to be about 20 to 35 mg/L in both shake flasks and 2 liter fermentors.

Western blot analysis was employed to confirm that ELISA signal corresponded to specific proteins. Multiple bands were subsequently observed with the Ep-CAM supernatant. These multimers are also observed with purified Ep-CAM and were not an artifact of running crude culture supernatant, and therefore did not adversely impact the use of supernatants in an ELISA-based direct binding assay. Moreover, the lack of detection on a reduced gel is consistent with the non-linear nature of the known Ep-CAM epitope structure recognized by immunoglobulin polypeptides with antigen binding like ING-1.

Immulon II plates were precoated with the sEp-CAM antigen to immobilize it to the microplate. In preparation for pre-coating, the sEp-CAM antigen was first diluted in PBS coating. sEp-CAM test concentrations ranging from 0.25 to 20 μg/ml were added at 50 μl/well and incubated at 4° C. overnight. The plates were then washed 3 times with PBS-0.05% Tween. The plates were blocked by adding in PBS-0.05% Tween 1% BSA followed by a 30 minute incubation at 37° C.

Dilutions of immunoglobulin polypeptides were prepared in PBS-0.05% Tween, 1% BSA solution. Two- or three-fold serial dilutions were prepared and added (100 μl/well) in duplicate or triplicate. After a 90 minute incubation at 37° C., the microplate was washed 3 times with PBS-0.05% Tween. For signal development, goat anti-human IgG (gamma- or Fc-specific) secondary antibody conjugated to peroxidase was added to each well and incubated for 60 minutes at 37° C. followed by addition of OPD at 0.4 mg/ml in citrate buffer plus 0.012% $H_2O_2$. After 5-10 minutes at room temperature, the assay was stopped by the addition of 100 µl 1M H$_2$SO$_4$ and the plates were read at 490 nm. Both goat and anti-human IgG (gamma-specific) and goat anti-human IgG (Fc-specific) antibodies have been employed. Results of the direct binding ELISA for human engineered (low risk) ING-1 on soluble Ep-CAM is shown in FIG. 28.

EXAMPLE 13

Construction of Additional Expression Vectors

This example describes the construction of expression vectors that comprise multiple copies of additional exemplary transcription units. Exemplary vector constructs are also described comprising multiple copies of exemplary gene sequences encoding polypeptides of interest, for example additional immunoglobulin gene sequences including light and/or heavy chain sequences.

Figure 29:
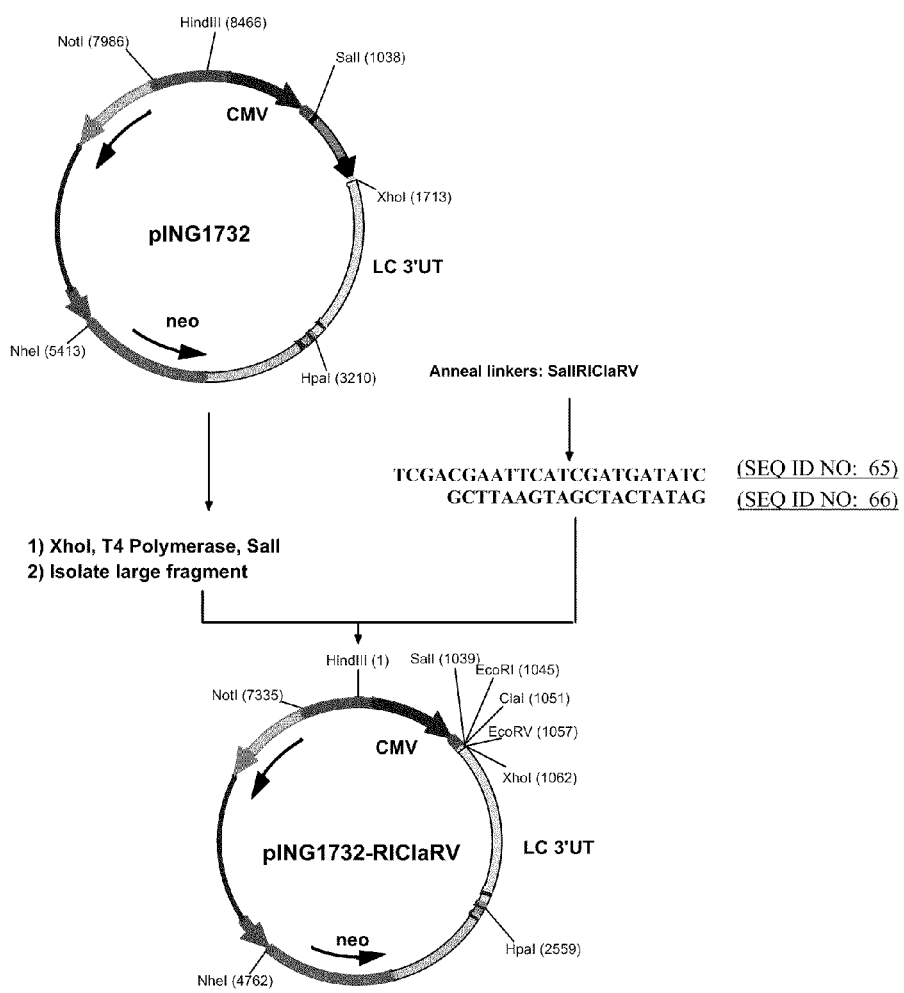
FIG. 29 depicts a construction map for vector pING1732-R1ClaRV.
Figure 30:
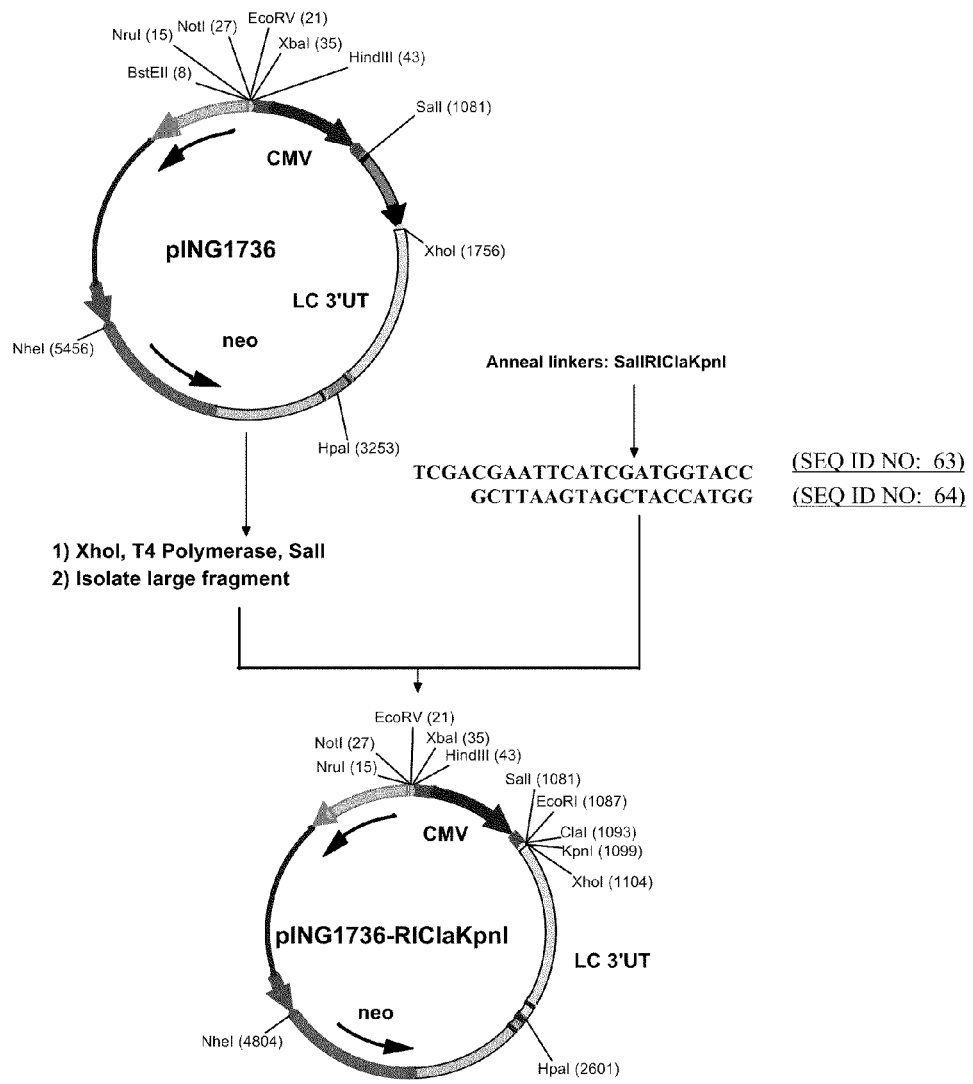
FIG. 30 depicts a construction map for vector pING1736-R1Cla Kpnl.

To facilitate cloning of additional genes into exemplary expression vectors useful according to the invention, modular expression vectors containing a multicloning site between a CMV promoter and a light chain 3' untranslated region were constructed. A polylinker, assembled from two complementary DNA oligonucleotides (pING1736 polylinker 5'TCGACGAATTCATCGATGGTACC3' (SEQ ID NO: 63) and 3'GCTTAAGTAGCTACCATGG5' (SEQ ID NO: 64)) (pING1732 polylinker 5'TCGACGAATTCATCGATGATATC3' (SEQ ID NO: 65)) and 3'GCTTAAGTAGCTACTATAG5' (SEQ ID NO: 66)) which when annealed form a duplex insert containing several unique sites (SalI, EcoRI, ClaI, EcoRV for pING1732 and SalI, EcoRI, ClaI, KpnI for pING1736) and overhangs for cloning into two separate vectors, pING1732 and pING1736, each containing a neo gene for selection of G418-resistant clones. Both pING1732 and pING1736 were first digested with XhoI, treated with T4 polymerase and then the linear vectors digested a second time with SalI. The purified linear vectors and the polylinker inserts were purified and ligated. As shown in FIGS. 29 and 30, the two resultant vectors, pING1732-RIClaRV and pING1736-RIClaKpnI, are designed with several unique restriction sites between the 3' end of the promoter/splice region and the 5' end of the polyadenylation region and useful for expression of any inserted gene encoding a polypeptide of interest.

Figure 31:
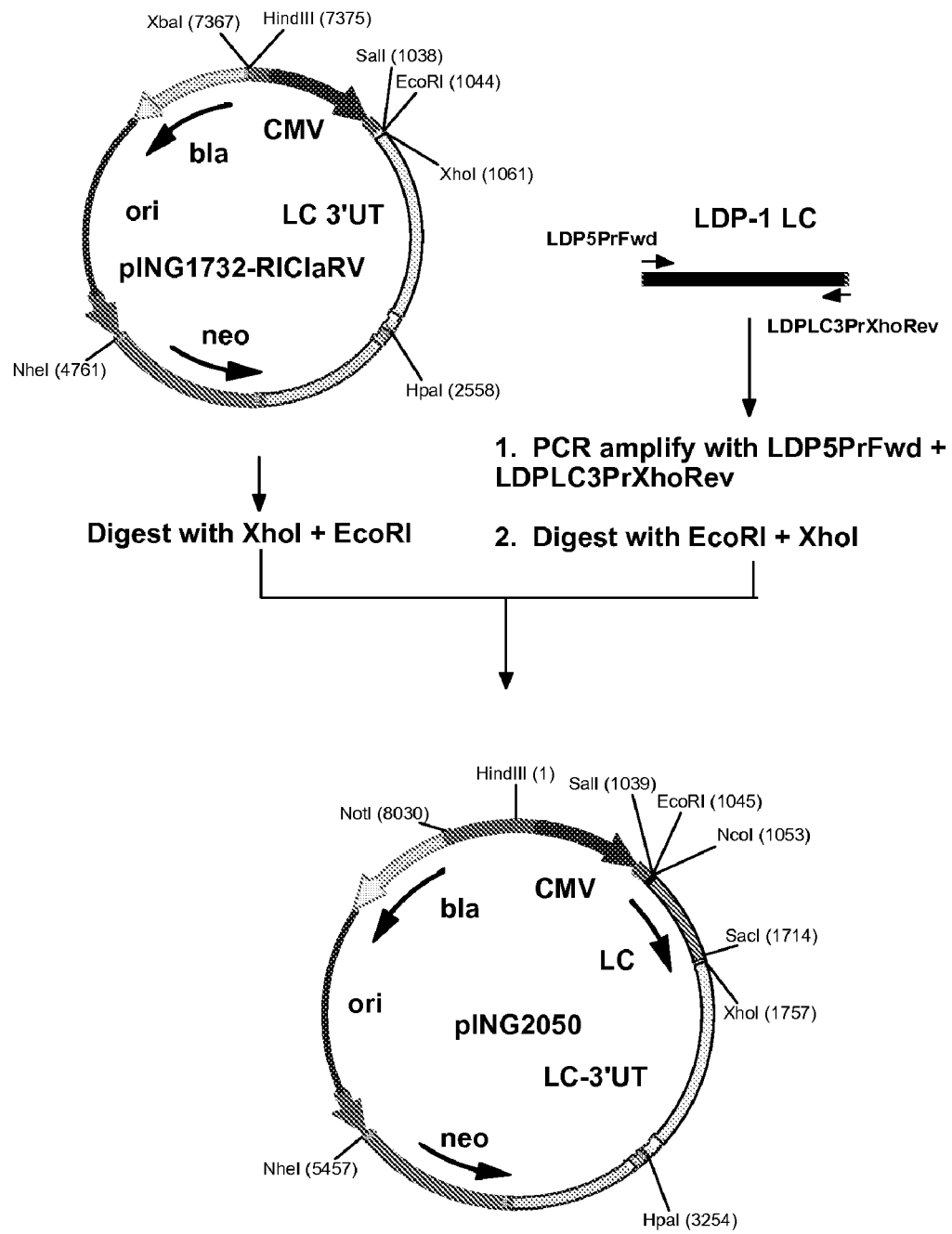
FIG. 31 depicts a construction map for vector pING2050.
Figure 32:
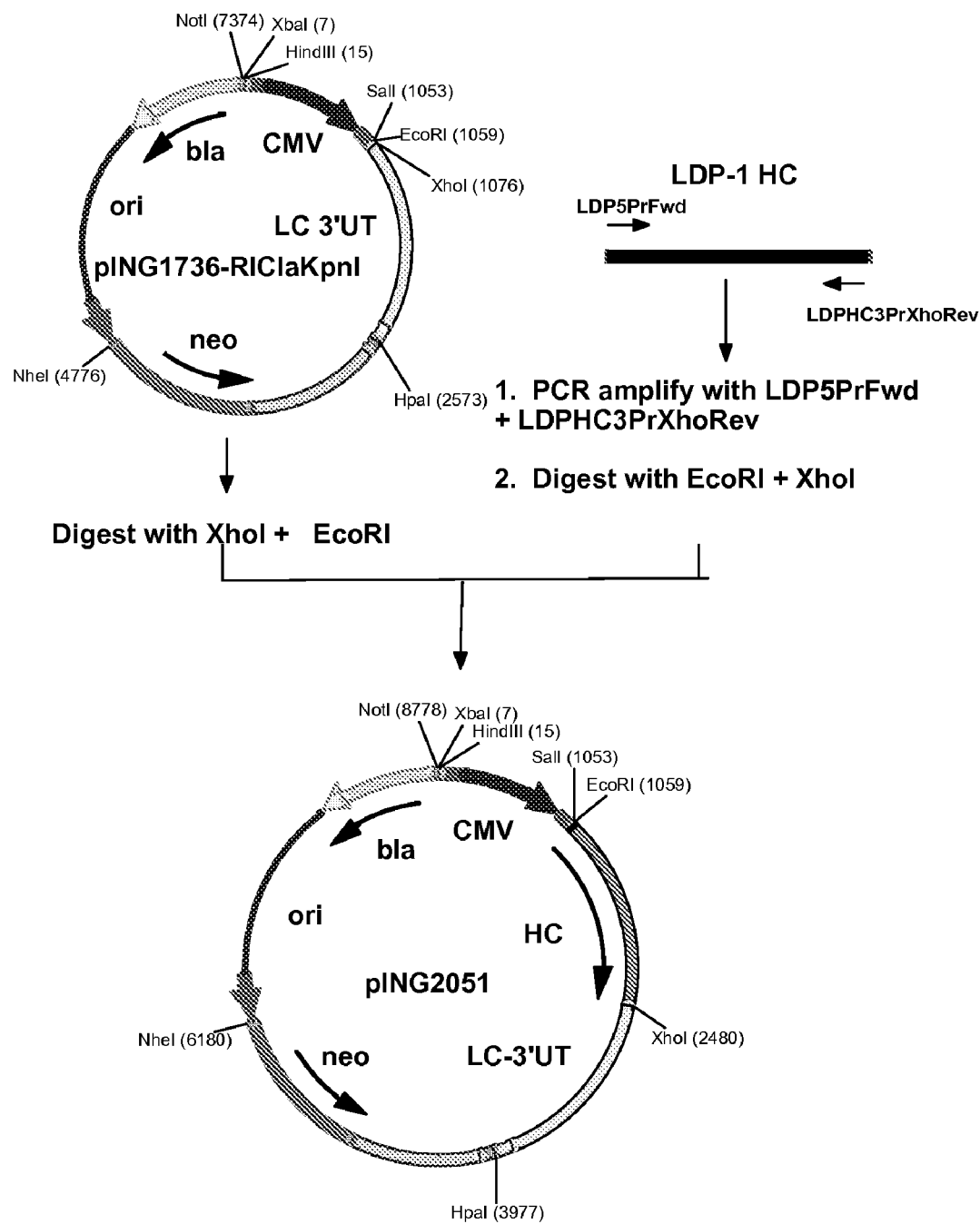
FIG. 32 depicts a construction map for vector pING2051.

Light and heavy chains from a humanized antibody against CD18 (see, U.S. Pat. Nos. 5,985,279 and 5,997,867) were cloned as shown in FIGS. 31 and 32 into pING1732-RIClaRV and pING1736-RIClaKpnI, respectively, by PCR from a vector having light and heavy chain genes. A new light chain vector, designated pING2050, was prepared as outlined in FIG. 3, and was constructed by first digesting the vector pING1732-RIClaRV with XhoI and EcoRI followed by purification of the linear vector. A gene encoding an anti-CD18 light chain (designated LDP-1 LC in FIG. 31; SEQ ID NOS: 67 and 68), was then amplified by PCR from a vector having that gene employing a forward primer LDP5PrFwd (5'TGTATTGAATTCACCATGGGATGGAGCTG 3'; SEQ ID NO: 69) and a reverse primer LDPLC3PrXhoRev (sequence=5'GATAACTCGAGCTAACACTCTCCCCTGTTG 3' (SEQ ID NO: 70)). The resultant PCR product was then purified, digested with the restriction enzymes EcoRI and XhoI, and ligated with the pING1732-RIClaRV made linear by digestion with EcoRI and XhoI. The resulting light chain vector was designated pING2050 as shown in FIG. 31.

A new heavy chain vector, designated pING2051, was prepared as outlined in FIG. 32. The vector pING1736-RIClaKpnI was first digested with XhoI and EcoRI followed by purification of the linear vector. A gene encoding an anti-CD18 heavy chain (designated LDP-1 HC in FIG. 32; SEQ ID NOS: 71 and 72) was then amplified by PCR from a vector having that gene employing a forward primer LDP 5PrFwd (5'TGTATTGAATTCACCATGGGATGGAGCTG3'; SEQ ID NO: 73) and a reverse primer LDPLX3PrXhoRev (5'CTTATCTCGAGTCATTTACCCGGAGACAGG3' (SEQ ID NO: 74)). The resultant PCR product was then purified, digested with the restriction enzymes EcoRI and XhoI, and ligated with the pING1736-RIClaKpnI made linear by digestion with EcoRI and XhoI. The resulting heavy chain vector was designated pING2051 as shown in FIG. 32. The DNA sequences of the light and heavy chain genes in pING2050 and pING2051, respectively, were verified by DNA sequence analysis. The light and heavy chain DNA and amino acid sequences are shown in FIGS. 33 (SEQ ID NOS: 64 and 70) and 34 (SEQ ID NOS: 68 and 72), respectively.

Figure 35:
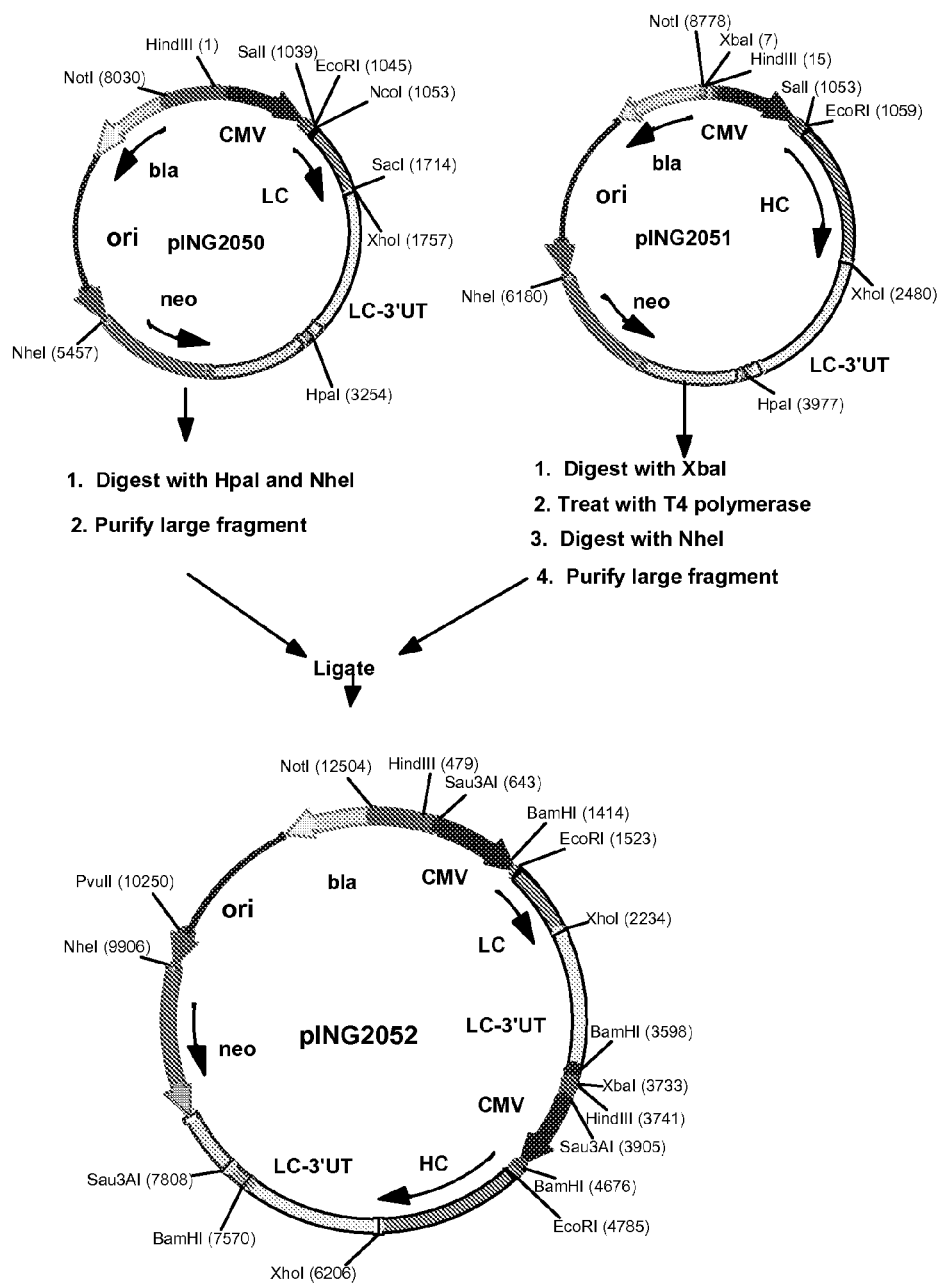
FIG. 35 depicts a construction map for vector pING2052.

The ping2052 a vector comprising anti-CD18 light plus heavy chain genes and a neo gene encoding resistance to G418 was constructed as shown in FIG. 35. The vector pING2050 was first digested with the restriction enzymes HpaI and NheI, and the large linear vector fragment purified. The vector pING2051 was digested with XbaI, blunt ended by treatment with T4 polymerase, digested with NheI, followed by purification of the large linear vector fragment. Both the pING2050 and pING2051 digested and purified vectors were then ligated to form a light plus heavy chain expression vector pING2052, which contains a neo gene encoding resistance to G418. As shown in FIG. 35, the pING2052 vector contains several unique restriction sites for generation of linear DNA in preparation for transfection. The features of pING2052 are summarized in Table 2.

TABLE 2

Description of pING2052 vector.

| Plasmid region | Start nt | End nt | Description |
|---|---|---|---|
| NotI-HindIII | 1 | 479 | =pUC12 2616-399 (includes pBR322 4291-4361, 2069-2354 and part of lac gene) |
| HindIII-1/2BamHI (Sau3AI) | 479 | 643 | upstream region of Abelson murine leukemia virus 3' LTR enhancer/promoter (=4627-4804 of Reddy et al., 1983 sequence; ref 5) |
| 1/2HincII-BamHI | 643 | 1414 | hCMV promoter (=−598 to 174 of Boshart et al., ref 1; includes splice donor) |
| BamHI-EcoRI | 1414 | 1523 | SV40 16S splice acceptor (1421-1509 = SV40 1410-1497) |
| EcoRI-XhoI | 1523 | 2234 | LDP-01 light chain gene |
| XhoI-BamHI | 2234 | 3598 | LC genomic DNA including poly A site |
| BamHI-1/2HpaI (XbaI-HindIII) | 3598 | 3741 | portion of SV40 polyadenylation (=SV40 2532-2668) |

TABLE 2-continued

Description of pING2052 vector.

| Plasmid region | Start nt | End nt | Description |
| --- | --- | --- | --- |
| HindIII-1/2BamHI (Sau3AI) | 3741 | 3905 | upstream region of Abelson murine leukemia virus 3' LTR enhancer/promoter (=4627-4804 of Reddy et al, 1983 sequence; ref 5) |
| 1/2HincII-BamHI | 3905 | 4676 | hCMV promoter, including splice donor |
| BamHI-EcoRI | 4676 | 4785 | SV40 16S splice acceptor |
| EcoRI-XhoI | 4785 | 6206 | LDP-01 heavy chain gene |
| XhoI-BamHI | 6206 | 7570 | LC genomic DNA including poly A site |
| BamHI-1/2BclI (Sau3AI) | 7570 | 7808 | SV40 polyadenylation (=SV40 2532-2774) |
| 1/2BstYI(Sau3AI)-NS[a] | 7808 | 8415 | SV40 small T intron (=SV40 4769-4099) |
| 1/2 SalI-NheI | 8415 | 9927 | bacterial neomycin phoshotransferase (neo) gene from pSV2neo (coding region = 9583-8761) |
| NheI-PvuII | 9927 | 10250 | SV40 promoter (=SV40 5172-272) |
| PvuII-NotI | 10250 | 12504 | bacterial origin of replication and beta-lactamase (ampicillin resistance) gene (=pBR322 2069-4290) |

[a]NS - restriction site not identified.

Figure 36:
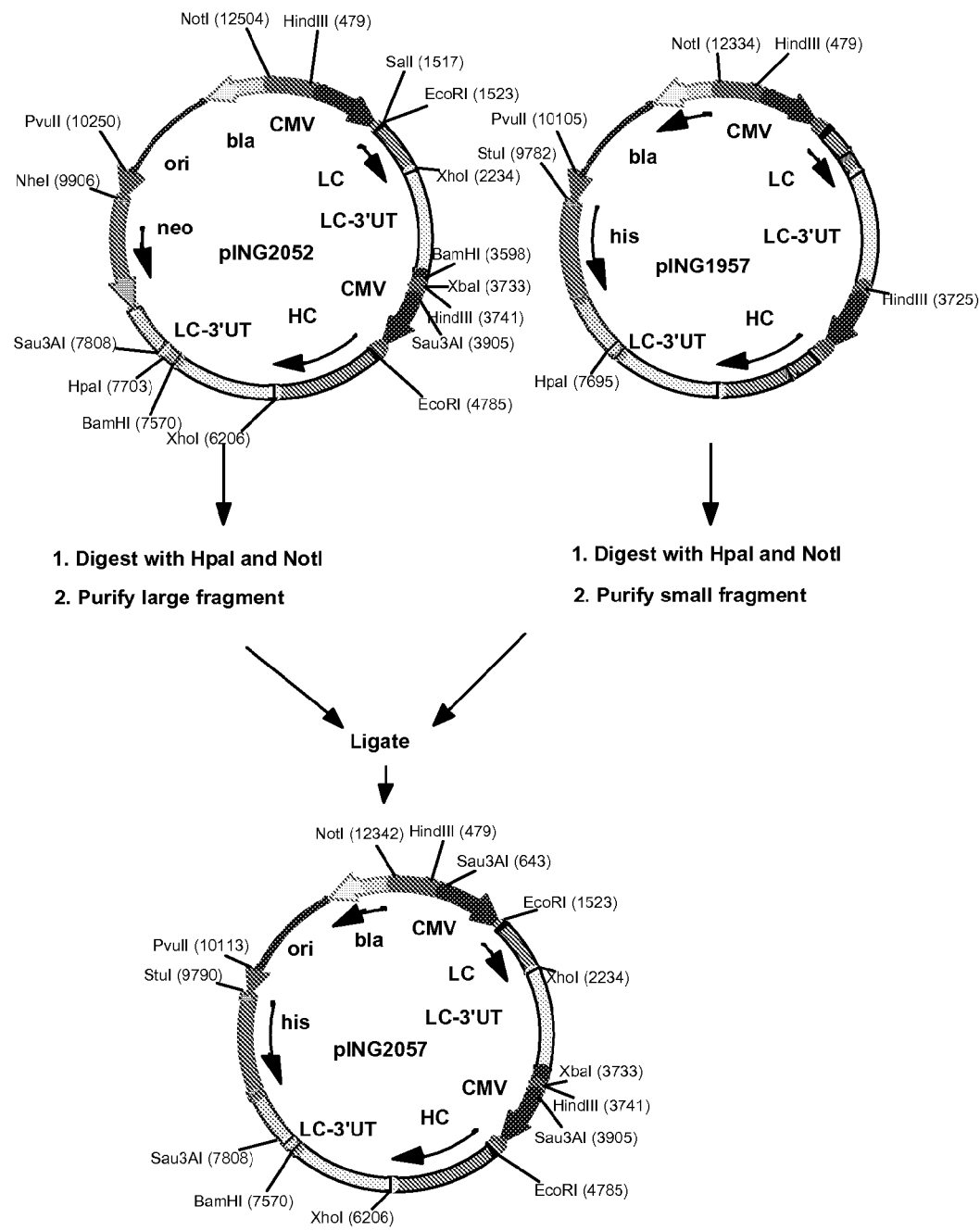
FIG. 36 depicts a construction map for vector pING2057.

A second anti-CD18 light plus heavy chain expression vector, pING2057, containing a his gene for selection of histidinol-resistant transfectants, was also constructed by exchanging the neo gene in pING2052 with a his gene from pING1957 (described in Example 6 and FIG. 18). The vector pING2052 was first digested with the restriction enzymes HpaI and NotI followed by purification of the large linear vector fragment. The vector pING1957 was then digested with HpaI and NotI followed by purification of the smaller his gene fragment. The linear vector pING2052 and his gene fragments were then ligated to form a light plus heavy chain expression vector pING2057 as shown in FIG. 36, which contains a his gene for selection of histidinol-resistant transfectants. The features of pING2057 are summarized in Table 3.

EXAMPLE 14

Development and Characterization of Additional Transfected Clones and Cell Lines This example describes the development and characterization of additional clones and cell lines transfected with additional exemplary vectors according to the present invention, the development and characterization of additional immunoglobulin producing cell lines is described from transfections with vectors, including multigene vectors, as described in Example 13.

Cell lines were developed by electroporation of Ex-Cell 301-adapted CHO-K1 cells. Prior to transfection, the anti-CD18 light plus heavy chain neo vector, pING2052, was

TABLE 3

Description of pING2057 vector.

| Plasmid region | Start nt | End nt | Description |
| --- | --- | --- | --- |
| NotI-HindIII | 1 | 479 | =pUC12 2616-399 (includes pBR322 4291-4361, 2069-2354 and part of lac gene) |
| HindIII-1/2BamHI (Sau3AI) | 479 | 643 | upstream region of Abelson murine leukemia virus 3' LTR enhancer/promoter (=4627-4804 of Reddy et al., 1983 sequence; ref 5) |
| 1/2HincII-BamHI | 643 | 1414 | hCMV promoter (=−598 to 174 of Boshart et al., ref 1; includes splice donor) |
| BamHI-EcoRI | 1414 | 1523 | SV40 16S splice acceptor (1421-1509 = SV40 1410-1497) |
| EcoRI-XhoI | 1523 | 2234 | LDP-01 light chain gene |
| XhoI-BamHI | 2234 | 3598 | LC genomic DNA including poly A site |
| BamHI-1/2HpaI (XbaI-HindIII) | 3598 | 3741 | Part of SV40 polyadenylation (=SV40 2532-2668) |
| HindIII-1/2BamHI (Sau3AI) | 3741 | 3905 | upstream region of Abelson murine leukemia virus 3' LTR enhancer/promoter (=4627-4804 of Reddy et al., 1983 sequence; ref 5) |
| 1/2HincII-BamHI | 3905 | 4676 | hCMV promoter, including splice donor |
| BamHI-EcoRI | 4676 | 4785 | SV40 16S splice acceptor |
| EcoRI-XhoI | 4785 | 6206 | LDP-01 heavy chain gene |
| XhoI-BamHI | 6206 | 7570 | LC genomic DNA including poly A site |
| BamHI-1/2BclI (Sau3AI) | 7570 | 7808 | SV40 polyadenylation (=SV40 2532-2774) |
| 1/2BstYI (Sau3AI)-NS[a] | 7808 | 8415 | SV40 small T intron (=SV40 4769-4099) |
| 1/2 SalI-StuI | 8415 | 9790 | bacterial histidine (his) gene from pSV2his (coding region = 9760-8458) |
| StuI-PvuII | 9790 | 10113 | SV40 promoter (=SV40 5172-272) |
| PvuII-NotI | 10113 | 12342 | bacterial origin of replication and beta-lactamase (ampicillin resistance) gene (=pBR322 2069-4290) |

Figure 37:
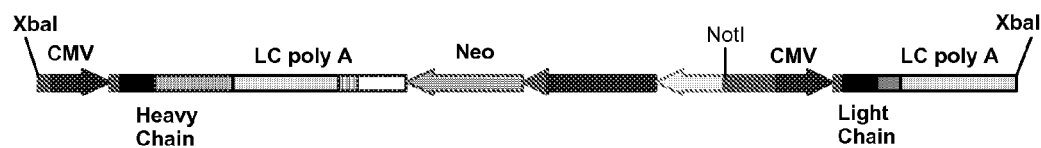
FIG. 37 shows the structure of vector pING2052 linearized with XbaI.

[a]NS - restriction site not identified.

linearized with XbaI as shown in FIG. 37. Forty µg of linearized DNA typically was used in conjunction with ~1×10$^7$ cells for transfection by electroporation. At least 3 electroporations were performed on any given day (for a total of ~120 µg DNA used with ~3×10$^7$ cells). Following a 2 day recovery period in non-selective Ex-Cell 301 medium supplemented with 2% FBS and 50 µg/ml gentamicin, the cells were plate at ~4000 cells/well (200 µL/well) in 96 well plates in Ex-Cell 301 medium supplemented with Glutamine/Penicillin/Streptomycin, 1% FBS and with 0.8 mg/mL G418 sulfate; Geneticin® (Invitrogen, Carlsbad, Calif. _____) for transfectants with neo vectors. The plates were incubated at 37° C. in a $CO_2$ incubator. Starting at days 10-12, the 96 well plates were scanned for wells containing single clones and the supernatants were sampled and screened by ELISA.

For the ELISA, culture supernatants from 96 or 24 well plates or from shake flasks were pipetted into 96 well dilution plates containing PBS, 1% BSA and 0.05% Tween 20 and stored overnight at 4° C. The supernatants were assayed for levels of immunoglobulin polypeptides by ELISA using Immulon 4 plates precoated overnight at 4° C. with an anti-Human IgG gamma coating antibody (Anti-Human IgG, Fd Fragment, Catalog No. 411411 or Anti-Human IgG, J Chain, Catalog No. 401441, Calbiochem, San Diego, Calif.). Following a blocking step with PBS containing 1% BSA and 0.05% Tween 20, the diluted supernatants were added to the plates. After incubation at room temperature for 1 hour on a plate shaker, the plates were washed three times with PBS supplemented with 0.05% Tween. A biotinylated anti-Human Kappa-specific secondary antibody (Pierce, Rockford, Ill., Product No. 31780) was added and the plates were incubated for 30 minutes at room temperature on a plate shaker. After additional washes, Extravidin (Sigma Chemical Co., St. Louis, Mo.) was added and the plates incubated for 30 minutes. Detection was performed with a KPL/ABTS system (KPL, Gaithersburg, Md.). After color development, the reaction was stopped by adding an equal volume of KPL stop buffer. Plates were read at 405 nm and concentrations were calculated using a program with a 4 parameter curve fit.

A total of 3-4 ELISAs were performed over ~17 days for any given transfection. Clones secreting immunoglobulin polypeptides above an established level were transferred to 24 well plates and when confluent, replica 24 well plates were prepared. Screening was performed by ELISA on the original 24 well plate cultures once they reached extinction at ~14 days post plating. The top-producing clones in 24 well plates were transferred to 6 well plates and then to shake flasks. CHO-K1 transfectants were inoculated into 25 mL Ex-Cell 301 medium in 125 mL shake flasks at ~1-2×10$^5$ cells per mL, depending on the assay. Ex-Cell 301 media was supplemented with Glutamine/Penicillin/Streptomycin as described above. Selective agents generally were not incorporated into media used for the shake flask tests except in cases in which maintenance cultures were allowed to incubate to extinction. The cells were incubated at 37° C., 100 RPM until viability was ≦20% (usually ~14 days). For growth and productivity experiments, viable cell density was determined either by hemocytometer and/or with the Guava flow cytometer (Guava Technologies, Inc., Burlingame, Calif. 94010) every 2 to 4 days. For studies in which the viable cell density was not determined, the flasks were opened and swirled in the biosafety hood every 2 to 3 days to provide some gas exchange. At the end of the incubation period, cells were removed by centrifugation and supernatants were assayed for immunoglobulin polypeptide concentration by ELISA. The highest producers identified by ELISA also were assayed by Protein A HPLC. For the Protein A HPLC, concentrations of immunoglobulin polypeptides in samples from transfectants were determined using a Shimadzu LC-10A HPLC System (Torrance, Calif.) and a Perceptive Biosystems' Protein A column (Albertville, Minn.; Poros A affinity, 20 µm, A/M, 4.6×100 mm, Catalog number 1-5022-26). HPLC Buffer A was phosphate buffered saline (PBS) at pH 7.2 and HPLC Buffer B was 0.1 M glycine/2% acetic acid, pH 3.0. The flow rate of the column was 4.0 ml/minute and the gradient was as follows: 100% A at 0-3 minutes; 100% B at 3.1-5 minutes; and 100% A at 5.1-8 minutes, with detection at 280 nm.

Three independent sets of transfections each consisting of three electroporations were performed using the neo vector, pING2052. A total of 3564 clones were screened from the 96 well plates. Of these clones, 471 were transferred from 96 well to 24 well plates and extinct cultures were screened by ELISA. The top 80 clones were transferred to shake flasks and extinct cultures were screened by ELISA and for some of the top clones, by Protein A HPLC. The results for the top 8 clones demonstrated that Clone 128D12 appeared to be the highest producer in Ex-Cell 301 medium with 14 day (extinct) shake flask productivities (determined by HPLC) of 134, 89, 157, and 127 µg/mL. Productivities determined by ELISA appeared to be up to ~2-fold higher than those obtained by HPLC.

Six of the top clones were evaluated in a growth and productivity test in 125 mL shake flasks. The cultures were inoculated at 1×10$^5$ cells/mL in Ex-Cell 301 medium and incubated for 13 days. The results as shown in FIG. 38 demonstrated that Clone 128D12 was an optimal clone with respect to both growth and productivity. Cells containing only the neo selective marker were grown in the presence of a maintenance level of G418.

EXAMPLE 15

Increasing Expression through a Second Sequential Vector Transfection: Development and Characterization of Additional Transfected Clones and Cell Lines This example describes a further increase in expression and production of polypeptides, including additional immunoglobulins, through a second transfection of an exemplary cell line with a second multi-transcription unit vector.

The top-producing clone, Clone 128D12, selected from transfections with pING2052, the anti-CD18 light plus heavy chain neo vector as described in Example 13 above, were re-transfected with the pING2057 his vector also described in Example 13 above. For example, Clone 128D12 was re-transfected with pING2057 in two sets of transfections (3 electroporations per set). In preparation for transfection, vector pING2057 was made linear by digestion with XbaI. A total of 1101 clones from 96 well plates were screened by ELISA. The top 218 clones were transferred to 24 well plates and extinct replica cultures were screened by ELISA. The top 8 clones expressed immunoglobulin polypeptides at levels up to ~3-fold higher than Clone 128D12 at the 24 well stage of screening. The top 120 clones were transferred to shake flasks. The top 10 clones secreted up to ~290 µg/mL in extinct shake flask cultures in Ex-Cell 301 medium. Cells containing both neo and his selective markers were grown in the presence of a maintenance levels of geneticin and histidinol.

Clones 264E2, 254G12, 257G8, 262E8, 259B6, and 253E10 secreted from 250-290 µg/ml in shake flasks, with Clone 264E2 selected as a top producer. Clone 264E2, in several shake flash tests in Ex-Cell 301 medium produced ~1.5 to greater than 2 times as much immunoglobulin POLYPEPTIDE as Clone 128D12 as measured by Protein A-HPLC.

EXAMPLE 16

Polypeptide Expression in Several Commercially Available Media

This example describes the use of a number of additional cell culture media. A number of chemically-defined and/or animal-product free media have been designed for high protein production in CHO cells and are commercially available. Four such media were utilized for culture of transfectants, including ProCHO3, ProCHO4 and ProCHO5, produced by BioWhittaker, now known as Cambrex (Catalog No. 12-762Q, 12-029Q, and 12-766Q, respectively) and HyQ-PFCHO, produced by HyClone (Catalog No. SH30359.02). Each of these media was supplemented with Glutamine/Penecillin/Streptomycin and selective agents (e.g., G418 Geneticin® and/or histidinol). Shake flask tests were performed in the absence of selective agents. Titers were determined by Protein A HPLC on Day 14 or when culture viability dropped below 20%.

Clones 264E2 and 254G12, both Clone 128D12 re-transfectants, were passaged directly into these media and after a period of adaptation, production was assessed in shake flask tests. The cells readily adapted to all of these media where they grew quickly and to high cell densities (3-4 million cells/mL). The results of four Clone 254G12 or five Clone 264E2 sequential shake flask tests in ProCHO4 and ProCHO5 as shown in FIG. 39 demonstrate that Clone 264E2 expressed at up to ~400 µg/ml in ProCHO4 and ProCHO5 while Clone 254G12 expressed up to ~340 µg/ml in each of these media. The titers in HyQ and ProCHO3 media were lower than those in the other commercial media. For instance, in ProCHO3, Clone 264E2 produced 321 µg/mL and Clone 254G12 produced 252 µg/mL whereas in HyQ, Clone 264E2 produced 146 µg/mL and Clone 254G12 produced 140 µg/mL. A variety of cell culture media is useful for transfectants, including clones and cell lines obtained as described herein.

EXAMPLE 17

Construction of Additional Expression Vectors

Figure 40:
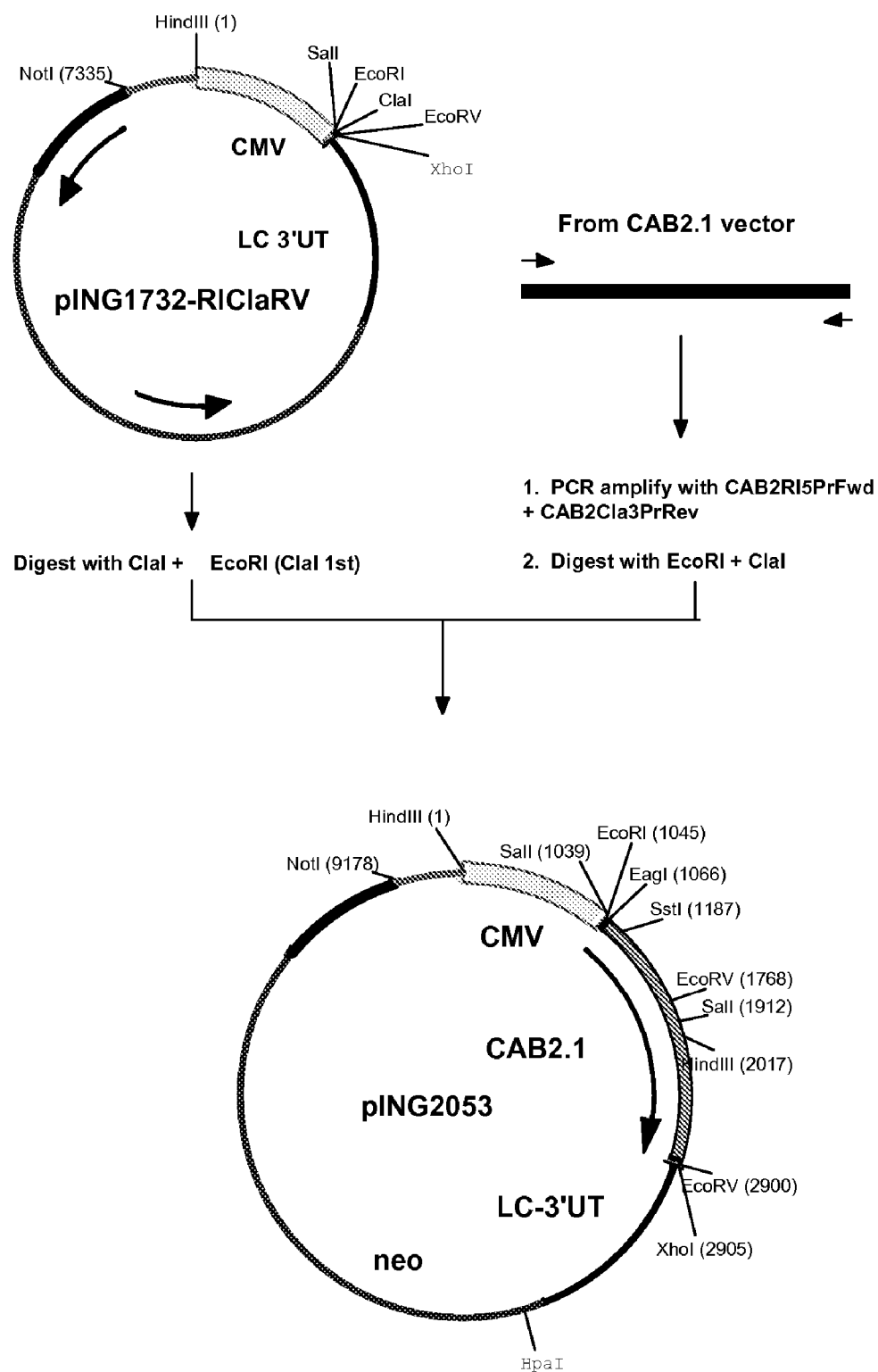
FIG. 40 depicts a construction map for vector pING2053.
Figure 41:
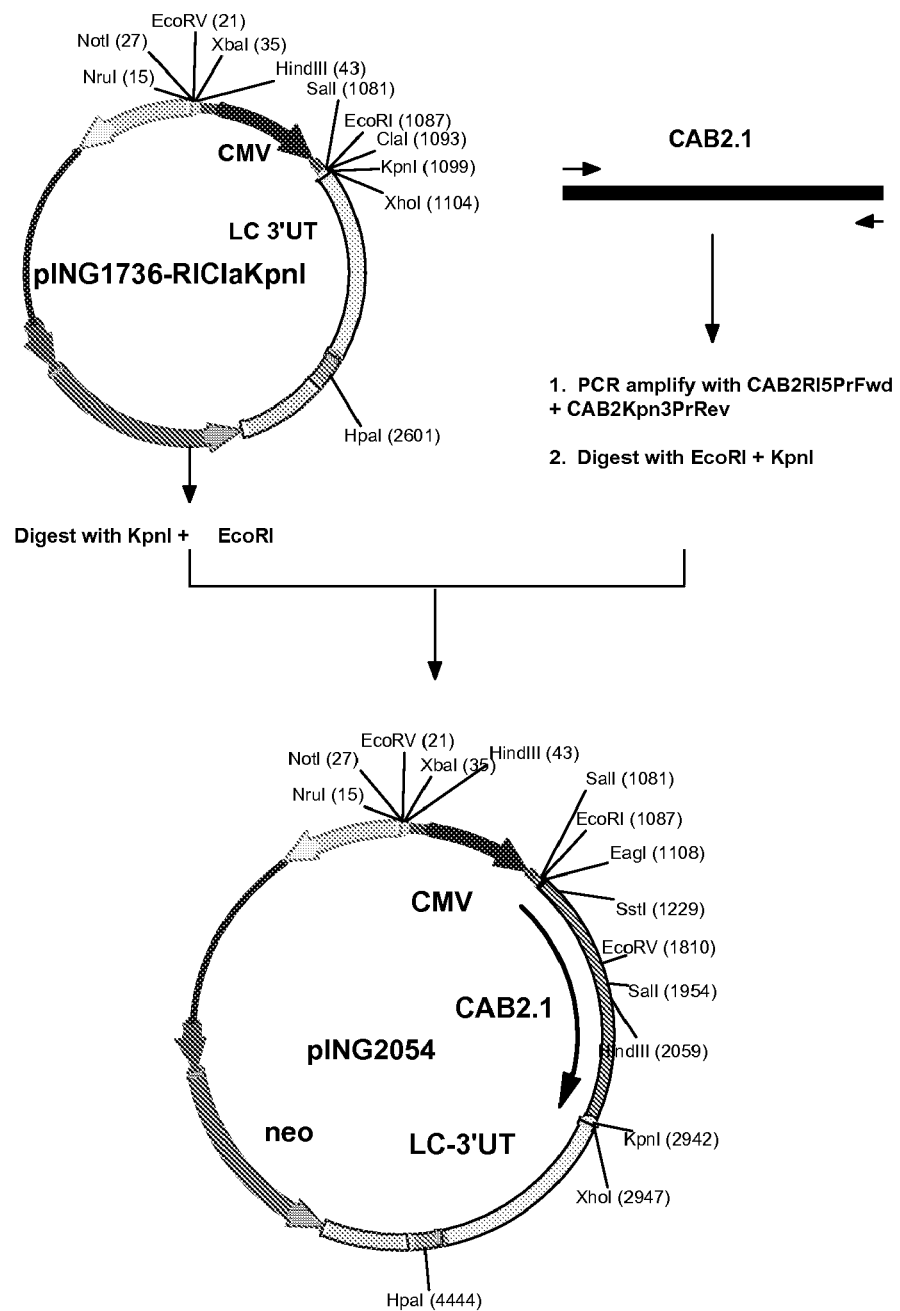
FIG. 41 depicts a construction map for vector pING2054.

This example describes the construction of expression vectors that contain multiple copies of additional exemplary transcription units. Exemplary vector constructs are also described containing multiple copies of exemplary gene sequences encoding polypeptides of interest, for example, polypeptides with complement inhibitory activities including chimeric or fusion proteins with such activities. Several modular expression vectors that contain a multicloning site between a CMV promoter and a light chain 3' untranslated region were constructed as described in Example 13 and utilized for the construction of additional expression vectors encoding complement inhibitory proteins. These expression vectors, pING1732-RIClaRV and pING1736-RIClaKpnI, are shown in FIGS. 29 and 30. A vector containing a CAB2.1 gene (see FIG. 1 of U.S. Pat. No. 6,316,253; SEQ ID NOS: 76 and 77) was cloned by PCR into the multiple cloning site of the neo (G418-resistance) expression vectors pING1732-RIClaRV and pING1736-RIClaKpnI as shown in FIGS. 40 and 41 respectively. The resulting CAB 2.1-containing vectors were designated pING2053 as shown in FIG. 40 and pING2054 as shown in FIG. 41. As shown in FIG. 40, pING2053 was constructed by first digesting the vector pING1732-RIClaRV with the restriction enzyme ClaI followed by digestion with the restriction enzyme EcoRI. Next, the gene encoding CAB2.1 was then amplified by PCR employing a forward primer CAB2RI5PrFwd (5'GTTAA-GAATTCCACCATGGAGCCTCCCGG3' (SEQ ID NO: 78) and a reverse primer CAB2Cla3PrRev 3'GAAGTCCAT-GATGGGCAACTTAGCTAAATCT5' (SEQ ID NO: 79). the resultant PCR product was then purified, digested with the restriction enzymes EcoRI and ClaI, and ligated with the pING1732-RIClaRV made linear by digestion with EcoRI and ClaI to form a CAB2.1 vector, pING2053, comprising a CAB2.1 gene (SEQ ID NO: 76).

An additional CAB2.1 single gene expression vector, designated pING2054, was prepared as shown in FIG. 41. The vector pING1736-RIClaKpnI was first digested with KpnI and EcoRI followed by purification of the linear vector. A gene encoding CAB2.1 was then amplified by PCR employing the forward primer CAB2RI5PrFwd as described above (SEQ ID NO: 78) and the reverse primer CAB2.1Kpn3PrRev (3'GAAGTCCATCATGGGCAACTCCATGGAATCT5' SEQ ID NO: 80). The resultant PCR product was then purified, digested with the restriction enzymes EcoRI and KpnI, and ligated with the pING1736-RIClaKpnI made linear by digestion with EcoRI and KpnI. This additional vector comprising CAB2.1 gene (SEQ ID NO: 76) was designated pING2054 as shown in FIG. 41. The features of pING2054 are summarized in Table 4.

TABLE 4

Description of pING2054.

| Plasmid region | Start nt | End nt | Description |
| --- | --- | --- | --- |
| NotI-HindIII | 1 | 16 | Part of multilinker site |
| HindIII-1/2BamHI (Sau3AI) | 16 | 179 | upstream region of Abelson murine leukemia virus 3' LTR enhancer/promoter (=4627-4804 of Reddy et al., (1983) sequence) |
| 1/2HincII-BamHI | 179 | 951 | hCMV promoter (=−598 to 174 of Boshart et al., Cell 41: 521-530 (1985) includes splice donor) |
| BamHI-EcoRI | 951 | 1060 | SV40 16S splice acceptor (=SV40 1410-1497) |
| EcoRI-KpnI | 1060 | 2910 | CAB2.1 gene |
| XhoI-BamHI | 2910 | 4275 | LC genomic DNA including poly A site |
| BamHI-1/2BclI (Sau3AI) | 4275 | 4512 | SV40 polyadenylation (=SV40 2532-2774) |
| 1/2BstYI(Sau3AI)-NS[a] | 4512 | 5123 | SV40 small T intron (=SV40 4769-4099) |
| 1/2 SalI-NheI | 5123 | 6611 | bacterial neomycin phoshotransferase (neo) gene from pSV2neo (coding region = 9583-8761) |
| NheI-PvuII | 6611 | 6951 | SV40 promoter (=SV40 5172-272) |
| PvuII-NotI | 6951 | 9910 | bacterial origin of replication and beta-lactamase (ampicillin resistance) gene (=pBR322 2069-4290) |

[a]NS - restriction site not identified.

Figure 42:
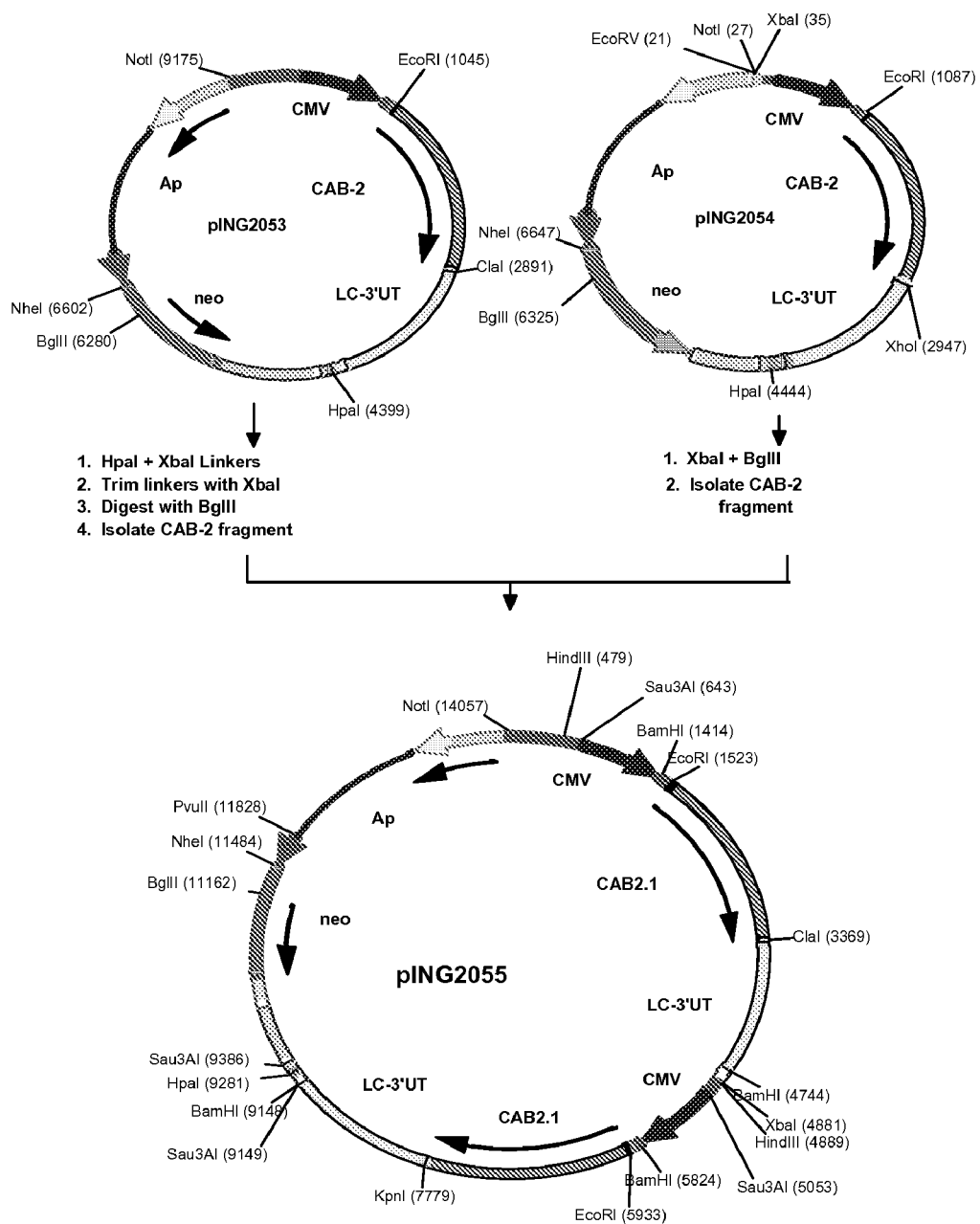
FIG. 42 depicts a construction map for vector pING2055.

An additional vector with two copies of a CAB 2.1 gene, designated pING2055, with a neo gene for selection of G418-resistant transfectants was constructed as shown in FIG. 42. The vector pING2053 was first digested with the restriction enzyme HpaI blunt-end ligated to XbaI linkers and the linkers were trimmed with XbaI. The DNA was then digested with BglII and the large linear vector fragment comprising a CAB2.1 gene was purified. The vector pING2054 was digested with XbaI and BglII followed by purification of the large linear vector fragment with a CAB2.1 gene. Both the pING2053 and pING2054 digested and purified fragments were then ligated to form the two-gene expression vector pING2055 as shown in FIG. 42. The features of pING2055 are summarized in Table 5.

TABLE 5

Description of pING2055.

| Plasmid region | Start nt | End nt | Description |
| --- | --- | --- | --- |
| NotI-HindIII | 1 | 479 | =pUC12 2616-399 (includes pBR322 4291-4361, 2069-2354 and part of lac gene) |
| HindIII-1/2BamHI (Sau3AI) | 479 | 643 | upstream region of Abelson murine leukemia virus 3' LTR enhancer/promoter (=4627-4804 of Reddy et al., Proc Natl. Acad. Sci (USA) 80: 3623-3627 (1983) |
| 1/2HincII-BamHI | 643 | 1414 | hCMV promoter (=−598 to 174 of Boshart et al., Cell 41: 521-530 (1985) includes splice donor) |
| BamHI-EcoRI | 1414 | 1523 | SV40 16S splice acceptor (1421-1509 = SV40 1410-1497) |
| EcoRI-ClaI | 1523 | 3369 | CAB2.1 gene |
| ClaI-BamHI | 3369 | 4744 | LC genomic DNA including poly A site |
| BamHI-1/2HpaI (XbaI-HindIII) | 4745 | 4889 | portion of SV40 polyadenylation (=SV40 2532-2668) |
| HindIII-1/2BamHI (Sau3AI) | 4889 | 5053 | upstream region of Abelson murine leukemia virus 3' LTR enhancer/promoter (=4627-4804 of Reddy et al., Proc Natl. Acad. Sci (USA) 80: 3623-3627 (1983) |
| 1/2HincII-BamHI | 5053 | 5825 | hCMV promoter, including splice donor |
| BamHI-EcoRI | 5825 | 5934 | SV40 16S splice acceptor |
| EcoRI-XhoI | 5933 | 7779 | CAB2.1 gene |
| XhoI-BamHI | 7779 | 9149 | LC genomic DNA including poly A site |
| BamHI-1/2BclI (Sau3AI) | 9149 | 9386 | SV40 polyadenylation (=SV40 2532-2774) |
| 1/2BstYI(Sau3AI)-NS[a] | 9386 | 9997 | SV40 small T intron (=SV40 4769-4099) |
| 1/2 SalI-NheI | 9997 | 11485 | bacterial neomycin phoshotransferase (neo) gene from pSV2neo (coding region = 9583-8761) |
| NheI-PvuII | 11485 | 11831 | SV40 promoter (=SV40 5172-272) |
| PvuII-NotI | 11831 | 14059 | bacterial origin of replication and beta-lactamase (ampicillin resistance) gene (=pBR322 2069-4290) |

[a]NS - restriction site not identified.

Figure 43:
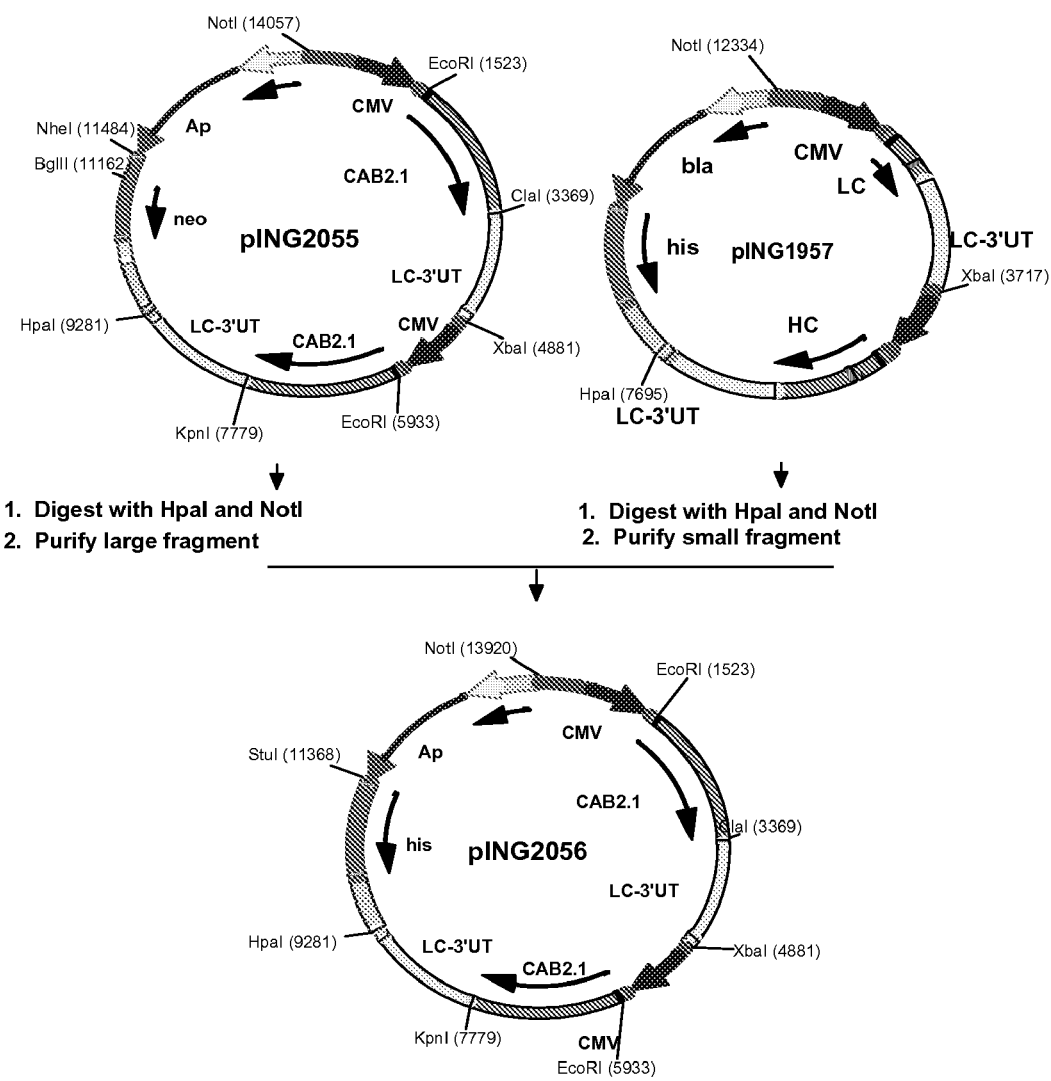
FIG. 43 depicts a construction map for vector pING2056.

Another vector with two copies of a CAB2.1 gene, designated pING2056 was also constructed as shown in FIG. 43. ping2056 which has the same structure as the neo two-gene vector pING2055, except that it encodes a his gene for histinol-resistance to facilitate multiple transfections. The features of pING2056 are summarized in Table 6.

TABLE 6

Description of pING2056.

| Plasmid region | Start nt | End nt | Description |
| --- | --- | --- | --- |
| NotI-HindIII | 1 | 479 | =pUC12 2616-399 (includes pBR322 4291-4361, 2069-2354 and part of lac gene) |
| HindIII-1/2BamHI (Sau3AI) | 479 | 643 | upstream region of Abelson murine leukemia virus 3' LTR enhancer/promoter (=4627-4804 of Reddy et al., Proc Natl. Acad. Sci (USA) 80: 3623-3627 (1983) |
| 1/2HincII-BamHI | 643 | 1414 | hCMV promoter (=−598 to 174 of Boshart et al., cell 41: 521-530 (1985); includes splice donor) |
| BamHI-EcoRI | 1414 | 1523 | SV40 16S splice acceptor (1421-1509 = SV40 1410-1497) |
| EcoRI-XhoI | 1523 | 3369 | CAB2.1 gene |
| XhoI-BamHI | 3369 | 4745 | LC genomic DNA including poly A site |
| BamHI-1/2HpaI (XbaI-HindIII) | 4745 | 4890 | Part of SV40 polyadenylation (=SV40 2532-2668) |
| HindIII-1/2BamHI (Sau3AI) | 4890 | 5053 | upstream region of Abelson murine leukemia virus 3' LTR enhancer/promoter (=4627-4804 of Reddy et al., Proc Natl. Acad. Sci (USA) 80: 3623-3627 (1983) |
| 1/2HincII-BamHI | 5053 | 5825 | hCMV promoter, including splice donor |
| BamHI-EcoRI | 5825 | 5934 | SV40 16S splice acceptor |
| EcoRI-XhoI | 5933 | 7779 | CAB2.1 gene |
| XhoI-BamHI | 7779 | 9149 | LC genomic DNA including poly A site |
| BamHI-1/2BclI (Sau3AI) | 9149 | 9386 | SV40 polyadenylation (=SV40 2532-2774) |

TABLE 6-continued

Description of pING2056.

| Plasmid region | Start nt | End nt | Description |
| --- | --- | --- | --- |
| 1/2BstYI (Sau3AI)-NS[a] | 9386 | 9997 | SV40 small T intron (=SV40 4769-4099) |
| 1/2 SalI-StuI | 9997 | 11368 | bacterial histidine (his) gene from pSV2his (coding region = 9760-8458) |
| StuI-PvuII | 11368 | 11694 | SV40 promoter (=SV40 5172-272) |
| PvuII-NotI | 11694 | 13920 | bacterial origin of replication and beta-lactamase (ampicillin resistance) gene (=pBR322 2069-4290) |

[a]NS - restriction site not identified.

EXAMPLE 18

Development and Characterization of Additional Transfected Clones and Cell Lines This example describes the development and characterization of clones and cell lines transfected with additional exemplary vectors according to the present invention. The development and characterization of polypeptide-producing cell lines is described from transfections with vectors, including multigene vectors, as described in Example 17.

Transfections were performed first with a single gene (pING2054) and a two gene (pING2055) neo vector. Cell lines were developed by electroporation of Ex-Cell 301-adapted CHO-K1 cells by the procedure of [Andreason, et al., *BioTechniques* 6:650 (1988)]. CHO-k1 cells were obtained from ATCC (CCL61).

Prior to transfection, 40 μg of either the single-gene neo vector pING2054 or the two-gene neo vector pING2055 was digested with XbaI yielding a linearized DNA structure shown in FIGS. 44A and B respectively. Forty μg of linearized DNA typically was used in conjunction with ~1×10$^7$ cells for each transfection. Generally, one to three electroporations were performed on any given day. Following a 2 day recovery period in non-selective Ex-Cell 301 medium supplemented with 2% FBS, the cells were plated at ~4000 cells/well in 96 well plates in Ex-Cell 301 medium supplemented with Glutamine-Pen-Strep, 1% FBS and with 0.8 mg/ml G418 (Geneticin®, Invitrogen). The plates were incubated at 37° C. in a CO$_2$ incubator.

Starting at days 10-12, the 96 well plates for either the single gene neo vector pING2054 or the two gene neo vector pING2055 transfections, were scanned for single clone colonies that were then sampled and screened by ELISA. A total of 3-4 ELISAs was performed over ~7 days. ELISAs were performed by removing culture supernatants from the 96 well plates (same for 24 well plates and shake flasks) and pipetting into 96 well dilution plates containing PBS and 1% BSA and stored overnight at 4° C. The supernatants were assayed for expressed polypeptide levels by ELISA using Immulon 4 plates precoated overnight at 4° C. with GB24, a mouse anti-DAF monoclonal antibody, diluted to 2 μg/ml in PBS. Following two washes with wash buffer (PBS+0.1% Tween 20) and a blocking step with PBS containing 0.05% Tween and 1% BSA, the diluted supernatants were added to the PBS-1% BSA buffer in the plates and incubated at 37° C. for 1 hour. The plates then were washed three times with PBS supplemented with 0.05% Tween and 0.5 μg/mL of a rabbit anti-Human CAB2.1 secondary antibody was added and incubated for 1 hour at 37° C. After three washes, a 1:15,000 dilution of horse radish peroxidase-conjugated goat anti-rabbit IgG (Pierce) was added and incubated for 1 hour. Detection was performed with the TMB system (KPL). After color development, the reaction was stopped by adding an equal volume of 1N H$_2$SO$_4$ and plates read at 450 nm.

Clones secreting polypeptides above an established baseline level, as determined by ELISA, were transferred from the 96 well plates to 24 well plates and replica plates prepared. Screening was performed by ELISA on extinct 24 well plate cultures as described above for 96 well plates. The top-producing clones in 24 well plates were then transferred to shake flasks. Shake flask experiments were performed by inoculating into 25 ml Ex-Cell 301 at ~1-2×10$^5$ cells per ml, depending on the assay. Ex-Cell 301 medium was supplemented as described above. Selective agents generally were not incorporated into media used for the shake flask tests except in cases in which maintenance cultures were allowed to incubate to extinction. The cells were incubated at 37° C., 100 RPM until viability was ≦20% (usually ~14 days). For growth and productivity experiments, viable cell density was determined either by hemocytometer and/or with the Guava Personal Flow Cytometer every 2 to 4 days. For studies in which the viable cell density was not determined, the flasks were opened for a few seconds in the biosafety hood every 2 to 3 days to provide some gas exchange. At the end of the experiment, cells were removed by centrifugation and filtration and the supernatants were assayed for CAB2.1 concentration either by ELISA as described above or by reverse-phase HPLC.

Specifically, for the transfections with pING2054, two independent sets of transfections were performed, on consisting of a single electroporation and the other consisting of two. A total of thirty eight 96 well plates were prepared from each of these transfections. Multiple colonies were observed in a number of wells following the 10-12 day incubation. 528 wells containing single colonies were screened by ELISA as described above. Wells with multiple colonies were triturated, pooled, labeled with a FITC conjugated mouse anti-human CD46 monoclonal antibody and subjected to Fluorescence activated cell sorting (FACS) analysis using a FACS Vantage SE-Diva (BD Biosciences, _____). FACS sorted clones were re-plated in 96 well plates and 223 individual clones were screened by ELISA.

The top 125 pING2054 transfectants from the 96 well format, of which 29 were from the FACS stored pool, were transferred to 24 well plates and extinct cultures were screened by ELISA as described above. The results demonstrated that the top transfectants produced between ~9 to ~16 μg/ml in 24 well plates (including, for example, Clones 3G8, 13A5, and 19A6). The top 30 of these clones, of which 4 were from the FACS stored pool, were transferred to shake flasks and grown in ExCell 301 (without FBS) to ~20% viability as described above. Extinct cultures were screened by ELISA. The top three producing clones, based on shake flask tests, included Clone 3G8, 13A5, and 19A6. Clone 3G8 appeared to be the highest produced in Ex-Cell 301 medium with 14 day (extinct) shake flask productivities (determined by HPLC) of 107, 86, and 116 µg/mL.

To select further for high expression, Clone 3G8 was subcloned. Cells were plated at in 96 well plates 5, 3 and 1 cells/well in Excell 301 medium. A total of 417 subclones were screened at the 96 well plate level as described above, with the top subclones secreting up to ~14 µg/ml (including, for example, 3G8-G5-F1, 3,G8-G13-C12, and 3G8-G10-H4). The top 50 subclones were next screened in 24 well plates, with the top producers secreting ~48 µg/ml (including, for example, 3G8-G5-F1, 3G8-G13-C-12, 3G8-G5E8, and 3G8-GA11). Twelve clones were selected and transferred to shake flask in ExCell medium without FBS. The cells were grown to extinction and the culture supernatant was assayed by reverse phase HPLC. Clone G5F1 appeared to be the highest producing clone in Ex-Cell 301 medium with 14 day (extinct) shake flask productivities (determined by HPLC) of 184, 194 and 182 µg/ml. This level was almost 2-fold higher than observed with the parent, Clone 3G8. Clone G5F1 was evaluated in a growth and productivity test in a 125 mL shake flask. The culture was inoculated at $1 \times 10^5$ cells/mL and incubated for 12-13 days. The results as shown in FIG. 45 demonstrate that Clone G5F1 was satisfactory with respect to both growth and productivity, maintaining a viability of 49% at Day 12 and ~175 µg/ml at Day 13.

Transfections and clonal development using pING2055, were performed as described for Clone 3G8, transfected with pING2054. Specifically, two independent sets of transfections each consisting of three electroporations were performed using pING2055 prepared as described above. A total of 3374 individual clones were screened from the 96 well plates. The top 263 clones were transferred to 24 well plates and extinct cultures were screened by ELISA. The results demonstrated that the top transfectants produced between ~9 to ~37 µg/ml in 24 well plates (including, for example, 44C8, 11C8, 122B10, 176C6, 156B8, and 134G3). The top 85 of these clones were transferred to shake flasks and extinct cultures were screened by ELISA or RP-HPLC as described above. Clones 156B8 and 176C6 appeared to be the highest producers in Ex-Cell 301 medium with 14 day (extinct) shake flask productivities (determined by HPLC) up to ~140 µg/ml for both.

EXAMPLE 19

Increasing Expression through a Second Sequential Vector Transfection: Development and Characterization of Additional Transfected Clones and Cell Lines This example describes the further increase in expression and production of polypeptides, including polypeptides with complement inhibitory activities, through a second transfection of an exemplary cell line with a multi-transcription unit vector.

The top CAB2.1-producing clones developed with the single-gene neo vector (Clone 3G8) and the two-gene neo vector (Clones 156B8 and 176C6) were re-transfected with the CAB2.1 two-gene histidinol vector, pING2056. Specifically, Clone 3G8, transfected with a neo single gene vector pING2054, was re-transfected the with a his two gene vector pING2056 linearized to position the histinol-resistant selective marker gene between the two CAB2.1 genes as shown in FIG. 44 for the neo vector. Cells were transfected as described above. A total of 387 clones were screened in 96 well plates in ExCell 301 medium and 120 clones were selected for screening in 24 well plates. Twenty of the top producing clones, secreting up to a ~68 µg/ml, were selected to be transferred to shake flasks in ExCell medium without FBS. Cells were grown to extinction and culture supernatants assayed by reverse phase HPLC. The top producing clones secreted in the range of ~142 to ~218 µg/ml (including, for example, 3G8-217B4, 3G8-206C3, 3G8-196E3, 3G8-190C7, 3G8-185E9, 3G8-178G2, 3G8-190E5). For example, for these top producing clones, Clone 217B4 consistently secreted more than ~200 µg/ml, and Clone 206C3 secreted up to ~199 µg/ml, Clone 185E9 secreted up to ~177 µg/ml.

The top re-transfectants of Clone 3G8, clones 217B4, 206C3, and 185E9, were subcloned. Specifically, Clones 217B4, 206C3 and 185E9 were subcloned by plating at 1, 3 or 5 cells/well in Ex-Cell 301 medium. A total of 282 individual subclones of Clone 217B4, 301 of Clone 206C3 and 308 of Clone 185E9 were screened in 96 well plates as described above for the development of clone 3G8. Of these, 59 subclones of Clone 217B4, 55 subclones of Clone 206C3 and 52 subclones of Clone 185E9 were transferred to 24 well plates and extinct cultures screened by ELISA as described above for the development of Clone 3G8. The top producing 217B4 subclones secreted in the range of ~35 to ~57 µg/ml. The top producing 206C3 subclones secreted in the range of ~31 to ~40 µg/ml and the top producing 185E9 subclones secreted from ~17 to ~61 µg/ml. Of these, the top 20, 16 and 16 clones for 217B4, 206C3 and 185E9 respectively, were transferred to shake flasks. Extinct cultures were screened by ELISA as previously described and in some cases by RP-HPLC. The top 217B4 subclones, including clones B3B8, B5B10, B4E11, B6E3, B7C4, B7B7, and B9B4, secreted between ~170 to 216 µg/ml in shake flasks. The top 206C3 subclones including clones C2B7, C2D10, C4F1, C7H7, and C9A2, secreted in the range ~147 to ~188 µg/ml in shake flasks. The top 185E9 subclones, including clones E7E9, E3C11, E10H5, and E2D5, secreted in the range of ~163 to ~210 µg/ml in shake flasks. These subclones did not produce higher levels of CAB2.1 than their parent clones in Ex-Cell 301 medium and their titers remained similar to those of their parental clones.

To further evaluate expression in Ex-Cell 301 medium, Clone 217B4, Clone 206C3, Subclones C2B7 and C7H7 of Clone 206C3 and Subclones B6E3 and B5B10 of Clone 217B4 were evaluated in shake flask test in which growth and productivity were measured over the course of the study. For this study, cells grown in Ex-Cell 301 were inoculated at $1 \times 10^5$ cells/ml. The cells were grown as described for the development of Clone 3G8. The growth and productivity for the re-transfectants of Clone 3G8, Clones 217B4 and 206C3, were measured. At 2 weeks the cells were still viable ($1 \times 10^6$ cells/ml for Clone 206C3 and $4 \times 10^5$ cells/ml for Clone 217B4) and supported a titer of ~150 µg/ml. The growth and productivity results for the Clone 206C3 Subclones C2B7 and C7H7 were also measured. The results are similar to those for the parent Clone 206C3 with a measurable decrease in cell viability at 2 weeks and productivity at or just below ~150 µg/ml. Growth and productivity results for Clone 217B4 Subclones B6E3 and B5B10 were also measured. When compared to Clone 206C3 and its subclones C2B7 and C7H7, these results demonstrate in productivities at two weeks, of ~200 µg/ml for B6E3 and above ~150 µg/ml for B5B10.

In view of the current problems and limitations in the art, there are many advantages of the present invention over the art, increased polypeptide production, production efficiency, greater control and regulation over the quantities of polypeptide expressed, increased stability of cell lines, and decreased costs for materials, reagents, and other resources. Thus, the present invention solves many of the problems previously existing in the art. One way in which the present invention solves these problems and is advantageous compared to the prior art is through the disclosed methods of vector construction that, when linearized, avoid homologous recombination of multiple copies of transcription units by separating the transcription unit DNA sequences with at least one selective marker gene. While the above examples demonstrate the use of two and four transcription unit vectors, the present invention contemplates use of all multiple transcription unit vectors, including three, four, five, six, and so on copies of transcription unit DNA sequences. Such vectors are constructed with at least one selective marker gene separating the transcription units in a manner which results in the avoidance or nullification of homologous recombination. All such permutations of multiple transcription unit copies are contemplated by this invention as one skilled in the art would recognize through this disclosure. A second way in which the present invention solves the problems of the prior art is through the disclosed methods to further increase expression through sequential transfections with multiple-transcription unit constructs. This leads to clones which can produce substantially increased levels of proteins and polypeptides, while still maintaining viability and stability in growth medium, thus, solving many problems in the art.

All patents, patent applications, literature publications and test methods cited herein are hereby incorporated by reference. The reader's attention is directed to all papers and documents which are filed concurrently with or previous to this specification in connection with this application and which are open to public inspection with this specification, and the contents of all such papers and documents are incorporated herein by reference.

All the features disclosed in this specification (including any accompanying claims, abstract, and drawings) may be replaced by alternative features serving the same, equivalent or similar purpose, unless expressly stated otherwise. Thus, unless expressly stated otherwise, each feature disclosed is only one example of a generic series of equivalent or similar features.

Although the present invention has been described in considerable detail with reference to certain preferred versions thereof, other versions are possible. Many variations of the present invention will suggest themselves to those skilled in the art in light of the above detailed disclosure. All such modifications are within the full intended scope of the appended claims. Therefore, the spirit and scope of the appended claims should not be limited to the description of the preferred embodiments contained herein.

---

What is claimed is:

1. A vector or segment thereof comprising multiple copies of a transcription unit separated by at least one selective marker gene wherein the transcription unit encodes a polypeptide,
  wherein the vector is linearized with a restriction enzyme, such that the selective marker gene is positioned between at least two transcription unit copies, as [(transcription unit)$_x$-selective marker gene-(transcription unit)$_x$], and wherein x is 1-4, and
  wherein the multiple copies of the transcription unit encode immunoglobulin light and heavy chain polypeptides.

2. A vector or segment thereof comprising multiple copies of a transcription unit separated by at least one selective marker gene wherein the transcription unit encodes a polypeptide,
  wherein the vector is linearized with a restriction enzyme, such that the selective marker gene is positioned between at least two transcription unit copies, as [(transcription unit)$_x$-selective marker gene-(transcription unit)$_x$], and wherein x is 1-4, and
  wherein the multiple copies of the transcription unit encode at least the variable regions of immunoglobulin light and heavy chain polypeptides.

3. A vector or segment thereof comprising multiple copies of a transcription unit separated by at least one selective marker gene wherein the transcription unit encodes a polypeptide,
  wherein the vector is linearized with a restriction enzyme, such that the selective marker gene is positioned between at least two transcription unit copies, as [(transcription unit)$_x$-selective marker gene-(transcription unit)$_x$], and wherein x is 1-4, and
  wherein the transcription unit encodes a BPI protein product.

4. A vector or segment thereof comprising multiple copies of a transcription unit separated by at least one selective marker gene wherein the transcription unit encodes a polypeptide,
  wherein the vector is linearized with a restriction enzyme, such that the selective marker gene is positioned between at least two transcription unit copies, as [(transcription unit)$_x$-selective marker gene-(transcription unit)$_x$], and wherein x is 1-4, and
  wherein the transcription unit encodes a BPI fragment, BPI analog, BPI variant, or BPI-derived peptide.

5. The vector or segment thereof of any one of claims 1 to 4 wherein the number of multiple copies of the transcription unit is two.

6. The vector or segment thereof of any one of claims 1 to 4 wherein each transcription unit is under the control of its own promoter and 3' untranslated region.

7. The vector or segment thereof of any one of claims 1 to 4 wherein the multiple copies of the transcription unit are in a direct repeat orientation.

8. The vector or segment thereof of any one of claims 1 to 4 wherein the multiple copies of the transcription unit are in an inverted repeat orientation.

9. The vector or segment thereof of any one of claims 1 to 4 wherein the transcription unit comprises an internal ribosome entry site.

10. The vector or segment thereof of any one of claims 1 to 4 wherein the multiple copies of the transcription unit are between 25% and 100% identical.

11. The vector or segment thereof of any one of claims 1 to 4 wherein the multiple copies of the transcription unit are 25% identical.

12. The vector or segment thereof of any one of claims 1 to 4 wherein the multiple copies of the transcription unit are at least 70%, at least 80%, or at least 90% identical.

13. The vector or segment thereof of any one of claims 1 to 4 wherein the multiple copies of the transcription unit are 80%, 81%, 82%, 83%, 84%, 85%, 86%, 87% 88%, 89%, 90%, 91%, 92%, 93%, 94%, 95%, 96%, 97%, 98% or 99% identical.

14. The vector or segment thereof of any one of claims 1 to 4 wherein the multiple copies of the transcription unit are 100% identical.

15. The vector or segment thereof of any one of claims 1 to 4 wherein the selective marker gene is a gpt, res, neo, his, DHFR, GS, adenosine deaminase (ADA), thymidine kinase (TK), adenine phosphoribosyl transferase (APRT), zeocin resistance, hygromycin resistance or puromycin resistance gene.

16. The vector or segment thereof of claims 3 or 4 wherein the transcription unit encodes $rBPI_{21}$ and is under the control of an hCMV promoter and mouse light chain 3' untranslated region, and wherein the vector further comprises 0, 1 or 2 copies of a human heavy chain enhancer and either a gpt or neo gene.

17. An expression vector or segment thereof according to any one of claims 1 to 4.

18. A host cell comprising an expression vector or segment thereof according to claim 17.

19. The host cell according to claim 18 comprising an additional expression vector or segment thereof comprising multiple copies of a transcription unit separated by at least one selective marker gene wherein the transcription unit encodes a polypeptide,
wherein the vector is linearized with a restriction enzyme such that the selective marker gene is positioned between at least two transcription unit copies, as [(transcription unit)$_x$-selective marker gene-(transcription unit)$_x$], and wherein x is 1-4, said additional expression vector or segment thereof comprising a different selective marker gene.

20. The host cell according to claim 18 wherein the host cell is a eukaryotic cell.

21. The host cell according to claim 18, wherein the host cell is a plant, insect, mammalian or yeast cell.

22. The host cell according to claim 18 wherein the host cell is a Chinese hamster ovary (CHO) cell or CHO-K1 cell.

23. The host cell according to claim 18 wherein the expression vector or segment thereof is integrated into the host cell chromosome.

24. A stable cell line comprising an expression vector or segment thereof according to claim 17.

25. The stable cell line according to claim 24 wherein the cells are transformed or transfected by at least one and not more than six expression vectors or segments thereof.

26. The vector or segment of claim 1, comprising two copies of a transcription unit encoding an immunoglobulin light chain polypeptide and two copies of a transcription unit encoding an immunoglobulin heavy chain polypeptide.

27. A vector or segment thereof comprising multiple copies of a transcription unit each separated by a selective marker gene wherein the transcription unit encodes a polypeptide,
wherein the vector is linearized with a restriction enzyme such that the selective marker gene is positioned between at least two transcription unit copies, as [(transcription unit)$_x$-selective marker gene-(transcription unit)$_x$], and wherein x is 1-4, and
wherein the multiple copies of the transcription unit encode immunoglobulin light and heavy chain polypeptides.

28. A vector or segment thereof comprising multiple copies of a transcription unit each separated by a selective marker gene wherein the transcription unit encodes a polypeptide,
wherein the vector is linearized with a restriction enzyme such that the selective marker gene is positioned between at least two transcription unit copies, as [transcription unit)$_x$-selective marker gene-(transcription unit)$_x$], and wherein x is 1-4, and
wherein the multiple copies of the transcription unit encode at least the variable regions of immunoglobulin light and heavy chain polypeptides.

29. A vector or segment thereof comprising multiple copies of a transcription unit each separated by a selective marker gene wherein the transcription unit encodes a polypeptide,
wherein the vector is linearized with a restriction enzyme such that the selective marker gene is positioned between at least two transcription unit copies, as [(transcription unit)$_x$-selective marker gene-(transcription unit)$_x$], and wherein x is 1-4, and
wherein the transcription unit encodes a BPI protein product.

30. A vector or segment thereof comprising multiple copies of a transcription unit each separated by a selective marker gene wherein the transcription unit encodes a polypeptide,
wherein the vector is linearized with a restriction enzyme such that the selective marker gene is positioned between at least two transcription unit copies, as [(transcription unit)$_x$-selective marker gene-(transcription unit)$_x$], and wherein x is 1-4, and
wherein the transcription unit encodes a BPI fragment, BPI analog, BPI variant, or BPI-derived peptide.

31. The vector or segment thereof of any one of claims 27 to 30 wherein the number of multiple copies of the transcription unit is two.

32. The vector or segment thereof of any one of claims 27 to 30 wherein each transcription unit is under the control of its own promoter and 3' untranslated region.

33. The vector or segment thereof of any one of claims 27 to 30 wherein the multiple copies of the transcription unit are in a direct repeat orientation.

34. The vector or segment thereof of any one of claims 27 to 30 wherein the multiple copies of the transcription unit are in an inverted repeat orientation.

35. The vector or segment thereof of any one of claims 27 to 30 wherein the transcription unit comprises an internal ribosome entry site.

36. The vector or segment thereof of any one of claims 27 to 30 wherein the multiple copies of the transcription unit are between 25% and 100% identical.

37. The vector or segment thereof of any one of claims 27 to 30 wherein the multiple copies of the transcription unit are 25% identical.

38. The vector or segment thereof of any one of claims 27 to 30 wherein the multiple copies of the transcription unit are at least 70%, at least 80%, or at least 90% identical.

39. The vector or segment thereof of any one of claims 27 to 30 wherein the multiple copies of the transcription unit are 80%, 81%, 82%, 83%, 84%, 85%, 86%, 87%, 88%, 89%, 90%, 91%, 92%, 93%, 94%, 95%, 96%, 97%, 98% or 99% identical.

40. The vector or segment thereof of any one of claims 27 to 30 wherein the multiple copies of the transcription unit are 100% identical.

41. The vector or segment thereof of any one of claims 27 to 30 wherein the selective marker gene is a gpt, res, neo, his, DHFR, GS, adenosine deaminase (ADA), thymidine kinase (TK), adenine phosphoribosyl transferase (APRT), zeocin resistance, hygromycin resistance or puromycin resistance gene.

42. An expression vector or segment thereof according to any one of claims 27 to 30.

43. A host cell comprising an expression vector or segment thereof according to claim 42.

44. The host cell according to claim 43 comprising an additional expression vector or segment thereof comprising multiple copies of a transcription unit each separated by a selective marker gene wherein the transcription unit encodes a polypeptide,
wherein the vector is linearized with a restriction enzyme such that the selective marker gene is positioned between at least two transcription unit copies, as [(transcription unit)$_x$-selective marker gene-(transcription unit)$_x$], and wherein x is 1-4, said additional expression vector or segment thereof comprising a different selective marker gene.

45. The host cell according to claim 43 wherein the host cell is a eukaryotic cell.

46. The host cell according to claim 43, wherein the host cell is a plant, insect, mammalian or yeast cell.

47. The host cell according to claim 43 wherein the host cell is a Chinese hamster ovary (CHO) cell or CHO-K1 cell.

48. The host cell according to claim 43 wherein the expression vector or segment thereof is integrated into the host cell chromosome.

49. A stable cell line comprising an expression vector or segment thereof according to claim 42.

50. The stable cell line according to claim 49 wherein the cells are transformed or transfected by at least one and not more than six expression vectors or segments thereof.

\* \* \* \* \*

SEQUENCE LISTING

```
<160> NUMBER OF SEQ ID NOS: 87

<210> SEQ ID NO 1
<211> LENGTH: 1813
<212> TYPE: DNA
<213> ORGANISM: Homo sapiens
<220> FEATURE:
<221> NAME/KEY: CDS
<222> LOCATION: (31)..(1491)
<220> FEATURE:
<221> NAME/KEY: mat_peptide
<222> LOCATION: (124)..()

<400> SEQUENCE: 1
caggccttga ggttttggca gctctggagg atg aga gag aac atg gcc agg ggc         54
                                Met Arg Glu Asn Met Ala Arg Gly
                                 -30                 -25 cct tgc aac gcg ccg aga tgg gtg tcc ctg atg gtg ctc gtc gcc ata        102
Pro Cys Asn Ala Pro Arg Trp Val Ser Leu Met Val Leu Val Ala Ile
            -20                 -15                 -10 ggc acc gcc gtg aca gcg gcc gtc aac cct ggc gtg gtg gtc agg atc        150
Gly Thr Ala Val Thr Ala Ala Val Asn Pro Gly Val Val Val Arg Ile
         -5                  -1   1               5 tcc cag aag ggc ctg gac tac gcc agc cag cag ggg acg gcc gct ctg        198
Ser Gln Lys Gly Leu Asp Tyr Ala Ser Gln Gln Gly Thr Ala Ala Leu
 10              15                  20                  25 cag aag gag ctg aag agg atc aag att cct gac tac tca gac agc ttt        246
Gln Lys Glu Leu Lys Arg Ile Lys Ile Pro Asp Tyr Ser Asp Ser Phe
             30                  35                  40 aag atc aag cat ctt ggg aag ggg cat tat agc ttc tac agc atg gac        294
Lys Ile Lys His Leu Gly Lys Gly His Tyr Ser Phe Tyr Ser Met Asp
                 45                  50                  55 atc cgt gaa ttc cag ctt ccc agt tcc cag ata agc atg gtg ccc aat        342
Ile Arg Glu Phe Gln Leu Pro Ser Ser Gln Ile Ser Met Val Pro Asn
             60                  65                  70 gtg ggc ctt aag ttc tcc atc agc aac gcc aat atc aag atc agc ggg        390
Val Gly Leu Lys Phe Ser Ile Ser Asn Ala Asn Ile Lys Ile Ser Gly
 75                  80                  85
```

```
aaa tgg aag gca caa aag aga ttc tta aaa atg agc ggc aat ttt gac        438
Lys Trp Lys Ala Gln Lys Arg Phe Leu Lys Met Ser Gly Asn Phe Asp
 90              95                 100                 105 ctg agc ata gaa ggc atg tcc att tcg gct gat ctg aag ctg ggc agt        486
Leu Ser Ile Glu Gly Met Ser Ile Ser Ala Asp Leu Lys Leu Gly Ser
                 110                 115                 120 aac ccc acg tca ggc aag ccc acc atc acc tgc tcc agc tgc agc agc        534
Asn Pro Thr Ser Gly Lys Pro Thr Ile Thr Cys Ser Ser Cys Ser Ser
             125                 130                 135 cac atc aac agt gtc cac gtg cac atc tca aag agc aaa gtc ggg tgg        582
His Ile Asn Ser Val His Val His Ile Ser Lys Ser Lys Val Gly Trp
         140                 145                 150 ctg atc caa ctc ttc cac aaa aaa att gag tct gcg ctt cga aac aag        630
Leu Ile Gln Leu Phe His Lys Lys Ile Glu Ser Ala Leu Arg Asn Lys
     155                 160                 165 atg aac agc cag gtc tgc gag aaa gtg acc aat tct gta tcc tcc aag        678
Met Asn Ser Gln Val Cys Glu Lys Val Thr Asn Ser Val Ser Ser Lys
170                 175                 180                 185 ctg caa cct tat ttc cag act ctg cca gta atg acc aaa ata gat tct        726
Leu Gln Pro Tyr Phe Gln Thr Leu Pro Val Met Thr Lys Ile Asp Ser
                 190                 195                 200 gtg gct gga atc aac tat ggt ctg gtg gca cct cca gca acc acg gct        774
Val Ala Gly Ile Asn Tyr Gly Leu Val Ala Pro Pro Ala Thr Thr Ala
             205                 210                 215 gag acc ctg gat gta cag atg aag ggg gag ttt tac agt gag aac cac        822
Glu Thr Leu Asp Val Gln Met Lys Gly Glu Phe Tyr Ser Glu Asn His
         220                 225                 230 cac aat cca cct ccc ttt gct cca cca gtg atg gag ttt ccc gct gcc        870
His Asn Pro Pro Pro Phe Ala Pro Pro Val Met Glu Phe Pro Ala Ala
     235                 240                 245 cat gac cgc atg gta tac ctg ggc ctc tca gac tac ttc ttc aac aca        918
His Asp Arg Met Val Tyr Leu Gly Leu Ser Asp Tyr Phe Phe Asn Thr
250                 255                 260                 265 gcc ggg ctt gta tac caa gag gct ggg gtc ttg aag atg acc ctt aga        966
Ala Gly Leu Val Tyr Gln Glu Ala Gly Val Leu Lys Met Thr Leu Arg
                 270                 275                 280 gat gac atg att cca aag gag tcc aaa ttt cga ctg aca acc aag ttc       1014
Asp Asp Met Ile Pro Lys Glu Ser Lys Phe Arg Leu Thr Thr Lys Phe
             285                 290                 295 ttt gga acc ttc cta cct gag gtg gcc aag aag ttt ccc aac atg aag       1062
Phe Gly Thr Phe Leu Pro Glu Val Ala Lys Lys Phe Pro Asn Met Lys
         300                 305                 310 ata cag atc cat gtc tca gcc tcc acc ccg cca cac ctg tct gtg cag       1110
Ile Gln Ile His Val Ser Ala Ser Thr Pro Pro His Leu Ser Val Gln
     315                 320                 325 ccc acc ggc ctt acc ttc tac cct gcc gtg gat gtc cag gcc ttt gcc       1158
Pro Thr Gly Leu Thr Phe Tyr Pro Ala Val Asp Val Gln Ala Phe Ala
330                 335                 340                 345 gtc ctc ccc aac tcc tcc ctg gct tcc ctc ttc ctg att ggc atg cac       1206
Val Leu Pro Asn Ser Ser Leu Ala Ser Leu Phe Leu Ile Gly Met His
                 350                 355                 360 aca act ggt tcc atg gag gtc agc gcc gag tcc aac agg ctt gtt gga       1254
Thr Thr Gly Ser Met Glu Val Ser Ala Glu Ser Asn Arg Leu Val Gly
             365                 370                 375 gag ctc aag ctg gat agg ctg ctc ctg gaa ctg aag cac tca aat att       1302
Glu Leu Lys Leu Asp Arg Leu Leu Leu Glu Leu Lys His Ser Asn Ile
         380                 385                 390 ggc ccc ttc ccg gtt gaa ttg ctg cag gat atc atg aac tac att gta       1350
Gly Pro Phe Pro Val Glu Leu Leu Gln Asp Ile Met Asn Tyr Ile Val
     395                 400                 405
```

```
ccc att ctt gtg ctg ccc agg gtt aac gag aaa cta cag aaa ggc ttc    1398
Pro Ile Leu Val Leu Pro Arg Val Asn Glu Lys Leu Gln Lys Gly Phe
410                 415                 420                 425 cct ctc ccg acg ccg gcc aga gtc cag ctc tac aac gta gtg ctt cag    1446
Pro Leu Pro Thr Pro Ala Arg Val Gln Leu Tyr Asn Val Val Leu Gln
            430                 435                 440 cct cac cag aac ttc ctg ctg ttc ggt gca gac gtt gtc tat aaa        1491
Pro His Gln Asn Phe Leu Leu Phe Gly Ala Asp Val Val Tyr Lys
            445                 450                 455 tgaaggcacc aggggtgccg ggggctgtca gccgcacctg ttcctgatgg gctgtggggc   1551
accggctgcc tttccccagg gaatcctctc cagatcttaa ccaagagccc cttgcaaact   1611
tcttcgactc agattcagaa atgatctaaa cacgaggaaa cattattcat tggaaaagtg   1671
catggtgtgt attttaggga ttatgagctt ctttcaaggg ctaaggctgc agagatattt   1731
cctccaggaa tcgtgtttca attgtaacca agaaatttcc atttgtgctt catgaaaaaa   1791
aacttctggt ttttttcatg tg                                           1813

<210> SEQ ID NO 2
<211> LENGTH: 487
<212> TYPE: PRT
<213> ORGANISM: Homo sapiens

<400> SEQUENCE: 2

Met Arg Glu Asn Met Ala Arg Gly Pro Cys Asn Ala Pro Arg Trp Val
        -30                 -25                 -20

Ser Leu Met Val Leu Val Ala Ile Gly Thr Ala Val Thr Ala Ala Val
-15                 -10                 -5                  -1  1

Asn Pro Gly Val Val Arg Ile Ser Gln Lys Gly Leu Asp Tyr Ala
                5                  10                  15

Ser Gln Gln Gly Thr Ala Ala Leu Gln Lys Glu Leu Lys Arg Ile Lys
            20                  25                  30

Ile Pro Asp Tyr Ser Asp Ser Phe Lys Ile Lys His Leu Gly Lys Gly
        35                  40                  45

His Tyr Ser Phe Tyr Ser Met Asp Ile Arg Glu Phe Gln Leu Pro Ser
50                  55                  60                  65

Ser Gln Ile Ser Met Val Pro Asn Val Gly Leu Lys Phe Ser Ile Ser
            70                  75                  80

Asn Ala Asn Ile Lys Ile Ser Gly Lys Trp Lys Ala Gln Lys Arg Phe
                85                  90                  95

Leu Lys Met Ser Gly Asn Phe Asp Leu Ser Ile Glu Gly Met Ser Ile
            100                 105                 110

Ser Ala Asp Leu Lys Leu Gly Ser Asn Pro Thr Ser Gly Lys Pro Thr
        115                 120                 125

Ile Thr Cys Ser Ser Cys Ser Ser His Ile Asn Ser Val His Val His
130                 135                 140                 145

Ile Ser Lys Ser Lys Val Gly Trp Leu Ile Gln Leu Phe His Lys Lys
            150                 155                 160

Ile Glu Ser Ala Leu Arg Asn Lys Met Asn Ser Gln Val Cys Glu Lys
        165                 170                 175

Val Thr Asn Ser Val Ser Ser Lys Leu Gln Pro Tyr Phe Gln Thr Leu
            180                 185                 190

Pro Val Met Thr Lys Ile Asp Ser Val Ala Gly Ile Asn Tyr Gly Leu
        195                 200                 205

Val Ala Pro Pro Ala Thr Thr Ala Glu Thr Leu Asp Val Gln Met Lys
210                 215                 220                 225
```

-continued

```
Gly Glu Phe Tyr Ser Glu Asn His His Asn Pro Pro Phe Ala Pro
            230                 235                 240

Pro Val Met Glu Phe Pro Ala Ala His Asp Arg Met Val Tyr Leu Gly
        245                 250                 255

Leu Ser Asp Tyr Phe Phe Asn Thr Ala Gly Leu Val Tyr Gln Glu Ala
    260                 265                 270

Gly Val Leu Lys Met Thr Leu Arg Asp Asp Met Ile Pro Lys Glu Ser
275                 280                 285

Lys Phe Arg Leu Thr Thr Lys Phe Phe Gly Thr Phe Leu Pro Glu Val
290                 295                 300                 305

Ala Lys Lys Phe Pro Asn Met Lys Ile Gln Ile His Val Ser Ala Ser
                310                 315                 320

Thr Pro Pro His Leu Ser Val Gln Pro Thr Gly Leu Thr Phe Tyr Pro
                325                 330                 335

Ala Val Asp Val Gln Ala Phe Ala Val Leu Pro Asn Ser Ser Leu Ala
            340                 345                 350

Ser Leu Phe Leu Ile Gly Met His Thr Thr Gly Ser Met Glu Val Ser
    355                 360                 365

Ala Glu Ser Asn Arg Leu Val Gly Glu Leu Lys Leu Asp Arg Leu Leu
370                 375                 380                 385

Leu Glu Leu Lys His Ser Asn Ile Gly Pro Phe Pro Val Glu Leu Leu
                390                 395                 400

Gln Asp Ile Met Asn Tyr Ile Val Pro Ile Leu Val Leu Pro Arg Val
                405                 410                 415

Asn Glu Lys Leu Gln Lys Gly Phe Pro Leu Pro Thr Pro Ala Arg Val
            420                 425                 430

Gln Leu Tyr Asn Val Val Leu Gln Pro His Gln Asn Phe Leu Leu Phe
    435                 440                 445

Gly Ala Asp Val Val Tyr Lys
450                 455

<210> SEQ ID NO 3
<211> LENGTH: 663
<212> TYPE: DNA
<213> ORGANISM: Homo Sapiens
<220> FEATURE:
<221> NAME/KEY: misc_feature
<223> OTHER INFORMATION: rBPI21 Sequence DNA and Protein Sequence
<220> FEATURE:
<221> NAME/KEY: CDS
<222> LOCATION: (1)..(660)
<220> FEATURE:
<221> NAME/KEY: mat_peptide
<222> LOCATION: (82)..()

<400> SEQUENCE: 3 atg gcc agg ggc cct tgc aac gcg ccg aga tgg gtg tcc ctg atg gtg      48
Met Ala Arg Gly Pro Cys Asn Ala Pro Arg Trp Val Ser Leu Met Val
        -25                 -20                 -15 ctc gtc gcc ata ggc acc gcc gtg aca gcg gcc gtc aac cct ggc gtc      96
Leu Val Ala Ile Gly Thr Ala Val Thr Ala Ala Val Asn Pro Gly Val
    -10                  -5                  -1   1               5 gtg gtc agg atc tcc cag aag ggc ctg gac tac gcc agc cag cag ggg     144
Val Val Arg Ile Ser Gln Lys Gly Leu Asp Tyr Ala Ser Gln Gln Gly
                 10                  15                  20 acg gcc gct ctg cag aag gag ctg aag agg atc aag att cct gac tac     192
Thr Ala Ala Leu Gln Lys Glu Leu Lys Arg Ile Lys Ile Pro Asp Tyr
            25                  30                  35 tca gac agc ttt aag atc aag cat ctt ggg aag ggg cat tat agc ttc     240
```

```
tac agc atg gac atc cgt gaa ttc cag ctt ccc agt tcc cag ata agc      288
Tyr Ser Met Asp Ile Arg Glu Phe Gln Leu Pro Ser Ser Gln Ile Ser
 55                  60                  65 atg gtg ccc aat gtg ggc ctt aag ttc tcc atc agc aac gcc aat atc      336
Met Val Pro Asn Val Gly Leu Lys Phe Ser Ile Ser Asn Ala Asn Ile
 70                  75                  80                  85 aag atc agc ggg aaa tgg aag gca caa aag aga ttc tta aaa atg agc      384
Lys Ile Ser Gly Lys Trp Lys Ala Gln Lys Arg Phe Leu Lys Met Ser
                 90                  95                 100 ggc aat ttt gac ctg agc ata gaa ggc atg tcc att tcg gct gat ctg      432
Gly Asn Phe Asp Leu Ser Ile Glu Gly Met Ser Ile Ser Ala Asp Leu
                105                 110                 115 aag ctg ggc agt aac ccc acg tca ggc aag ccc acc atc acc gcc tcc      480
Lys Leu Gly Ser Asn Pro Thr Ser Gly Lys Pro Thr Ile Thr Ala Ser
            120                 125                 130 agc tgc agc agc cac atc aac agt gtc cac gtg cac atc tca aag agc      528
Ser Cys Ser Ser His Ile Asn Ser Val His Val His Ile Ser Lys Ser
    135                 140                 145 aaa gtc ggg tgg ctg atc caa ctc ttc cac aaa aaa att gag tct gcg      576
Lys Val Gly Trp Leu Ile Gln Leu Phe His Lys Lys Ile Glu Ser Ala
150                 155                 160                 165 ctt cga aac aag atg aac agc cag gtc tgc gag aaa gtg acc aat tct      624
Leu Arg Asn Lys Met Asn Ser Gln Val Cys Glu Lys Val Thr Asn Ser
                170                 175                 180 gta tcc tcc aag ctg caa cct tat ttc cag act ctg tag                  663
Val Ser Ser Lys Leu Gln Pro Tyr Phe Gln Thr Leu
            185                 190

<210> SEQ ID NO 4
<211> LENGTH: 220
<212> TYPE: PRT
<213> ORGANISM: Homo Sapiens

<400> SEQUENCE: 4

Met Ala Arg Gly Pro Cys Asn Ala Pro Arg Trp Val Ser Leu Met Val
        -25                 -20                 -15

Leu Val Ala Ile Gly Thr Ala Val Thr Ala Ala Val Asn Pro Gly Val
    -10                  -5                  -1   1               5

Val Val Arg Ile Ser Gln Lys Gly Leu Asp Tyr Ala Ser Gln Gln Gly
                 10                  15                  20

Thr Ala Ala Leu Gln Lys Glu Leu Lys Arg Ile Lys Ile Pro Asp Tyr
             25                  30                  35

Ser Asp Ser Phe Lys Ile Lys His Leu Gly Lys Gly His Tyr Ser Phe
         40                  45                  50

Tyr Ser Met Asp Ile Arg Glu Phe Gln Leu Pro Ser Ser Gln Ile Ser
 55                  60                  65

Met Val Pro Asn Val Gly Leu Lys Phe Ser Ile Ser Asn Ala Asn Ile
 70                  75                  80                  85

Lys Ile Ser Gly Lys Trp Lys Ala Gln Lys Arg Phe Leu Lys Met Ser
                 90                  95                 100

Gly Asn Phe Asp Leu Ser Ile Glu Gly Met Ser Ile Ser Ala Asp Leu
                105                 110                 115

Lys Leu Gly Ser Asn Pro Thr Ser Gly Lys Pro Thr Ile Thr Ala Ser
            120                 125                 130

Ser Cys Ser Ser His Ile Asn Ser Val His Val His Ile Ser Lys Ser
    135                 140                 145
```

```
Lys Val Gly Trp Leu Ile Gln Leu Phe His Lys Lys Ile Glu Ser Ala
150                 155                 160                 165

Leu Arg Asn Lys Met Asn Ser Gln Val Cys Glu Lys Val Thr Asn Ser
                170                 175                 180

Val Ser Ser Lys Leu Gln Pro Tyr Phe Gln Thr Leu
                185                 190

<210> SEQ ID NO 5
<211> LENGTH: 720
<212> TYPE: DNA
<213> ORGANISM: Homo Sapiens
<220> FEATURE:
<221> NAME/KEY: misc_feature
<223> OTHER INFORMATION: Mouse Human Chimeric Light Chain DNA and
      Protein
<220> FEATURE:
<221> NAME/KEY: CDS
<222> LOCATION: (1)..(717)
<220> FEATURE:
<221> NAME/KEY: mat_peptide
<222> LOCATION: (61)..()

<400> SEQUENCE: 5
```

| | | | | | | | | | | | | | | | | |
|---|---|---|---|---|---|---|---|---|---|---|---|---|---|---|---|---|
| atg | agg | ttc | tct | gct | cag | ctt | ctg | ggg | ctg | ctt | gtg | ctc | tgg | atc | cct | 48 |
| Met | Arg | Phe | Ser | Ala | Gln | Leu | Leu | Gly | Leu | Leu | Val | Leu | Trp | Ile | Pro | |
| -20 | | | | | -15 | | | | | -10 | | | | | -5 | |
| gga | tcc | act | gca | gat | att | gtg | atg | acg | cag | gct | gca | ttc | tcc | aat | cca | 96 |
| Gly | Ser | Thr | Ala | Asp | Ile | Val | Met | Thr | Gln | Ala | Ala | Phe | Ser | Asn | Pro | |
| | | | -1 | 1 | | | | 5 | | | | | | 10 | | |
| gtc | act | ctt | gga | aca | tca | ggt | tcc | atc | tcc | tgc | agg | tct | agt | aag | agt | 144 |
| Val | Thr | Leu | Gly | Thr | Ser | Gly | Ser | Ile | Ser | Cys | Arg | Ser | Ser | Lys | Ser | |
| | | 15 | | | | | 20 | | | | | 25 | | | | |
| ctc | cta | cat | agt | aat | ggc | atc | act | tat | ttg | tat | tgg | tat | ctg | cag | aag | 192 |
| Leu | Leu | His | Ser | Asn | Gly | Ile | Thr | Tyr | Leu | Tyr | Trp | Tyr | Leu | Gln | Lys | |
| | | 30 | | | | | 35 | | | | | 40 | | | | |
| cca | ggc | cag | tct | cct | cag | ctc | ctg | att | tat | cag | atg | tcc | aac | ctt | gcc | 240 |
| Pro | Gly | Gln | Ser | Pro | Gln | Leu | Leu | Ile | Tyr | Gln | Met | Ser | Asn | Leu | Ala | |
| 45 | | | | | 50 | | | | | 55 | | | | | 60 | |
| tca | gga | gtc | cca | gac | agg | ttc | agt | agc | agt | ggg | tca | gga | act | gat | ttc | 288 |
| Ser | Gly | Val | Pro | Asp | Arg | Phe | Ser | Ser | Ser | Gly | Ser | Gly | Thr | Asp | Phe | |
| | | | | 65 | | | | | 70 | | | | | 75 | | |
| aca | ctg | aga | atc | agc | aga | gtg | gag | gct | gag | gat | gtg | ggt | gtt | tat | tac | 336 |
| Thr | Leu | Arg | Ile | Ser | Arg | Val | Glu | Ala | Glu | Asp | Val | Gly | Val | Tyr | Tyr | |
| | | | 80 | | | | | 85 | | | | | 90 | | | |
| tgt | gct | caa | aat | cta | gaa | ctt | cct | cgg | acg | ttc | ggt | gga | ggc | acc | aag | 384 |
| Cys | Ala | Gln | Asn | Leu | Glu | Leu | Pro | Arg | Thr | Phe | Gly | Gly | Gly | Thr | Lys | |
| | | | 95 | | | | | 100 | | | | | 105 | | | |
| ctt | gag | atg | aaa | cga | act | gtg | gct | gca | cca | tct | gtc | ttc | atc | ttc | ccg | 432 |
| Leu | Glu | Met | Lys | Arg | Thr | Val | Ala | Ala | Pro | Ser | Val | Phe | Ile | Phe | Pro | |
| | 110 | | | | | 115 | | | | | 120 | | | | | |
| cca | tct | gat | gag | cag | ttg | aaa | tct | gga | act | gcc | tct | gtt | gtg | tgc | ctg | 480 |
| Pro | Ser | Asp | Glu | Gln | Leu | Lys | Ser | Gly | Thr | Ala | Ser | Val | Val | Cys | Leu | |
| 125 | | | | | 130 | | | | | 135 | | | | | 140 | |
| ctg | aat | aac | ttc | tat | ccc | aga | gag | gcc | aaa | gta | cag | tgg | aag | gtg | gat | 528 |
| Leu | Asn | Asn | Phe | Tyr | Pro | Arg | Glu | Ala | Lys | Val | Gln | Trp | Lys | Val | Asp | |
| | | | | 145 | | | | | 150 | | | | | 155 | | |
| aac | gcc | ctc | caa | tcg | ggt | aac | tcc | cag | gag | agt | gtc | aca | gag | cag | gac | 576 |
| Asn | Ala | Leu | Gln | Ser | Gly | Asn | Ser | Gln | Glu | Ser | Val | Thr | Glu | Gln | Asp | |
| | | | | 160 | | | | | 165 | | | | | 170 | | |
| agc | aag | gac | agc | acc | tac | agc | ctc | agc | agc | acc | ctg | acg | ctg | agc | aaa | 624 |
| Ser | Lys | Asp | Ser | Thr | Tyr | Ser | Leu | Ser | Ser | Thr | Leu | Thr | Leu | Ser | Lys | |
| | | 175 | | | | | 180 | | | | | 185 | | | | |
| gca | gac | tac | gag | aaa | cac | aaa | gtc | tac | gcc | tgc | gaa | gtc | acc | cat | cag | 672 |

```
Ala Asp Tyr Glu Lys His Lys Val Tyr Ala Cys Glu Val Thr His Gln
190                 195                 200 ggc ctg agc tcg ccc gtc aca aag agc ttc aac agg gga gag tgt tag    720
Gly Leu Ser Ser Pro Val Thr Lys Ser Phe Asn Arg Gly Glu Cys
205                 210                 215
```

<210> SEQ ID NO 6
<211> LENGTH: 239
<212> TYPE: PRT
<213> ORGANISM: Homo Sapiens

<400> SEQUENCE: 6

```
Met Arg Phe Ser Ala Gln Leu Leu Gly Leu Leu Val Leu Trp Ile Pro
-20                 -15                 -10                 -5

Gly Ser Thr Ala Asp Ile Val Met Thr Gln Ala Ala Phe Ser Asn Pro
            -1  1                   5                   10

Val Thr Leu Gly Thr Ser Gly Ser Ile Ser Cys Arg Ser Ser Lys Ser
                15                  20                  25

Leu Leu His Ser Asn Gly Ile Thr Tyr Leu Tyr Trp Tyr Leu Gln Lys
        30                  35                  40

Pro Gly Gln Ser Pro Gln Leu Leu Ile Tyr Gln Met Ser Asn Leu Ala
45                  50                  55                  60

Ser Gly Val Pro Asp Arg Phe Ser Ser Ser Gly Ser Gly Thr Asp Phe
                65                  70                  75

Thr Leu Arg Ile Ser Arg Val Glu Ala Glu Asp Val Gly Val Tyr Tyr
            80                  85                  90

Cys Ala Gln Asn Leu Glu Leu Pro Arg Thr Phe Gly Gly Gly Thr Lys
                95                  100                 105

Leu Glu Met Lys Arg Thr Val Ala Ala Pro Ser Val Phe Ile Phe Pro
110                 115                 120

Pro Ser Asp Glu Gln Leu Lys Ser Gly Thr Ala Ser Val Val Cys Leu
125                 130                 135                 140

Leu Asn Asn Phe Tyr Pro Arg Glu Ala Lys Val Gln Trp Lys Val Asp
                145                 150                 155

Asn Ala Leu Gln Ser Gly Asn Ser Gln Glu Ser Val Thr Glu Gln Asp
                160                 165                 170

Ser Lys Asp Ser Thr Tyr Ser Leu Ser Ser Thr Leu Thr Leu Ser Lys
            175                 180                 185

Ala Asp Tyr Glu Lys His Lys Val Tyr Ala Cys Glu Val Thr His Gln
190                 195                 200

Gly Leu Ser Ser Pro Val Thr Lys Ser Phe Asn Arg Gly Glu Cys
205                 210                 215
```

<210> SEQ ID NO 7
<211> LENGTH: 1398
<212> TYPE: DNA
<213> ORGANISM: Homo Sapiens
<220> FEATURE:
<221> NAME/KEY: misc_feature
<223> OTHER INFORMATION: Mouse-Human chimeric Heavy Chain DNA and
      Protein Sequence
<220> FEATURE:
<221> NAME/KEY: CDS
<222> LOCATION: (1)..(1395)
<220> FEATURE:
<221> NAME/KEY: mat_peptide
<222> LOCATION: (58)..()

<400> SEQUENCE: 7

```
atg gct tgg gtg tcc acc ttg cta ttc ctg atg gca gct gcc caa agt    48
Met Ala Trp Val Ser Thr Leu Leu Phe Leu Met Ala Ala Ala Gln Ser
```

|   |   |
|---|---|
| <pre>                -15               -10                -5
gcc caa gca cag atc cag ttg gtg cag tct gga cct gag ctg aag aag
Ala Gln Ala Gln Ile Gln Leu Val Gln Ser Gly Pro Glu Leu Lys Lys
        -1  1              5                 10 cct gga gag aca gtc aag atc tcc tgc aag gct tct gga tat acc ttc
Pro Gly Glu Thr Val Lys Ile Ser Cys Lys Ala Ser Gly Tyr Thr Phe
 15              20                 25 aca aaa tat gga atg aac tgg gtg aag cag gct cca gga aag ggt tta
Thr Lys Tyr Gly Met Asn Trp Val Lys Gln Ala Pro Gly Lys Gly Leu
 30              35                 40                 45 aag tgg atg ggc tgg ata aac acc tac act gaa gag cca aca tat ggt
Lys Trp Met Gly Trp Ile Asn Thr Tyr Thr Glu Glu Pro Thr Tyr Gly
                 50                 55                 60 gat gac ttc aag gga cgg ttt gcc ttc tct ttg gaa acc tct gcc agc
Asp Asp Phe Lys Gly Arg Phe Ala Phe Ser Leu Glu Thr Ser Ala Ser
             65                 70                 75 act gcc aat ttg cag atc aac aac ctc aaa agt gag gac acg gct aca
Thr Ala Asn Leu Gln Ile Asn Asn Leu Lys Ser Glu Asp Thr Ala Thr
             80                 85                 90 tat ttc tgt gca aga ttt ggc tct gct gtg gac tac tgg ggt caa gga
Tyr Phe Cys Ala Arg Phe Gly Ser Ala Val Asp Tyr Trp Gly Gln Gly
 95                 100                105 acc tcg gtc acc gtc tcc tca gcc agc aca aag ggc cca tcg gtc ttc
Thr Ser Val Thr Val Ser Ser Ala Ser Thr Lys Gly Pro Ser Val Phe
110             115                 120                 125 ccc ctg gca ccc tcc tcc aag agc acc tct ggg ggc aca gcg gcc ctg
Pro Leu Ala Pro Ser Ser Lys Ser Thr Ser Gly Gly Thr Ala Ala Leu
                130                 135                 140 ggc tgc ctg gtc aag gac tac ttc ccc gaa ccg gtg acg gtg tcg tgg
Gly Cys Leu Val Lys Asp Tyr Phe Pro Glu Pro Val Thr Val Ser Trp
             145                 150                 155 aac tca ggc gcc ctg acc agc ggc gtg cac acc ttc ccg gct gtc cta
Asn Ser Gly Ala Leu Thr Ser Gly Val His Thr Phe Pro Ala Val Leu
             160                 165                 170 cag tcc tca gga ctc tac tcc ctc agc agc gtg gtg acc gtg ccc tcc
Gln Ser Ser Gly Leu Tyr Ser Leu Ser Ser Val Val Thr Val Pro Ser
175             180                 185 agc agc ttg ggc acc cag acc tac atc tgc aac gtg aat cac aag ccc
Ser Ser Leu Gly Thr Gln Thr Tyr Ile Cys Asn Val Asn His Lys Pro
190                 195                 200                 205 agc aac acc aag gtg gac aag aga gtt gag ccc aaa tct tgt gac aaa
Ser Asn Thr Lys Val Asp Lys Arg Val Glu Pro Lys Ser Cys Asp Lys
                210                 215                 220 act cac aca tgc cca ccg tgc cca gca cct gaa ctc ctg ggg gga ccg
Thr His Thr Cys Pro Pro Cys Pro Ala Pro Glu Leu Leu Gly Gly Pro
                225                 230                 235 tca gtc ttc ctc ttc ccc cca aaa ccc aag gac acc ctc atg atc tcc
Ser Val Phe Leu Phe Pro Pro Lys Pro Lys Asp Thr Leu Met Ile Ser
            240                 245                 250 cgg acc cct gag gtc aca tgc gtg gtg gtg gac gtg agc cac gaa gac
Arg Thr Pro Glu Val Thr Cys Val Val Val Asp Val Ser His Glu Asp
255                 260                 265 cct gag gtc aag ttc aac tgg tac gtg gac ggc gtg gag gtg cat aat
Pro Glu Val Lys Phe Asn Trp Tyr Val Asp Gly Val Glu Val His Asn
270                 275                 280                 285 gcc aag aca aag ccg cgg gag gag cag tac aac agc acg tac cgg gtg
Ala Lys Thr Lys Pro Arg Glu Glu Gln Tyr Asn Ser Thr Tyr Arg Val
                290                 295                 300 gtc agc gtc ctc acc gtc ctg cac cag gac tgg ctg aat ggc aag gag
Val Ser Val Leu Thr Val Leu His Gln Asp Trp Leu Asn Gly Lys Glu</pre> | 96<br><br><br><br>144<br><br><br><br>192<br><br><br><br>240<br><br><br><br>288<br><br><br><br>336<br><br><br><br>384<br><br><br><br>432<br><br><br><br>480<br><br><br><br>528<br><br><br><br>576<br><br><br><br>624<br><br><br><br>672<br><br><br><br>720<br><br><br><br>768<br><br><br><br>816<br><br><br><br>864<br><br><br><br>912<br><br><br><br>960<br><br><br><br>1008 |

```
                     305                 310                 315
tac aag tgc aag gtc tcc aac aaa gcc ctc cca gcc ccc atc gag aaa      1056
Tyr Lys Cys Lys Val Ser Asn Lys Ala Leu Pro Ala Pro Ile Glu Lys
                320                 325                 330 acc atc tcc aaa gcc aaa ggg cag ccc cga gaa cca cag gtg tac acc      1104
Thr Ile Ser Lys Ala Lys Gly Gln Pro Arg Glu Pro Gln Val Tyr Thr
            335                 340                 345 ctg ccc cca tcc cgg gat gag ctg acc aag aac cag gtc agc ctg acc      1152
Leu Pro Pro Ser Arg Asp Glu Leu Thr Lys Asn Gln Val Ser Leu Thr
350                 355                 360                 365 tgc ctg gtc aaa ggc ttc tat ccc agc gac atc gcc gtg gag tgg gag      1200
Cys Leu Val Lys Gly Phe Tyr Pro Ser Asp Ile Ala Val Glu Trp Glu
                370                 375                 380 agc aat ggg cag ccg gag aac aac tac aag acc acg cct ccc gtg ctg      1248
Ser Asn Gly Gln Pro Glu Asn Asn Tyr Lys Thr Thr Pro Pro Val Leu
                385                 390                 395 gac tcc gac ggc tcc ttc ttc ctc tac agc aag ctc acc gtg gac aag      1296
Asp Ser Asp Gly Ser Phe Phe Leu Tyr Ser Lys Leu Thr Val Asp Lys
            400                 405                 410 agc agg tgg cag cag ggg aac gtc ttc tca tgc tcc gtg atg cat gag      1344
Ser Arg Trp Gln Gln Gly Asn Val Phe Ser Cys Ser Val Met His Glu
        415                 420                 425 gct ctg cac aac cac tac acg cag aag agc ctc tcc ctg tct ccg ggt      1392
Ala Leu His Asn His Tyr Thr Gln Lys Ser Leu Ser Leu Ser Pro Gly
430                 435                 440                 445 aaa tga                                                               1398
Lys

<210> SEQ ID NO 8
<211> LENGTH: 465
<212> TYPE: PRT
<213> ORGANISM: Homo Sapiens

<400> SEQUENCE: 8

Met Ala Trp Val Ser Thr Leu Leu Phe Leu Met Ala Ala Ala Gln Ser
                -15                 -10                  -5

Ala Gln Ala Gln Ile Gln Leu Val Gln Ser Gly Pro Glu Leu Lys Lys
        -1   1               5                  10

Pro Gly Glu Thr Val Lys Ile Ser Cys Lys Ala Ser Gly Tyr Thr Phe
 15                  20                  25

Thr Lys Tyr Gly Met Asn Trp Val Lys Gln Ala Pro Gly Lys Gly Leu
 30                  35                  40                  45

Lys Trp Met Gly Trp Ile Asn Thr Tyr Thr Glu Glu Pro Thr Tyr Gly
                 50                  55                  60

Asp Asp Phe Lys Gly Arg Phe Ala Phe Ser Leu Glu Thr Ser Ala Ser
                 65                  70                  75

Thr Ala Asn Leu Gln Ile Asn Asn Leu Lys Ser Glu Asp Thr Ala Thr
             80                  85                  90

Tyr Phe Cys Ala Arg Phe Gly Ser Ala Val Asp Tyr Trp Gly Gln Gly
     95                 100                 105

Thr Ser Val Thr Val Ser Ser Ala Ser Thr Lys Gly Pro Ser Val Phe
110                 115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
                145                 150                 155

Asn Ser Gly Ala Leu Thr Ser Gly Val His Thr Phe Pro Ala Val Leu
            160                 165                 170
```

```
Gln Ser Ser Gly Leu Tyr Ser Leu Ser Ser Val Val Thr Val Pro Ser
    175                 180                 185

Ser Ser Leu Gly Thr Gln Thr Tyr Ile Cys Asn Val Asn His Lys Pro
190                 195                 200                 205

Ser Asn Thr Lys Val Asp Lys Arg Val Glu Pro Lys Ser Cys Asp Lys
                210                 215                 220

Thr His Thr Cys Pro Pro Cys Pro Ala Pro Glu Leu Leu Gly Gly Pro
                225                 230                 235

Ser Val Phe Leu Phe Pro Pro Lys Pro Lys Asp Thr Leu Met Ile Ser
            240                 245                 250

Arg Thr Pro Glu Val Thr Cys Val Val Val Asp Val Ser His Glu Asp
    255                 260                 265

Pro Glu Val Lys Phe Asn Trp Tyr Val Asp Gly Val Glu Val His Asn
270                 275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
                305                 310                 315

Tyr Lys Cys Lys Val Ser Asn Lys Ala Leu Pro Ala Pro Ile Glu Lys
            320                 325                 330

Thr Ile Ser Lys Ala Lys Gly Gln Pro Arg Glu Pro Gln Val Tyr Thr
    335                 340                 345

Leu Pro Pro Ser Arg Asp Glu Leu Thr Lys Asn Gln Val Ser Leu Thr
350                 355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
                385                 390                 395

Asp Ser Asp Gly Ser Phe Phe Leu Tyr Ser Lys Leu Thr Val Asp Lys
            400                 405                 410

Ser Arg Trp Gln Gln Gly Asn Val Phe Ser Cys Ser Val Met His Glu
    415                 420                 425

Ala Leu His Asn His Tyr Thr Gln Lys Ser Leu Ser Leu Ser Pro Gly
430                 435                 440                 445

Lys

<210> SEQ ID NO 9
<211> LENGTH: 720
<212> TYPE: DNA
<213> ORGANISM: Homo Sapiens
<220> FEATURE:
<221> NAME/KEY: misc_feature
<223> OTHER INFORMATION: Low Risk ING-1 Light Chain (LC)
<220> FEATURE:
<221> NAME/KEY: misc_feature
<223> OTHER INFORMATION: Variable Region of the Light Chain is Amino
      Acids 1-112
<220> FEATURE:
<221> NAME/KEY: CDS
<222> LOCATION: (1)..(717)
<220> FEATURE:
<221> NAME/KEY: mat_peptide
<222> LOCATION: (61)..()

<400> SEQUENCE: 9 atg agg ttc tct gct cag ctt ctg ggg ctg ctt gtg ctc tgg atc cct      48
Met Arg Phe Ser Ala Gln Leu Leu Gly Leu Leu Val Leu Trp Ile Pro
-20                 -15                 -10                  -5 gga tcc act gca gac atc gtg atg acc cag tct gca ctc tcc aat cca     96
```

```
Gly Ser Thr Ala Asp Ile Val Met Thr Gln Ser Ala Leu Ser Asn Pro
        -1  1           5                  10 gtc act ctg gga gag tca ggt tcc atc tcc tgc cgg tct agt aag agt    144
Val Thr Leu Gly Glu Ser Gly Ser Ile Ser Cys Arg Ser Ser Lys Ser
        15                  20                  25 ctc cta cat agt aat ggc atc act tat ttg tat tgg tat ctg cag aaa    192
Leu Leu His Ser Asn Gly Ile Thr Tyr Leu Tyr Trp Tyr Leu Gln Lys
        30                  35                  40 cca ggg cag tct cct cag ctg ctc atc tat cag atg tct aac aga gcc    240
Pro Gly Gln Ser Pro Gln Leu Leu Ile Tyr Gln Met Ser Asn Arg Ala
45          50                  55                  60 tca ggg gtc cca gac agg ttc agt agc agt gga tct ggg aca gat ttc    288
Ser Gly Val Pro Asp Arg Phe Ser Ser Ser Gly Ser Gly Thr Asp Phe
                65                  70                  75 act ctc aag atc agc aga gtg gag gct gaa gat gtg gga gtt tat tac    336
Thr Leu Lys Ile Ser Arg Val Glu Ala Glu Asp Val Gly Val Tyr Tyr
            80                  85                  90 tgt gct cag aac cta gag ctt ccg cgg acg ttc ggt cag ggc acc aag    384
Cys Ala Gln Asn Leu Glu Leu Pro Arg Thr Phe Gly Gln Gly Thr Lys
                95                  100                 105 ctt gag atg aaa cga act gtg gct gca cca tct gtc ttc atc ttc ccg    432
Leu Glu Met Lys Arg Thr Val Ala Ala Pro Ser Val Phe Ile Phe Pro
    110                 115                 120 cca tct gat gag cag ttg aaa tct gga act gcc tct gtt gtg tgc ctg    480
Pro Ser Asp Glu Gln Leu Lys Ser Gly Thr Ala Ser Val Val Cys Leu
125             130                 135                 140 ctg aat aac ttc tat ccc aga gag gcc aaa gta cag tgg aag gtg gat    528
Leu Asn Asn Phe Tyr Pro Arg Glu Ala Lys Val Gln Trp Lys Val Asp
                    145                 150                 155 aac gcc ctc caa tcg ggt aac tcc cag gag agt gtc aca gag cag gac    576
Asn Ala Leu Gln Ser Gly Asn Ser Gln Glu Ser Val Thr Glu Gln Asp
                160                 165                 170 agc aag gac agc acc tac agc ctc agc agc acc ctg acg ctg agc aaa    624
Ser Lys Asp Ser Thr Tyr Ser Leu Ser Ser Thr Leu Thr Leu Ser Lys
            175                 180                 185 gca gac tac gag aaa cac aaa gtc tac gcc tgc gaa gtc acc cat cag    672
Ala Asp Tyr Glu Lys His Lys Val Tyr Ala Cys Glu Val Thr His Gln
        190                 195                 200 ggc ctg agc tcg ccc gtc aca aag agc ttc aac agg gga gag tgt tag    720
Gly Leu Ser Ser Pro Val Thr Lys Ser Phe Asn Arg Gly Glu Cys
205                 210                 215

<210> SEQ ID NO 10
<211> LENGTH: 239
<212> TYPE: PRT
<213> ORGANISM: Homo Sapiens

<400> SEQUENCE: 10

Met Arg Phe Ser Ala Gln Leu Leu Gly Leu Leu Val Leu Trp Ile Pro
-20             -15                 -10                  -5

Gly Ser Thr Ala Asp Ile Val Met Thr Gln Ser Ala Leu Ser Asn Pro
        -1  1           5                  10

Val Thr Leu Gly Glu Ser Gly Ser Ile Ser Cys Arg Ser Ser Lys Ser
        15                  20                  25

Leu Leu His Ser Asn Gly Ile Thr Tyr Leu Tyr Trp Tyr Leu Gln Lys
        30                  35                  40

Pro Gly Gln Ser Pro Gln Leu Leu Ile Tyr Gln Met Ser Asn Arg Ala
45          50                  55                  60

Ser Gly Val Pro Asp Arg Phe Ser Ser Ser Gly Ser Gly Thr Asp Phe
                65                  70                  75
```

```
Thr Leu Lys Ile Ser Arg Val Glu Ala Glu Asp Val Gly Val Tyr Tyr
            80                  85                  90

Cys Ala Gln Asn Leu Glu Leu Pro Arg Thr Phe Gly Gln Gly Thr Lys
                95                 100                 105

Leu Glu Met Lys Arg Thr Val Ala Ala Pro Ser Val Phe Ile Phe Pro
    110                 115                 120

Pro Ser Asp Glu Gln Leu Lys Ser Gly Thr Ala Ser Val Val Cys Leu
125                 130                 135                 140

Leu Asn Asn Phe Tyr Pro Arg Glu Ala Lys Val Gln Trp Lys Val Asp
                145                 150                 155

Asn Ala Leu Gln Ser Gly Asn Ser Gln Glu Ser Val Thr Glu Gln Asp
            160                 165                 170

Ser Lys Asp Ser Thr Tyr Ser Leu Ser Ser Thr Leu Thr Leu Ser Lys
        175                 180                 185

Ala Asp Tyr Glu Lys His Lys Val Tyr Ala Cys Glu Val Thr His Gln
    190                 195                 200

Gly Leu Ser Ser Pro Val Thr Lys Ser Phe Asn Arg Gly Glu Cys
205                 210                 215

<210> SEQ ID NO 11
<211> LENGTH: 720
<212> TYPE: DNA
<213> ORGANISM: Homo Sapiens
<220> FEATURE:
<221> NAME/KEY: misc_feature
<223> OTHER INFORMATION: Low + Moderate Risk ING-1 Light Chain (LC)
<220> FEATURE:
<221> NAME/KEY: CDS
<222> LOCATION: (1)..(717)
<220> FEATURE:
<221> NAME/KEY: mat_peptide
<222> LOCATION: (61)..()

<400> SEQUENCE: 11 atg agg ttc tct gct cag ctt ctg ggg ctg ctt gtg ctc tgg atc cct        48
Met Arg Phe Ser Ala Gln Leu Leu Gly Leu Leu Val Leu Trp Ile Pro
-20                 -15                 -10                  -5 gga tcc act gca gac atc gtg atg acc cag tct cca ctc tcc ctg cca        96
Gly Ser Thr Ala Asp Ile Val Met Thr Gln Ser Pro Leu Ser Leu Pro
            -1   1               5                  10 gtc act cct gga gag ccg ggt tcc atc tcc tgc agg tct agt aag agt       144
Val Thr Pro Gly Glu Pro Gly Ser Ile Ser Cys Arg Ser Ser Lys Ser
        15                  20                  25 ctc cta cat agt aat ggc atc act tat ttg tat tgg tat ctg cag aaa       192
Leu Leu His Ser Asn Gly Ile Thr Tyr Leu Tyr Trp Tyr Leu Gln Lys
    30                  35                  40 cca ggg cag tct cct cag ctg ctc atc tat cag atg tct aac aga gcc       240
Pro Gly Gln Ser Pro Gln Leu Leu Ile Tyr Gln Met Ser Asn Arg Ala
45                  50                  55                  60 tca ggg gtc cca gac agg ttc agt agc agt gga tct ggg aca gat ttc       288
Ser Gly Val Pro Asp Arg Phe Ser Ser Ser Gly Ser Gly Thr Asp Phe
                65                  70                  75 act ctc aag atc agc aga gtg gag gct gaa gat gtg gga gtt tat tac       336
Thr Leu Lys Ile Ser Arg Val Glu Ala Glu Asp Val Gly Val Tyr Tyr
            80                  85                  90 tgt gct cag aac cta gag ctt cca cgg acg ttc ggt cag ggc acc aag       384
Cys Ala Gln Asn Leu Glu Leu Pro Arg Thr Phe Gly Gln Gly Thr Lys
                95                 100                 105 ctt gag atg aaa cga act gtg gct gca cca tct gtc ttc atc ttc ccg       432
Leu Glu Met Lys Arg Thr Val Ala Ala Pro Ser Val Phe Ile Phe Pro
    110                 115                 120
```

```
cca tct gat gag cag ttg aaa tct gga act gcc tct gtt gtg tgc ctg      480
Pro Ser Asp Glu Gln Leu Lys Ser Gly Thr Ala Ser Val Val Cys Leu
125                 130                 135                 140 ctg aat aac ttc tat ccc aga gag gcc aaa gta cag tgg aag gtg gat      528
Leu Asn Asn Phe Tyr Pro Arg Glu Ala Lys Val Gln Trp Lys Val Asp
            145                 150                 155 aac gcc ctc caa tcg ggt aac tcc cag gag agt gtc aca gag cag gac      576
Asn Ala Leu Gln Ser Gly Asn Ser Gln Glu Ser Val Thr Glu Gln Asp
        160                 165                 170 agc aag gac agc acc tac agc ctc agc agc acc ctg acg ctg agc aaa      624
Ser Lys Asp Ser Thr Tyr Ser Leu Ser Ser Thr Leu Thr Leu Ser Lys
    175                 180                 185 gca gac tac gag aaa cac aaa gtc tac gcc tgc gaa gtc acc cat cag      672
Ala Asp Tyr Glu Lys His Lys Val Tyr Ala Cys Glu Val Thr His Gln
190                 195                 200 ggc ctg agc tcg ccc gtc aca aag agc ttc aac agg gga gag tgt tag      720
Gly Leu Ser Ser Pro Val Thr Lys Ser Phe Asn Arg Gly Glu Cys
205                 210                 215

<210> SEQ ID NO 12
<211> LENGTH: 239
<212> TYPE: PRT
<213> ORGANISM: Homo Sapiens

<400> SEQUENCE: 12

Met Arg Phe Ser Ala Gln Leu Leu Gly Leu Leu Val Leu Trp Ile Pro
-20                 -15                 -10                 -5

Gly Ser Thr Ala Asp Ile Val Met Thr Gln Ser Pro Leu Ser Leu Pro
            -1  1                   5                  10

Val Thr Pro Gly Glu Pro Gly Ser Ile Ser Cys Arg Ser Ser Lys Ser
        15                  20                  25

Leu Leu His Ser Asn Gly Ile Thr Tyr Leu Tyr Trp Tyr Leu Gln Lys
    30                  35                  40

Pro Gly Gln Ser Pro Gln Leu Leu Ile Tyr Gln Met Ser Asn Arg Ala
45                  50                  55                  60

Ser Gly Val Pro Asp Arg Phe Ser Ser Gly Ser Gly Thr Asp Phe
                65                  70                  75

Thr Leu Lys Ile Ser Arg Val Glu Ala Glu Asp Val Gly Val Tyr Tyr
            80                  85                  90

Cys Ala Gln Asn Leu Glu Leu Pro Arg Thr Phe Gly Gln Gly Thr Lys
        95                  100                 105

Leu Glu Met Lys Arg Thr Val Ala Ala Pro Ser Val Phe Ile Phe Pro
    110                 115                 120

Pro Ser Asp Glu Gln Leu Lys Ser Gly Thr Ala Ser Val Val Cys Leu
125                 130                 135                 140

Leu Asn Asn Phe Tyr Pro Arg Glu Ala Lys Val Gln Trp Lys Val Asp
            145                 150                 155

Asn Ala Leu Gln Ser Gly Asn Ser Gln Glu Ser Val Thr Glu Gln Asp
        160                 165                 170

Ser Lys Asp Ser Thr Tyr Ser Leu Ser Ser Thr Leu Thr Leu Ser Lys
    175                 180                 185

Ala Asp Tyr Glu Lys His Lys Val Tyr Ala Cys Glu Val Thr His Gln
190                 195                 200

Gly Leu Ser Ser Pro Val Thr Lys Ser Phe Asn Arg Gly Glu Cys
205                 210                 215

<210> SEQ ID NO 13
```

-continued

```
<211> LENGTH: 88
<212> TYPE: DNA
<213> ORGANISM: Homo Sapiens
<220> FEATURE:
<221> NAME/KEY: misc_feature
<223> OTHER INFORMATION: KL1 V Region Oligios ING-1 Light Chain (Kappa
      low)

<400> SEQUENCE: 13
tgtcgacacc atgaggttct ctgctcagct tctggggctg cttgtgctct ggatccctgg      60
atccactgca gacatcgtga tgacccag                                         88

<210> SEQ ID NO 14
<211> LENGTH: 85
<212> TYPE: DNA
<213> ORGANISM: Homo Sapiens
<220> FEATURE:
<221> NAME/KEY: misc_feature
<223> OTHER INFORMATION: KL2 V Region Oligios ING-1 Light Chain (Kappa
      low)

<400> SEQUENCE: 14
actcttacta gaccggcagg agatggaacc tgactctccc agagtgactg gattggagag      60
tgcagactgg gtcatcacga tgtct                                            85

<210> SEQ ID NO 15
<211> LENGTH: 88
<212> TYPE: DNA
<213> ORGANISM: Homo Sapiens
<220> FEATURE:
<221> NAME/KEY: misc_feature
<223> OTHER INFORMATION: KL3 V Region Oligios ING-1 Light Chain (Kappa
      low)

<400> SEQUENCE: 15
ctgccggtct agtaagagtc tcctacatag taatggcatc acttatttgt attggtatct      60
gcagaaacca gggcagtctc ctcagctg                                         88

<210> SEQ ID NO 16
<211> LENGTH: 86
<212> TYPE: DNA
<213> ORGANISM: Homo Sapiens
<220> FEATURE:
<221> NAME/KEY: misc_feature
<223> OTHER INFORMATION: KL4 V Region Oligios ING-1 Light Chain (Kappa
      low)

<400> SEQUENCE: 16
tgtcccagat ccactgctac tgaacctgtc tgggaccccct gaggctctgt tagacatctg     60
atagatgagc agctgaggag actgcc                                           86

<210> SEQ ID NO 17
<211> LENGTH: 77
<212> TYPE: DNA
<213> ORGANISM: Homo Sapiens
<220> FEATURE:
<221> NAME/KEY: misc_feature
<223> OTHER INFORMATION: KL5 V Region Oligios ING-1 Light Chain (Kappa
      low)

<400> SEQUENCE: 17
agcagtggat ctgggacaga tttcactctc aagatcagca gagtggaggc tgaagatgtg      60
ggagtttatt actgtgc                                                     77

<210> SEQ ID NO 18
```

```
<211> LENGTH: 75
<212> TYPE: DNA
<213> ORGANISM: Homo Sapiens
<220> FEATURE:
<221> NAME/KEY: misc_feature
<223> OTHER INFORMATION: KL6 V Region Oligios ING-1 Light Chain (Kappa
      low)

<400> SEQUENCE: 18
tttgatttca agcttggtgc cctgaccgaa cgtccgtgga agctctaggt tctgagcaca      60
gtaataaact cccac                                                     75

<210> SEQ ID NO 19
<211> LENGTH: 22
<212> TYPE: DNA
<213> ORGANISM: Homo Sapiens
<220> FEATURE:
<221> NAME/KEY: misc_feature
<223> OTHER INFORMATION: Low Risk Primers Forward Primer: KF Ing-1 Light
      Chain Oligos

<400> SEQUENCE: 19
ttatgtcgac accatgaggt tc                                             22

<210> SEQ ID NO 20
<211> LENGTH: 21
<212> TYPE: DNA
<213> ORGANISM: Homo Sapiens
<220> FEATURE:
<221> NAME/KEY: misc_feature
<223> OTHER INFORMATION: Low risk Primers Reverse Primer: KR Ing-1 Light
      Chain Oligos

<400> SEQUENCE: 20
tttgatttca agcttggtgc c                                              21

<210> SEQ ID NO 21
<211> LENGTH: 85
<212> TYPE: DNA
<213> ORGANISM: Homo Sapiens
<220> FEATURE:
<221> NAME/KEY: misc_feature
<223> OTHER INFORMATION: Moderate Risk Primer: KM2 Ing-1 Light Chain
      Oligos

<400> SEQUENCE: 21
actcttacta gaccggcagg agatggaacc cggctctcca ggagtgactg gcagggagag      60
tggagactgg gtcatcacga tgtct                                          85

<210> SEQ ID NO 22
<211> LENGTH: 1398
<212> TYPE: DNA
<213> ORGANISM: Homo Sapiens
<220> FEATURE:
<221> NAME/KEY: misc_feature
<223> OTHER INFORMATION: Low Risk ING-1 Risk Heavy Chain (HC)
<220> FEATURE:
<221> NAME/KEY: misc_feature
<223> OTHER INFORMATION: Variable region of HC is Amino Acids is 1-116
<220> FEATURE:
<221> NAME/KEY: CDS
<222> LOCATION: (1)..(1395)
<220> FEATURE:
<221> NAME/KEY: mat_peptide
<222> LOCATION: (58)..()

<400> SEQUENCE: 22 atg gct tgg gtg tcc acc ttg cta ttc ctg atg gca gct gcc caa agt      48
Met Ala Trp Val Ser Thr Leu Leu Phe Leu Met Ala Ala Ala Gln Ser
```

|  |  |  |  |  |  |  |  |  |  |  |  |  |  |  |  |
|---|---|---|---|---|---|---|---|---|---|---|---|---|---|---|---|
|  |  | -15 |  |  |  |  | -10 |  |  |  |  | -5 |  |  |  |

```
gcc caa gca cag atc cag ttg gtg cag tct gga cct gag gtg aag aag       96
Ala Gln Ala Gln Ile Gln Leu Val Gln Ser Gly Pro Glu Val Lys Lys
     -1   1              5                  10 cct gga gag tcc gtc aag atc tcc tgc aag gct tct gga tat acc ttc      144
Pro Gly Glu Ser Val Lys Ile Ser Cys Lys Ala Ser Gly Tyr Thr Phe
 15                  20                  25 aca aaa tat gga atg aac tgg gtg aag cag gct cca gga cag ggt tta      192
Thr Lys Tyr Gly Met Asn Trp Val Lys Gln Ala Pro Gly Gln Gly Leu
 30                  35                  40                  45 aag tgg atg ggc tgg ata aac acc tac act gaa gag cca aca tat ggt      240
Lys Trp Met Gly Trp Ile Asn Thr Tyr Thr Glu Glu Pro Thr Tyr Gly
                 50                  55                  60 gat gac ttc aag gga cgg ttt acc ttc acc ttg gac acc tct act agc      288
Asp Asp Phe Lys Gly Arg Phe Thr Phe Thr Leu Asp Thr Ser Thr Ser
             65                  70                  75 act gcc tat ttg gaa atc tct tct ctc cgg agt gag gac acg gct aca      336
Thr Ala Tyr Leu Glu Ile Ser Ser Leu Arg Ser Glu Asp Thr Ala Thr
         80                  85                  90 tat ttc tgt gca aga ttt ggc tct gct gtg gac tac tgg ggt caa gga      384
Tyr Phe Cys Ala Arg Phe Gly Ser Ala Val Asp Tyr Trp Gly Gln Gly
     95                 100                 105 acc ttg gtc acc gtc tcc tca gcc agc aca aag ggc cca tcg gtc ttc      432
Thr Leu Val Thr Val Ser Ser Ala Ser Thr Lys Gly Pro Ser Val Phe
110                 115                 120                 125 ccc ctg gca ccc tcc tcc aag agc acc tct ggg ggc aca gcg gcc ctg      480
Pro Leu Ala Pro Ser Ser Lys Ser Thr Ser Gly Gly Thr Ala Ala Leu
                130                 135                 140 ggc tgc ctg gtc aag gac tac ttc ccc gaa ccg gtg acg gtg tcg tgg      528
Gly Cys Leu Val Lys Asp Tyr Phe Pro Glu Pro Val Thr Val Ser Trp
            145                 150                 155 aac tca ggc gcc ctg acc agc ggc gtg cac acc ttc ccg gct gtc cta      576
Asn Ser Gly Ala Leu Thr Ser Gly Val His Thr Phe Pro Ala Val Leu
        160                 165                 170 cag tcc tca gga ctc tac tcc ctc agc agc gtg gtg acc gtg ccc tcc      624
Gln Ser Ser Gly Leu Tyr Ser Leu Ser Ser Val Val Thr Val Pro Ser
    175                 180                 185 agc agc ttg ggc acc cag acc tac atc tgc aac gtg aat cac aag ccc      672
Ser Ser Leu Gly Thr Gln Thr Tyr Ile Cys Asn Val Asn His Lys Pro
190                 195                 200                 205 agc aac acc aag gtg gac aag aga gtt gag ccc aaa tct tgt gac aaa      720
Ser Asn Thr Lys Val Asp Lys Arg Val Glu Pro Lys Ser Cys Asp Lys
                210                 215                 220 act cac aca tgc cca ccg tgc cca gca cct gaa ctc ctg ggg gga ccg      768
Thr His Thr Cys Pro Pro Cys Pro Ala Pro Glu Leu Leu Gly Gly Pro
            225                 230                 235 tca gtc ttc ctc ttc ccc cca aaa ccc aag gac acc ctc atg atc tcc      816
Ser Val Phe Leu Phe Pro Pro Lys Pro Lys Asp Thr Leu Met Ile Ser
        240                 245                 250 cgg acc cct gag gtc aca tgc gtg gtg gtg gac gtg agc cac gaa gac      864
Arg Thr Pro Glu Val Thr Cys Val Val Val Asp Val Ser His Glu Asp
    255                 260                 265 cct gag gtc aag ttc aac tgg tac gtg gac ggc gtg gag gtg cat aat      912
Pro Glu Val Lys Phe Asn Trp Tyr Val Asp Gly Val Glu Val His Asn
270                 275                 280                 285 gcc aag aca aag ccg cgg gag gag cag tac aac agc acg tac cgg gtg      960
Ala Lys Thr Lys Pro Arg Glu Glu Gln Tyr Asn Ser Thr Tyr Arg Val
                290                 295                 300 gtc agc gtc ctc acc gtc ctg cac cag gac tgg ctg aat ggc aag gag     1008
Val Ser Val Leu Thr Val Leu His Gln Asp Trp Leu Asn Gly Lys Glu
```

```
                     305                 310                 315
tac aag tgc aag gtc tcc aac aaa gcc ctc cca gcc ccc atc gag aaa         1056
Tyr Lys Cys Lys Val Ser Asn Lys Ala Leu Pro Ala Pro Ile Glu Lys
                320                 325                 330 acc atc tcc aaa gcc aaa ggg cag ccc cga gaa cca cag gtg tac acc         1104
Thr Ile Ser Lys Ala Lys Gly Gln Pro Arg Glu Pro Gln Val Tyr Thr
            335                 340                 345 ctg ccc cca tcc cgg gat gag ctg acc aag aac cag gtc agc ctg acc         1152
Leu Pro Pro Ser Arg Asp Glu Leu Thr Lys Asn Gln Val Ser Leu Thr
350                 355                 360                 365 tgc ctg gtc aaa ggc ttc tat ccc agc gac atc gcc gtg gag tgg gag         1200
Cys Leu Val Lys Gly Phe Tyr Pro Ser Asp Ile Ala Val Glu Trp Glu
                370                 375                 380 agc aat ggg cag ccg gag aac aac tac aag acc acg cct ccc gtg ctg         1248
Ser Asn Gly Gln Pro Glu Asn Asn Tyr Lys Thr Thr Pro Pro Val Leu
            385                 390                 395 gac tcc gac ggc tcc ttc ttc ctc tac agc aag ctc acc gtg gac aag         1296
Asp Ser Asp Gly Ser Phe Phe Leu Tyr Ser Lys Leu Thr Val Asp Lys
        400                 405                 410 agc agg tgg cag cag ggg aac gtc ttc tca tgc tcc gtg atg cat gag         1344
Ser Arg Trp Gln Gln Gly Asn Val Phe Ser Cys Ser Val Met His Glu
    415                 420                 425 gct ctg cac aac cac tac acg cag aag agc ctc tcc ctg tct ccg ggt         1392
Ala Leu His Asn His Tyr Thr Gln Lys Ser Leu Ser Leu Ser Pro Gly
430                 435                 440                 445 aaa tga                                                                 1398
Lys <210> SEQ ID NO 23
<211> LENGTH: 465
<212> TYPE: PRT
<213> ORGANISM: Homo Sapiens

<400> SEQUENCE: 23

Met Ala Trp Val Ser Thr Leu Leu Phe Leu Met Ala Ala Ala Gln Ser
                -15                 -10                 -5

Ala Gln Ala Gln Ile Gln Leu Val Gln Ser Gly Pro Glu Val Lys Lys
    -1  1               5                   10

Pro Gly Glu Ser Val Lys Ile Ser Cys Lys Ala Ser Gly Tyr Thr Phe
15                  20                  25

Thr Lys Tyr Gly Met Asn Trp Val Lys Gln Ala Pro Gly Gln Gly Leu
30                  35                  40                  45

Lys Trp Met Gly Trp Ile Asn Thr Tyr Thr Glu Glu Pro Thr Tyr Gly
                50                  55                  60

Asp Asp Phe Lys Gly Arg Phe Thr Phe Thr Leu Asp Thr Ser Thr Ser
            65                  70                  75

Thr Ala Tyr Leu Glu Ile Ser Ser Leu Arg Ser Glu Asp Thr Ala Thr
        80                  85                  90

Tyr Phe Cys Ala Arg Phe Gly Ser Ala Val Asp Tyr Trp Gly Gln Gly
    95                  100                 105

Thr Leu Val Thr Val Ser Ser Ala Ser Thr Lys Gly Pro Ser Val Phe
110                 115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
            145                 150                 155

Asn Ser Gly Ala Leu Thr Ser Gly Val His Thr Phe Pro Ala Val Leu
        160                 165                 170
```

```
Gln Ser Ser Gly Leu Tyr Ser Leu Ser Val Val Thr Val Pro Ser
    175                 180                 185

Ser Ser Leu Gly Thr Gln Thr Tyr Ile Cys Asn Val Asn His Lys Pro
190                 195                 200                 205

Ser Asn Thr Lys Val Asp Lys Arg Val Glu Pro Lys Ser Cys Asp Lys
                210                 215                 220

Thr His Thr Cys Pro Pro Cys Pro Ala Pro Glu Leu Leu Gly Gly Pro
            225                 230                 235

Ser Val Phe Leu Phe Pro Pro Lys Pro Lys Asp Thr Leu Met Ile Ser
        240                 245                 250

Arg Thr Pro Glu Val Thr Cys Val Val Val Asp Val Ser His Glu Asp
    255                 260                 265

Pro Glu Val Lys Phe Asn Trp Tyr Val Asp Gly Val Glu Val His Asn
270                 275                 280                 285

Ala Lys Thr Lys Pro Arg Glu Glu Gln Tyr Asn Ser Thr Tyr Arg Val
                290                 295                 300

Val Ser Val Leu Thr Val Leu His Gln Asp Trp Leu Asn Gly Lys Glu
            305                 310                 315

Tyr Lys Cys Lys Val Ser Asn Lys Ala Leu Pro Ala Pro Ile Glu Lys
        320                 325                 330

Thr Ile Ser Lys Ala Lys Gly Gln Pro Arg Glu Pro Gln Val Tyr Thr
    335                 340                 345

Leu Pro Pro Ser Arg Asp Glu Leu Thr Lys Asn Gln Val Ser Leu Thr
350                 355                 360                 365

Cys Leu Val Lys Gly Phe Tyr Pro Ser Asp Ile Ala Val Glu Trp Glu
                370                 375                 380

Ser Asn Gly Gln Pro Glu Asn Asn Tyr Lys Thr Thr Pro Pro Val Leu
            385                 390                 395

Asp Ser Asp Gly Ser Phe Phe Leu Tyr Ser Lys Leu Thr Val Asp Lys
        400                 405                 410

Ser Arg Trp Gln Gln Gly Asn Val Phe Ser Cys Ser Val Met His Glu
    415                 420                 425

Ala Leu His Asn His Tyr Thr Gln Lys Ser Leu Ser Leu Ser Pro Gly
430                 435                 440                 445

Lys

<210> SEQ ID NO 24
<211> LENGTH: 1398
<212> TYPE: DNA
<213> ORGANISM: Homo Sapiens
<220> FEATURE:
<221> NAME/KEY: misc_feature
<223> OTHER INFORMATION: Low + Moderate ING-1 Heavy Chain (HC)
<220> FEATURE:
<221> NAME/KEY: CDS
<222> LOCATION: (1)..(1395)
<220> FEATURE:
<221> NAME/KEY: mat_peptide
<222> LOCATION: (58)..()

<400> SEQUENCE: 24 atg gct tgg gtg tcc acc ttg cta ttc ctg atg gca gct gcc caa agt    48
Met Ala Trp Val Ser Thr Leu Leu Phe Leu Met Ala Ala Ala Gln Ser
            -15                 -10                  -5 gcc caa gca cag atc cag ttg gtg cag tct gga gct gag gtg aag aag    96
Ala Gln Ala Gln Ile Gln Leu Val Gln Ser Gly Ala Glu Val Lys Lys
        -1   1                   5                  10 cct gga gag tca gtc aag atc tcc tgc aag gct tct gga tat acc ttc   144
```

```
              Pro Gly Glu Ser Val Lys Ile Ser Cys Lys Ala Ser Gly Tyr Thr Phe
                  15                  20                  25 aca aaa tat gga atg aac tgg gtg cga cag gct cca gga caa ggt tta        192
Thr Lys Tyr Gly Met Asn Trp Val Arg Gln Ala Pro Gly Gln Gly Leu
 30                  35                  40                  45 gag tgg atg ggc tgg ata aac acc tac act gaa gag cca aca tat ggt        240
Glu Trp Met Gly Trp Ile Asn Thr Tyr Thr Glu Glu Pro Thr Tyr Gly
                     50                  55                  60 cag aag ttc cag gga cgg ttt acc ttc acc ttg gac acc tct act agc        288
Gln Lys Phe Gln Gly Arg Phe Thr Phe Thr Leu Asp Thr Ser Thr Ser
                 65                  70                  75 act gcc tat ttg gaa atc tct tcg ctc cgg agt gag gac acg gct gtg        336
Thr Ala Tyr Leu Glu Ile Ser Ser Leu Arg Ser Glu Asp Thr Ala Val
             80                  85                  90 tat ttc tgt gca aga ttt ggc tct gct gtg gac tac tgg ggt caa gga        384
Tyr Phe Cys Ala Arg Phe Gly Ser Ala Val Asp Tyr Trp Gly Gln Gly
         95                 100                 105 acc ttg gtc acc gtc tcc tca gcc agc aca aag ggc cca tcg gtc ttc        432
Thr Leu Val Thr Val Ser Ser Ala Ser Thr Lys Gly Pro Ser Val Phe
110                 115                 120                 125 ccc ctg gca ccc tcc tcc aag agc acc tct ggg ggc aca gcg gcc ctg        480
Pro Leu Ala Pro Ser Ser Lys Ser Thr Ser Gly Gly Thr Ala Ala Leu
                    130                 135                 140 ggc tgc ctg gtc aag gac tac ttc ccc gaa ccg gtg acg gtg tcg tgg        528
Gly Cys Leu Val Lys Asp Tyr Phe Pro Glu Pro Val Thr Val Ser Trp
                145                 150                 155 aac tca ggc gcc ctg acc agc ggc gtg cac acc ttc ccg gct gtc cta        576
Asn Ser Gly Ala Leu Thr Ser Gly Val His Thr Phe Pro Ala Val Leu
            160                 165                 170 cag tcc tca gga ctc tac tcc ctc agc agc gtg gtg acc gtg ccc tcc        624
Gln Ser Ser Gly Leu Tyr Ser Leu Ser Ser Val Val Thr Val Pro Ser
        175                 180                 185 agc agc ttg ggc acc cag acc tac atc tgc aac gtg aat cac aag ccc        672
Ser Ser Leu Gly Thr Gln Thr Tyr Ile Cys Asn Val Asn His Lys Pro
190                 195                 200                 205 agc aac acc aag gtg gac aag aga gtt gag ccc aaa tct tgt gac aaa        720
Ser Asn Thr Lys Val Asp Lys Arg Val Glu Pro Lys Ser Cys Asp Lys
                    210                 215                 220 act cac aca tgc cca ccg tgc cca gca cct gaa ctc ctg ggg gga ccg        768
Thr His Thr Cys Pro Pro Cys Pro Ala Pro Glu Leu Leu Gly Gly Pro
                225                 230                 235 tca gtc ttc ctc ttc ccc cca aaa ccc aag gac acc ctc atg atc tcc        816
Ser Val Phe Leu Phe Pro Pro Lys Pro Lys Asp Thr Leu Met Ile Ser
            240                 245                 250 cgg acc cct gag gtc aca tgc gtg gtg gtg gac gtg agc cac gaa gac        864
Arg Thr Pro Glu Val Thr Cys Val Val Val Asp Val Ser His Glu Asp
        255                 260                 265 cct gag gtc aag ttc aac tgg tac gtg gac ggc gtg gag gtg cat aat        912
Pro Glu Val Lys Phe Asn Trp Tyr Val Asp Gly Val Glu Val His Asn
270                 275                 280                 285 gcc aag aca aag ccg cgg gag gag cag tac aac agc acg tac cgg gtg        960
Ala Lys Thr Lys Pro Arg Glu Glu Gln Tyr Asn Ser Thr Tyr Arg Val
                    290                 295                 300 gtc agc gtc ctc acc gtc ctg cac cag gac tgg ctg aat ggc aag gag       1008
Val Ser Val Leu Thr Val Leu His Gln Asp Trp Leu Asn Gly Lys Glu
                305                 310                 315 tac aag tgc aag gtc tcc aac aaa gcc ctc cca gcc ccc atc gag aaa       1056
Tyr Lys Cys Lys Val Ser Asn Lys Ala Leu Pro Ala Pro Ile Glu Lys
            320                 325                 330 acc atc tcc aaa gcc aaa ggg cag ccc cga gaa cca cag gtg tac acc       1104
```

```
Thr Ile Ser Lys Ala Lys Gly Gln Pro Arg Glu Pro Gln Val Tyr Thr
    335                 340                 345 ctg ccc cca tcc cgg gat gag ctg acc aag aac cag gtc agc ctg acc      1152
Leu Pro Pro Ser Arg Asp Glu Leu Thr Lys Asn Gln Val Ser Leu Thr
350                 355                 360                 365 tgc ctg gtc aaa ggc ttc tat ccc agc gac atc gcc gtg gag tgg gag      1200
Cys Leu Val Lys Gly Phe Tyr Pro Ser Asp Ile Ala Val Glu Trp Glu
                370                 375                 380 agc aat ggg cag ccg gag aac aac tac aag acc acg cct ccc gtg ctg      1248
Ser Asn Gly Gln Pro Glu Asn Asn Tyr Lys Thr Thr Pro Pro Val Leu
            385                 390                 395 gac tcc gac ggc tcc ttc ttc ctc tac agc aag ctc acc gtg gac aag      1296
Asp Ser Asp Gly Ser Phe Phe Leu Tyr Ser Lys Leu Thr Val Asp Lys
        400                 405                 410 agc agg tgg cag cag ggg aac gtc ttc tca tgc tcc gtg atg cat gag      1344
Ser Arg Trp Gln Gln Gly Asn Val Phe Ser Cys Ser Val Met His Glu
    415                 420                 425 gct ctg cac aac cac tac acg cag aag agc ctc tcc ctg tct ccg ggt      1392
Ala Leu His Asn His Tyr Thr Gln Lys Ser Leu Ser Leu Ser Pro Gly
430                 435                 440                 445 aaa tga                                                              1398
Lys

<210> SEQ ID NO 25
<211> LENGTH: 465
<212> TYPE: PRT
<213> ORGANISM: Homo Sapiens

<400> SEQUENCE: 25

Met Ala Trp Val Ser Thr Leu Leu Phe Leu Met Ala Ala Gln Ser
                -15                 -10                 -5

Ala Gln Ala Gln Ile Gln Leu Val Gln Ser Gly Ala Glu Val Lys Lys
        -1  1               5                   10

Pro Gly Glu Ser Val Lys Ile Ser Cys Lys Ala Ser Gly Tyr Thr Phe
 15                  20                  25

Thr Lys Tyr Gly Met Asn Trp Val Arg Gln Ala Pro Gly Gln Gly Leu
30                  35                  40                  45

Glu Trp Met Gly Trp Ile Asn Thr Tyr Thr Glu Pro Thr Tyr Gly
                50                  55                  60

Gln Lys Phe Gln Gly Arg Phe Thr Phe Thr Leu Asp Thr Ser Thr Ser
            65                  70                  75

Thr Ala Tyr Leu Glu Ile Ser Ser Leu Arg Ser Glu Asp Thr Ala Val
        80                  85                  90

Tyr Phe Cys Ala Arg Phe Gly Ser Ala Val Asp Tyr Trp Gly Gln Gly
    95                  100                 105

Thr Leu Val Thr Val Ser Ser Ala Ser Thr Lys Gly Pro Ser Val Phe
110                 115                 120                 125

Pro Leu Ala Pro Ser Ser Lys Ser Thr Ser Gly Gly Thr Ala Ala Leu
                130                 135                 140

Gly Cys Leu Val Lys Asp Tyr Phe Pro Glu Pro Val Thr Val Ser Trp
            145                 150                 155

Asn Ser Gly Ala Leu Thr Ser Gly Val His Thr Phe Pro Ala Val Leu
        160                 165                 170

Gln Ser Ser Gly Leu Tyr Ser Leu Ser Ser Val Val Thr Val Pro Ser
    175                 180                 185

Ser Ser Leu Gly Thr Gln Thr Tyr Ile Cys Asn Val Asn His Lys Pro
190                 195                 200                 205
```

```
Ser Asn Thr Lys Val Asp Lys Arg Val Glu Pro Lys Ser Cys Asp Lys
            210                 215                 220
Thr His Thr Cys Pro Pro Cys Pro Ala Pro Glu Leu Leu Gly Gly Pro
        225                 230                 235
Ser Val Phe Leu Phe Pro Pro Lys Pro Lys Asp Thr Leu Met Ile Ser
        240                 245                 250
Arg Thr Pro Glu Val Thr Cys Val Val Val Asp Val Ser His Glu Asp
        255                 260                 265
Pro Glu Val Lys Phe Asn Trp Tyr Val Asp Gly Val Glu Val His Asn
270                 275                 280                 285
Ala Lys Thr Lys Pro Arg Glu Glu Gln Tyr Asn Ser Thr Tyr Arg Val
            290                 295                 300
Val Ser Val Leu Thr Val Leu His Gln Asp Trp Leu Asn Gly Lys Glu
        305                 310                 315
Tyr Lys Cys Lys Val Ser Asn Lys Ala Leu Pro Ala Pro Ile Glu Lys
        320                 325                 330
Thr Ile Ser Lys Ala Lys Gly Gln Pro Arg Glu Pro Gln Val Tyr Thr
        335                 340                 345
Leu Pro Pro Ser Arg Asp Glu Leu Thr Lys Asn Gln Val Ser Leu Thr
350                 355                 360                 365
Cys Leu Val Lys Gly Phe Tyr Pro Ser Asp Ile Ala Val Glu Trp Glu
            370                 375                 380
Ser Asn Gly Gln Pro Glu Asn Asn Tyr Lys Thr Thr Pro Pro Val Leu
            385                 390                 395
Asp Ser Asp Gly Ser Phe Phe Leu Tyr Ser Lys Leu Thr Val Asp Lys
        400                 405                 410
Ser Arg Trp Gln Gln Gly Asn Val Phe Ser Cys Ser Val Met His Glu
        415                 420                 425
Ala Leu His Asn His Tyr Thr Gln Lys Ser Leu Ser Leu Ser Pro Gly
430                 435                 440                 445
Lys
```

```
<210> SEQ ID NO 26
<211> LENGTH: 91
<212> TYPE: DNA
<213> ORGANISM: HomoSapiens
<220> FEATURE:
<221> NAME/KEY: misc_feature
<223> OTHER INFORMATION: GL1 V Region Oligos: ING-1 Heavy Chain Oligos

<400> SEQUENCE: 26
tgtcgacacc atggcttggg tgtccacctt gctattcctg atggcagctg cccaaagtgc    60
ccaagcacag atccagttgg tgcagtctgg a                                   91

<210> SEQ ID NO 27
<211> LENGTH: 90
<212> TYPE: DNA
<213> ORGANISM: HomoSapiens
<220> FEATURE:
<221> NAME/KEY: misc_feature
<223> OTHER INFORMATION: GL2 V Region Oligos: ING-1 Heavy Chain Oligos

<400> SEQUENCE: 27
atattttgtg aaggtatatc cagaagcctt gcaggagatc ttgacggact ctccaggctt    60
cttcacctca ggtccagact gcaccaactg                                     90

<210> SEQ ID NO 28
<211> LENGTH: 91
```

```
<212> TYPE: DNA
<213> ORGANISM: HomoSapiens
<220> FEATURE:
<221> NAME/KEY: misc_feature
<223> OTHER INFORMATION: GL3 V Region Oligos: ING-1 Heavy Chain Oligos

<400> SEQUENCE: 28
tggatatacc ttcacaaaat atggaatgaa ctgggtgaag caggctccag gacagggttt      60
aaagtggatg ggctggataa acacctacac t                                    91

<210> SEQ ID NO 29
<211> LENGTH: 90
<212> TYPE: DNA
<213> ORGANISM: HomoSapiens
<220> FEATURE:
<221> NAME/KEY: misc_feature
<223> OTHER INFORMATION: GL4 V Region Oligos: ING-1 Heavy Chain Oligos

<400> SEQUENCE: 29
cagtgctagt agaggtgtcc aaggtgaagg taaaccgtcc cttgaagtca tcaccatatg      60
ttggctcttc agtgtaggtg tttatccagc                                      90

<210> SEQ ID NO 30
<211> LENGTH: 90
<212> TYPE: DNA
<213> ORGANISM: HomoSapiens
<220> FEATURE:
<221> NAME/KEY: misc_feature
<223> OTHER INFORMATION: GL5 V Region Oligos:  ING-1 Heavy Chain Oligos

<400> SEQUENCE: 30
gacacctcta ctagcactgc ctatttggaa atctcttctc tccggagtga ggacacggct      60
acatatttct gtgcaagatt tggctctgct                                      90

<210> SEQ ID NO 31
<211> LENGTH: 85
<212> TYPE: DNA
<213> ORGANISM: HomoSapiens
<220> FEATURE:
<221> NAME/KEY: misc_feature
<223> OTHER INFORMATION: GL6 V Region Oligos: ING-1 Heavy Chain Oligos

<400> SEQUENCE: 31
gaccgatggg ccctttgtgc tggctgagga cacggtgacc aaggttcctt gaccccagta      60
gtccacagca gagccaaatc ttgca                                           85

<210> SEQ ID NO 32
<211> LENGTH: 22
<212> TYPE: DNA
<213> ORGANISM: HomoSapiens
<220> FEATURE:
<221> NAME/KEY: misc_feature
<223> OTHER INFORMATION: ING-1 Heavy Chain Oligos-Low Risk Primers
      Forward primer:GF

<400> SEQUENCE: 32
ttatgtcgac accatggctt gg                                              22

<210> SEQ ID NO 33
<211> LENGTH: 17
<212> TYPE: DNA
<213> ORGANISM: HomoSapiens
<220> FEATURE:
<221> NAME/KEY: misc_feature
<223> OTHER INFORMATION: ING-1 Heavy Chain Oligos Low Risk Primers
      -Reverse Primer GR
```

-continued

```
<220> FEATURE:
<221> NAME/KEY: misc_feature
<223> OTHER INFORMATION: ING-1 Heavy Chain Oligos Low Risk Primers
      Reverse Primer GR

<400> SEQUENCE: 33
gaccgatggg ccctttg                                                   17

<210> SEQ ID NO 34
<211> LENGTH: 90
<212> TYPE: DNA
<213> ORGANISM: HomoSapiens
<220> FEATURE:
<221> NAME/KEY: misc_feature
<223> OTHER INFORMATION: GM2 V Region Oligos ING-1 Heavy Chain
      Oligos-Low + Moderate Risk Primers

<400> SEQUENCE: 34
atattttgtg aaggtatatc cagaagcctt gcaggagatc ttgactgact ctccaggctt   60
cttcacctca gctccagact gcaccaactg                                    90

<210> SEQ ID NO 35
<211> LENGTH: 91
<212> TYPE: DNA
<213> ORGANISM: HomoSapiens
<220> FEATURE:
<221> NAME/KEY: misc_feature
<223> OTHER INFORMATION: GM3 V Region Oligos ING-1 Heavy Chain
      Oligos-Low + Moderate Risk Primers

<400> SEQUENCE: 35
tggatatacc ttcacaaaat atggaatgaa ctgggtgcga caggctccag acaaggttt   60 agagtggatg ggctggataa acacctacac t                                  91

<210> SEQ ID NO 36
<211> LENGTH: 90
<212> TYPE: DNA
<213> ORGANISM: HomoSapiens
<220> FEATURE:
<221> NAME/KEY: misc_feature
<223> OTHER INFORMATION: GM4 V Region Oligos ING-1 Heavy Chain
      Oligos-Low + Moderate Risk Primers

<400> SEQUENCE: 36
cagtgctagt agaggtgtcc aaggtgaagg taaaccgtcc ctggaacttc tgaccatatg   60
ttggctcttc agtgtaggtg tttatccagc                                    90

<210> SEQ ID NO 37
<211> LENGTH: 90
<212> TYPE: DNA
<213> ORGANISM: HomoSapiens
<220> FEATURE:
<221> NAME/KEY: misc_feature
<223> OTHER INFORMATION: GM5 V Region Oligos ING-1 Heavy Chain
      Oligos-Low + Moderate Risk Primers

<400> SEQUENCE: 37
gacacctcta ctagcactgc ctatttggaa atctcttcgc tccggagtga ggacacggct   60
gtgtatttct gtgcaagatt tggctctgct                                    90

<210> SEQ ID NO 38
<211> LENGTH: 720
<212> TYPE: DNA
<213> ORGANISM: Homo sapiens
<220> FEATURE:
<221> NAME/KEY: misc_feature
```

```
<223> OTHER INFORMATION: P1=P Human Engineered (low risk) ING1 light
      Chain with one moderate risk proline change; proline at position 8
      (P1)
<220> FEATURE:
<221> NAME/KEY: CDS
<222> LOCATION: (1)..(717)
<220> FEATURE:
<221> NAME/KEY: mat_peptide
<222> LOCATION: (61)..()

<400> SEQUENCE: 38 atg agg ttc tct gct cag ctt ctg ggg ctg ctt gtg ctc tgg atc cct      48
Met Arg Phe Ser Ala Gln Leu Leu Gly Leu Leu Val Leu Trp Ile Pro
-20             -15                 -10                 -5 gga tcc act gca gac atc gtg atg acc cag tct cca ctc tcc aat cca      96
Gly Ser Thr Ala Asp Ile Val Met Thr Gln Ser Pro Leu Ser Asn Pro
            -1  1               5                   10 gtc act ctg gga gag tca ggt tcc atc tcc tgc agg tct agt aag agt     144
Val Thr Leu Gly Glu Ser Gly Ser Ile Ser Cys Arg Ser Ser Lys Ser
        15                  20                  25 ctc cta cat agt aat ggc atc act tat ttg tat tgg tat ctg cag aaa     192
Leu Leu His Ser Asn Gly Ile Thr Tyr Leu Tyr Trp Tyr Leu Gln Lys
        30                  35                  40 cca ggg cag tct cct cag ctg ctc atc tat cag atg tct aac aga gcc     240
Pro Gly Gln Ser Pro Gln Leu Leu Ile Tyr Gln Met Ser Asn Arg Ala
45                  50                  55                  60 tca ggg gtc cca gac agg ttc agt agc agt gga tct ggg aca gat ttc     288
Ser Gly Val Pro Asp Arg Phe Ser Ser Ser Gly Ser Gly Thr Asp Phe
                65                  70                  75 act ctc aag atc agc aga gtg gag gct gaa gat gtg gga gtt tat tac     336
Thr Leu Lys Ile Ser Arg Val Glu Ala Glu Asp Val Gly Val Tyr Tyr
            80                  85                  90 tgt gct cag aac cta gag ctt ccg cgg acg ttc ggt cag ggc acc aag     384
Cys Ala Gln Asn Leu Glu Leu Pro Arg Thr Phe Gly Gln Gly Thr Lys
        95                  100                 105 ctt gag atg aaa cga act gtg gct gca cca tct gtc ttc atc ttc ccg     432
Leu Glu Met Lys Arg Thr Val Ala Ala Pro Ser Val Phe Ile Phe Pro
    110                 115                 120 cca tct gat gag cag ttg aaa tct gga act gcc tct gtt gtg tgc ctg     480
Pro Ser Asp Glu Gln Leu Lys Ser Gly Thr Ala Ser Val Val Cys Leu
125                 130                 135                 140 ctg aat aac ttc tat ccc aga gag gcc aaa gta cag tgg aag gtg gat     528
Leu Asn Asn Phe Tyr Pro Arg Glu Ala Lys Val Gln Trp Lys Val Asp
                145                 150                 155 aac gcc ctc caa tcg ggt aac tcc cag gag agt gtc aca gag cag gac     576
Asn Ala Leu Gln Ser Gly Asn Ser Gln Glu Ser Val Thr Glu Gln Asp
            160                 165                 170 agc aag gac agc acc tac agc ctc agc agc acc ctg acg ctg agc aaa     624
Ser Lys Asp Ser Thr Tyr Ser Leu Ser Ser Thr Leu Thr Leu Ser Lys
        175                 180                 185 gca gac tac gag aaa cac aaa gtc tac gcc tgc gaa gtc acc cat cag     672
Ala Asp Tyr Glu Lys His Lys Val Tyr Ala Cys Glu Val Thr His Gln
    190                 195                 200 ggc ctg agc tcg ccc gtc aca aag agc ttc aac agg gga gag tgt tag     720
Gly Leu Ser Ser Pro Val Thr Lys Ser Phe Asn Arg Gly Glu Cys
205                 210                 215

<210> SEQ ID NO 39
<211> LENGTH: 239
<212> TYPE: PRT
<213> ORGANISM: Homo sapiens

<400> SEQUENCE: 39
```

```
Met Arg Phe Ser Ala Gln Leu Leu Gly Leu Leu Val Leu Trp Ile Pro
-20                 -15                 -10                 -5

Gly Ser Thr Ala Asp Ile Val Met Thr Gln Ser Pro Leu Ser Asn Pro
            -1  1               5                   10

Val Thr Leu Gly Glu Ser Gly Ser Ile Ser Cys Arg Ser Ser Lys Ser
        15              20              25

Leu Leu His Ser Asn Gly Ile Thr Tyr Leu Tyr Trp Tyr Leu Gln Lys
    30              35                  40

Pro Gly Gln Ser Pro Gln Leu Leu Ile Tyr Gln Met Ser Asn Arg Ala
45              50                  55                  60

Ser Gly Val Pro Asp Arg Phe Ser Ser Gly Ser Gly Thr Asp Phe
                65              70                  75

Thr Leu Lys Ile Ser Arg Val Glu Ala Glu Asp Val Gly Val Tyr Tyr
            80              85                  90

Cys Ala Gln Asn Leu Glu Leu Pro Arg Thr Phe Gly Gln Gly Thr Lys
            95              100                 105

Leu Glu Met Lys Arg Thr Val Ala Ala Pro Ser Val Phe Ile Phe Pro
    110             115                 120

Pro Ser Asp Glu Gln Leu Lys Ser Gly Thr Ala Ser Val Val Cys Leu
125             130                 135                 140

Leu Asn Asn Phe Tyr Pro Arg Glu Ala Lys Val Gln Trp Lys Val Asp
                145                 150                 155

Asn Ala Leu Gln Ser Gly Asn Ser Gln Glu Ser Val Thr Glu Gln Asp
            160                 165                 170

Ser Lys Asp Ser Thr Tyr Ser Leu Ser Ser Thr Leu Thr Leu Ser Lys
            175                 180                 185

Ala Asp Tyr Glu Lys His Lys Val Tyr Ala Cys Glu Val Thr His Gln
190                 195                 200

Gly Leu Ser Ser Pro Val Thr Lys Ser Phe Asn Arg Gly Glu Cys
205                 210                 215

<210> SEQ ID NO 40
<211> LENGTH: 720
<212> TYPE: DNA
<213> ORGANISM: Homo sapiens
<220> FEATURE:
<221> NAME/KEY: misc_feature
<223> OTHER INFORMATION: P2=P Human Engineered (low risk) ING1 light
      Chain with one moderate risk proline change; proline at position
      15 (P2)
<220> FEATURE:
<221> NAME/KEY: CDS
<222> LOCATION: (1)..(717)
<220> FEATURE:
<221> NAME/KEY: mat_peptide
<222> LOCATION: (61)..()

<400> SEQUENCE: 40 atg agg ttc tct gct cag ctt ctg ggg ctg ctt gtg ctc tgg atc cct     48
Met Arg Phe Ser Ala Gln Leu Leu Gly Leu Leu Val Leu Trp Ile Pro
-20                 -15                 -10                 -5 gga tcc act gca gac atc gtg atg acc cag tct gca ctc tcc aat cca     96
Gly Ser Thr Ala Asp Ile Val Met Thr Gln Ser Ala Leu Ser Asn Pro
            -1  1               5                   10 gtc act cct gga gag tca ggt tcc atc tcc tgc agg tct agt aag agt    144
Val Thr Pro Gly Glu Ser Gly Ser Ile Ser Cys Arg Ser Ser Lys Ser
        15              20              25 ctc cta cat agt aat ggc atc act tat ttg tat tgg tat ctg cag aaa    192
Leu Leu His Ser Asn Gly Ile Thr Tyr Leu Tyr Trp Tyr Leu Gln Lys
    30              35                  40
```

```
cca ggg cag tct cct cag ctg ctc atc tat cag atg tct aac aga gcc     240
Pro Gly Gln Ser Pro Gln Leu Leu Ile Tyr Gln Met Ser Asn Arg Ala
 45              50                  55                  60 tca ggg gtc cca gac agg ttc agt agc agt gga tct ggg aca gat ttc     288
Ser Gly Val Pro Asp Arg Phe Ser Ser Ser Gly Ser Gly Thr Asp Phe
                 65                  70                  75 act ctc aag atc agc aga gtg gag gct gaa gat gtg gga gtt tat tac     336
Thr Leu Lys Ile Ser Arg Val Glu Ala Glu Asp Val Gly Val Tyr Tyr
             80                  85                  90 tgt gct cag aac cta gag ctt ccg cgg acg ttc ggt cag ggc acc aag     384
Cys Ala Gln Asn Leu Glu Leu Pro Arg Thr Phe Gly Gln Gly Thr Lys
         95                 100                 105 ctt gag atg aaa cga act gtg gct gca cca tct gtc ttc atc ttc ccg     432
Leu Glu Met Lys Arg Thr Val Ala Ala Pro Ser Val Phe Ile Phe Pro
     110                 115                 120 cca tct gat gag cag ttg aaa tct gga act gcc tct gtt gtg tgc ctg     480
Pro Ser Asp Glu Gln Leu Lys Ser Gly Thr Ala Ser Val Val Cys Leu
125                 130                 135                 140 ctg aat aac ttc tat ccc aga gag gcc aaa gta cag tgg aag gtg gat     528
Leu Asn Asn Phe Tyr Pro Arg Glu Ala Lys Val Gln Trp Lys Val Asp
                145                 150                 155 aac gcc ctc caa tcg ggt aac tcc cag gag agt gtc aca gag cag gac     576
Asn Ala Leu Gln Ser Gly Asn Ser Gln Glu Ser Val Thr Glu Gln Asp
            160                 165                 170 agc aag gac agc acc tac agc ctc agc agc acc ctg acg ctg agc aaa     624
Ser Lys Asp Ser Thr Tyr Ser Leu Ser Ser Thr Leu Thr Leu Ser Lys
        175                 180                 185 gca gac tac gag aaa cac aaa gtc tac gcc tgc gaa gtc acc cat cag     672
Ala Asp Tyr Glu Lys His Lys Val Tyr Ala Cys Glu Val Thr His Gln
    190                 195                 200 ggc ctg agc tcg ccc gtc aca aag agc ttc aac agg gga gag tgt tag    720
Gly Leu Ser Ser Pro Val Thr Lys Ser Phe Asn Arg Gly Glu Cys
205                 210                 215

<210> SEQ ID NO 41
<211> LENGTH: 239
<212> TYPE: PRT
<213> ORGANISM: Homo sapiens

<400> SEQUENCE: 41

Met Arg Phe Ser Ala Gln Leu Leu Gly Leu Leu Val Leu Trp Ile Pro
-20                 -15                 -10                  -5

Gly Ser Thr Ala Asp Ile Val Met Thr Gln Ser Ala Leu Ser Asn Pro
             -1  1                   5                  10

Val Thr Pro Gly Glu Ser Gly Ser Ile Ser Cys Arg Ser Ser Lys Ser
         15                  20                  25

Leu Leu His Ser Asn Gly Ile Thr Tyr Leu Tyr Trp Tyr Leu Gln Lys
     30                  35                  40

Pro Gly Gln Ser Pro Gln Leu Leu Ile Tyr Gln Met Ser Asn Arg Ala
 45                  50                  55                  60

Ser Gly Val Pro Asp Arg Phe Ser Ser Ser Gly Ser Gly Thr Asp Phe
                 65                  70                  75

Thr Leu Lys Ile Ser Arg Val Glu Ala Glu Asp Val Gly Val Tyr Tyr
             80                  85                  90

Cys Ala Gln Asn Leu Glu Leu Pro Arg Thr Phe Gly Gln Gly Thr Lys
         95                 100                 105

Leu Glu Met Lys Arg Thr Val Ala Ala Pro Ser Val Phe Ile Phe Pro
     110                 115                 120

Pro Ser Asp Glu Gln Leu Lys Ser Gly Thr Ala Ser Val Val Cys Leu
```

```
                        125                 130                 135                 140
Leu Asn Asn Phe Tyr Pro Arg Glu Ala Lys Val Gln Trp Lys Val Asp
                    145                 150                 155

Asn Ala Leu Gln Ser Gly Asn Ser Gln Glu Ser Val Thr Glu Gln Asp
                160                 165                 170

Ser Lys Asp Ser Thr Tyr Ser Leu Ser Ser Thr Leu Thr Leu Ser Lys
            175                 180                 185

Ala Asp Tyr Glu Lys His Lys Val Tyr Ala Cys Glu Val Thr His Gln
        190                 195                 200

Gly Leu Ser Ser Pro Val Thr Lys Ser Phe Asn Arg Gly Glu Cys
205                 210                 215

<210> SEQ ID NO 42
<211> LENGTH: 720
<212> TYPE: DNA
<213> ORGANISM: Homo sapiens
<220> FEATURE:
<221> NAME/KEY: misc_feature
<223> OTHER INFORMATION: P3=P Human Engineered (low risk) ING1 light
      Chain with one moderate risk proline change; proline at position
      18 (P3)
<220> FEATURE:
<221> NAME/KEY: CDS
<222> LOCATION: (1)..(717)
<220> FEATURE:
<221> NAME/KEY: mat_peptide
<222> LOCATION: (61)..()

<400> SEQUENCE: 42 atg agg ttc tct gct cag ctt ctg ggg ctg ctt gtg ctc tgg atc cct      48
Met Arg Phe Ser Ala Gln Leu Leu Gly Leu Leu Val Leu Trp Ile Pro
-20                 -15                 -10                 -5 gga tcc act gca gac atc gtg atg acc cag tct gca ctc tcc aat cca      96
Gly Ser Thr Ala Asp Ile Val Met Thr Gln Ser Ala Leu Ser Asn Pro
            -1   1               5                   10 gtc act ctg gga gag ccg ggt tcc atc tcc tgc cgg tct agt aag agt     144
Val Thr Leu Gly Glu Pro Gly Ser Ile Ser Cys Arg Ser Ser Lys Ser
         15                  20                  25 ctc cta cat agt aat ggc atc act tat ttg tat tgg tat ctg cag aaa     192
Leu Leu His Ser Asn Gly Ile Thr Tyr Leu Tyr Trp Tyr Leu Gln Lys
     30                  35                  40 cca ggg cag tct cct cag ctg ctc atc tat cag atg tct aac aga gcc     240
Pro Gly Gln Ser Pro Gln Leu Leu Ile Tyr Gln Met Ser Asn Arg Ala
45                  50                  55                  60 tca ggg gtc cca gac agg ttc agt agc agt gga tct ggg aca gat ttc     288
Ser Gly Val Pro Asp Arg Phe Ser Ser Ser Gly Ser Gly Thr Asp Phe
                 65                  70                  75 act ctc aag atc agc aga gtg gag gct gaa gat gtg gga gtt tat tac     336
Thr Leu Lys Ile Ser Arg Val Glu Ala Glu Asp Val Gly Val Tyr Tyr
             80                  85                  90 tgt gct cag aac cta gag ctt ccg cgg acg ttc ggt cag ggc acc aag     384
Cys Ala Gln Asn Leu Glu Leu Pro Arg Thr Phe Gly Gln Gly Thr Lys
         95                 100                 105 ctt gag atg aaa cga act gtg gct gca cca tct gtc ttc atc ttc ccg     432
Leu Glu Met Lys Arg Thr Val Ala Ala Pro Ser Val Phe Ile Phe Pro
     110                 115                 120 cca tct gat gag cag ttg aaa tct gga act gcc tct gtt gtg tgc ctg     480
Pro Ser Asp Glu Gln Leu Lys Ser Gly Thr Ala Ser Val Val Cys Leu
125                 130                 135                 140 ctg aat aac ttc tat ccc aga gag gcc aaa gta cag tgg aag gtg gat     528
Leu Asn Asn Phe Tyr Pro Arg Glu Ala Lys Val Gln Trp Lys Val Asp
                145                 150                 155
```

```
aac gcc ctc caa tcg ggt aac tcc cag gag agt gtc aca gag cag gac    576
Asn Ala Leu Gln Ser Gly Asn Ser Gln Glu Ser Val Thr Glu Gln Asp
        160                 165                 170 agc aag gac agc acc tac agc ctc agc agc acc ctg acg ctg agc aaa    624
Ser Lys Asp Ser Thr Tyr Ser Leu Ser Ser Thr Leu Thr Leu Ser Lys
    175                 180                 185 gca gac tac gag aaa cac aaa gtc tac gcc tgc gaa gtc acc cat cag    672
Ala Asp Tyr Glu Lys His Lys Val Tyr Ala Cys Glu Val Thr His Gln
190                 195                 200 ggc ctg agc tcg ccc gtc aca aag agc ttc aac agg gga gag tgt tag    720
Gly Leu Ser Ser Pro Val Thr Lys Ser Phe Asn Arg Gly Glu Cys
205                 210                 215

<210> SEQ ID NO 43
<211> LENGTH: 239
<212> TYPE: PRT
<213> ORGANISM: Homo sapiens

<400> SEQUENCE: 43

Met Arg Phe Ser Ala Gln Leu Leu Gly Leu Leu Val Leu Trp Ile Pro
-20                 -15                 -10                 -5

Gly Ser Thr Ala Asp Ile Val Met Thr Gln Ser Ala Leu Ser Asn Pro
            -1  1               5                   10

Val Thr Leu Gly Glu Pro Gly Ser Ile Ser Cys Arg Ser Ser Lys Ser
        15                  20                  25

Leu Leu His Ser Asn Gly Ile Thr Tyr Leu Tyr Trp Tyr Leu Gln Lys
    30                  35                  40

Pro Gly Gln Ser Pro Gln Leu Leu Ile Tyr Gln Met Ser Asn Arg Ala
45                  50                  55                  60

Ser Gly Val Pro Asp Arg Phe Ser Ser Ser Gly Ser Gly Thr Asp Phe
                65                  70                  75

Thr Leu Lys Ile Ser Arg Val Glu Ala Glu Asp Val Gly Val Tyr Tyr
            80                  85                  90

Cys Ala Gln Asn Leu Glu Leu Pro Arg Thr Phe Gly Gln Gly Thr Lys
        95                  100                 105

Leu Glu Met Lys Arg Thr Val Ala Ala Pro Ser Val Phe Ile Phe Pro
    110                 115                 120

Pro Ser Asp Glu Gln Leu Lys Ser Gly Thr Ala Ser Val Val Cys Leu
125                 130                 135                 140

Leu Asn Asn Phe Tyr Pro Arg Glu Ala Lys Val Gln Trp Lys Val Asp
                145                 150                 155

Asn Ala Leu Gln Ser Gly Asn Ser Gln Glu Ser Val Thr Glu Gln Asp
            160                 165                 170

Ser Lys Asp Ser Thr Tyr Ser Leu Ser Ser Thr Leu Thr Leu Ser Lys
        175                 180                 185

Ala Asp Tyr Glu Lys His Lys Val Tyr Ala Cys Glu Val Thr His Gln
    190                 195                 200

Gly Leu Ser Ser Pro Val Thr Lys Ser Phe Asn Arg Gly Glu Cys
205                 210                 215

<210> SEQ ID NO 44
<211> LENGTH: 720
<212> TYPE: DNA
<213> ORGANISM: Homo sapiens
<220> FEATURE:
<221> NAME/KEY: misc_feature
<223> OTHER INFORMATION: P1P2=Human Engineered (low risk) ING1 light
      Chain with one moderate risk proline change; proline at position 8
      (P1) 15(P2)
<220> FEATURE:
```

```
<221> NAME/KEY: CDS
<222> LOCATION: (1)..(717)
<220> FEATURE:
<221> NAME/KEY: mat_peptide
<222> LOCATION: (61)..()

<400> SEQUENCE: 44 atg agg ttc tct gct cag ctt ctg ggg ctg ctt gtg ctc tgg atc cct        48
Met Arg Phe Ser Ala Gln Leu Leu Gly Leu Leu Val Leu Trp Ile Pro
-20             -15                 -10                 -5 gga tcc act gca gac atc gtg atg acc cag tct cca ctc tcc aat cca        96
Gly Ser Thr Ala Asp Ile Val Met Thr Gln Ser Pro Leu Ser Asn Pro
            -1  1               5                   10 gtc act cct gga gag tca ggt tcc atc tcc tgc cgg tct agt aag agt       144
Val Thr Pro Gly Glu Ser Gly Ser Ile Ser Cys Arg Ser Ser Lys Ser
        15                  20                  25 ctc cta cat agt aat ggc atc act tat ttg tat tgg tat ctg cag aaa       192
Leu Leu His Ser Asn Gly Ile Thr Tyr Leu Tyr Trp Tyr Leu Gln Lys
    30                  35                  40 cca ggg cag tct cct cag ctg ctc atc tat cag atg tct aac aga gcc       240
Pro Gly Gln Ser Pro Gln Leu Leu Ile Tyr Gln Met Ser Asn Arg Ala
45                  50                  55                  60 tca ggg gtc cca gac agg ttc agt agc agt gga tct ggg aca gat ttc       288
Ser Gly Val Pro Asp Arg Phe Ser Ser Ser Gly Ser Gly Thr Asp Phe
                65                  70                  75 act ctc aag atc agc aga gtg gag gct gaa gat gtg gga gtt tat tac       336
Thr Leu Lys Ile Ser Arg Val Glu Ala Glu Asp Val Gly Val Tyr Tyr
            80                  85                  90 tgt gct cag aac cta gag ctt ccg cgg acg ttc ggt cag ggc acc aag       384
Cys Ala Gln Asn Leu Glu Leu Pro Arg Thr Phe Gly Gln Gly Thr Lys
        95                  100                 105 ctt gag atg aaa cga act gtg gct gca cca tct gtc ttc atc ttc ccg       432
Leu Glu Met Lys Arg Thr Val Ala Ala Pro Ser Val Phe Ile Phe Pro
    110                 115                 120 cca tct gat gag cag ttg aaa tct gga act gcc tct gtt gtg tgc ctg       480
Pro Ser Asp Glu Gln Leu Lys Ser Gly Thr Ala Ser Val Val Cys Leu
125                 130                 135                 140 ctg aat aac ttc tat ccc aga gag gcc aaa gta cag tgg aag gtg gat       528
Leu Asn Asn Phe Tyr Pro Arg Glu Ala Lys Val Gln Trp Lys Val Asp
                145                 150                 155 aac gcc ctc caa tcg ggt aac tcc cag gag agt gtc aca gag cag gac       576
Asn Ala Leu Gln Ser Gly Asn Ser Gln Glu Ser Val Thr Glu Gln Asp
            160                 165                 170 agc aag gac agc acc tac agc ctc agc agc acc ctg acg ctg agc aaa       624
Ser Lys Asp Ser Thr Tyr Ser Leu Ser Ser Thr Leu Thr Leu Ser Lys
        175                 180                 185 gca gac tac gag aaa cac aaa gtc tac gcc tgc gaa gtc acc cat cag       672
Ala Asp Tyr Glu Lys His Lys Val Tyr Ala Cys Glu Val Thr His Gln
    190                 195                 200 ggc ctg agc tcg ccc gtc aca aag agc ttc aac agg gga gag tgt tag       720
Gly Leu Ser Ser Pro Val Thr Lys Ser Phe Asn Arg Gly Glu Cys
205                 210                 215

<210> SEQ ID NO 45
<211> LENGTH: 239
<212> TYPE: PRT
<213> ORGANISM: Homo sapiens

<400> SEQUENCE: 45

Met Arg Phe Ser Ala Gln Leu Leu Gly Leu Leu Val Leu Trp Ile Pro
-20             -15                 -10                 -5

Gly Ser Thr Ala Asp Ile Val Met Thr Gln Ser Pro Leu Ser Asn Pro
```

```
                      -1   1               5                    10
Val Thr Pro Gly Glu Ser Gly Ser Ile Ser Cys Arg Ser Ser Lys Ser
             15                   20                   25

Leu Leu His Ser Asn Gly Ile Thr Tyr Leu Tyr Trp Tyr Leu Gln Lys
         30                   35                   40

Pro Gly Gln Ser Pro Gln Leu Leu Ile Tyr Gln Met Ser Asn Arg Ala
45                   50                   55                   60

Ser Gly Val Pro Asp Arg Phe Ser Ser Gly Ser Gly Thr Asp Phe
                 65                   70                   75

Thr Leu Lys Ile Ser Arg Val Glu Ala Glu Asp Val Gly Val Tyr Tyr
             80                   85                   90

Cys Ala Gln Asn Leu Glu Leu Pro Arg Thr Phe Gly Gln Gly Thr Lys
             95                  100                  105

Leu Glu Met Lys Arg Thr Val Ala Ala Pro Ser Val Phe Ile Phe Pro
        110                  115                  120

Pro Ser Asp Glu Gln Leu Lys Ser Gly Thr Ala Ser Val Val Cys Leu
125                  130                  135                  140

Leu Asn Asn Phe Tyr Pro Arg Glu Ala Lys Val Gln Trp Lys Val Asp
                 145                  150                  155

Asn Ala Leu Gln Ser Gly Asn Ser Gln Glu Ser Val Thr Glu Gln Asp
             160                  165                  170

Ser Lys Asp Ser Thr Tyr Ser Leu Ser Ser Thr Leu Thr Leu Ser Lys
             175                  180                  185

Ala Asp Tyr Glu Lys His Lys Val Tyr Ala Cys Glu Val Thr His Gln
         190                  195                  200

Gly Leu Ser Ser Pro Val Thr Lys Ser Phe Asn Arg Gly Glu Cys
205                  210                  215

<210> SEQ ID NO 46
<211> LENGTH: 720
<212> TYPE: DNA
<213> ORGANISM: Homo sapiens
<220> FEATURE:
<221> NAME/KEY: misc_feature
<223> OTHER INFORMATION: P1P3= Human Engineered (low risk) ING1 light
      Chain with one moderate risk proline change; proline at position 8
      (P1) 18 (P3)
<220> FEATURE:
<221> NAME/KEY: CDS
<222> LOCATION: (1)..(717)
<220> FEATURE:
<221> NAME/KEY: mat_peptide
<222> LOCATION: (61)..()

<400> SEQUENCE: 46 atg agg ttc tct gct cag ctt ctg ggg ctg ctt gtg ctc tgg atc cct    48
Met Arg Phe Ser Ala Gln Leu Leu Gly Leu Leu Val Leu Trp Ile Pro
-20                 -15                  -10                   -5 gga tcc act gca gac atc gtg atg acc cag tct cca ctc tcc aat cca    96
Gly Ser Thr Ala Asp Ile Val Met Thr Gln Ser Pro Leu Ser Asn Pro
              -1   1                   5                    10 gtc act ctg gga gag ccg ggt tcc atc tcc tgc cgg tct agt aag agt   144
Val Thr Leu Gly Glu Pro Gly Ser Ile Ser Cys Arg Ser Ser Lys Ser
             15                   20                   25 ctc cta cat agt aat ggc atc act tat ttg tat tgg tat ctg cag aaa   192
Leu Leu His Ser Asn Gly Ile Thr Tyr Leu Tyr Trp Tyr Leu Gln Lys
         30                   35                   40 cca ggg cag tct cct cag ctg ctc atc tat cag atg tct aac aga gcc   240
Pro Gly Gln Ser Pro Gln Leu Leu Ile Tyr Gln Met Ser Asn Arg Ala
45                   50                   55                   60
```

| tca ggg gtc cca gac agg ttc agt agc agt gga tct ggg aca gat ttc | 288 |
|---|---|
| Ser Gly Val Pro Asp Arg Phe Ser Ser Ser Gly Ser Gly Thr Asp Phe | |
| 65 70 75 | |

| act ctc aag atc agc aga gtg gag gct gaa gat gtg gga gtt tat tac | 336 |
|---|---|
| Thr Leu Lys Ile Ser Arg Val Glu Ala Glu Asp Val Gly Val Tyr Tyr | |
| 80 85 90 | |

| tgt gct cag aac cta gag ctt ccg cgg acg ttc ggt cag ggc acc aag | 384 |
|---|---|
| Cys Ala Gln Asn Leu Glu Leu Pro Arg Thr Phe Gly Gln Gly Thr Lys | |
| 95 100 105 | |

| ctt gag atg aaa cga act gtg gct gca cca tct gtc ttc atc ttc ccg | 432 |
|---|---|
| Leu Glu Met Lys Arg Thr Val Ala Ala Pro Ser Val Phe Ile Phe Pro | |
| 110 115 120 | |

| cca tct gat gag cag ttg aaa tct gga act gcc tct gtt gtg tgc ctg | 480 |
|---|---|
| Pro Ser Asp Glu Gln Leu Lys Ser Gly Thr Ala Ser Val Val Cys Leu | |
| 125 130 135 140 | |

| ctg aat aac ttc tat ccc aga gag gcc aaa gta cag tgg aag gtg gat | 528 |
|---|---|
| Leu Asn Asn Phe Tyr Pro Arg Glu Ala Lys Val Gln Trp Lys Val Asp | |
| 145 150 155 | |

| aac gcc ctc caa tcg ggt aac tcc cag gag agt gtc aca gag cag gac | 576 |
|---|---|
| Asn Ala Leu Gln Ser Gly Asn Ser Gln Glu Ser Val Thr Glu Gln Asp | |
| 160 165 170 | |

| agc aag gac agc acc tac agc ctc agc agc acc ctg acg ctg agc aaa | 624 |
|---|---|
| Ser Lys Asp Ser Thr Tyr Ser Leu Ser Ser Thr Leu Thr Leu Ser Lys | |
| 175 180 185 | |

| gca gac tac gag aaa cac aaa gtc tac gcc tgc gaa gtc acc cat cag | 672 |
|---|---|
| Ala Asp Tyr Glu Lys His Lys Val Tyr Ala Cys Glu Val Thr His Gln | |
| 190 195 200 | |

| ggc ctg agc tcg ccc gtc aca aag agc ttc aac agg gga gag tgt tag | 720 |
|---|---|
| Gly Leu Ser Ser Pro Val Thr Lys Ser Phe Asn Arg Gly Glu Cys | |
| 205 210 215 | |

<210> SEQ ID NO 47
<211> LENGTH: 239
<212> TYPE: PRT
<213> ORGANISM: Homo sapiens

<400> SEQUENCE: 47

Met Arg Phe Ser Ala Gln Leu Leu Gly Leu Leu Val Leu Trp Ile Pro
-20                 -15                 -10                  -5

Gly Ser Thr Ala Asp Ile Val Met Thr Gln Ser Pro Leu Ser Asn Pro
         -1  1               5                  10

Val Thr Leu Gly Glu Pro Gly Ser Ile Ser Cys Arg Ser Ser Lys Ser
             15                  20                  25

Leu Leu His Ser Asn Gly Ile Thr Tyr Leu Tyr Trp Tyr Leu Gln Lys
         30                  35                  40

Pro Gly Gln Ser Pro Gln Leu Leu Ile Tyr Gln Met Ser Asn Arg Ala
45                  50                  55                  60

Ser Gly Val Pro Asp Arg Phe Ser Ser Ser Gly Ser Gly Thr Asp Phe
                 65                  70                  75

Thr Leu Lys Ile Ser Arg Val Glu Ala Glu Asp Val Gly Val Tyr Tyr
             80                  85                  90

Cys Ala Gln Asn Leu Glu Leu Pro Arg Thr Phe Gly Gln Gly Thr Lys
         95                  100                 105

Leu Glu Met Lys Arg Thr Val Ala Ala Pro Ser Val Phe Ile Phe Pro
     110                 115                 120

Pro Ser Asp Glu Gln Leu Lys Ser Gly Thr Ala Ser Val Val Cys Leu
125                 130                 135                 140

Leu Asn Asn Phe Tyr Pro Arg Glu Ala Lys Val Gln Trp Lys Val Asp
                 145                 150                 155

```
Asn Ala Leu Gln Ser Gly Asn Ser Gln Glu Ser Val Thr Glu Gln Asp
            160                 165                 170

Ser Lys Asp Ser Thr Tyr Ser Leu Ser Ser Thr Leu Thr Leu Ser Lys
        175                 180                 185

Ala Asp Tyr Glu Lys His Lys Val Tyr Ala Cys Glu Val Thr His Gln
        190                 195                 200

Gly Leu Ser Ser Pro Val Thr Lys Ser Phe Asn Arg Gly Glu Cys
205                 210                 215

<210> SEQ ID NO 48
<211> LENGTH: 720
<212> TYPE: DNA
<213> ORGANISM: Homo sapiens
<220> FEATURE:
<221> NAME/KEY: misc_feature
<223> OTHER INFORMATION: P2P3=Human Engineered (low risk) ING1 light
      Chain with one moderate risk proline change; proline at position 8
      (P1) 18 (P3)
<220> FEATURE:
<221> NAME/KEY: CDS
<222> LOCATION: (1)..(717)
<220> FEATURE:
<221> NAME/KEY: mat_peptide
<222> LOCATION: (61)..()

<400> SEQUENCE: 48
```

| | | | | | | | | | | | | | | | | |
|---|---|---|---|---|---|---|---|---|---|---|---|---|---|---|---|---|
| atg | agg | ttc | tct | gct | cag | ctt | ctg | ggg | ctg | ctt | gtg | ctc | tgg | atc | cct | 48 |
| Met | Arg | Phe | Ser | Ala | Gln | Leu | Leu | Gly | Leu | Leu | Val | Leu | Trp | Ile | Pro | |
| -20 | | | | -15 | | | | -10 | | | | | | | -5 | |

```
gga tcc act gca gac atc gtg atg acc cag tct gca ctc tcc aat cca    96
Gly Ser Thr Ala Asp Ile Val Met Thr Gln Ser Ala Leu Ser Asn Pro
            -1  1               5                  10 gtc act cct gga gag ccg ggt tcc atc tcc tgc cgg tct agt aag agt   144
Val Thr Pro Gly Glu Pro Gly Ser Ile Ser Cys Arg Ser Ser Lys Ser
            15                  20                  25 ctc cta cat agt aat ggc atc act tat ttg tat tgg tat ctg cag aaa   192
Leu Leu His Ser Asn Gly Ile Thr Tyr Leu Tyr Trp Tyr Leu Gln Lys
        30                  35                  40 cca ggg cag tct cct cag ctg ctc atc tat cag atg tct aac aga gcc   240
Pro Gly Gln Ser Pro Gln Leu Leu Ile Tyr Gln Met Ser Asn Arg Ala
45                  50                  55                  60 tca ggg gtc cca gac agg ttc agt agc agt gga tct ggg aca gat ttc   288
Ser Gly Val Pro Asp Arg Phe Ser Ser Ser Gly Ser Gly Thr Asp Phe
                65                  70                  75 act ctc aag atc agc aga gtg gag gct gaa gat gtg gga gtt tat tac   336
Thr Leu Lys Ile Ser Arg Val Glu Ala Glu Asp Val Gly Val Tyr Tyr
            80                  85                  90 tgt gct cag aac cta gag ctt ccg cgg acg ttc ggt cag ggc acc aag   384
Cys Ala Gln Asn Leu Glu Leu Pro Arg Thr Phe Gly Gln Gly Thr Lys
        95                 100                 105 ctt gag atg aaa cga act gtg gct gca cca tct gtc ttc atc ttc ccg   432
Leu Glu Met Lys Arg Thr Val Ala Ala Pro Ser Val Phe Ile Phe Pro
    110                 115                 120 cca tct gat gag cag ttg aaa tct gga act gcc tct gtt gtg tgc ctg   480
Pro Ser Asp Glu Gln Leu Lys Ser Gly Thr Ala Ser Val Val Cys Leu
125                 130                 135                 140 ctg aat aac ttc tat ccc aga gag gcc aaa gta cag tgg aag gtg gat   528
Leu Asn Asn Phe Tyr Pro Arg Glu Ala Lys Val Gln Trp Lys Val Asp
                145                 150                 155 aac gcc ctc caa tcg ggt aac tcc cag gag agt gtc aca gag cag gac   576
Asn Ala Leu Gln Ser Gly Asn Ser Gln Glu Ser Val Thr Glu Gln Asp
            160                 165                 170
```

```
agc aag gac agc acc tac agc ctc agc agc acc ctg acg ctg agc aaa        624
Ser Lys Asp Ser Thr Tyr Ser Leu Ser Ser Thr Leu Thr Leu Ser Lys
        175                 180                 185 gca gac tac gag aaa cac aaa gtc tac gcc tgc gaa gtc acc cat cag        672
Ala Asp Tyr Glu Lys His Lys Val Tyr Ala Cys Glu Val Thr His Gln
        190                 195                 200 ggc ctg agc tcg ccc gtc aca aag agc ttc aac agg gga gag tgt tag        720
Gly Leu Ser Ser Pro Val Thr Lys Ser Phe Asn Arg Gly Glu Cys
205                 210                 215

<210> SEQ ID NO 49
<211> LENGTH: 239
<212> TYPE: PRT
<213> ORGANISM: Homo sapiens

<400> SEQUENCE: 49

Met Arg Phe Ser Ala Gln Leu Leu Gly Leu Leu Val Leu Trp Ile Pro
-20                 -15                 -10                  -5

Gly Ser Thr Ala Asp Ile Val Met Thr Gln Ser Ala Leu Ser Asn Pro
                -1   1              5                      10

Val Thr Pro Gly Glu Pro Gly Ser Ile Ser Cys Arg Ser Ser Lys Ser
            15                  20                  25

Leu Leu His Ser Asn Gly Ile Thr Tyr Leu Tyr Trp Tyr Leu Gln Lys
        30                  35                  40

Pro Gly Gln Ser Pro Gln Leu Leu Ile Tyr Gln Met Ser Asn Arg Ala
45                  50                  55                  60

Ser Gly Val Pro Asp Arg Phe Ser Ser Ser Gly Ser Gly Thr Asp Phe
                65                  70                  75

Thr Leu Lys Ile Ser Arg Val Glu Ala Glu Asp Val Gly Val Tyr Tyr
            80                  85                  90

Cys Ala Gln Asn Leu Glu Leu Pro Arg Thr Phe Gly Gln Gly Thr Lys
        95                  100                 105

Leu Glu Met Lys Arg Thr Val Ala Ala Pro Ser Val Phe Ile Phe Pro
        110                 115                 120

Pro Ser Asp Glu Gln Leu Lys Ser Gly Thr Ala Ser Val Val Cys Leu
125                 130                 135                 140

Leu Asn Asn Phe Tyr Pro Arg Glu Ala Lys Val Gln Trp Lys Val Asp
                145                 150                 155

Asn Ala Leu Gln Ser Gly Asn Ser Gln Glu Ser Val Thr Glu Gln Asp
            160                 165                 170

Ser Lys Asp Ser Thr Tyr Ser Leu Ser Ser Thr Leu Thr Leu Ser Lys
        175                 180                 185

Ala Asp Tyr Glu Lys His Lys Val Tyr Ala Cys Glu Val Thr His Gln
        190                 195                 200

Gly Leu Ser Ser Pro Val Thr Lys Ser Phe Asn Arg Gly Glu Cys
205                 210                 215

<210> SEQ ID NO 50
<211> LENGTH: 85
<212> TYPE: DNA
<213> ORGANISM: Homo Sapiens
<220> FEATURE:
<221> NAME/KEY: misc_feature
<223> OTHER INFORMATION: P1 Oligo ING-1 with proline oligos

<400> SEQUENCE: 50
actcttacta gaccggcagg agatggaacc tgactctccc agagtgactg gattggagag      60
tggagactgg gtcatcacga tgtct                                            85
```

```
<210> SEQ ID NO 51
<211> LENGTH: 85
<212> TYPE: DNA
<213> ORGANISM: Homo Sapiens
<220> FEATURE:
<221> NAME/KEY: misc_feature
<223> OTHER INFORMATION: P2 Oligo ING-1 with proline oligos

<400> SEQUENCE: 51
actcttacta gaccggcagg agatggaacc tgactctcca ggagtgactg gattggagag      60
tgcagactgg gtcatcacga tgtct                                           85

<210> SEQ ID NO 52
<211> LENGTH: 85
<212> TYPE: DNA
<213> ORGANISM: Homo Sapiens
<220> FEATURE:
<221> NAME/KEY: misc_feature
<223> OTHER INFORMATION: P3 Oligo ING-1 with proline oligos

<400> SEQUENCE: 52
actcttacta gaccggcagg agatggaacc cggctctccc agagtgactg gattggagag      60
tgcagactgg gtcatcacga tgtct                                           85

<210> SEQ ID NO 53
<211> LENGTH: 85
<212> TYPE: DNA
<213> ORGANISM: Homo Sapiens
<220> FEATURE:
<221> NAME/KEY: misc_feature
<223> OTHER INFORMATION: P1P2 Oligo ING-1 with proline oligos

<400> SEQUENCE: 53
actcttacta gaccggcagg agatggaacc cggctctcca ggagtgactg gattggagag      60
tgcagactgg gtcatcacga tgtct                                           85

<210> SEQ ID NO 54
<211> LENGTH: 85
<212> TYPE: DNA
<213> ORGANISM: Homo Sapiens
<220> FEATURE:
<221> NAME/KEY: misc_feature
<223> OTHER INFORMATION: P1P3 Oligo ING-1 with proline oligos

<400> SEQUENCE: 54
actcttacta gaccggcagg agatggaacc cggctctccc agagtgactg gattggagag      60
tggagactgg gtcatcacga tgtct                                           85

<210> SEQ ID NO 55
<211> LENGTH: 85
<212> TYPE: DNA
<213> ORGANISM: Homo Sapiens
<220> FEATURE:
<221> NAME/KEY: misc_feature
<223> OTHER INFORMATION: P2P3 Oligo ING-1 with proline oligos

<400> SEQUENCE: 55
actcttacta gaccggcagg agatggaacc cggctctcca ggagtgactg gattggagag      60
tgcagactgg gtcatcacga tgtct                                           85

<210> SEQ ID NO 56
<211> LENGTH: 19
<212> TYPE: DNA
<213> ORGANISM: Homo Sapiens
```

```
<220> FEATURE:
<221> NAME/KEY: misc_feature
<223> OTHER INFORMATION: Reverse Primer KBsr ING-1 Light Chain

<400> SEQUENCE: 56
cttactagac cggcaggag                                                    19

<210> SEQ ID NO 57
<211> LENGTH: 798
<212> TYPE: DNA
<213> ORGANISM: Homo sapiens
<220> FEATURE:
<221> NAME/KEY: misc_feature
<223> OTHER INFORMATION: EpCam truncated sequence
<220> FEATURE:
<221> NAME/KEY: CDS
<222> LOCATION: (1)..(795)

<400> SEQUENCE: 57
```

| | | | | | | | | | | | | | | | | |
|---|---|---|---|---|---|---|---|---|---|---|---|---|---|---|---|---|
| atg | gcg | ccc | ccg | cag | gtc | ctc | gcg | ttc | ggg | ctt | ctg | ctt | gcc | gcg | gcg | 48 |
| Met | Ala | Pro | Pro | Gln | Val | Leu | Ala | Phe | Gly | Leu | Leu | Leu | Ala | Ala | Ala | |
| 1 | | | | 5 | | | | | 10 | | | | | 15 | | |
| acg | gcg | act | ttt | gcc | gca | gct | cag | gaa | gaa | tgt | gtc | tgt | gaa | aac | tac | 96 |
| Thr | Ala | Thr | Phe | Ala | Ala | Ala | Gln | Glu | Glu | Cys | Val | Cys | Glu | Asn | Tyr | |
| | | | 20 | | | | | 25 | | | | | 30 | | | |
| aag | ctg | gcc | gta | aac | tgc | ttt | gtg | aat | aat | aat | cgt | caa | tgc | cag | tgt | 144 |
| Lys | Leu | Ala | Val | Asn | Cys | Phe | Val | Asn | Asn | Asn | Arg | Gln | Cys | Gln | Cys | |
| | | 35 | | | | | 40 | | | | | 45 | | | | |
| act | tca | gtt | ggt | gca | caa | aat | act | gtc | att | tgc | tca | aag | ctg | gct | gcc | 192 |
| Thr | Ser | Val | Gly | Ala | Gln | Asn | Thr | Val | Ile | Cys | Ser | Lys | Leu | Ala | Ala | |
| | 50 | | | | | 55 | | | | | 60 | | | | | |
| aaa | tgt | ttg | gtg | atg | aag | gca | gaa | atg | aat | ggc | tca | aaa | ctt | ggg | aga | 240 |
| Lys | Cys | Leu | Val | Met | Lys | Ala | Glu | Met | Asn | Gly | Ser | Lys | Leu | Gly | Arg | |
| 65 | | | | | 70 | | | | | 75 | | | | | 80 | |
| aga | gca | aaa | cct | gaa | ggg | gcc | ctc | cag | aac | aat | gat | ggg | ctt | tat | gat | 288 |
| Arg | Ala | Lys | Pro | Glu | Gly | Ala | Leu | Gln | Asn | Asn | Asp | Gly | Leu | Tyr | Asp | |
| | | | | 85 | | | | | 90 | | | | | 95 | | |
| cct | gac | tgc | gat | gag | agc | ggg | ctc | ttt | aag | gcc | aag | cag | tgc | aac | ggc | 336 |
| Pro | Asp | Cys | Asp | Glu | Ser | Gly | Leu | Phe | Lys | Ala | Lys | Gln | Cys | Asn | Gly | |
| | | | 100 | | | | | 105 | | | | | 110 | | | |
| acc | tcc | acg | tgc | tgg | tgt | gtg | aac | act | gct | ggg | gtc | aga | aga | aca | gac | 384 |
| Thr | Ser | Thr | Cys | Trp | Cys | Val | Asn | Thr | Ala | Gly | Val | Arg | Arg | Thr | Asp | |
| | | 115 | | | | | 120 | | | | | 125 | | | | |
| aag | gac | act | gaa | ata | acc | tgc | tct | gag | cga | gtg | aga | acc | tac | tgg | atc | 432 |
| Lys | Asp | Thr | Glu | Ile | Thr | Cys | Ser | Glu | Arg | Val | Arg | Thr | Tyr | Trp | Ile | |
| | 130 | | | | | 135 | | | | | 140 | | | | | |
| atc | att | gaa | cta | aaa | cac | aaa | gca | aga | gaa | aaa | cct | tat | gat | agt | aaa | 480 |
| Ile | Ile | Glu | Leu | Lys | His | Lys | Ala | Arg | Glu | Lys | Pro | Tyr | Asp | Ser | Lys | |
| 145 | | | | | 150 | | | | | 155 | | | | | 160 | |
| agt | ttg | cgg | act | gca | ctt | cag | aag | gag | atc | aca | acg | cgt | tat | caa | ctg | 528 |
| Ser | Leu | Arg | Thr | Ala | Leu | Gln | Lys | Glu | Ile | Thr | Thr | Arg | Tyr | Gln | Leu | |
| | | | 165 | | | | | 170 | | | | | 175 | | | |
| gat | cca | aaa | ttt | atc | acg | agt | att | ttg | tat | gag | aat | aat | gtt | atc | act | 576 |
| Asp | Pro | Lys | Phe | Ile | Thr | Ser | Ile | Leu | Tyr | Glu | Asn | Asn | Val | Ile | Thr | |
| | | | | 180 | | | | | 185 | | | | | 190 | | |
| att | gat | ctg | gtt | caa | aat | tct | tct | caa | aaa | act | cag | aat | gat | gtg | gac | 624 |
| Ile | Asp | Leu | Val | Gln | Asn | Ser | Ser | Gln | Lys | Thr | Gln | Asn | Asp | Val | Asp | |
| | | 195 | | | | | 200 | | | | | 205 | | | | |
| ata | gct | gat | gtg | gct | tat | tat | ttt | gaa | aaa | gat | gtt | aaa | ggt | gaa | tcc | 672 |
| Ile | Ala | Asp | Val | Ala | Tyr | Tyr | Phe | Glu | Lys | Asp | Val | Lys | Gly | Glu | Ser | |
| | 210 | | | | | 215 | | | | | 220 | | | | | |
| ttg | ttt | cat | tct | aag | aaa | atg | gac | ctg | aca | gta | aat | ggg | gaa | caa | ctg | 720 |
| Leu | Phe | His | Ser | Lys | Lys | Met | Asp | Leu | Thr | Val | Asn | Gly | Glu | Gln | Leu | |

```
                225                 230                 235                 240
gat ctg gat cct ggt caa act tta att tat tat gtt gat gaa aaa gca      768
Asp Leu Asp Pro Gly Gln Thr Leu Ile Tyr Tyr Val Asp Glu Lys Ala
            245                 250                 255 cct gaa ttc tca atg cag ggt cta aaa taa                              798
Pro Glu Phe Ser Met Gln Gly Leu Lys
        260                 265

<210> SEQ ID NO 58
<211> LENGTH: 265
<212> TYPE: PRT
<213> ORGANISM: Homo sapiens

<400> SEQUENCE: 58

Met Ala Pro Pro Gln Val Leu Ala Phe Gly Leu Leu Leu Ala Ala Ala
1               5                   10                  15

Thr Ala Thr Phe Ala Ala Ala Gln Glu Glu Cys Val Cys Glu Asn Tyr
            20                  25                  30

Lys Leu Ala Val Asn Cys Phe Val Asn Asn Asn Arg Gln Cys Gln Cys
        35                  40                  45

Thr Ser Val Gly Ala Gln Asn Thr Val Ile Cys Ser Lys Leu Ala Ala
    50                  55                  60

Lys Cys Leu Val Met Lys Ala Glu Met Asn Gly Ser Lys Leu Gly Arg
65                  70                  75                  80

Arg Ala Lys Pro Glu Gly Ala Leu Gln Asn Asn Asp Gly Leu Tyr Asp
                85                  90                  95

Pro Asp Cys Asp Glu Ser Gly Leu Phe Lys Ala Lys Gln Cys Asn Gly
            100                 105                 110

Thr Ser Thr Cys Trp Cys Val Asn Thr Ala Gly Val Arg Arg Thr Asp
        115                 120                 125

Lys Asp Thr Glu Ile Thr Cys Ser Glu Arg Val Arg Thr Tyr Trp Ile
    130                 135                 140

Ile Ile Glu Leu Lys His Lys Ala Arg Glu Lys Pro Tyr Asp Ser Lys
145                 150                 155                 160

Ser Leu Arg Thr Ala Leu Gln Lys Glu Ile Thr Thr Arg Tyr Gln Leu
                165                 170                 175

Asp Pro Lys Phe Ile Thr Ser Ile Leu Tyr Glu Asn Asn Val Ile Thr
            180                 185                 190

Ile Asp Leu Val Gln Asn Ser Ser Gln Lys Thr Gln Asn Asp Val Asp
        195                 200                 205

Ile Ala Asp Val Ala Tyr Tyr Phe Glu Lys Asp Val Lys Gly Glu Ser
    210                 215                 220

Leu Phe His Ser Lys Lys Met Asp Leu Thr Val Asn Gly Glu Gln Leu
225                 230                 235                 240

Asp Leu Asp Pro Gly Gln Thr Leu Ile Tyr Tyr Val Asp Glu Lys Ala
                245                 250                 255

Pro Glu Phe Ser Met Gln Gly Leu Lys
            260                 265

<210> SEQ ID NO 59
<211> LENGTH: 945
<212> TYPE: DNA
<213> ORGANISM: Homo sapiens
<220> FEATURE:
<221> NAME/KEY: misc_feature
<223> OTHER INFORMATION: Full-Length EpCam
<220> FEATURE:
<221> NAME/KEY: CDS
<222> LOCATION: (1)..(942)
```

```
<220> FEATURE:
<221> NAME/KEY: mat_peptide
<222> LOCATION: (70)..()

<400> SEQUENCE: 59 atg gcg ccc ccg cag gtc ctc gcg ttc ggg ctt ctg ctt gcc gcg gcg      48
Met Ala Pro Pro Gln Val Leu Ala Phe Gly Leu Leu Leu Ala Ala Ala
        -20                 -15                 -10 acg gcg act ttt gcc gca gct cag gaa gaa tgt gtc tgt gaa aac tac      96
Thr Ala Thr Phe Ala Ala Ala Gln Glu Glu Cys Val Cys Glu Asn Tyr
         -5             -1   1                   5 aag ctg gcc gta aac tgc ttt gtg aat aat aat cgt caa tgc cag tgt     144
Lys Leu Ala Val Asn Cys Phe Val Asn Asn Asn Arg Gln Cys Gln Cys
 10                  15                  20                  25 act tca gtt ggt gca caa aat act gtc att tgc tca aag ctg gct gcc     192
Thr Ser Val Gly Ala Gln Asn Thr Val Ile Cys Ser Lys Leu Ala Ala
                 30                  35                  40 aaa tgt ttg gtg atg aag gca gaa atg aat ggc tca aaa ctt ggg aga     240
Lys Cys Leu Val Met Lys Ala Glu Met Asn Gly Ser Lys Leu Gly Arg
             45                  50                  55 aga gca aaa cct gaa ggg gcc ctc cag aac aat gat ggg ctt tat gat     288
Arg Ala Lys Pro Glu Gly Ala Leu Gln Asn Asn Asp Gly Leu Tyr Asp
         60                  65                  70 cct gac tgc gat gag agc ggg ctc ttt aag gcc aag cag tgc aac ggc     336
Pro Asp Cys Asp Glu Ser Gly Leu Phe Lys Ala Lys Gln Cys Asn Gly
 75                  80                  85 acc tcc acg tgc tgg tgt gtg aac act gct ggg gtc aga aga aca gac     384
Thr Ser Thr Cys Trp Cys Val Asn Thr Ala Gly Val Arg Arg Thr Asp
 90                  95                 100                 105 aag gac act gaa ata acc tgc tct gag cga gtg aga acc tac tgg atc     432
Lys Asp Thr Glu Ile Thr Cys Ser Glu Arg Val Arg Thr Tyr Trp Ile
                 110                 115                 120 atc att gaa cta aaa cac aaa gca aga gaa aaa cct tat gat agt aaa     480
Ile Ile Glu Leu Lys His Lys Ala Arg Glu Lys Pro Tyr Asp Ser Lys
             125                 130                 135 agt ttg cgg act gca ctt cag aag gag atc aca acg cgt tat caa ctg     528
Ser Leu Arg Thr Ala Leu Gln Lys Glu Ile Thr Thr Arg Tyr Gln Leu
         140                 145                 150 gat cca aaa ttt atc acg agt att ttg tat gag aat aat gtt atc act     576
Asp Pro Lys Phe Ile Thr Ser Ile Leu Tyr Glu Asn Asn Val Ile Thr
 155                 160                 165 att gat ctg gtt caa aat tct tct caa aaa act cag aat gat gtg gac     624
Ile Asp Leu Val Gln Asn Ser Ser Gln Lys Thr Gln Asn Asp Val Asp
170                 175                 180                 185 ata gct gat gtg gct tat tat ttt gaa aaa gat gtt aaa ggt gaa tcc     672
Ile Ala Asp Val Ala Tyr Tyr Phe Glu Lys Asp Val Lys Gly Glu Ser
                 190                 195                 200 ttg ttt cat tct aag aaa atg gac ctg aca gta aat ggg gaa caa ctg     720
Leu Phe His Ser Lys Lys Met Asp Leu Thr Val Asn Gly Glu Gln Leu
             205                 210                 215 gat ctg gat cct ggt caa act tta att tat tat gtt gat gaa aaa gca     768
Asp Leu Asp Pro Gly Gln Thr Leu Ile Tyr Tyr Val Asp Glu Lys Ala
         220                 225                 230 cct gaa ttc tca atg cag ggt cta aaa gct ggt gtt att gct gtt att     816
Pro Glu Phe Ser Met Gln Gly Leu Lys Ala Gly Val Ile Ala Val Ile
 235                 240                 245 gtg gtt gtg gtg ata gca gtt gtt gct gga att gtt gtg ctg gtt att     864
Val Val Val Val Ile Ala Val Val Ala Gly Ile Val Val Leu Val Ile
250                 255                 260                 265 tcc aga aag aag aga atg gca aag tat gag aag gct gag ata aag gag     912
Ser Arg Lys Lys Arg Met Ala Lys Tyr Glu Lys Ala Glu Ile Lys Glu
```

```
                      270               275               280
atg ggt gag atg cat agg gaa ctc aat gca taa                              945
Met Gly Glu Met His Arg Glu Leu Asn Ala
            285               290
```

<210> SEQ ID NO 60
<211> LENGTH: 314
<212> TYPE: PRT
<213> ORGANISM: Homo sapiens

<400> SEQUENCE: 60

```
Met Ala Pro Pro Gln Val Leu Ala Phe Gly Leu Leu Ala Ala Ala
            -20              -15              -10
Thr Ala Thr Phe Ala Ala Ala Gln Glu Glu Cys Val Cys Glu Asn Tyr
            -5           -1  1               5
Lys Leu Ala Val Asn Cys Phe Val Asn Asn Arg Gln Cys Gln Cys
 10               15              20              25
Thr Ser Val Gly Ala Gln Asn Thr Val Ile Cys Ser Lys Leu Ala Ala
                 30              35              40
Lys Cys Leu Val Met Lys Ala Glu Met Asn Gly Ser Lys Leu Gly Arg
         45              50              55
Arg Ala Lys Pro Glu Gly Ala Leu Gln Asn Asn Asp Gly Leu Tyr Asp
         60              65              70
Pro Asp Cys Asp Glu Ser Gly Leu Phe Lys Ala Lys Gln Cys Asn Gly
 75              80              85
Thr Ser Thr Cys Trp Cys Val Asn Thr Ala Gly Val Arg Arg Thr Asp
 90              95              100             105
Lys Asp Thr Glu Ile Thr Cys Ser Glu Arg Val Arg Thr Tyr Trp Ile
                 110             115             120
Ile Ile Glu Leu Lys His Lys Ala Arg Glu Lys Pro Tyr Asp Ser Lys
                 125             130             135
Ser Leu Arg Thr Ala Leu Gln Lys Glu Ile Thr Thr Arg Tyr Gln Leu
         140             145             150
Asp Pro Lys Phe Ile Thr Ser Ile Leu Tyr Glu Asn Asn Val Ile Thr
         155             160             165
Ile Asp Leu Val Gln Asn Ser Ser Gln Lys Thr Gln Asn Asp Val Asp
 170             175             180             185
Ile Ala Asp Val Ala Tyr Tyr Phe Glu Lys Asp Val Lys Gly Glu Ser
                 190             195             200
Leu Phe His Ser Lys Lys Met Asp Leu Thr Val Asn Gly Glu Gln Leu
                 205             210             215
Asp Leu Asp Pro Gly Gln Thr Leu Ile Tyr Tyr Val Asp Glu Lys Ala
         220             225             230
Pro Glu Phe Ser Met Gln Gly Leu Lys Ala Gly Val Ile Ala Val Ile
         235             240             245
Val Val Val Val Ile Ala Val Val Ala Gly Ile Val Val Leu Val Ile
 250             255             260             265
Ser Arg Lys Lys Arg Met Ala Lys Tyr Glu Lys Ala Glu Ile Lys Glu
                 270             275             280
Met Gly Glu Met His Arg Glu Leu Asn Ala
            285             290
```

<210> SEQ ID NO 61
<211> LENGTH: 26
<212> TYPE: DNA
<213> ORGANISM: Homo sapiens
<220> FEATURE:

<221> NAME/KEY: misc_feature
<223> OTHER INFORMATION: Forward Primer (for both soluble and full
      length EpCam:  EC-1

<400> SEQUENCE: 61
ttatgtcgac agcatggcgc ccccgc                                          26

<210> SEQ ID NO 62
<211> LENGTH: 31
<212> TYPE: DNA
<213> ORGANISM: Homo sapiens
<220> FEATURE:
<221> NAME/KEY: misc_feature
<223> OTHER INFORMATION: EpCAM Reverse Primer

<400> SEQUENCE: 62
gagttacgtc ccagatttta ttgggccccc t                                    31

<210> SEQ ID NO 63
<211> LENGTH: 23
<212> TYPE: DNA
<213> ORGANISM: Homo Sapiens
<220> FEATURE:
<221> NAME/KEY: misc_feature
<223> OTHER INFORMATION: Polylinker pING1736 oligonucleotides

<400> SEQUENCE: 63
tcgacgaatt catcgatggt acc                                             23

<210> SEQ ID NO 64
<211> LENGTH: 19
<212> TYPE: DNA
<213> ORGANISM: Homo Sapiens
<220> FEATURE:
<221> NAME/KEY: misc_feature
<223> OTHER INFORMATION: Polylinker pING1736 oligonucleotides reverse 3'
      to 5'

<400> SEQUENCE: 64
ggtaccatcg atgaattcg                                                  19

<210> SEQ ID NO 65
<211> LENGTH: 23
<212> TYPE: DNA
<213> ORGANISM: Homo Sapiens
<220> FEATURE:
<221> NAME/KEY: misc_feature
<223> OTHER INFORMATION: Polylinker pING1732 oligonucleotides

<400> SEQUENCE: 65
tcgacgaatt catcgatgat atc                                             23

<210> SEQ ID NO 66
<211> LENGTH: 19
<212> TYPE: DNA
<213> ORGANISM: Homo Sapiens
<220> FEATURE:
<221> NAME/KEY: misc_feature
<223> OTHER INFORMATION: Polylinker pING1732 oligonucleotides reverse 3'
      to 5'

<400> SEQUENCE: 66
gatatcatcg atgaattcg                                                  19

<210> SEQ ID NO 67
<211> LENGTH: 702
<212> TYPE: DNA
<213> ORGANISM: Homo Sapiens
<220> FEATURE:
<221> NAME/KEY: misc_feature
<223> OTHER INFORMATION: LDP-01 Light Chain
<220> FEATURE:
<221> NAME/KEY: CDS
<222> LOCATION: (1)..(699)
<220> FEATURE:
<221> NAME/KEY: mat_peptide
<222> LOCATION: (58)..()

<400> SEQUENCE: 67

```
atg gga tgg agc tgt atc atc ctc ttc ttg gta gca aca gct aca ggt     48
Met Gly Trp Ser Cys Ile Ile Leu Phe Leu Val Ala Thr Ala Thr Gly
            -15                 -10                 -5 gtc cac tcc gac atc cag atg acc cag agc cca agc agc ctg agc gcc     96
Val His Ser Asp Ile Gln Met Thr Gln Ser Pro Ser Ser Leu Ser Ala
        -1   1               5                  10 agc gtg ggt gac aga gtg acc atc acc tgt aaa gca agt aag agc att    144
Ser Val Gly Asp Arg Val Thr Ile Thr Cys Lys Ala Ser Lys Ser Ile
        15                  20                  25 agc aat tat tta gcc tgg tac cag cag aag cca ggt aag gct cca aag    192
Ser Asn Tyr Leu Ala Trp Tyr Gln Gln Lys Pro Gly Lys Ala Pro Lys
 30                  35                  40                  45 ctg ctg atc tac tat ggg tca act ttg cga tct ggt gtg cca agc aga    240
Leu Leu Ile Tyr Tyr Gly Ser Thr Leu Arg Ser Gly Val Pro Ser Arg
                 50                  55                  60 ttc agc ggt agc ggt agc ggt acc gac ttc acc ttc acc atc agc agc    288
Phe Ser Gly Ser Gly Ser Gly Thr Asp Phe Thr Phe Thr Ile Ser Ser
             65                  70                  75 ctc cag cca gag gac atc gcc acc tac tac tgc caa cag tat tat gaa    336
Leu Gln Pro Glu Asp Ile Ala Thr Tyr Tyr Cys Gln Gln Tyr Tyr Glu
         80                  85                  90 aga ccg ctc acg ttc ggc caa ggg acc aag gtg gaa atc aaa cga act    384
Arg Pro Leu Thr Phe Gly Gln Gly Thr Lys Val Glu Ile Lys Arg Thr
 95                 100                 105 gtg gct gca cca tct gtc ttc atc ttc ccg cca tct gat gag cag ttg    432
Val Ala Ala Pro Ser Val Phe Ile Phe Pro Pro Ser Asp Glu Gln Leu
110                 115                 120                 125 aaa tct gga act gcc tct gtt gtg tgc ctg ctg aat aac ttc tat ccc    480
Lys Ser Gly Thr Ala Ser Val Val Cys Leu Leu Asn Asn Phe Tyr Pro
                130                 135                 140 aga gag gcc aaa gta cag tgg aag gtg gat aac gcc ctc caa tcg ggt    528
Arg Glu Ala Lys Val Gln Trp Lys Val Asp Asn Ala Leu Gln Ser Gly
            145                 150                 155 aac tcc cag gag agt gtc aca gag cag gac agc aag gac agc acc tac    576
Asn Ser Gln Glu Ser Val Thr Glu Gln Asp Ser Lys Asp Ser Thr Tyr
        160                 165                 170 agc ctc agc agc acc ctg acg ctg agc aaa gca gac tac gag aaa cac    624
Ser Leu Ser Ser Thr Leu Thr Leu Ser Lys Ala Asp Tyr Glu Lys His
    175                 180                 185 aaa gtc tac gcc tgc gaa gtc acc cat cag ggc ctg agc tcg ccc gtc    672
Lys Val Tyr Ala Cys Glu Val Thr His Gln Gly Leu Ser Ser Pro Val
190                 195                 200                 205 aca aag agc ttc aac agg gga gag tgt tag                            702
Thr Lys Ser Phe Asn Arg Gly Glu Cys
                210
```

<210> SEQ ID NO 68
<211> LENGTH: 233
<212> TYPE: PRT
<213> ORGANISM: Homo Sapiens

<400> SEQUENCE: 68

| | | | | | | | | | | | |
|---|---|---|---|---|---|---|---|---|---|---|---|
|Met|Gly|Trp|Ser|Cys|Ile|Ile|Leu|Phe|Leu|Val|Ala|Thr|Ala|Thr|Gly|
| | | |-15| | | |-10| | | |-5|

Met Gly Trp Ser Cys Ile Ile Leu Phe Leu Val Ala Thr Ala Thr Gly
                -15              -10              -5

Val His Ser Asp Ile Gln Met Thr Gln Ser Pro Ser Ser Leu Ser Ala
     -1  1               5                      10

Ser Val Gly Asp Arg Val Thr Ile Thr Cys Lys Ala Ser Lys Ser Ile
     15              20              25

Ser Asn Tyr Leu Ala Trp Tyr Gln Gln Lys Pro Gly Lys Ala Pro Lys
30              35              40              45

Leu Leu Ile Tyr Tyr Gly Ser Thr Leu Arg Ser Gly Val Pro Ser Arg
             50              55              60

Phe Ser Gly Ser Gly Ser Gly Thr Asp Phe Thr Phe Thr Ile Ser Ser
         65              70              75

Leu Gln Pro Glu Asp Ile Ala Thr Tyr Tyr Cys Gln Gln Tyr Tyr Glu
     80              85              90

Arg Pro Leu Thr Phe Gly Gln Gly Thr Lys Val Glu Ile Lys Arg Thr
     95              100             105

Val Ala Ala Pro Ser Val Phe Ile Phe Pro Pro Ser Asp Glu Gln Leu
110             115             120             125

Lys Ser Gly Thr Ala Ser Val Val Cys Leu Leu Asn Asn Phe Tyr Pro
             130             135             140

Arg Glu Ala Lys Val Gln Trp Lys Val Asp Asn Ala Leu Gln Ser Gly
             145             150             155

Asn Ser Gln Glu Ser Val Thr Glu Gln Asp Ser Lys Asp Ser Thr Tyr
             160             165             170

Ser Leu Ser Ser Thr Leu Thr Leu Ser Lys Ala Asp Tyr Glu Lys His
     175             180             185

Lys Val Tyr Ala Cys Glu Val Thr His Gln Gly Leu Ser Ser Pro Val
190             195             200             205

Thr Lys Ser Phe Asn Arg Gly Glu Cys
                210

<210> SEQ ID NO 69
<211> LENGTH: 29
<212> TYPE: DNA
<213> ORGANISM: Homo Sapiens
<220> FEATURE:
<221> NAME/KEY: misc_feature
<223> OTHER INFORMATION: forward primer LDP5PrFwd

<400> SEQUENCE: 69
tgtattgaat tcaccatggg atggagctg                                  29

<210> SEQ ID NO 70
<211> LENGTH: 30
<212> TYPE: DNA
<213> ORGANISM: Homo Sapiens
<220> FEATURE:
<221> NAME/KEY: misc_feature
<223> OTHER INFORMATION: reverse primer LDPLC3PrXhoRev

<400> SEQUENCE: 70
gataactcga gctaacactc tcccctgttg                                 30

<210> SEQ ID NO 71
<211> LENGTH: 1410
<212> TYPE: DNA
<213> ORGANISM: Homo Sapiens
<220> FEATURE:
<221> NAME/KEY: misc_feature
<223> OTHER INFORMATION: LDP-01 Heavy Chain
<220> FEATURE:

```
<221> NAME/KEY: CDS
<222> LOCATION: (1)..(1407)
<220> FEATURE:
<221> NAME/KEY: mat_peptide
<222> LOCATION: (58)..()

<400> SEQUENCE: 71 atg gga tgg agc tgt atc atc ctc ttc ttg gta gca aca gct aca ggt      48
Met Gly Trp Ser Cys Ile Ile Leu Phe Leu Val Ala Thr Ala Thr Gly
            -15             -10              -5 gtc cac tcc cag gtc caa ctg cag gag agc ggt cca ggt ctt gtg aga      96
Val His Ser Gln Val Gln Leu Gln Glu Ser Gly Pro Gly Leu Val Arg
         -1  1               5                  10 cct agc cag acc ctg agc ctg acc tgc acc gtg tct ggc ttc acc ttc     144
Pro Ser Gln Thr Leu Ser Leu Thr Cys Thr Val Ser Gly Phe Thr Phe
         15              20                  25 acc gat tac ctt ctg cac tgg gtg aga cag cca cct gga cga ggt ctt     192
Thr Asp Tyr Leu Leu His Trp Val Arg Gln Pro Pro Gly Arg Gly Leu
30              35                  40                  45 gag tgg att gga tgg att gat cct gag gat ggt gaa aca aag tat ggt     240
Glu Trp Ile Gly Trp Ile Asp Pro Glu Asp Gly Glu Thr Lys Tyr Gly
                50                  55                  60 cag aag ttt caa agc aga gtg aca atg ctg gta gac acc agc aag aac     288
Gln Lys Phe Gln Ser Arg Val Thr Met Leu Val Asp Thr Ser Lys Asn
            65                  70                  75 cag ttc agc ctg aga ctc agc agc gtg aca gcc gcc gac acc gcg gtc     336
Gln Phe Ser Leu Arg Leu Ser Ser Val Thr Ala Ala Asp Thr Ala Val
        80                  85                  90 tat tat tgt gca aga ggc gaa tat aga tac aac tcg tgg ttt gat tac     384
Tyr Tyr Cys Ala Arg Gly Glu Tyr Arg Tyr Asn Ser Trp Phe Asp Tyr
95                  100                 105 tgg ggt caa ggc tca cta gtc aca gtc tcc tca gcc tcc acc aag ggc     432
Trp Gly Gln Gly Ser Leu Val Thr Val Ser Ser Ala Ser Thr Lys Gly
110                 115                 120                 125 cca tcg gtc ttc ccc ctg gca ccc tcc tcc aag agc acc tct ggg ggc     480
Pro Ser Val Phe Pro Leu Ala Pro Ser Ser Lys Ser Thr Ser Gly Gly
                130                 135                 140 aca gcg gcc ctg ggc tgc ctg gtc aag gac tac ttc ccc gaa ccg gtg     528
Thr Ala Ala Leu Gly Cys Leu Val Lys Asp Tyr Phe Pro Glu Pro Val
            145                 150                 155 acg gtg tcg tgg aac tca ggc gcc ctg acc agc ggc gtg cac acc ttc     576
Thr Val Ser Trp Asn Ser Gly Ala Leu Thr Ser Gly Val His Thr Phe
        160                 165                 170 ccg gct gtc cta cag tcc tca gga ctc tac tcc ctc agc agc gtg gtg     624
Pro Ala Val Leu Gln Ser Ser Gly Leu Tyr Ser Leu Ser Ser Val Val
    175                 180                 185 acc gtg ccc tcc agc agc ttg ggc acc cag acc tac atc tgc aac gtg     672
Thr Val Pro Ser Ser Ser Leu Gly Thr Gln Thr Tyr Ile Cys Asn Val
190                 195                 200                 205 aat cac aag ccc agc aac acc aag gtg gac aag aaa gtt gag ccc aaa     720
Asn His Lys Pro Ser Asn Thr Lys Val Asp Lys Lys Val Glu Pro Lys
                210                 215                 220 tct tgt gac aaa act cac aca tgc cca ccg tgc cca gca cct gaa ctc     768
Ser Cys Asp Lys Thr His Thr Cys Pro Pro Cys Pro Ala Pro Glu Leu
            225                 230                 235 gcg ggg gca ccg tca gtc ttc ctc ttc ccc cca aaa ccc aag cac acc     816
Ala Gly Ala Pro Ser Val Phe Leu Phe Pro Pro Lys Pro Lys His Thr
        240                 245                 250 ctc atg atc tcc cgg acc cct gag gtc aca tgc gtg gtg gtg gac gtg     864
Leu Met Ile Ser Arg Thr Pro Glu Val Thr Cys Val Val Val Asp Val
    255                 260                 265
```

```
agc cac gaa gac cct gag gtc aag ttc aac tgg tac gtg gac ggc gtg    912
Ser His Glu Asp Pro Glu Val Lys Phe Asn Trp Tyr Val Asp Gly Val
270             275                 280                 285 gag gtg cat aat gcc aag aca aag ccg cgg gag gag cag tac aac agc    960
Glu Val His Asn Ala Lys Thr Lys Pro Arg Glu Glu Gln Tyr Asn Ser
        290                 295                 300 acg tac cgt gtg gtc agc gtc ctc acc gtc ctg cac cag gac tgg ctg   1008
Thr Tyr Arg Val Val Ser Val Leu Thr Val Leu His Gln Asp Trp Leu
            305                 310                 315 aat ggc aag gag tac aag tgc aag gtc tcc aac aaa gcc ctc cca gcc   1056
Asn Gly Lys Glu Tyr Lys Cys Lys Val Ser Asn Lys Ala Leu Pro Ala
                320                 325                 330 ccc atc gag aaa acc atc tcc aaa gcc aaa ggg cag ccc cga gaa cca   1104
Pro Ile Glu Lys Thr Ile Ser Lys Ala Lys Gly Gln Pro Arg Glu Pro
                    335                 340                 345 cag gtg tac acc ctg ccc cca tcc cgg gat gag ctg acc aag aac cag   1152
Gln Val Tyr Thr Leu Pro Pro Ser Arg Asp Glu Leu Thr Lys Asn Gln
350                 355                 360                 365 gtc agc ctg acc tgc ctg gtc aaa ggc ttc tat ccc agc gac atc gcc   1200
Val Ser Leu Thr Cys Leu Val Lys Gly Phe Tyr Pro Ser Asp Ile Ala
            370                 375                 380 gtg gag tgg gag agc aat ggg cag ccg gag aac aac tac aag acc acg   1248
Val Glu Trp Glu Ser Asn Gly Gln Pro Glu Asn Asn Tyr Lys Thr Thr
                385                 390                 395 cct ccc gtg ctg gac tcc gac ggc tcc ttc ttc ctc tac agc aag ctc   1296
Pro Pro Val Leu Asp Ser Asp Gly Ser Phe Phe Leu Tyr Ser Lys Leu
                    400                 405                 410 acc gtg gac aag agc agg tgg cag cag ggg aac gtc ttc tca tgc tcc   1344
Thr Val Asp Lys Ser Arg Trp Gln Gln Gly Asn Val Phe Ser Cys Ser
                        415                 420                 425 gtg atg cat gag gct ctg cac aac cac tac acg cag aag agc ctc tcc   1392
Val Met His Glu Ala Leu His Asn His Tyr Thr Gln Lys Ser Leu Ser
430                 435                 440                 445 ctg tct ccg ggt aaa tga                                           1410
Leu Ser Pro Gly Lys
                450

<210> SEQ ID NO 72
<211> LENGTH: 469
<212> TYPE: PRT
<213> ORGANISM: Homo Sapiens

<400> SEQUENCE: 72

Met Gly Trp Ser Cys Ile Ile Leu Phe Leu Val Ala Thr Ala Thr Gly
                -15                 -10                 -5

Val His Ser Gln Val Gln Leu Gln Glu Ser Gly Pro Gly Leu Val Arg
        -1   1               5                  10

Pro Ser Gln Thr Leu Ser Leu Thr Cys Thr Val Ser Gly Phe Thr Phe
    15                  20                  25

Thr Asp Tyr Leu Leu His Trp Val Arg Gln Pro Pro Gly Arg Gly Leu
30                  35                  40                  45

Glu Trp Ile Gly Trp Ile Asp Pro Glu Asp Gly Glu Thr Lys Tyr Gly
                50                  55                  60

Gln Lys Phe Gln Ser Arg Val Thr Met Leu Val Asp Thr Ser Lys Asn
            65                  70                  75

Gln Phe Ser Leu Arg Leu Ser Ser Val Thr Ala Ala Asp Thr Ala Val
        80                  85                  90

Tyr Tyr Cys Ala Arg Gly Glu Tyr Arg Tyr Asn Ser Trp Phe Asp Tyr
    95                  100                 105
```

Trp Gly Gln Gly Ser Leu Val Thr Val Ser Ser Ala Ser Thr Lys Gly
110                 115                 120                 125

Pro Ser Val Phe Pro Leu Ala Pro Ser Ser Lys Ser Thr Ser Gly Gly
            130                 135                 140

Thr Ala Ala Leu Gly Cys Leu Val Lys Asp Tyr Phe Pro Glu Pro Val
        145                 150                 155

Thr Val Ser Trp Asn Ser Gly Ala Leu Thr Ser Gly Val His Thr Phe
    160                 165                 170

Pro Ala Val Leu Gln Ser Ser Gly Leu Tyr Ser Leu Ser Ser Val Val
175                 180                 185

Thr Val Pro Ser Ser Ser Leu Gly Thr Gln Thr Tyr Ile Cys Asn Val
190                 195                 200                 205

Asn His Lys Pro Ser Asn Thr Lys Val Asp Lys Lys Val Glu Pro Lys
                210                 215                 220

Ser Cys Asp Lys Thr His Thr Cys Pro Pro Cys Pro Ala Pro Glu Leu
            225                 230                 235

Ala Gly Ala Pro Ser Val Phe Leu Phe Pro Pro Lys Pro Lys His Thr
        240                 245                 250

Leu Met Ile Ser Arg Thr Pro Glu Val Thr Cys Val Val Val Asp Val
255                 260                 265

Ser His Glu Asp Pro Glu Val Lys Phe Asn Trp Tyr Val Asp Gly Val
270                 275                 280                 285

Glu Val His Asn Ala Lys Thr Lys Pro Arg Glu Glu Gln Tyr Asn Ser
                290                 295                 300

Thr Tyr Arg Val Val Ser Val Leu Thr Val Leu His Gln Asp Trp Leu
            305                 310                 315

Asn Gly Lys Glu Tyr Lys Cys Lys Val Ser Asn Lys Ala Leu Pro Ala
        320                 325                 330

Pro Ile Glu Lys Thr Ile Ser Lys Ala Lys Gly Gln Pro Arg Glu Pro
335                 340                 345

Gln Val Tyr Thr Leu Pro Pro Ser Arg Asp Glu Leu Thr Lys Asn Gln
350                 355                 360                 365

Val Ser Leu Thr Cys Leu Val Lys Gly Phe Tyr Pro Ser Asp Ile Ala
                370                 375                 380

Val Glu Trp Glu Ser Asn Gly Gln Pro Glu Asn Asn Tyr Lys Thr Thr
            385                 390                 395

Pro Pro Val Leu Asp Ser Asp Gly Ser Phe Phe Leu Tyr Ser Lys Leu
        400                 405                 410

Thr Val Asp Lys Ser Arg Trp Gln Gln Gly Asn Val Phe Ser Cys Ser
415                 420                 425

Val Met His Glu Ala Leu His Asn His Tyr Thr Gln Lys Ser Leu Ser
430                 435                 440                 445

Leu Ser Pro Gly Lys
            450

<210> SEQ ID NO 73
<211> LENGTH: 30
<212> TYPE: DNA
<213> ORGANISM: Homo Sapiens
<220> FEATURE:
<221> NAME/KEY: misc_feature
<223> OTHER INFORMATION: reverse primer LDPLX3PrXhoRev

<400> SEQUENCE: 73
cttatctcga gtcatttacc cggagacagg                                    30

<210> SEQ ID NO 74
<211> LENGTH: 1836
<212> TYPE: DNA
<213> ORGANISM: Homo Sapiens
<220> FEATURE:
<221> NAME/KEY: misc_feature
<223> OTHER INFORMATION: CAB2.1
<220> FEATURE:
<221> NAME/KEY: CDS
<222> LOCATION: (1)..(1833)
<220> FEATURE:
<221> NAME/KEY: mat_peptide
<222> LOCATION: (103)..()

<400> SEQUENCE: 74

```
atg gag cct ccc ggc cgc cgc gag tgt ccc ttt cct tcc tgg cgc ttt      48
Met Glu Pro Pro Gly Arg Arg Glu Cys Pro Phe Pro Ser Trp Arg Phe
            -30                 -25                 -20 cct ggg ttg ctt ctg gcg gcc atg gtg ttg ctg tac tcc ttc tcc          96
Pro Gly Leu Leu Leu Ala Ala Met Val Leu Leu Tyr Ser Phe Ser
        -15                 -10                  -5 gat gcc tgt gag gag cca cca aca ttt gaa gct atg gag ctc atc ggg     144
Asp Ala Cys Glu Glu Pro Pro Thr Phe Glu Ala Met Glu Leu Ile Gly
 -1   1               5                  10 aaa cca aaa ccc tac tat gag att ggt gaa cga gta gat tat aag tgt     192
Lys Pro Lys Pro Tyr Tyr Glu Ile Gly Glu Arg Val Asp Tyr Lys Cys
 15              20                  25                  30 aaa aaa gga tac ttc tat ata cct cct ctt gcc acc cat act att tgt     240
Lys Lys Gly Tyr Phe Tyr Ile Pro Pro Leu Ala Thr His Thr Ile Cys
             35                  40                  45 gat cgg aat cat aca tgg cta cct gtc tca gat gac gcc tgt tat aga     288
Asp Arg Asn His Thr Trp Leu Pro Val Ser Asp Asp Ala Cys Tyr Arg
         50                  55                  60 gaa aca tgt cca tat ata cgg gat cct tta aat ggc caa gca gtc cct     336
Glu Thr Cys Pro Tyr Ile Arg Asp Pro Leu Asn Gly Gln Ala Val Pro
     65                  70                  75 gca aat ggg act tac gag ttt ggt tat cag atg cac ttt att tgt aat     384
Ala Asn Gly Thr Tyr Glu Phe Gly Tyr Gln Met His Phe Ile Cys Asn
 80                  85                  90 gag ggt tat tac tta att ggt gaa gaa att cta tat tgt gaa ctt aaa     432
Glu Gly Tyr Tyr Leu Ile Gly Glu Glu Ile Leu Tyr Cys Glu Leu Lys
 95                 100                 105                 110 gga tca gta gca att tgg agc gga aaa ccc ccc ata tgt gaa aag gtt     480
Gly Ser Val Ala Ile Trp Ser Gly Lys Pro Pro Ile Cys Glu Lys Val
                115                 120                 125 ttg tgt aca cca cct cca aaa ata aaa aat gga aaa cac acc ttt agt     528
Leu Cys Thr Pro Pro Pro Lys Ile Lys Asn Gly Lys His Thr Phe Ser
            130                 135                 140 gaa gta gaa gta ttt gag tat ctt gat gca gta act tat agt tgt gat     576
Glu Val Glu Val Phe Glu Tyr Leu Asp Ala Val Thr Tyr Ser Cys Asp
        145                 150                 155 cct gca cct gga cca gat cca ttt tca ctt att gga gag agc acg att     624
Pro Ala Pro Gly Pro Asp Pro Phe Ser Leu Ile Gly Glu Ser Thr Ile
    160                 165                 170 tat tgt ggt gac aat tca gtg tgg agt cgt gct gct cca gag tgt aaa     672
Tyr Cys Gly Asp Asn Ser Val Trp Ser Arg Ala Ala Pro Glu Cys Lys
175                 180                 185                 190 gtg gtc aaa tgt cga ttt cca gta gtc gaa aat gga aaa cag ata tca     720
Val Val Lys Cys Arg Phe Pro Val Val Glu Asn Gly Lys Gln Ile Ser
                195                 200                 205 gga ttt gga aaa aaa ttt tac tac aaa gca aca gtt atg ttt gaa tgc     768
Gly Phe Gly Lys Lys Phe Tyr Tyr Lys Ala Thr Val Met Phe Glu Cys
            210                 215                 220
```

```
gat aag ggt ttt tac ctc gat ggc agc gac aca att gtc tgt gac agt    816
Asp Lys Gly Phe Tyr Leu Asp Gly Ser Asp Thr Ile Val Cys Asp Ser
        225                 230                 235 aac agt act tgg gat ccc cca gtt cca aag tgt ctt aaa gtg tcg act    864
Asn Ser Thr Trp Asp Pro Pro Val Pro Lys Cys Leu Lys Val Ser Thr
    240                 245                 250 gac tgt ggc ctt ccc cca gat gta cct aat gcc cag cca gct ttg gaa    912
Asp Cys Gly Leu Pro Pro Asp Val Pro Asn Ala Gln Pro Ala Leu Glu
255                 260                 265                 270 ggc cgt aca agt ttt ccc gag gat act gta ata acg tac aaa tgt gaa    960
Gly Arg Thr Ser Phe Pro Glu Asp Thr Val Ile Thr Tyr Lys Cys Glu
                275                 280                 285 gaa agc ttt gtg aaa att cct ggc gag aag gac tca gtg atc tgc ctt   1008
Glu Ser Phe Val Lys Ile Pro Gly Glu Lys Asp Ser Val Ile Cys Leu
        290                 295                 300 aag ggc agt caa tgg tca gat att gaa gag ttc tgc aat cgt agc tgc   1056
Lys Gly Ser Gln Trp Ser Asp Ile Glu Glu Phe Cys Asn Arg Ser Cys
    305                 310                 315 gag gtg cca aca agg cta aat tct gca tcc ctc aaa cag cct tat atc   1104
Glu Val Pro Thr Arg Leu Asn Ser Ala Ser Leu Lys Gln Pro Tyr Ile
320                 325                 330 act cag aat tac ttc cct gtc ggt act gtt gtg gaa tat gag tgc cgt   1152
Thr Gln Asn Tyr Phe Pro Val Gly Thr Val Val Glu Tyr Glu Cys Arg
335                 340                 345                 350 cca ggt tac aga aga gaa cct tct cta tca cca aaa cta act tgc ctt   1200
Pro Gly Tyr Arg Arg Glu Pro Ser Leu Ser Pro Lys Leu Thr Cys Leu
                355                 360                 365 cag aat tta aaa tgg tcc aca gca gtc gaa ttt tgt aaa aag aaa tca   1248
Gln Asn Leu Lys Trp Ser Thr Ala Val Glu Phe Cys Lys Lys Lys Ser
        370                 375                 380 tgc cct aat ccg gga gaa ata cga aat ggt cag att gat gta cca ggt   1296
Cys Pro Asn Pro Gly Glu Ile Arg Asn Gly Gln Ile Asp Val Pro Gly
    385                 390                 395 ggc ata tta ttt ggt gca acc atc tcc ttc tca tgt aac aca ggg tac   1344
Gly Ile Leu Phe Gly Ala Thr Ile Ser Phe Ser Cys Asn Thr Gly Tyr
400                 405                 410 aaa tta ttt ggc tcg act tct agt ttt tgt cta ata agc ggc tcg agt   1392
Lys Leu Phe Gly Ser Thr Ser Ser Phe Cys Leu Ile Ser Gly Ser Ser
415                 420                 425                 430 gtc cag tgg agt gac ccg ttg cca gag tgc aga gaa att tat tgt cca   1440
Val Gln Trp Ser Asp Pro Leu Pro Glu Cys Arg Glu Ile Tyr Cys Pro
                435                 440                 445 gca cca cca caa att gac aat gga ata att caa ggg gaa cgt gac cat   1488
Ala Pro Pro Gln Ile Asp Asn Gly Ile Ile Gln Gly Glu Arg Asp His
        450                 455                 460 tat gga tat aga cag tct gta acg tat gca tgt aat aaa gga ttc acc   1536
Tyr Gly Tyr Arg Gln Ser Val Thr Tyr Ala Cys Asn Lys Gly Phe Thr
    465                 470                 475 atg att gga gag cac tct att tat tgt act gtg aat aat gat gaa gga   1584
Met Ile Gly Glu His Ser Ile Tyr Cys Thr Val Asn Asn Asp Glu Gly
480                 485                 490 gag tgg agt ggc cca cca cct gaa tgc aga gga aaa tct cta act tcc   1632
Glu Trp Ser Gly Pro Pro Pro Glu Cys Arg Gly Lys Ser Leu Thr Ser
495                 500                 505                 510 aag gtc cca cca aca gtt cag aaa cct acc aca gta aat gtt cca act   1680
Lys Val Pro Pro Thr Val Gln Lys Pro Thr Thr Val Asn Val Pro Thr
                515                 520                 525 aca gaa gtc tca cca act tct cag aaa acc acc aca aaa acc acc aca   1728
Thr Glu Val Ser Pro Thr Ser Gln Lys Thr Thr Thr Lys Thr Thr Thr
        530                 535                 540
```

```
cca aat gct caa gca aca cgg agt aca cct gtt tcc agg aca acc aag    1776
Pro Asn Ala Gln Ala Thr Arg Ser Thr Pro Val Ser Arg Thr Thr Lys
        545                 550                 555 cat ttt cat gaa aca acc cca aat aaa gga agt gga acc act tca ggt    1824
His Phe His Glu Thr Thr Pro Asn Lys Gly Ser Gly Thr Thr Ser Gly
    560                 565                 570 act acc cgt tga                                                    1836
Thr Thr Arg
575

<210> SEQ ID NO 75
<211> LENGTH: 611
<212> TYPE: PRT
<213> ORGANISM: Homo Sapiens

<400> SEQUENCE: 75

Met Glu Pro Pro Gly Arg Arg Glu Cys Pro Phe Pro Ser Trp Arg Phe
                -30                 -25                 -20

Pro Gly Leu Leu Leu Ala Ala Met Val Leu Leu Leu Tyr Ser Phe Ser
            -15                 -10                  -5

Asp Ala Cys Glu Glu Pro Pro Thr Phe Glu Ala Met Glu Leu Ile Gly
     -1  1                  5                  10

Lys Pro Lys Pro Tyr Tyr Glu Ile Gly Glu Arg Val Asp Tyr Lys Cys
 15              20                  25                  30

Lys Lys Gly Tyr Phe Tyr Ile Pro Pro Leu Ala Thr His Thr Ile Cys
            35                  40                  45

Asp Arg Asn His Thr Trp Leu Pro Val Ser Asp Asp Ala Cys Tyr Arg
         50                  55                  60

Glu Thr Cys Pro Tyr Ile Arg Asp Pro Leu Asn Gly Gln Ala Val Pro
     65                  70                  75

Ala Asn Gly Thr Tyr Glu Phe Gly Tyr Gln Met His Phe Ile Cys Asn
 80                  85                  90

Glu Gly Tyr Tyr Leu Ile Gly Glu Glu Ile Leu Tyr Cys Glu Leu Lys
 95                 100                 105                 110

Gly Ser Val Ala Ile Trp Ser Gly Lys Pro Pro Ile Cys Glu Lys Val
            115                 120                 125

Leu Cys Thr Pro Pro Lys Ile Lys Asn Gly Lys His Thr Phe Ser
        130                 135                 140

Glu Val Glu Val Phe Glu Tyr Leu Asp Ala Val Thr Tyr Ser Cys Asp
        145                 150                 155

Pro Ala Pro Gly Pro Asp Pro Phe Ser Leu Ile Gly Glu Ser Thr Ile
        160                 165                 170

Tyr Cys Gly Asp Asn Ser Val Trp Ser Arg Ala Ala Pro Glu Cys Lys
175                 180                 185                 190

Val Val Lys Cys Arg Phe Pro Val Val Glu Asn Gly Lys Gln Ile Ser
            195                 200                 205

Gly Phe Gly Lys Lys Phe Tyr Tyr Lys Ala Thr Val Met Phe Glu Cys
            210                 215                 220

Asp Lys Gly Phe Tyr Leu Asp Gly Ser Asp Thr Ile Val Cys Asp Ser
            225                 230                 235

Asn Ser Thr Trp Asp Pro Pro Val Pro Lys Cys Leu Lys Val Ser Thr
240                 245                 250

Asp Cys Gly Leu Pro Pro Asp Val Pro Asn Ala Gln Pro Ala Leu Glu
255                 260                 265                 270

Gly Arg Thr Ser Phe Pro Glu Asp Thr Val Ile Thr Tyr Lys Cys Glu
            275                 280                 285
```

```
Glu Ser Phe Val Lys Ile Pro Gly Glu Lys Asp Ser Val Ile Cys Leu
            290                 295                 300

Lys Gly Ser Gln Trp Ser Asp Ile Glu Glu Phe Cys Asn Arg Ser Cys
        305                 310                 315

Glu Val Pro Thr Arg Leu Asn Ser Ala Ser Leu Lys Gln Pro Tyr Ile
320                 325                 330

Thr Gln Asn Tyr Phe Pro Val Gly Thr Val Val Glu Tyr Glu Cys Arg
335                 340                 345                 350

Pro Gly Tyr Arg Arg Glu Pro Ser Leu Ser Pro Lys Leu Thr Cys Leu
                355                 360                 365

Gln Asn Leu Lys Trp Ser Thr Ala Val Glu Phe Cys Lys Lys Lys Ser
            370                 375                 380

Cys Pro Asn Pro Gly Glu Ile Arg Asn Gly Gln Ile Asp Val Pro Gly
        385                 390                 395

Gly Ile Leu Phe Gly Ala Thr Ile Ser Phe Ser Cys Asn Thr Gly Tyr
400                 405                 410

Lys Leu Phe Gly Ser Thr Ser Ser Phe Cys Leu Ile Ser Gly Ser Ser
415                 420                 425                 430

Val Gln Trp Ser Asp Pro Leu Pro Glu Cys Arg Glu Ile Tyr Cys Pro
                435                 440                 445

Ala Pro Pro Gln Ile Asp Asn Gly Ile Ile Gln Gly Glu Arg Asp His
            450                 455                 460

Tyr Gly Tyr Arg Gln Ser Val Thr Tyr Ala Cys Asn Lys Gly Phe Thr
        465                 470                 475

Met Ile Gly Glu His Ser Ile Tyr Cys Thr Val Asn Asn Asp Glu Gly
480                 485                 490

Glu Trp Ser Gly Pro Pro Glu Cys Arg Gly Lys Ser Leu Thr Ser
495                 500                 505                 510

Lys Val Pro Pro Thr Val Gln Lys Pro Thr Thr Val Asn Val Pro Thr
                515                 520                 525

Thr Glu Val Ser Pro Thr Ser Gln Lys Thr Thr Thr Lys Thr Thr Thr
            530                 535                 540

Pro Asn Ala Gln Ala Thr Arg Ser Thr Pro Val Ser Arg Thr Thr Lys
        545                 550                 555

His Phe His Glu Thr Thr Pro Asn Lys Gly Ser Gly Thr Thr Ser Gly
560                 565                 570

Thr Thr Arg
575

<210> SEQ ID NO 76
<211> LENGTH: 29
<212> TYPE: DNA
<213> ORGANISM: Homo Sapiens
<220> FEATURE:
<221> NAME/KEY: misc_feature
<223> OTHER INFORMATION: CAB2RI5PrFwd-CAB-2 Oligos and Primers

<400> SEQUENCE: 76
gttaagaatt ccaccatgga gcctcccgg                                29

<210> SEQ ID NO 77
<211> LENGTH: 31
<212> TYPE: DNA
<213> ORGANISM: Homo Sapiens
<220> FEATURE:
<221> NAME/KEY: misc_feature
<223> OTHER INFORMATION: CAB2Cla3PrRev-Cab-2 Oligos and Primers

<400> SEQUENCE: 77
```

```
tctaaatcga ttcaacgggt agtacctgaa g                                              31
```

<210> SEQ ID NO 78
<211> LENGTH: 31
<212> TYPE: DNA
<213> ORGANISM: Homo Sapiens
<220> FEATURE:
<221> NAME/KEY: misc_feature
<223> OTHER INFORMATION: CAB2Kpn3PrRev-Cab-2 Oligos and Primers

<400> SEQUENCE: 78

```
tctaaggtac ctcaacgggt agtacctgaa g                                              31
```

<210> SEQ ID NO 79
<211> LENGTH: 30
<212> TYPE: DNA
<213> ORGANISM: Homo sapiens

<400> SEQUENCE: 79

```
gtatcccttg agttacgtat tgagctcgtt                                                30
```

<210> SEQ ID NO 80
<211> LENGTH: 112
<212> TYPE: PRT
<213> ORGANISM: Artificial Sequence
<220> FEATURE:
<223> OTHER INFORMATION: Synthesized: Murine ING-1 light chain variable
      region (amino acids 1-112)

<400> SEQUENCE: 80

Asp Ile Val Met Thr Gln Ala Ala Phe Ser Asn Pro Val Thr Leu Gly
1               5                   10                  15

Thr Ser Gly Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Leu Ala Ser Gly Val Pro
    50                  55                  60

Asp Arg Phe Ser Ser Ser Gly Ser Gly Thr Asp Phe Thr Leu Arg Ile
65                  70                  75                  80

Ser Arg Val Glu Ala Glu Asp Val Gly Val Tyr Tyr Cys Ala Gln Asn
                85                  90                  95

Leu Glu Leu Pro Arg Thr Phe Gly Gly Gly Thr Lys Leu Glu Met Lys
            100                 105                 110

<210> SEQ ID NO 81
<211> LENGTH: 107
<212> TYPE: PRT
<213> ORGANISM: Artificial Sequence
<220> FEATURE:
<223> OTHER INFORMATION: Synthesized: Human ING-1 light chain variable
      region (amino acids 1-112)
<220> FEATURE:
<221> NAME/KEY: misc_feature
<222> LOCATION: (92)..(92)
<223> OTHER INFORMATION: Xaa can be any naturally occurring amino acid
<220> FEATURE:
<221> NAME/KEY: misc_feature
<222> LOCATION: (94)..(94)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid

<400> SEQUENCE: 81

-continued

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Leu Asn Trp Tyr Leu Gln Lys Pro Gly Gln Ser Pro Gln Leu Leu Ile
        35                  40                  45

Tyr Leu Val Ser Asn Arg Ala Ser Gly Val Pro Asp Arg Phe Ser Gly
    50                  55                  60

Ser Gly Ser Gly Thr Asp Phe Thr Leu Lys Ile Ser Arg Val Glu Ala
65                  70                  75                  80

Glu Asp Val Gly Val Tyr Tyr Cys Met Gln Ala Xaa Gln Xaa Pro Xaa
                85                  90                  95

Thr Phe Gly Gln Gly Thr Lys Val Glu Ile Lys
                100                 105
```

<210> SEQ ID NO 82
<211> LENGTH: 112
<212> TYPE: PRT
<213> ORGANISM: Artificial Sequence
<220> FEATURE:
<223> OTHER INFORMATION: Synthesized: ING-1 light chain variable region
      (amino acids 1-112); low risk changes

<400> SEQUENCE: 82

```
Asp Ile Val Met Thr Gln Ser Ala Leu Ser Asn Pro Val Thr Leu Gly
1               5                   10                  15

Glu Ser Gly Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Ser Ser Gly Ser Gly Thr Asp Phe Thr Leu Lys Ile
65                  70                  75                  80

Ser Arg Val Glu Ala Glu Asp Val Gly Val Tyr Tyr Cys Ala Gln Asn
                85                  90                  95

Leu Glu Leu Pro Arg Thr Phe Gly Gln Gly Thr Lys Leu Glu Met Lys
                100                 105                 110
```

<210> SEQ ID NO 83
<211> LENGTH: 112
<212> TYPE: PRT
<213> ORGANISM: Artificial Sequence
<220> FEATURE:
<223> OTHER INFORMATION: Synthesized: ING-1 light chain variable region
      (amino acids 1-112); low plus moderate risk changes

<400> SEQUENCE: 83

```
Asp Ile Val Met Thr Gln Ser Pro Leu Ser Leu Pro Val Thr Pro Gly
1               5                   10                  15

Glu Pro Gly Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
        35                  40                  45

Pro Gln Leu Leu Ile Tyr Gln Met Ser Asn Arg Ala Ser Gly Val Pro
    50                  55                  60

Asp Arg Phe Ser Ser Ser Gly Ser Gly Thr Asp Phe Thr Leu Lys Ile
65                  70                  75                  80
```

-continued

```
Ser Arg Val Glu Ala Glu Asp Val Gly Val Tyr Tyr Cys Ala Gln Asn
                85                  90                  95

Leu Glu Leu Pro Arg Thr Phe Gly Gln Gly Thr Lys Leu Glu Met Lys
            100                 105                 110

<210> SEQ ID NO 84
<211> LENGTH: 116
<212> TYPE: PRT
<213> ORGANISM: Artificial Sequence
<220> FEATURE:
<223> OTHER INFORMATION: Synthesized: Murine ING-1 heavy chain variable
      region (amino acids 1-116)

<400> SEQUENCE: 84

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Lys Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Glu Glu Pro Thr Tyr Gly Asp Asp Phe
    50                  55                  60

Lys Gly Arg Phe Ala Phe Ser Leu Glu Thr Ser Ala Ser Thr Ala Asn
65                  70                  75                  80

Leu Gln Ile Asn Asn Leu Lys Ser Glu Asp Thr Ala Thr Tyr Phe Cys
                85                  90                  95

Ala Arg Phe Gly Ser Ala Val Asp Tyr Trp Gly Gln Gly Thr Ser Val
            100                 105                 110

Thr Val Ser Ser
        115

<210> SEQ ID NO 85
<211> LENGTH: 115
<212> TYPE: PRT
<213> ORGANISM: Artificial Sequence
<220> FEATURE:
<223> OTHER INFORMATION: Synthesized: Human ING-1 heavy chain variable
      region (amino acids 1-116)
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (30)..(30)
<223> OTHER INFORMATION: Xaa can be any naturally occurring amino acid
<220> FEATURE:
<221> NAME/KEY: misc_feature
<222> LOCATION: (33)..(33)
<223> OTHER INFORMATION: Xaa can be any naturally occurring amino acid
<220> FEATURE:
<221> NAME/KEY: misc_feature
<222> LOCATION: (35)..(35)
<223> OTHER INFORMATION: Xaa can be any naturally occurring amino acid
<220> FEATURE:
<221> NAME/KEY: misc_feature
<222> LOCATION: (50)..(50)
<223> OTHER INFORMATION: Xaa can be any naturally occurring amino acid
<220> FEATURE:
<221> NAME/KEY: misc_feature
<222> LOCATION: (52)..(52)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (56)..(56)
```

-continued

```
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
<220> FEATURE:
<221> NAME/KEY: misc_feature
<222> LOCATION: (98)..(104)
<223> OTHER INFORMATION: Xaa can be any naturally occurring amino acid

<400> SEQUENCE: 85

Gln Val Gln Leu Val Gln Ser Gly Ala Glu Val Lys Lys Pro Gly Xaa
1               5                   10                  15

Ser Val Lys Val Ser Cys Lys Ala Ser Gly Tyr Thr Phe Xaa Ser Tyr
            20                  25                  30

Xaa Ile Xaa Trp Val Arg Gln Ala Pro Gly Gln Gly Leu Glu Trp Met
        35                  40                  45

Gly Xaa Ile Xaa Pro Xaa Gly Xaa Thr Xaa Tyr Ala Gln Lys Phe Gln
    50                  55                  60

Gly Arg Val Thr Ile Thr Xaa Asp Xaa Ser Thr Ser Thr Ala Tyr Met
65                  70                  75                  80

Glu Leu Ser Ser Leu Arg Ser Glu Asp Thr Ala Val Tyr Tyr Cys Ala
                85                  90                  95

Arg Xaa Xaa Xaa Xaa Xaa Xaa Xaa Trp Gly Gln Gly Thr Leu Val Thr
            100                 105                 110

Val Ser Ser
        115

<210> SEQ ID NO 86
<211> LENGTH: 116
<212> TYPE: PRT
<213> ORGANISM: Artificial Sequence
<220> FEATURE:
<223> OTHER INFORMATION: Synthesized: ING-1 heavy chain variable region
      (amino acids 1-116); low risk changes

<400> SEQUENCE: 86

Gln Ile Gln Leu Val Gln Ser Gly Pro Glu Val Lys Lys Pro Gly Glu
1               5                   10                  15

Ser Val Lys Ile Ser Cys Lys Ala Ser Gly Tyr Thr Phe Thr Lys Tyr
            20                  25                  30

Gly Met Asn Trp Val Lys Gln Ala Pro Gly Gln Gly Leu Lys Trp Met
        35                  40                  45

Gly Trp Ile Asn Thr Tyr Thr Glu Glu Pro Thr Tyr Gly Asp Asp Phe
    50                  55                  60

Lys Gly Arg Phe Thr Phe Thr Leu Asp Thr Ser Thr Ser Thr Ala Tyr
65                  70                  75                  80

Leu Glu Ile Ser Ser Leu Arg Ser Glu Asp Thr Ala Thr Tyr Phe Cys
                85                  90                  95

Ala Arg Phe Gly Ser Ala Val Asp Tyr Trp Gly Gln Gly Thr Leu Val
            100                 105                 110

Thr Val Ser Ser
        115
```

```
<210> SEQ ID NO 87
<211> LENGTH: 116
<212> TYPE: PRT
<213> ORGANISM: Artificial Sequence
<220> FEATURE:
<223> OTHER INFORMATION: Synthesized: ING-1 heavy chain variable region
      (amino acids 1-116); low plus moderate risk changes

<400> SEQUENCE: 87

Gln Ile Gln Leu Val Gln Ser Gly Ala Glu Val Lys Lys Pro Gly Glu
1               5                   10                  15

Ser Val Lys Ile Ser Cys Lys Ala Ser Gly Tyr Thr Phe Thr Lys Tyr
                20                  25                  30

Gly Met Asn Trp Val Arg Gln Ala Pro Gly Gln Gly Leu Glu Trp Met
            35                  40                  45

Gly Trp Ile Asn Thr Tyr Thr Glu Glu Pro Thr Tyr Gly Gln Lys Phe
        50                  55                  60

Gln Gly Arg Phe Thr Phe Thr Leu Asp Thr Ser Thr Ser Thr Ala Tyr
65                  70                  75                  80

Leu Glu Ile Ser Ser Leu Arg Ser Glu Asp Thr Ala Val Tyr Phe Cys
                85                  90                  95

Ala Arg Phe Gly Ser Ala Val Asp Tyr Trp Gly Gln Gly Thr Leu Val
            100                 105                 110

Thr Val Ser Ser
        115
```